(12) United States Patent
Benning et al.

(10) Patent No.: US 10,006,039 B2
(45) Date of Patent: Jun. 26, 2018

(54) PRODUCTION OF OIL IN VEGETATIVE TISSUES

(71) Applicant: Board of Trustees of Michigan State University, East Lansing, MI (US)

(72) Inventors: Christoph Benning, East Lansing, MI (US); Sanjaya, East Lansing, MI (US); Changcheng Xu, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 283 days.

(21) Appl. No.: 14/046,504

(22) Filed: Oct. 4, 2013

(65) Prior Publication Data

US 2014/0228585 A1    Aug. 14, 2014

Related U.S. Application Data

(60) Provisional application No. 61/709,447, filed on Oct. 4, 2012.

(51) Int. Cl.
*C12N 15/82* (2006.01)
*C07K 14/415* (2006.01)
*C12N 9/12* (2006.01)
*C12N 9/14* (2006.01)

(52) U.S. Cl.
CPC ........ *C12N 15/8247* (2013.01); *C07K 14/415* (2013.01); *C12N 9/1241* (2013.01); *C12N 9/14* (2013.01); *C12N 15/8218* (2013.01); *C12Y 207/07027* (2013.01); *C12Y 306/03* (2013.01)

(58) Field of Classification Search
None
See application file for complete search history.

(56) References Cited

U.S. PATENT DOCUMENTS

| 8,217,223 | B2 * | 7/2012 | Haertel | C07K 14/415 435/410 |
| 2007/0214517 | A1 * | 9/2007 | Alexandrov | C07K 14/415 800/278 |

FOREIGN PATENT DOCUMENTS

WO    WO 2008068498 A2 *    6/2008    ......... C12N 15/8203

OTHER PUBLICATIONS

Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*
Sanjaya et al (Increasing the energy density of vegetative tissues by diverting carbon from starch to oil biosynthesis in transgenic Arabidopsis, Plant Biotechnology Journal 9, pp. 874-883, 2011. Received Oct. 13, 2010; revised Dec. 29, 2010; accepted Jan. 7, 2011).*
Xu et al (A permease-like protein involved in ER to thylakoid lipid transfer in *Arabidopsis*. EMBO J. May 15; 22: 2370-2379, 2003), and Graham et al (WO2008068498, published Dec. 6, 2008).*
Xu et al (Lipid Trafficking between the Endoplasmic Reticulum and the Plastid in *Arabidopsis* Requires the ExtraplastidicTGD4 Protein. The Plant Cell, vol. 20: 2190-2204, Aug. 2008).*
Cernac, A., et al., "WRINKLED1 encodes an AP2/EREB domain protein involved in the control of storage compound biosynthesis in *Arabidopsis*", The Plant Journal,40. (2004), 575-585.*
Sanjaya et al (Increasing the energy density of vegetative tissues by diverting carbon from starch to oil biosynthesis in transgenic *Arabidopsis*, Plant Biotechnology Journal 9, pp. 874-883, 2011. Received Oct. 13, 2010).*
Lu et al (A Small ATPase Protein of *Arabidopsis*, TGD3, Involved in Chloroplast Lipid Import. The Journal of Biological Chemistry vol. 282, No. 49, pp. 35945-35953, Dec. 7, 2007).*
Xu et al (Mutation of the TGD1 Chloroplast Envelope Protein Affects Phosphatidate Metabolism in *Arabidopsis*. The Plant Cell, vol. 17, 3094-3110, 2005).*
Awai, K., et al., "A phosphatidic acid-binding protein of the chloroplast inner envelope membrane involved in lipid trafficking", Proc. Natl. Acad. Sci. USA, 103(28), (2006), 10817-10822.
Cernac, A., et al., "WRINKLED1 encodes an AP2/EREB domain protein involved in the control of storage compound biosynthesis in *Arabidopsis*", The Plant Journal. 40, (2004), 575-585.
Cernac, A., et al., "WRI1 Is Required for Seed Germination and Seedling Establishmentl", Plant Physiology, 141, (2006), 745-757.
Lu, B., et al., "A Small ATPase Protein of *Arabidopsis*, TGD3, Involved in Chloroplast Lipid Import", J. Biol. Chem., 282(49), (2007), 35945-35953.
Sanjaya, et al., "Increasing the energy density of vegetative tissues by diverting carbon from starch to oil biosynthesis in transgenic *Arabidopsis*", Plant Biotechnology Journal, 9, (2011), 874-883.

(Continued)

*Primary Examiner* — Medina A Ibrahim
*Assistant Examiner* — Wayne Zhong
(74) *Attorney, Agent, or Firm* — Schwegman Lundberg & Woessner, P.A.

(57) ABSTRACT

The present invention relates to compositions and methods for providing RNA interference (RNAi) vectors comprising trigalactosyldiacylglycerol (tgd) biosynthesis enzyme constructs for increasing oil content of plants. Further, the use of tgd RNAi silencing vectors in combination with co-expression of heterologous oil regulating transcription factors, such as WRINKLED1, are contemplated to overcome the reduced growth and variable levels of embryonic lethality in plants with reduced TGD protein. Additionally, plants having reduced APS1, a gene encoding a major catalytic isoform of the small subunit of AGPase (AGP(-) plants), co-expressing a heterologous oil modulating transcription factor are contemplated for use in combination with plants having reduced TGD. Oil harvested from vegetative tissues of plants comprising vectors and genes of the present invention is contemplated for use in biofuel and biodiesel products.

12 Claims, 31 Drawing Sheets
(4 of 31 Drawing Sheet(s) Filed in Color)

(56) References Cited

OTHER PUBLICATIONS

Xu, C., et al., "Lipid Trafficking between the Endoplasmic Reticulum and the Plastid in *Arabidopsis* Requires the Extraplastidic TGD4 Protein", *Plant Cell*. 20, (2008), 2190-2204.

Xu, C., et al., "Mutation of the TGD1 Chloroplast Envelope Protein Affects Phosphatidate Metabolism in *Arabidopsis*", *Plant Cell*. 17, (2005), 3094-3110.

* cited by examiner

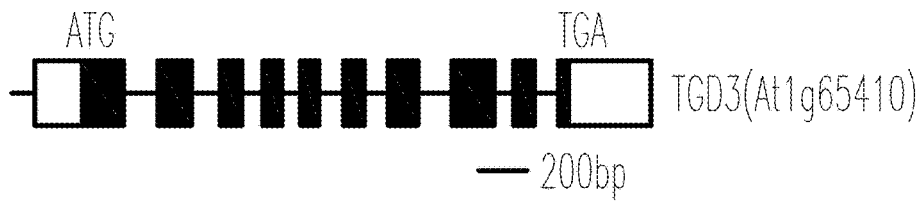

*Fig. 10A*

```
  1 AAAAATGGCA ATGTGACTCA CTCAATCGGT GACTCGCTAT AGTCTGTGAA
 51 GAAAGGCCAA TTTCGCCATA AAGTTCACAC CTTTGATCTC CTTTGTTTCT
101 GGGTTTCTCC TAAATCATCC AAATTGGTAT CGAATTTGCC CTTCTCCGAT
151 TCAATTTCTT CACGATCTCA AAACCCAGAA GAAAGAATCA TGCTTTCGTT
201 ATCATGCTCT TCTTCTTCTT CTTCGTTGCT TCCTCCGAGT TTACACTACC
251 ACGGTTCTTC TTCTGTTCAG TCCATCGTTG TACCAAGAAG GAGTCTTATC
301 TCGTTTCGTC GGAAAGTCTC TTGCTGTTGC ATAGCTCCAC CTCAGAACTT
351 GGACAACGAT GCCACCAAAT TCGAT
```

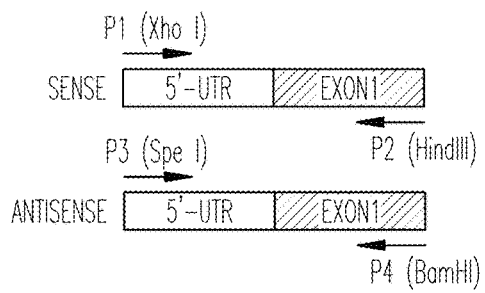

*Fig. 10B*

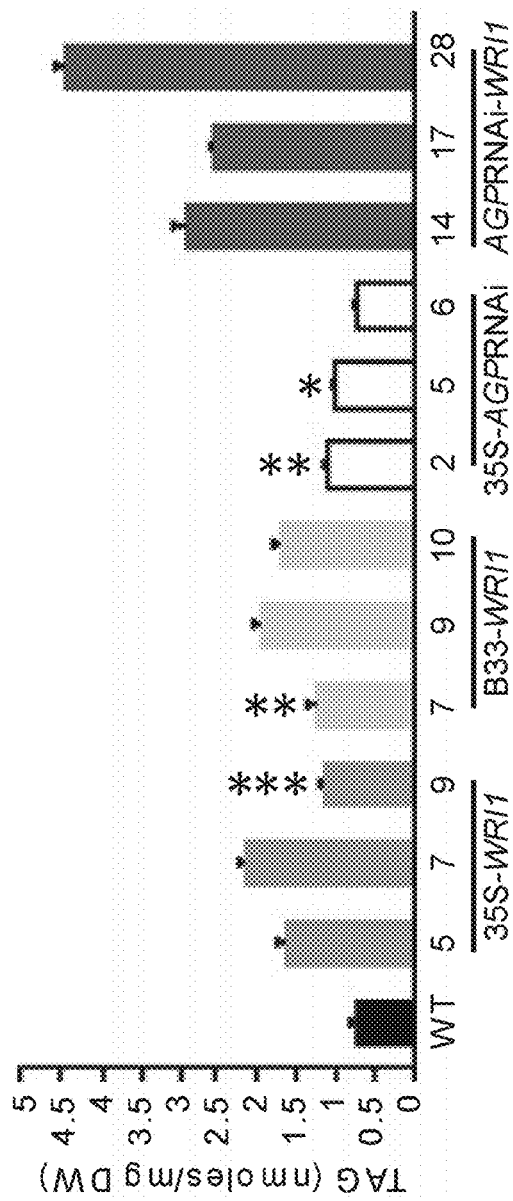
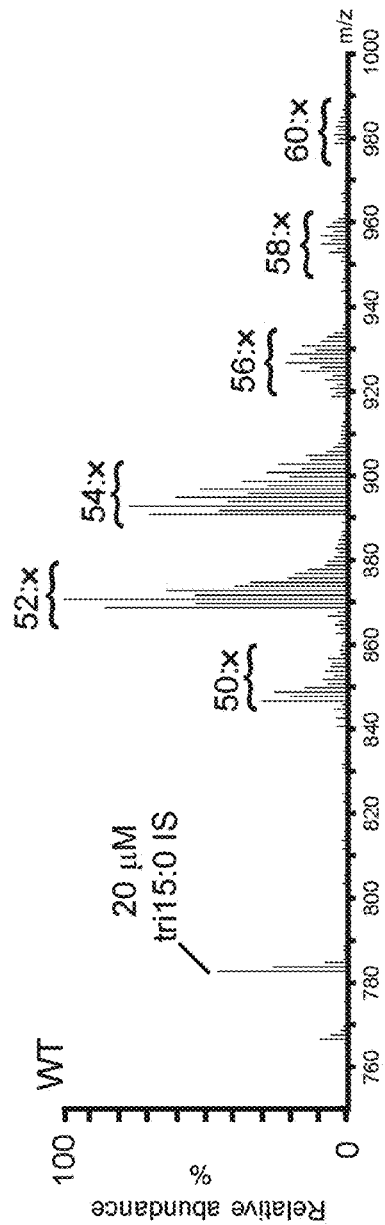
Fig. 22A
Fig. 22B

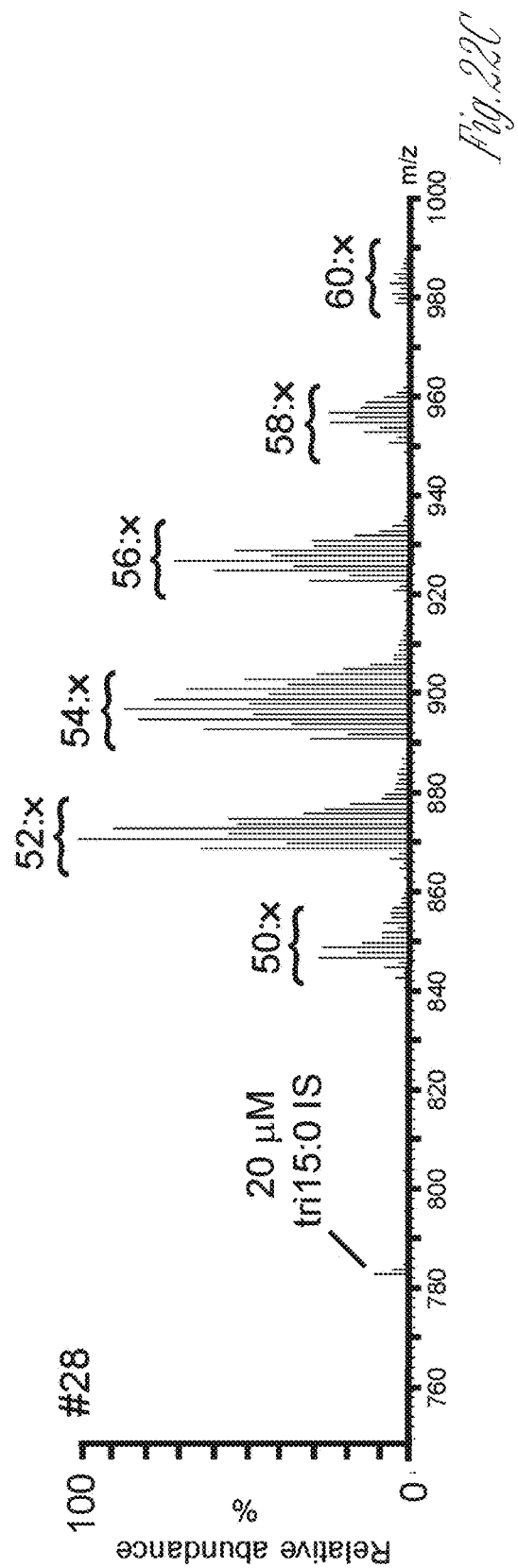
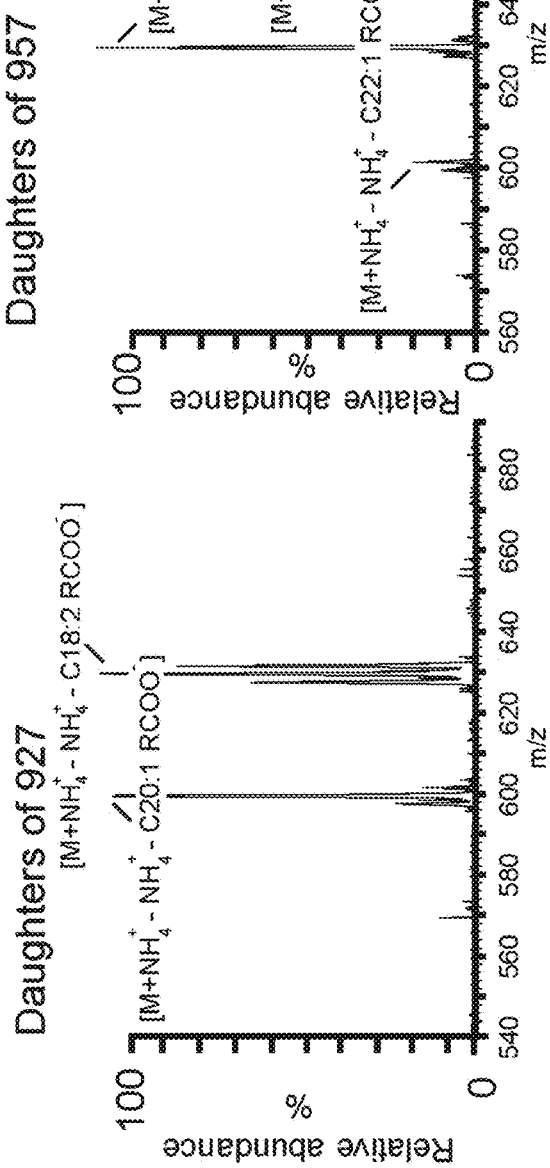

PRODUCTION OF OIL IN VEGETATIVE TISSUES

This patent application claims the benefit of priority, under 35 U.S.C. § 119(e), to U.S. Provisional Patent Application Ser. No. 61/709,447, filed on Oct. 4, 2013, the contents of which application is specifically incorporated by reference herein in its entirety.

This invention was made with government support under Grant No. MCB0453858 by The National Science Foundation (NSF), USDA-CSREES grant number 2005-35504-16195 from the United States Department of Agriculture, and Grant No. DE_FG02-07ER20356 from the Department of Energy (DOE) and Great Lakes Bioenergy Research Center Cooperative Agreement DE-FC02-07ER64494 by the DOE. The government has certain rights in the invention.

FIELD OF THE INVENTION

The present invention relates to compositions and methods for providing RNA interference (RNAi) vectors comprising trigalactosyldiacylglycerol (tgd) biosynthesis enzyme constructs for increasing the oil content of plants. Specifically, plant cells, plant tissues and whole plants are provided comprising novel tgd RNAi vectors for reducing TGD protein expression for increasing oil content (including relative amounts of triacylglycerols) in cells and in vegetative tissues. In particular, vectors are provided comprising tgd RNAi constructs for silencing tgd1 and tgd4 endogenous gene translation. Further, the use of tgd RNAi silencing vectors in combination with co-expression of heterologous oil regulating transcription factors, such as WRINKLED1, are contemplated to overcome the reduced growth and variable levels of embryonic lethality in plants with reduced TGD protein. Additionally, plants having reduced APS1, a gene encoding a major catalytic isoform of the small subunit of AGPase (AGP(−) plants), that also co-express a heterologous oil modulating transcription factor are contemplated for use in combination with plants having reduced TGD. Oil harvested from vegetative tissues of plants comprising vectors and genes of the present invention is contemplated for use in biofuel and biodiesel products.

BACKGROUND OF THE INVENTION

Oil produced by plants is one of the most energy-rich forms of reduced carbon available from nature. As crude oil supply declined, plant oils are gaining increasing interest as substitutes for petroleum-derived and non-renewable fuels. As one example, Hu et al., describes the use of microalgal TAGs as feedstocks for biofuel production, The Plant J., 54(4):621-639.

One of the biggest challenges in using plant oils is the limited growing areas available for plants whose oil is designated for the biofuel industry along with finite supplies of fertilizers, pesticides, and resources for growing these plants and processing their oils.

Thus, compositions and methods are needed for increasing the amount of harvestable amount of plant oils from plants per acre for decreasing the cost per liter of plant oil. Further, compositions and methods are needed for growing oil crop plants for increasing the amount of harvestable oil in plants destined as sources of biofuel.

SUMMARY OF THE INVENTION

The present invention relates to compositions and methods for providing RNA interference (RNAi) vectors comprising trigalactosyldiacylglycerol (tgd) biosynthesis enzyme constructs for increasing oil content of plants. Specifically, plant cells, plant tissues and whole plants are provided comprising novel tgd RNAi vectors for reducing TGD protein expression for increasing oil content (including relative amounts of triacylglycerols) in cells and in vegetative tissues. In particular, vectors are provided comprising tgd RNAi constructs for silencing tgd1 and tgd4 endogenous gene translation. Further, the use of tgd RNAi silencing vectors in combination with co-expression of heterologous oil regulating transcription factors, such as WRINKLED1, are contemplated to overcome the reduced growth and variable levels of embryonic lethality in plants with reduced TGD protein. Additionally, plants having reduced APS1, a gene encoding a major catalytic isoform of the small subunit of AGPase (AGP(−) plants), are contemplated for use in combination with plants having reduced TGD. Such plants can co-express a heterologous oil modulating transcription factor. Oil harvested from vegetative tissues of plants comprising vectors and genes of the present invention is contemplated for use in biofuel and biodiesel products.

The present invention relates to compositions and methods for providing RNA interference (RNAi) vectors with RNAi constructs for reducing protein translation from mRNA. Such compositions and method are provided in combination with heterologous oil modulating transcription factors for use in plants for increasing oil accumulation in vegetative tissues. Specifically, RNAi constructs for reducing expression of trigalactosyldiacylglycerol (TGD) enzymes are provided along with RNAi constructs for reducing expression of AGPase proteins. Further, these constructs are used in combination with oil modulating transcription factors. Specifically, plants comprising RNAi trigalactosyldiacylglycerol tgd gene fragment constructs expressed by plant silencing vectors are provided for increasing the amount of oil produced per plant or per acre of plants through increased production of oil in vegetative tissues. In some embodiments, a heterologous oil regulating transcription factor is expressed in these plants. Even further, these plants comprise an AGPRNAi construct. Therefore, the inventions relate to promoters, gene fragments and spacer sequences for use in these RNAi TGD and AGP silencing constructs.

The inventions provide, a double gene vector construct, comprising a RNAi silencing construct, wherein a first gene has a first promoter sequence in operable combination with a first fragment of a trigalactosyldiacylglycerol nucleic acid sequence in its sense orientation and a second fragment of a trigalactosyldiacylglycerol nucleic acid sequence it's antisense orientation and a second gene comprising a heterologous oil regulating transcription factor nucleic acid sequence. In one embodiment, said trigalactosyldiacylglycerol nucleic acid sequence is selected from the group consisting of trigalactosyldiacylglycerol 1, trigalactosyldiacylglycerol 2, trigalactosyldiacylglycerol 3, and trigalactosyldiacylglycerol 4. In one embodiment, said trigalactosyldiacylglycerol nucleic acid sense sequence is selected from the group consisting of SEQ ID NOs: 12-15. In one embodiment, said trigalactosyldiacylglycerol nucleic acid antisense sequence is selected from the group consisting of SEQ ID NOs: 51-54. In one embodiment, said first promoter is a constitutive promoter. In one embodiment, said first promoter is an inducible promoter. In one embodiment, said first promoter is a developmental promoter. In one embodiment, said construct, further comprises an intervening nucleic acid sequence located in between said sense sequence and said antisense sequence. In one embodiment, said intervening sequence is selected from the group consisting of an intron of a trigalactosyldiacylglycerol gene and a glucuronidase intron. In one embodiment, said RNAi construct nucleic acid sequence has a sense sequence in operable combination with a spacer sequence and an antisense sequence selected from the group consisting of SEQ ID NOs: 19-22. In one embodiment, said heterologous oil regulating transcription factor nucleic acid sequence encodes a WRINKLED1 protein. In one embodiment, said WRINKLED1 nucleic acid sequence is from a species selected from the group consisting of an *Arabidopsis*, *Brassica napus*, maize, soybean and sunflower plant species. In one embodiment, said WRINKLED1 nucleic acid sequence is SEQ ID NO: 44. In one embodiment, said heterologous oil regulating transcription factor nucleic acid sequence is in operable combination with a second promoter. In one embodiment, said second promoter is selected from the group consisting of a 35S cauliflower mosaic virus promoter and an OLE (Oleosin) promoter.

The invention provides, a reproductively competent plant comprising a double gene vector construct, further comprising a RNAi silencing construct, wherein a first gene has a first promoter sequence in operable combination with a first fragment of a trigalactosyldiacylglycerol nucleic acid sequence in its sense orientation and a second fragment of a trigalactosyldiacylglycerol nucleic acid sequence it's antisense orientation and a second gene comprising a heterologous oil regulating transcription factor nucleic acid sequence. In one embodiment, said plant has accumulated lipid in its vegetative tissues. In one embodiment, said plant has reduced ADP-glucose pyrophosphorylase protein, i.e. reduced AGPase.

The invention provides, a seed of the plant of a reproductively competent plant comprising a double gene vector construct, further comprising a RNAi silencing construct, wherein a first gene has a first promoter sequence in operable combination with a first fragment of a trigalactosyldiacylglycerol nucleic acid sequence in its sense orientation and a second fragment of a trigalactosyldiacylglycerol nucleic acid sequence it's antisense orientation and a second gene comprising a heterologous oil regulating transcription factor nucleic acid sequence.

The invention provides, an isolated oil from vegetative tissues of a reproductively competent plant comprising a double gene vector construct, further comprising a RNAi silencing construct, wherein a first gene has a first promoter sequence in operable combination with a first fragment of a trigalactosyldiacylglycerol nucleic acid sequence in its sense orientation and a second fragment of a trigalactosyldiacylglycerol nucleic acid sequence it's antisense orientation and a second gene comprising a heterologous oil regulating transcription factor nucleic acid sequence.

The invention provides, a method, comprising, a) providing, i) a plant tissue, wherein said plant tissue comprises a RNAi vector construct, comprising a first promoter sequence in operable combination with an RNAi gene silencing sequence having a first fragment of a trigalactosyldiacylglycerol nucleic acid sequence in its sense orientation and a second fragment of a trigalactosyldiacylglycerol nucleic acid sequence it's antisense orientation for reducing a trigalactosyldiacylglycerol protein, and ii) a double gene vector construct for a first gene comprising a RNAi silencing nucleic acid sequence for reducing an ADP-glucose pyrophosphorylase protein and a second gene encoding a heterologous oil regulating transcription factor for expressing transcription factor protein, and b) transfecting said plant tissue with said double gene vector and growing tissue into a whole plant, wherein said plant has reduced trigalactosyldiacylglycerol protein along with reduced AGPase protein with increased transcription factor protein for increased lipid in vegetative tissues of said plant. In one embodiment, said factor is WRINKLED1. In one embodiment, said trigalactosyldiacylglycerol protein is selected from the group consisting of trigalactosyldiacylglycerol 1, trigalactosyldiacylglycerol 2, trigalactosyldiacylglycerol 3, and trigalactosyldiacylglycerol 4. In one embodiment, said reduced ADP-glucose pyrophosphorylase protein (AGPase) is reduced translation of an APS1 gene. In one embodiment, said whole plant is a reproductively competent plant. In one embodiment, said lipid comprises triacylglycerol. In one embodiment, said method further comprises step c) isolating said vegetative lipid. In one embodiment, said trigalactosyldiacylglycerol protein is selected from the group consisting of monocotyledons and dicotyledons. It is not meant to limit the type of In one embodiment, said trigalactosyldiacylglycerol protein is selected from the group consisting of soybean, rutabaga, rapeseed, sunflower, cotton, corn, cocoa, safflower, oil palm, coconut palm, flax, castor, peanut and rice. In one embodiment, said silenced trigalactosyldiacylglycerol nucleic acid sequence is selected from the group consisting of SEQ ID NOs: 1, 3, 4, 6, 8, 9, 11, and a combination thereof for reducing expression of their encoded proteins (e.g., SEQ ID NOs: 2, 5, 7, 10). In one embodiment, said vegetative tissue is selected from the group consisting of a plant leaf, plant stem and plant stalk. In one embodiment, said plant is an oleaginous plant. In one embodiment, said plant is selected from the group consisting of soybean, rutabaga, rapeseed, sunflower, cotton, corn, cocoa, safflower, oil palm, coconut palm, flax, castor, peanut and rice plants. In one embodiment, said plant is selected from the group consisting of rice plants, beet plants, grape plants, *Arabidopsis* sp. plants, Brassicaceae sp. plants, *Brassica napus* plants, grass plants and algae plants. In one embodiment, said grass plant is selected form the group consisting of a rice plant, a Miscanthus plant, and a switchgrass plant.

The invention provides a method for making a plant, comprising, a) providing, i) a plant tissue, wherein said plant tissue has reduced ADP-glucose pyrophosphorylase (AGPase) protein and increased expression of a heterologous oil regulating transcription factor protein, ii) a RNAi silencing construct comprising a first promoter sequence in operable combination with a first fragment of a trigalactosyldiacylglycerol nucleic acid sequence in its sense orientation and a second fragment of a trigalactosyldiacylglycerol nucleic acid sequence it's antisense orientation, and b) transfecting said RNAi vector construct into said plant tissue, c) growing said plant tissue into a plant, wherein said plant accumulates lipid in its vegetative tissue. In one embodiment, said method, further comprises step d) harvesting said lipid.

The invention provides a method, comprising, a) providing, i) a first plant, wherein said plant has reduced ADP-glucose pyrophosphorylase protein and increased expression of a heterologous oil regulating transcription factor, ii) a second plant, wherein said plant has reduced trigalactosyldiacylglycerol protein, and b) breeding said first plant with said second plant for producing seed capable of growing into a third plant, and c) growing said seed into said third plant, wherein said third plant accumulates lipid in its vegetative tissue. In one embodiment, said third plant is reproductively competent. In one embodiment, said method, further comprises step d) of breeding said third plant with a fourth plant for use in producing a reproductively competent plant line. In one embodiment, said method, further comprising step d) of breeding said third plant with a fourth plant for use in producing a plant line having accumulation of oil in its vegetative tissues. In one embodiment, method, further comprises step d) of breeding said third plant with a fourth plant for use in producing a plant line having desired agronomic traits.

The invention provides a whole plant made by methods of the present inventions.

The invention provides a seed produced by plants made by methods of the present inventions.

The invention provides a composition, comprising a plant part of a plant made by methods of the present inventions.

The invention provides an isolated oil of plants made by methods of the present inventions.

The invention provides a plant line having increased oil in vegetative tissues bred from plants made by methods of the present inventions.

The invention provides seeds of plant lines made by methods of the present inventions.

The invention provides a biofuel comprising a lipid isolated from a plant made by methods of the present inventions.

The invention provides a biodiesel comprising a lipid isolated from a plant made by methods of the present inventions.

Definitions

To facilitate an understanding of the present invention, a number of terms and phrases are defined below:

The use of the article "a" or "an" is intended to include one or more. As used in this application, the singular form "a," "an," and "the" include plural references unless the context clearly dictates otherwise. For example, the term "an agent" includes a plurality of agents, including mixtures thereof.

As used herein, the term "trigalactosyldiacylglycerol" or "TGD" in general refers to a gene and its encoded protein (i.e. molecules) associated with a lipid transporter complex whose function is to transport lipid across a cell membrane. Specifically, a TGD term designation is made for a protein and it's gene when a gene's transcription (or translation or mutation in encoded polypeptide), either by genetic mutation or manipulation by man, renders it dysfunctional thus resulting in accumulation of oligogalactoglycerolipids on one side of a membrane, for example, "accumulated lipid" comprising primarily triacylglycerol within a chloroplast membrane, accumulation of lipid outside of a chloroplast membrane.

As used herein, the term "dysfunctional" or "nonfunctional" in reference to TGD refers to both a lipid transporter (such as a TGD complex) and an individual TGD protein, for example, a TGD protein or TGD complex which has reduced function compared to wild-type, i.e. does not transport lipid as well or as fast as a wild-type complex resulting in accumulation of lipid on one side of a membrane.

As used herein, the term "trigalactosyldiacylglycerol 1" or "TGD1" refers to a permease gene and its encoded protein associated with a lipid transporter complex.

As used herein, the term "trigalactosyldiacylglycerol 2" or "TGD2" refers to a substrate binding component gene and its encoded protein associated with a lipid transporter complex.

As used herein, the term "trigalactosyldiacylglycerol 3" or "TGD3" refers to a gene and its encoded protein associated with an ATPase (Adenosine triphosphatase) component of a lipid transporter involving TGD1 and TGD2.

The term "complex" as used herein, refers to any stable interaction between two compounds such that a close association is formed, for example a "TGD1, 2, 3 complex" or "TGD 1-3 complex," and the like. A complex may be stabilized by atomic interactions including, but not limited to, covalent bonding, non-covalent bonding, electrostatic interactions, hydrophobic interactions, or Van der Waals forces. A TGD 1-3 complex is contemplated to function in transferring compounds, e.g. phosphatidic acid through the inner envelope membrane of an organelle, i.e. "plastid."

As used herein, the term "plastid" refers to an organelle found in a plant or alga cell and is used interchangeably with a specialized plastid "chloroplast."

As used herein, the term "trigalactosyldiacylglycerol 4" or "TGD4" refers to a gene and it's encoded protein associated a function of mediating lipid transfer between the ER and the outer plastid envelope membrane, i.e. TGD4 function refers to a transfer of lipids to isolated plastids, and further associated with a lipid transporter TGD 1-3 complex. Unlike the TGD1, 2, 3 complex, which is proposed to transfer phosphatidic acid through the inner envelope membrane into the plastid/chloroplast, TGD4 appears to be part of the machinery that mediates lipid transfer between the endoplasmic reticulum and the outer plastid/chloroplast envelope membrane.

As used herein, the terms "accumulates lipid in vegetative tissues," "plant accumulates lipid in vegetative tissues," and "plant accumulates lipid in its vegetative tissues," refers to plants with increased amounts (over corresponding wild-type plants with a functional trigalactosyldiacylglycerol target gene) of the oligogalactolipid trigalactosyldiacylglycerol (TGDG), such as triacylglycerol, and the like, in any of the following plant tissues, leaf, stem, seed, root, stalk, etc. Additionally, the term "accumulates" or "accumulated" in reference to any lipid found in higher amounts in plant vegetative tissue (amounts higher than amounts in corresponding wild-type plants with a functional trigalactosyldiacylglycerol target gene) of the present inventions, for example, accumulates triacylglycerol, accumulates polar lipid, accumulates lipid staining with α-naphthol, and the like. In general, exemplary accumulated lipids include triacylglycerol, oligogalactolipid, and phosphatidate lipid including polar lipids.

As used herein, the term "biosynthetic oil" in reference to oil produced by an engineered plant as described herein, refers to the oil accumulated in vegetative tissues of plants having reduced TGD protein production compared to wild-type plants. In one embodiment, biosynthetic oil refers to the oil that accumulated in stems and leaves of plants having increased amounts of TAG lipids.

As used herein, the term "vegetative tissues" refer to a plant part such as a leaf, a stem, a root, a shoot, a stalk and a leaf bud.

As used herein, the term "mutant" in reference to a specific TGD molecule refers to a plant comprising an altered TGD molecule, for example, a plant comprising RNAi for silencing TGD3 is referred to as a "TGD3 mutant, a plant comprising an insertion in a TGD3 gene which reduces TGD3 function, and the like."

As used herein, the term "lipid" encompasses many types of lipid such as triacylglycerol, oligogalactolipid, phosphatidate lipid including polar lipids, DGDG, digalactosyldiacylglycerol; MGDG, monogalactosyldiacylglycerol, PC, phosphatidylcholine; PE, phosphatidylethanolamine; PG, phosphatidylglycerol; PI, phosphatidylinositol; SQDG, sulfoquinovosyldiacylglycerol; TAG, triacylglycerol; TGDG, trigalactosyldiacylglycerol, etc.

As used herein, the term "polar' in reference to a lipid refers to a lipid comprising a charged group, for example, a galactolipid such as monogalactosyldiacylglycerol; MGDG and digalactosyldiacylglycerol; DGDG.

As used herein, the term "α-naphthol" refers to a sugar-staining compound, for example, a stain for identifying a galactolipid and glycolipid, for example, a glycolipid comprising a hexose group.

As used herein, the term "isolated" when used in relation to a lipid in a vegetative tissue refers to removing a particular lipid from at least one plant contaminant with which it is ordinarily associated in its natural source.

As used herein, the term "allele" in reference to a gene refers to one of two or more alternative forms of a gene that may occur alternatively at a given site on a chromosome. Alleles may occur in pairs, or there may be multiple alleles affecting the expression of a particular trait. If paired alleles are the same, the organism is said to be homozygous for that trait; if they are different, the organism is heterozygous. A dominant allele will override the traits of a recessive allele in a heterozygous pairing (see dominance and recessive). In some traits, alleles may be codominant (i.e., neither acts as dominant or recessive). In even further traits, including manipulation by the hand of man, an allele may be a completely disrupted allele (i.e. dysfunctional) or an artificial construct of an allele may provide a dominant-negative effect, for example, an RNAi of the present invention.

As used herein, the term "leaky allele" refers to a gene allele expressed at variable levels from cell to cell, tissue to tissue, seed to seed, or plant to plant, typically at lower levels relative to that of the wild-type allele. For example, a mutant allele tgd1-1 is a leaky allele, as demonstrated in FIG. 3C (in Xu, et al., 2005, herein incorporated by reference in its entirety), tgd1-1, showing variable expression of tgd1-1 in seeds within the same silique of the same plant, for example, expression of tgd1-1 in viable green normal-looking seeds (seeds containing maturing/matured green plant embryos) located next to nonviable white seeds of the same size as the wild type/small white seed-like, and small white seed-like structures or 'empty' seed hulls of seeds (i.e. seeds lacking fully developed green plant embryos) in the same silique/pod due to lack of expression of the leaky allele tgd1-1, Xu, et al., 2005, herein incorporated by reference in its entirety. In other words, a leaky allele results in attenuated phenotypes.

As used herein, the term "attenuated phenotype" in reference to an organism refers to a related group of organisms with variable expression of a trait, for example, variable expression of a tgd1-1 allele as described herein and in Xu, et al., 2005, herein incorporated by reference in its entirety.

As used herein, the term "seed" in general refers to a fertilized ovule containing an embryo which forms a new plant upon germination or an empty hull or shell where a fertilized ovule should be located.

As used herein, the term "reproductively competent" in reference to a plant, i.e. "reproductively competent plant" or "reproductively viable plant" refers to a plant's capability to progress to reproductive maturation and produce viable seeds, unlike a plant comprising an embryonic lethal gene. For example, during its development, a plant shoot progresses from a juvenile to an adult phase of vegetative growth, i.e. progressing from a reproductively incompetent state to a reproductively competent state. Thus, a reproductively competent plant is a plant capable of producing viable seeds of which at least 50%, or at least 60% up to 100% viable. Seeds produced by a progeny plant derived from a reproductively competent plant in turn are viable seeds with the capability to germinate and develop in turn into a reproductively competent plant.

As used herein, the term "viable plant seed" or "viable seed" or "living seed" refers to a seed capable of germinating, growing and developing (maturing) into a reproductively competent plant. The length of time that a seed retains its viability varies in different species and depends on storage conditions. Thus, willow seeds generally remain viable for several days; in closed vessels at temperatures of 12°-13° C., however, they retain their viability 150 to 320 days. The hard seeds of certain legumes can sprout after 100 years, and lotus seeds preserved in a layer of peat for several hundred years have proved to be viable.

As used herein, the terms "nonviable plant seed" or "aborted seed" or "mutant seed" refers to a seed incapable of germinating or growing into a reproductively competent plant for example, a sterile seed or empty seed hull observed in seeds are nonviable (aborted).

As used herein, the term "germination" refers to a process whereby a viable seed takes up water and the radicle (primary root) or hypocotyl emerges from the seed under species-specific conditions of moisture, oxygen, and temperature.

As used herein, the term "embryonic stage" in general refers to one of a series of developmental points during maturation of an embryo, for example, a stage of chloroplast formation or heart stage in an *Arabidopsis* embryo (Mansfield and Briarty, 1991).

As used herein, the terms "embryo-lethality" refers to an individual comprising a dominant lethal allele die before it can produce the progeny. A fully dominant lethal allele kills the carrier individual both as a homozygous and heterozygous genotype while a recessive lethal kills the carrier in the homozygous genotype. Completely lethal genes usually cause death of the zygote anytime from late in embryonic development to after germination or growth. Complete lethality, thus is the case where individuals of a certain genotype do not attain reproduction maturation. In other cases lethal genes become operative at the time the individual becomes sexually mature. Such lethal genes that handicap but do not destroy their possessor are called subvital, sublethal or semilethal genes. An embryo-lethal example was previously shown for the ats1-1 tgd1-1 mutant plant (Xu et al., 2005, herein incorporated by reference in its entirety).

As used herein, the term "RNAi gene silencing vector construct" or "RNAi silencing construct" or "tgd RNAi" or "RNAi gene silencing construct" or "tgd RNAi" in reference to inhibiting trigalactosyldiacylglycerol protein production refers to a construct comprising an artificial DNA sequence encoding a trigalactosyldiacylglycerol RNA sequence in the sense direction and a copy in the antisense direction in operable combination with a promoter, wherein expression of the artificial DNA sequence is capable of inhibiting the translation of a trigalactosyldiacylglycerol protein molecule. When the RNAi construct has an inducible promoter it may be referred to as an "inducible RNAi" or inducible tgd RNAi."

As used herein, the term "RNA interference" or "RNAi" refers to the silencing of i.e. decreasing, RNA translation by inhibitory RNA. It is a process of sequence-specific, posttranscriptional gene silencing in animals and plants, initiated by double stranded siRNA (RNAi processed in cells) that is homologous in its duplex region to the sequence of the targeted gene.

As used herein, the term "posttranscriptional gene silencing" or "PTGS" or "gene silencing" refers to reducing, i.e.

silencing, gene expression in plants after transcription, in other words reducing translation of a target protein.

As used herein, the nucleic acid sequence, i.e. strand, complementary to a target RNA molecule is the "antisense strand;" the strand homologous to the target RNA molecule is the "sense strand," and is also complementary to the RNA antisense strand. RNAi molecules may also contain additional sequences; non-limiting examples of such sequences include linking sequences, or loops, as well as stem and other folded structures including spacers.

As used herein, the term "target RNA molecule" refers to an RNA molecule to which at least one strand of the endogenous RNA is homologous or complementary to at least a fragment of nucleic acid sequence in an RNAi construct of the present inventions. Typically, when such homology or complementary is up to 100%, the expressed and processed RNAi, for example, siRNA, is able to silence or inhibit translation of the target endogenous RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of RNAi. Such targets include unprocessed mRNA, ribosomal RNA, etc.

As used herein, the term "regulatory element" refers to a genetic element that controls some aspect of the expression of nucleic acid sequence(s). For example, a promoter is a regulatory element that facilitates the initiation of transcription of an operably linked coding region. Other regulatory elements are transcription factors, splicing signals, polyadenylation signals, termination signals, etc.

As used herein, the term "transcription factor" refers to a molecule involved with controlling gene expression by RNA polymerase.

As used herein, the term "oil regulating transcription factor" refers to a molecule involved with controlling gene expression by RNA polymerase where the gene is associated with oil biosynthesis, including genes and their encoded protein involved with fatty acid synthesis, elongation, oil accumulation and/or oil breakdown, as one example, WRINKLED1 (WRI1).

The term "recombinant" when made in reference to a nucleic acid molecule refers to a nucleic acid molecule that is comprised of segments of nucleic acid joined together by means of molecular biological techniques.

The term "recombinant" when made in reference to a protein or a polypeptide refers to a protein molecule that is expressed using a recombinant nucleic acid molecule. Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." For example, an endogenous nucleic acid sequence is one that is found naturally in the genome. As another example, a heterologous nucleic acid sequence has been isolated, such as a genomic fragment or mRNA sequence and positioned 3' to another gene for expression in an organism.

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. An expression cassette may also refer to a DNA molecule capable of expressing more than one gene or DNA encoding more than on mRNA sequence.

As used herein, the term "recombinant vector" or "vector construct" refers to a nucleic acid molecule which is capable of transferring nucleic acid sequences contained therein into a cell, and which is produced by means of molecular biological techniques. Recombinant vectors are exemplified by linear DNA, plasmid DNA, viruses, etc.

The term "gene expression" refers to the process of converting genetic information encoded in a gene into RNA (for example, mRNA, rRNA, tRNA, or snRNA) through "transcription" of the gene (in other words, via the enzymatic action of an RNA polymerase), and into protein, through "translation" of mRNA. Gene expression can be regulated at many stages in the process. "Up-regulation" or "activation" refers to regulation that increases the production of gene expression products (for example, RNA or protein), while "down-regulation" or "repression" refers to regulation that decrease production. Molecules (for example, transcription factors) that are involved in up-regulation or down-regulation are often called "activators" and "repressors," respectively.

As used herein, the terms "vector" and "vehicle" are used interchangeably in reference to nucleic acid molecules that transfer DNA segment(s) from one cell to another. Vectors may include plasmids, bacteriophages, viruses, cosmids, and the like.

The terms "targeting vector" and "targeting construct" refer to nucleic acid sequences comprising a sequence of interest flanked on either side by recognition sequences that are capable of homologous recombination with cognate sequences in the genome in such a way that the sequence of interest replaces any DNA sequences that are located between the cognate sequences in the genome. The sequence of interest can consist of recognition sites for restriction enzymes or site specific recombinases such as Flp or Cre, exogenous genes including but not limited to those that encode thymidine kinase or confer resistance to antibiotics such as neomycin and hygromycin, marker genes such as LacZ and enhanced green fluorescent protein (eGFP), as well as portions of the targeted gene itself or sequences from other genes of interest.

The term "ectopic expression" as used herein, refers to the expression of a gene in an abnormal place in an organism.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. For example, operably linking a promoter sequence to a nucleotide sequence of interest refers to linking the promoter sequence and the nucleotide sequence of interest in a manner such that the promoter sequence is capable of directing the transcription of the nucleotide sequence of interest into RNA, RNAi, mRNA and/or the synthesis of a polypeptide encoded by the nucleotide sequence of interest.

The term "selectable marker" as used herein, refers to a gene which encodes an enzyme having an activity that confers resistance to an antibiotic or drug upon the cell in which the selectable marker is expressed. Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV thymidine kinase (HSV-tk) gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV thymidine kinase enzyme.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987, herein incorporated by reference in its entirety). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987, all of which are herein incorporated by reference in its entirety).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. Promoters may be tissue specific or cell specific.

The term "tissue specific" as it applies to a promoter refers to a promoter that is capable of directing selective expression of a nucleotide sequence of interest to a specific type of tissue in the relative absence of expression of the same nucleotide sequence of interest in a different type of tissue. Tissue specificity of a promoter may be evaluated by, for example, operably linking a reporter gene to the promoter sequence to generate a reporter construct, introducing the reporter construct into the genome of an organism such that the reporter construct is integrated into every tissue of the resulting transgenic organism, and detecting the expression of the reporter gene (e.g., detecting mRNA, protein, or the activity of a protein encoded by the reporter gene) in different tissues of the transgenic. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue.

The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining Briefly, tissue sections are embedded in paraffin, and paraffin sections are reacted with a primary antibody that is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy. Alternatively, mRNA localization can be determined by in situ hybridization.

Promoters may be constitutive or regulatable. The term "constitutive" when made in reference to a promoter means that the promoter is capable of directing transcription of an operably linked nucleic acid sequence in the absence of a stimulus (for example, heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see for example, U.S. Pat. No. 5,352,605, herein incorporated by reference in its entirety), mannopine synthase, octopine synthase (ocs), superpromoter (see for example, WO 95/14098, herein incorporated by reference in its entirety), and ubi3 (see for example, Garbarino and Belknap (1994) Plant Mol. Biol. 24:119-127, herein incorporated by reference in its entirety) promoters. Such promoters have been used successfully to direct the expression of heterologous nucleic acid sequences in transformed plant tissue. In contrast, a "regulatable" or "inducible" promoter is a promoter sequence capable of directing a level of transcription of an operably linked nuclei acid sequence in the presence of a stimulus (e.g., heat shock, chemicals, light, etc.), such as beta-estradiol of the present inventions, which is different from the level of transcription of the operably linked nucleic acid sequence in the absence of the stimulus.

The term "upregulated" as used herein, should be interpreted in the most general sense possible. For example, a special type of molecule may be "upregulated" in a cell if it is produced at a level significantly and detectably higher (i.e., for example, 1.5-10 fold) than the natural expression rate.

The enhancer and/or promoter may be "endogenous" or "exogenous" or "heterologous." An "endogenous" enhancer or promoter is one that is naturally linked with a given gene in the genome. An "exogenous" or "heterologous", enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed and placed in operable combination with a second gene, thereby making it a "heterologous"

promoter in operable combination with said second gene. A variety of such combinations are contemplated (e.g. the first and second genes can be from the same species, or from different species).

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., Molecular Cloning: A Laboratory Manual, 2nd ed., Cold Spring Harbor Laboratory Press, New York (1989) pp. 16.7-16.8, herein incorporated by reference in its entirety). A commonly used splice donor and acceptor site is the splice junction from the 16S RNA of SV40.

The term "cosuppression" refers to the expression of a foreign gene that has substantial homology to an endogenous gene resulting in the suppression of expression of both the foreign and the endogenous gene.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6-16.7).

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (for example, particle bombardment) and the like. The terms "infecting" and "infection" when used with a bacterium refer to co-incubation of a target biological sample, (for example, cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (for example, nopaline, agropine, octopine etc.) by the infected cell. Thus, *Agrobacterium* strains which cause production of nopaline (for example, strain LBA4301, C58, A208, GV3101) are referred to as "nopaline-type" *Agrobacteria*; *Agrobacterium* strains which cause production of octopine (for example, strain LBA4404, Ach5, B6) are referred to as "octopine-type" *Agrobacteria*; and *Agrobacterium* strains which cause production of agropine (for example, strain EHA105, EHA101, A281) are referred to as "agropine-type" *Agrobacteria*.

The terms "bombarding, "bombardment," and "biolistic bombardment" refer to the process of accelerating particles towards a target biological sample (for example, cell, tissue, etc.) to effect wounding of the cell membrane of a cell in the target biological sample and/or entry of the particles into the target biological sample. Methods for biolistic bombardment are known in the art (for example, U.S. Pat. No. 5,584,807, the contents of which are incorporated herein by reference), and are commercially available (for example, the helium gas-driven microprojectile accelerator (PDS-1000/He, Bio-Rad).

The term "microwounding" when made in reference to plant tissue refers to the introduction of microscopic wounds in that tissue. Microwounding may be achieved by, for example, particle bombardment as described herein.

The term "transgenic" when used in reference to a plant or fruit or seed (in other words, a "transgenic plant" or "transgenic fruit" or a "transgenic seed") refers to a plant or fruit or seed that contains at least one heterologous gene in one or more of its cells. The term "transgenic plant material" refers broadly to a plant, a plant structure, a plant tissue, a plant seed or a plant cell that contains at least one heterologous gene in one or more of its cells. The term "transgenic" when used in reference to a cell refers to a cell which contains a transgene, or whose genome has been altered by the introduction of a transgene.

The term "transgenic" when used in reference to a tissue or to an organism, such as a mouse, refers to a tissue or organism, respectively, which comprises one or more cells that contain a transgene, or whose genome has been altered by the introduction of a transgene. Transgenic cells, tissues and organisms may be produced by several methods including the introduction of a "transgene" comprising nucleic acid (usually DNA) into a target cell or integration of the transgene into a chromosome of a target cell by way of human intervention, such as by the methods described herein.

The terms "transformants" or "transformed cells" include the primary transformed cell and cultures derived from that cell without regard to the number of transfers. Progeny may not be precisely identical in DNA content, due to deliberate or inadvertent mutations. Mutant progeny that have the same functionality as screened for in the originally transformed cell are included in the definition of transformants.

The term "transgene" as used herein refers to any nucleic acid sequence that is introduced into the genome of a cell by experimental manipulations. A transgene may be an "endogenous DNA sequence," or a "heterologous DNA sequence" (i.e., "foreign DNA").

The term "endogenous DNA sequence" refers to a nucleotide sequence that is naturally found in the cell into which it is introduced so long as it does not contain some modification (e.g., a point mutation, the presence of a selectable marker gene, etc.) relative to the naturally occurring sequence.

The term "heterologous DNA sequence" refers to a nucleotide sequence that is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence that contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "gene" refers to a nucleic acid (for example, DNA or RNA) sequence that comprises coding sequences necessary for the production of RNA, or a polypeptide or its precursor (for example, proinsulin). A functional polypeptide can be encoded by a full-length coding sequence or by any portion of the coding sequence as long as the desired activity or functional properties (for example, enzymatic activity, ligand binding, signal transduction, etc.) of the polypeptide are retained.

The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage and polyadenylation. The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "an oligonucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in cDNA, genomic DNA or RNA form. When present in a DNA form, the oligonucleotide may be single-stranded (in other words, the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "heterologous gene" refers to a gene encoding a factor that is not in its natural environment (in other words, has been altered by the hand of man). For example, a heterologous gene includes a gene from one species introduced into another species. A heterologous gene also includes a gene native to an organism that has been altered in some way (for example, mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (for example, genes expressed in loci where the gene is not normally expressed).

The term "foreign gene" refers to any nucleic acid (e.g., gene sequence) which is introduced into the genome of a cell by experimental manipulations and may include gene sequences found in that cell so long as the introduced gene contains some modification (e.g., in operable combination with a heterologous promoter, a point mutation in the gene, the presence of a selectable marker gene, etc.) relative to the naturally-occurring gene.

Transformation of a cell may be stable or transient. The term "transient transformation" or "transiently transformed" refers to the introduction of one or more trans genes into a cell in the absence of integration of the transgene into the host cell's genome. Transient transformation may be detected by, for example, enzyme-linked immunosorbent assay (ELISA), which detects the presence of a polypeptide encoded by one or more of the transgenes. Alternatively, transient transformation may be detected by detecting the activity of the protein (e.g., .beta.-glucuronidase) encoded by the transgene.

The term "transient transformant" refers to a cell that has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences that are capable of binding to one or more of the transgenes. Alternatively, stable transformation of a cell may also be detected by the polymerase chain reaction of genomic DNA of the cell to amplify transgene sequences.

The term "stable transformant" refers to a cell that has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

The term "plant" is used in its broadest sense. It includes, but is not limited to; any species of woody, ornamental or decorative, crop or cereal, fruit or vegetable plant, and photosynthetic green algae (for example, *Chlamydomonas reinhardtii*). It also refers to a plurality of plant cells that are largely differentiated into a structure that is present at any stage of a plant's development. Such structures include, but are not limited to, a fruit, shoot, stem, leaf, flower petal, etc.

The term "plant tissue" includes differentiated and undifferentiated tissues of plants including those present in roots, shoots, leaves, pollen, seeds and tumors, as well as cells in culture (for example, single cells, protoplasts, embryos, callus, etc.). Plant tissue may be in planta, in organ culture, tissue culture, or cell culture.

The term "plant part" as used herein refers to a plant structure or a plant tissue.

The term "wild-type" when made in reference to a gene refers to a gene that has the characteristics of a gene isolated from a naturally occurring source.

The term "wild-type" when made in reference to a gene product refers to a gene product that has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (in other words, altered characteristics) when compared to the wild-type gene or gene product. It is noted that naturally occurring mutants can be isolated; these are identified by the fact that they have altered characteristics when compared to the wild-type gene or gene product.

The term "host cell" refers to any cell capable of replicating and/or transcribing and/or translating a heterologous gene.

The term plant cell "compartments or organelles" is used in its broadest sense. The term includes, but is not limited to, the endoplasmic reticulum, Golgi apparatus, trans Golgi network, plastids, sarcoplasmic reticulum, glyoxysomes, mitochondrial, chloroplast, and nuclear membranes, and the like.

The term "crop" or "crop plant" is used in its broadest sense. The term includes, but is not limited to, any species of plant or algae edible by humans or used as a feed for animals or used, or consumed by humans, or any plant or algae used in industry or commerce.

The term "oil-producing species" refers to plant species that produce and store triacylglycerol in specific organs, primarily in seeds. Such species include, but are not limited to, green algae (*Chlamydomonas reinhardtii*), soybean (*Glycine max*), rutabaga (*Brassica napobrassica*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*), alfalfa (e.g., forage legume alfalfa), avocado, barley, broccoli, Brussels sprouts, cabbage, cassava, cauliflower, cole vegetables, collards, crucifers, grain legumes, grasses (e.g., forage grasses), jatropha, kale, kohlrabi, maize, miscanthus, mustards, nut sedge, oats, oil firewood trees, oilseeds, potato, radish, rice, rutabaga, sorghum, soybean, sugar beets, sugarcane, switchgrass, tobacco, tomato, turnips, and wheat. The group also includes non-agronomic species which are useful in developing appropriate expression vectors such as tobacco, rapid cycling *Brassica* species, and *Arabidopsis thaliana*, and wild species which may be a source of unique fatty acids.

As used herein, the term "sense strand" refers to a deoxyribonucleotide (i.e. nucleic acid) sequence which is transcribed by a cell in its natural state into a "sense mRNA." A sense nucleic acid sequence transcribed into a sense RNA is capable of being translated therefore a nucleic acid sequence encodes a polypeptide sequence.

As used herein, the term "antisense" refers to a deoxyribonucleotide (i.e. nucleic acid) sequence whose sequence of deoxyribonucleotide residues is in reverse 5' to 3' orientation in relation to the sequence of deoxyribonucleotide residues in a sense strand (i.e. coding strand for encoding a protein) of a DNA duplex. Antisense also refers to the "reverse complement orientation." By way of example, the reverse complement of the nucleotide sequence 5' GATCC-3' is 5'-CTAGG-3'. In other words an "antisense" sequence is a sequence having the same sequence as the non-coding strand in a DNA duplex (i.e. hybridized DNA).

The term "antisense RNA" refers to a RNA transcript that is complementary to all or part of a target primary DNA transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "inverted" when made in reference to two nucleotide sequences means that the two sequences are linked (in the presence or absence of intervening nucleotides) such that the first sequence is in a 5' to 3' orientation relative to the second sequence which is in a 3' to 5' orientation, where the 3' ends of the first and second sequences are arranged in proximity to one another, while the 5' ends of the first and second sequences are separated by the 3' ends of the first and second sequences.

Thus, the term "inverted terminal repeats" refers to a first and second terminal repeats whose 3' ends are linked (in the presence or absence of intervening nucleotides) together.

As used herein, the term "underexpression" refers to the production of a gene product, such as transcribed RNA, encoded polypeptides, and the like, in transgenic organisms that is lower than levels of production in normal or non-transformed organisms undergoing the same or similar growing conditions. Underexpression includes a lower amount and undetectable amounts of a gene product.

As used herein, the term "overexpression" refers to the production of a gene product in transgenic organisms that exceeds levels of production in normal or non-transformed organisms. As used herein, the term "altered levels" refers to the production of gene product(s) in transgenic organisms in amounts or proportions that differ from that of normal or non-transformed organisms, i.e. underexpressed or overexpressed.

As used herein the term "coding region" when used in reference to structural gene refers to the nucleotide sequences which encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, and TGA). In some cases the coding region is also known to initiate by a nucleotide triplet "TTG".

The terms "specific binding" or "specifically binding" when used in reference to the interaction of a lipid (i.e., for example, PA) and a protein or peptide (i.e., for example, TGD1, TGD2, TGD3, or TGD4 protein and/or a truncated TGD1, TGD2, TGD3, or TGD4 peptide) means that the interaction is dependent upon the presence of a particular structure (i.e., for example, a tertiary amino acid structure) on a protein; in other words a lipid is recognizing and binding to a specific protein structure rather than to proteins in general. For example, if a lipid is specific for tertiary structure "A", the presence of a protein containing tertiary structure A (or free, unlabeled A) in a reaction containing labeled "A", the lipid will reduce the amount of labeled A bound to the lipid. A "variant" of a protein is defined as an amino acid sequence that differs by one or more amino acids from a polypeptide sequence or any ortholog and/or homolog of the polypeptide sequence. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs including, but not limited to, DNAStar™ software. A "variant" of a nucleotide is defined as a novel nucleotide sequence that differs from a reference oligonucleotide by having deletions, insertions and substitutions. These may be detected using a variety of methods (e.g., sequencing, hybridization assays etc.). Included within this definition are alterations to the genomic DNA sequence which encodes TGD1, TGD2, TGD3, or TGD4 protein (for example, SEQ ID NOs: 1, 3, 4, 6, 8, 9, 11), the inability of a selected fragment of any of these SEQ ID NOs (e.g., of SEQ ID NO:1) to hybridize under high stringency conditions to a sample of genomic DNA (e.g., using allele-specific oligonucleotide probes), and improper or unexpected hybridization, such as hybridization to a locus other than a wild type chromosomal locus (e.g., using fluorescent in situ hybridization (FISH)). A "deletion" is defined as a change in either nucleotide or amino acid sequence in which one or more nucleotides or amino acid residues, respectively, are absent. An "insertion" or "addition" is that change in a nucleotide or amino acid sequence that has resulted in the addition of one or more nucleotides or amino acid residues, respectively, as compared to, for example, the naturally occurring protein. A "substitution" results from the replacement of one or more nucleotides or amino acids by different nucleotides or amino acids, respectively. As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids. The term "complement" of a nucleic acid sequence as used herein refers to a nucleotide sequence whose nucleic acids show total complementarity to the nucleic acids of the nucleic acid sequence.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target. When used in reference to nucleic acid hybridization those skilled in the art know that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution. For example, high stringency can be defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C. However, the stringency of hybridization is actually determined by the wash conditions. Thus, wash conditions in 0.1×SSC, 0.1% SDS at 65° C. are a sufficient definition of high stringent hybridization conditions.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads), fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241, all of which are herein incorporated by reference in their entirety). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) Molecular Cloning: A Laboratory Manual, Cold Spring Harbor Press, NY, pp 9.31-9.58, herein incorporated by reference in its entirety).

The term "Northern blot analysis" and "Northern blot" and "Northern" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39-7.52, herein incorporated by reference in its entirety).

The terms "protein" and "polypeptide" refer to compounds comprising amino acids joined via peptide bonds and are used interchangeably herein.

As used herein, "amino acid sequence" refers to an amino acid sequence of a protein molecule. "Amino acid sequence" and like terms, such as "polypeptide" or "protein," are not meant to limit the amino acid sequence to the complete, native amino acid sequence associated with the recited protein molecule. Furthermore, an "amino acid sequence" can be deduced from the nucleic acid sequence encoding the protein. Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. Typically, the terminus of a polypeptide at which a new linkage would be to the carboxy-terminus of the growing polypeptide chain, and polypeptide sequences are written from left to right beginning at the amino terminus.

The term "portion" when used in reference to a protein (as in "a portion of a given protein") refers to fragments of that protein. The fragments may range in size from four amino acid residues to the entire amino sequence minus one amino acid. The terms "homology" and "homologous" as used herein in reference to amino acid sequences refer to the degree of identity of sequence structure between two amino acid sequences. Such a degree of identity may be directed a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity. There may be partial homology or complete homology (in other words, identity). "Sequence identity" refers to a measure of relatedness between two or more proteins, and is given as a percentage with reference to the total comparison length. The identity calculation takes into account those amino acid residues that are identical and in the same relative positions in their respective larger sequences. Calculations of identity may be performed by algorithms contained within computer programs.

The term "isolated" when used in relation to an oil, as in "an isolated oil" refers to a plant oil that is separated from at least one contaminant plant part or other oil with which it is ordinarily associated in its natural source.

The term "purified" in reference to a plant oil, refers to oil obtained from vegetative parts and/or seed oil that makes up at least 30% of the extracted plant materials, or from 30-60% of the plants materials or from 60-90%, or up to at least 99% of the extracted plant materials.

The term "sample" is used in its broadest sense. In one sense it can refer to a plant cell or tissue. In another sense, it is meant to include a specimen or culture obtained from any source, including plants, as well as biological and environmental samples. Biological samples may be obtained from plants and encompass fluids, solids, tissues, and gases.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A graphically illustrates the percent radiolabeled polar lipids in wild type, a tgd1-1 mutant, and the tgd4-2 and tgd4-3 mutants were after 30 min in the presence of radiolabeled oleic acid (pulse). DGDG, SQDG, and phosphatidylinositol (PtdIns) could not be individually detected and were analyzed in a pool designated R. FIG. 3B graphically illustrates the percent radiolabeled polar lipids of polar lipid labeling following a 3 day chase. FIG. 3C shows a representative autoradiograph of labeled lipids separated by thin layer chromatography following a 3 day chase. For data shown in FIG. 3A and FIG. 3B, three independent replicates were averaged, and the standraf deviation is indicated.

FIG. 4A shows rescue of the tgd4-1 lipid phenotype by stable expression of a cDNA encoding a TGDcGFP fusion construct in Arabidopsis wild type (WT) and tgd4-1 mutant under the control of the 35S-CAMV promoter. Two independent transgenic lines are shown. Lipids from top to bottom: MDGD, monogalactosyldiacylglycerol; PtdGro, phosphatidylglycerol; DGDG, digalactosyldiacylglycerol; SQDG, sulfoquinovosyldiacylglycerol; PtdEtn, phosphatidyl-ethanolamine; TriGDG, trigalactosyldiacylglycerol; PtdCho, phosphatidylcholine; TetraGDG, tetragalactosyldiacylglycerol. FIG. 4B shows genotyping of lines using a tgd4-1 specific cut amplified polymorphism DNA marker. A C/T mutation disrupts an HpaII site in the tgd4-1 gene.

FIG. 5A shows a thin-layer chromatogram of lipid extracts. Lipids were visualized by iodine staining. Soy oil was included as a standard. FIG. 5B shows a thin-layer chromatogram of in vivo pulse-chase labeling with labeled oleic acid. Leaves of 3-week-old plants were incubated with labeled oleic acid for 30 min. Chase time was 4 h followed by a change to unlabeled medium. An autoradiograph of a thin-layer chromatogram is shown. Lipids: TAG, triacylglycerol; DAG, diacylglycerol.

FIG. 6A shows a thin-layer chromatogram of neutral lipids. Lipids were visualized by exposure to iodine vapor. FIG. 6B shows a thin-layer chromatogram of polar lipids. Lipids were visualized by sugar-specific α-naphthol staining DGDG, digalactosyldiacylglycerol; MGDG, monogalactosyldiacylglycerol; O, origin; PIG, pigments; TAG, triacylglycerol; TGDG, trigalactosyldiacylglycerol.

FIG. 7A graphically illustrates the polar lipid composition (relative mol %) determined by quantification of fatty acid methylesters derived from individual lipids. FIG. 7B shows the fatty acid composition of the MGDG galactolipids. FIG. 7C shows the fatty acid composition of the DGDG galactolipids. Fatty acids are indicated with number of carbons: number of double bonds. DGDG, digalactosyldiacylglycerol; MGDG, monogalactosyldiacylglycerol; PC, phosphatidylcholine; PE, phosphatidylethanolamine; PG, phosphatidylglycerol; PI, phosphatidylinositol; SQDG, sulfoquinovosyldiacylglycerol.

FIG. 8C shows a mass spectrum for the peak at retention time 21.32 min for the tgd3 mutant has additional peaks corresponding to [M+Cl]— and [M+formate] (unlabeled). FIGS. 8D and 8E shows positive mode electrospray XICs over the range of m/z 890-905 illustrating the abundance of triacylglycerols with 54 carbons and various numbers of double bonds for tgd3 mutant leaves (FIG. 8D) and Col-2 wild type leaves (FIG. 8E). FIG. 8F shows the summed mass spectrum over the peak eluting at 27.87 min illustrating the [M+NH$_4$]$^+$ peaks corresponding to triacylglycerols with 54 carbons and from 3-8 double bonds.

FIG. 10A-10C shows an exemplary inducible silencing constructs and constitutively expressed tgd RNAi constructs for reducing TGD3 in Arabidopsis plants. FIG. 10A is a schematic diagram of genomic tgd3 where black areas represent exons separated by linear introns, the left white box represents the tgd3 promoter, and the right white box represents 3' untranslated region. FIG. 10B shows a tgd nucleic acid sequence annotated to show the untranslated region (not boxed) and the exon with ATG start site of exon1 (boxed area) used for sense and antisense constructs (SEQ ID NO:74). The two schematic diagrams shown below sequence illustrate the structures of sense and antisense constructs. Endonuclease cut sites are shown that can be used for cloning sense nucleic acid sequences and antisense nucleic acid sequences into the pSK-multicloning sites shown in FIG. 10C. An intron (int) sequence can be inserted in between the coding regions. The pSK construct was then cloned into pER8 containing an inducible promoter PG10-90. A control pCAMBIA1300MCS was constructed by inserting pSK in operable combination with a 35S promoter. An exemplary inducible promoter is described in Zuo, (2000) An estrogen receptor-based transactivator XVE mediates highly inducible gene expression in transgenic plants. Plant J. 24, 265-273, herein incorporated by reference in its entirety.

FIG. 11A shows that use of 2 uM B estradiol and 5 μM to induce expression provides somewhat variable results in silencing TGD3. FIG. 11B illustrates associated results showing an increase of TAG in vegetative tissues correlating with estradiol treatment. Col-wild type showed no detectable TAG in tissues, whereas tgd3-1 Salk T-DNA insertion plants show high levels of TAG.

FIG. 12A shows the total fatty acids per seed for the untransformed mutant (wri1-1) and wild type (WT). FIG. 12B shows the total fatty acids per seed for transgenic WRI1 lines in a wri1-1 background. FIG. 12C shows the total fatty acids per seed for transgenic WRI1 lines in the wild type background.

FIG. 13A shows WRINKLED mRNA after semi-quantitative RT-PCR of total RNA from wild type (WRI1), mutant (wri1-1) and the transgenic lines 106 and 107 expressing the WRI1-1 cDNA in the wri1-1 mutant background. Seedlings were grown either in the absence (0) or presence of (2) of 2% sucrose. Diagnostic fragments for the mutant (wri1-1) and wild type (WRI1) species are indicated. Actin-specific primers were used for control purposes. FIG. 13B shows Northern analysis of wild type (WRI1), mutant (wri1-1), and independent transgenic lines expressing the WRI1 cDNA under the control of the 35S-CAMV promoter from a CAMBIA vector-derived construct. Transgenic lines were in the wild-type (WRI1-tf) or wri1-1 mutant (wri1-1-tf) mutant backgrounds. Transgenic lines except (lane 9) were producing abnormal seedlings in the presence of 2% sucrose. Total RNA was isolated from transgenic (mixed normal and abnormal) seedlings grown for 11 days in the presence of 2% sucrose. The blot was repeatedly probed with the WRI1 cDNA (WRI1) or a cDNA encoding a predicted plastidic pyruvate kinase (Pkc, GenBank AY048198). The ethidium bromide-stained rRNA band is shown as loading control.

FIG. 14A shows a thin layer chromatogram of lipid extracts from 10 seeds or ten 10-day-old seedlings as indicated. Visibly morphologically altered seedlings were selected for the transgenic lines. In addition to transgenic lines 106 and 107, two additional independent transgenic lines, 10 and 84, were included to demonstrate broad occurrence of the phenomenon in the transgenic lines, these lines expressed the WRI1 cDNA in the wri1-1 mutant background. Pig, pigments; TAG, triacylglycerol. (b-d) Long-chain fatty acids as makers for seed oil in developing seedlings of wild type, wri1-1, and line 106 ectopically expressing the WRI1-cDNA in the wri1-1 mutant background. FIG. 14B shows long chain fatty acid content over time in plants grown on MS agar plates without sucrose. FIG. 14C shows long chain fatty acid content over time in plants grown on plates with 2% sucrose. Squares, wild type; open triangles, line 106; circles, wri1-1 mutant. In general, six groups of 15 plants each were analyzed and averaged (+/−SE). In FIG. 14C, from 7 days on, individual seedlings of line 106 (15-25 individuals) grown on sucrose were analyzed and averaged (+/−SD). FIG. 14D shows the number of these seedlings (closed bar, 7 day seedlings; hatched bar, 9 day seedlings; open bar, 11-day-old seedlings) grouped into classes according to their long-chain fatty acid content to illustrate the distribution of phenotypes.

FIG. 15A illustrates the increased oil content of transgenic phaseolin-F-box lines compared with vector control lines. Data shown are average of 18 lines (T2) and error bars are SE. FIG. 15B shows the total seed fatty acid methyl esters (FAMEs) of F-box transgenic lines compared to WT, and vector control lines. Error bars are standard error (SE) based on 18 lines: 3 duplicate results were performed for each line.

FIG. 16 graphically illustrates total seed FAMEs of transgenic lines versus WT and vector control lines. Large dots are the two lines with highest oil content and were named Fbox2 and F-box3 later chosen for next generation analysis. FIG. 16B graphically illustrates the fatty acid profile and fatty acid molar ratio composition of F-box transgenic lines versus control plants.

FIG. 17A graphically total FAMEs per seed in F-box $T_3$ seeds versus WT and vector control lines. The error bars are SE based on data obtained from 12 plants for F-box2 and F-box3 lines; 6 plants for WT and vector control lines. The two lines here named F-box2 and F-box3 are the two data points indicated by large dots. FIG. 17B graphical representation of experiments demonstrating total seed FAMEs of transgenic lines (F-box2 and F-box3) versus WT and 30 vector control lines.

FIG. 18A shows the C:N ratios for two independent lines F-box2 and F-box3. Error bars are SE based on six replicates. FIG. 18B graphically illustrates the percent oil content and C:N ratios of F-box lines versus wild type. As shown there is a positive correlation between oil content and C:N ratio. Open bars are overexpressors F-box2 and F-box3; hatched bars are wild type *Arabidopsis* seeds.

FIG. 19A sows schematic diagrams of 35S-WRI1, B33-WRI1, 35S-AGPRNAi and AGPRNAi-WRI1 constructs that included combinations of (WRI1) WRINKLED1 (At3g54320; SEQ ID NO:44) sequences, with a (P35S) cauliflower mosaic virus 35S promoter, a (PatB33) Patatin B33 promoter, and/or (HptII) hygromycin phosphotransferase II, (NptII) neomycin phosphotransferase II, [ADP-glucose pyrophosphorylase (AGPase)] small subunit of AGPase (AJ271162), with (nos) nopaline synthase terminator sequence, or (T35S) cauliflower mosaic virus terminator sequence, and/or an (Int) intron/linker, (His) His tag, (LB) left border, (RB) right border. FIG. 19B shows that fifteen-day-old T3 seedlings developed a glossy pale green phenotype when germinated on ½ Murashige and Skoog (MS) media supplemented with 1% sucrose. Wild-type (WT; Col2; left image) and AGPRNAi-WRI1 line 28 (28; right image) seedlings are shown. FIG. 19C graphically illustrates the chlorophyll content of WT and AGPRNAi-WRI1 line 28 seedlings. Chlorophyll was extracted from 15-day-old seedlings with 80% acetone and its concentrations determined spectrophotometrically. The error bars represent the standard deviation of the mean of three independent experiments (n=3), *t-test significant at P<0.005 versus WT. FIG. 19D shows the morphology of soil grown WT plants compared to AGPRNAi-WRI1 lines 14, 17 and 18.

FIG. 20A illustrates the relative expression of WRI1 in 35S-AGPRNAi transgenic lines 2, 5 and 6; in 35S-WRI1 transgenic lines 5, 7 and 9; in B33-WRI1 transgenic lines 7, 9 and 10; and in AGPR-NAi-WRI1 transgenic lines 14, 17 and 28. FIG. 20B graphically illustrates the relative down-regulation of APS1 in 35S-AGPRNAi and AGPRNAi-WRI1 lines. The error bars represent the standard deviation of the mean of three independent experiments carried out from the three independent mRNA extractions.

FIG. 21A shows the starch content of the different lines, *t-test significant at P<0.006 or **P<0.0001 versus WT. FIG. 21B shows the sucrose content of the lines, *t-test significant at P<0.003 or **P<0.001 versus WT. FIG. 21C shows the glucose content of the lines, *t-test significant at P<0.008 or **P<0.004 versus WT. FIG. 21D shows the fructose content of the lines, *t-test significant at P<0.003 or **P<0.001 versus WT. The error bars represent the standard deviation of the mean of three independent experiments (n=3).

FIG. 22A-22D shows that exemplary *Arabidopsis* lines that overexpress WRINKLED1 (WRI1) with down-regulation of APS1 accumulated higher levels of triacylglycerols (TAGs) in their vegetative tissue when compared to wild-type. FIG. 22A shows electrospray ionization mass spectrographs (ESI-MS) illustrating triacylglycerol quantities in neutral lipid extracts of 15-day-old seedlings of wild type and of representative T3 homozygous transgenic plants expressing WRI1 alone or WRI1 in combination with AGPRNAi. The error bars represent the standard deviation of the mean of three independent experiments (n=4). *t-test significant at P<0.0005 or P<0.0002 or *P<10)$^5$ versus WT. FIG. 22B shows a positive-ion ESI mass spectra of neutral lipid extracts from wild-type seedlings. FIG. 22C shows a positive-ion ESI mass spectra of neutral lipid extracts from T3 homozygous AGPRNAi-WRINKLED1 line 28 seedlings. Tritridecanoin (tri13:0) and tripentadecanoin (tri15:0) TAGs were added as internal standards. FIG. 22D shows two ESI-MS analyses of neutral lipid extracts of line 28. Shown are the daughter fragment peaks from TAGs with [M+NH$_4$]+ adducts with m/z values of 927 and 957.

DETAILED DESCRIPTION OF THE INVENTION

Figure 1:
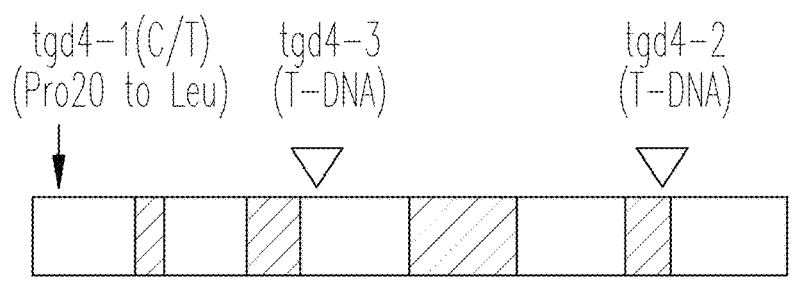
FIG. 1 shows a schematic diagram of tgd4-1, tgd4-2 and tgd4-3 mutation sites.

The present invention relates to compositions and methods for providing RNA interference (RNAi) vectors comprising trigalactosyldiacylglycerol (tgd) biosynthesis enzyme constructs for increasing oil content of plants. Specifically, plant cells, plant tissues and whole plants are provided comprising novel tgd RNAi vectors for reducing TGD protein expression for increasing oil content (including relative amounts of triacylglycerols) in cells and in vegetative tissues. In particular, vectors are provided comprising tgd RNAi constructs for silencing tgd1 and tgd4 endogenous gene translation. Further, the use of tgd RNAi silencing vectors in combination with co-expression of heterologous oil regulating transcription factors, such as WRINKLED1, are contemplated to overcome the reduced growth and variable levels of embryonic lethality in plants with reduced TGD protein. Additionally, plants having reduced APS1, a gene encoding a major catalytic isoform of the small subunit of AGPase (AGP(−) plants), co-expressing a heterologous oil modulating transcription factor are contemplated for use in combination with plants having reduced TGD. Oil harvested from vegetative tissues of plants comprising vectors and genes of the present invention is contemplated for use in biofuel and biodiesel products.

I. Biosynthetic Oil Production.

Production of alternative fuels such as biodiesel is on the rise around the world and in the U.S. due to a strong and growing desire to reduce dependency on petroleum derived diesel fuel. The acceptance of biodiesel has been slowed due to its higher cost relative to petroleum-derived diesel. The higher cost of biodiesel is directly related to the cost of feedstock used for biodiesel production, which is often derived from the same crops grown for use as human and animal food. Hence, many biodiesel producers and academic researchers are exploring technologies for alternative biodiesel feedstock, i.e. crop oils, particularly those technologies with the potential to lower feedstock costs. In some embodiments, the inventors contemplate the use of isolated vegetative lipids produced by plants and methods of the present inventions for use in biofuels. The use of these alternative plants and methods is contemplated to increase the amount of oil harvested per acreage of cultivated plant oil crop. In addition to biofuel uses for engineered oils, oils produced by engineered plants are contemplated to serve as renewable chemical feedstocks contemplated for use in replacing petroleum-based products in industrial applications (see, for examples, a review in Jaworski et al., Curr. Opin. Plant Biol. 6:178-184 (2003); Dyer et al., Seed Sci. Res. 15:255-267 (2005); and Singh et al., Curr. Opin. Plant Biol. 8:197-203 (2005), all of which are herein incorporated by reference in their entirety).

However large-scale production of oils from engineered plants and natural plant species through traditional farming is often impossible because of poor agronomic traits of these engineered or natural plants producing desired oils. Furthermore, efforts to transfer genes encoding the proteins responsible for making novel fatty acids from endogenous pathways or creating unusual fatty acid biosynthesis by inserting genes from exotic plants into higher yielding plants (i.e. plants with agronomic traits for commercial use) has generally met with limited success. Often lack of success is due to much lower amounts of the desired fatty acid accumulating in the seed oils of transgenic plants (15 to 30%) compared with the seeds of native plant species (up to 90%). Thelen et al., Metab. Eng. 4:12-21 (2002), herein incorporated by reference in its entirety. Thus, engineering of existing oil seed crop species is contemplated for increasing plant oil production and for making specific engineered oils.

One contemplated method for engineering existing oil seed crop plants is to increase the amount of desired oil produced and stored within a seed. However even if this was accomplished, there may be a limit on the total amount of oil a seed is capable of storing, in addition to a severe impact on the fertility of the plants. Further, plants need to be grown to maturity, using fertilizers, herbicides, and arable acreage for an entire growing season, in order to for the plant to produce fully formed seeds in order for seed oil isolation to be economically feasible. Therefore, compositions and methods involved in plant oil biosynthesis are needed for providing engineered plants producing increased amounts of industrially important oils in plants with agronomic traits suitable for commercial production.

Many genes encoding enzymes affecting oil biosynthesis were isolated from plants for use in engineering plant fatty acid production with the hope of discovering novel oil compositions or increasing the amounts of oil produced per plant for commercial purposes. The majority of these genes were discovered using various methods, including natural plant mutants, artificially mutagenized plants and plants with insertions, i.e. T-DNA insertions, which changed fatty acid synthesis, primarily in seeds, often along with phenotypic changes in plant morphology when plants were grown from these seeds. Isolated genes were then used transgenically as heterologous genes to produce plants in hopes of discovering useful novel fatty acid compositions i.e. 'designer oils' that could be successfully incorporated into commercially viable plant lines. Examples of fatty acid altering enzymes included fatty acid biosynthetic enzymes, such as acyltransferases, ketoacyl-acyl carrier protein synthetases, desaturases, and related enzymes were discovered and used for producing plants with novel fatty acid content.

However the majority of the plants, or their isolated oils, are not commercially used. Many of these transgenic plants or isolated oils were not used due to lacking the type of oil compositions effective for commercial use, low production of desired oils, plants with poor agronomic traits, plants with poor fitness (in general an unhealthy plant), such as plants with reduced oil yield per plant, plants with stunted growth, infertile plants, etc.

Thus, current commercial use of oils from plants engineered for designer alterations in oil production is limited to merely a few plant lines producing limited types of oils. Despite a few commercial successes with engineered plant lines having altered oil production, such as certain soybean seed oils, there are no known engineered commercial plant lines where fatty acids accumulated in vegetative tissues. Furthermore, there are no known engineered commercial plant lines where TAGs accumulated in vegetative tissues, in part due to undesirable agronomic traits when TAG production is increased in plants where at least one tgd gene is knocked out (or mutated) for undetectable or barely detectable levels of expression (see summary in Table 1 and schematic of tgd4-1, tgd4-2 and tgd4-3 insertion mutation sites in FIG. 1). Further, there are no known engineered commercial plant lines where TAGs accumulated in both vegetative tissues and seeds.

TABLE 1

Loss of TDG function phenotypes

| Gene | Loss of tgd function phenotypes, The *Arabidopsis* Information Resource (TAIR) | References |
|---|---|---|
| tgd4-1 tgd4-2 tgd4-3 | The tgd4-1 point mutation produced plants that were slightly pale green but otherwise indistinguishable from the wild type plants. Plants carrying the tgd4-2 and tgd4-3 T-DNA insertion allele were stunted, pale yellow in color, and infertile. More lipid accumulated in tgd4-2 and tgd4-3 plants than in tgd4-1 plants. | Xu et al., Plant Cell. 20(8): 2190-2204 (2008). |
| tgd3-1 | No mutant plant phenotype described for tgd3-1, lipid accumulated in leaves comprising polar fatty acids, polar lipid extracts of the tgd3-1 mutant contained a new lipid staining with α-naphthol additional. | Lu et al., J. Biol. Chem., 282: 35945-53 (2007). |
| tgd2-1 | Compared to the wild type, mutant plants were consistently smaller and slightly pale, as was observed for the tgd1-1 mutants. Mutant plants had aberrant accumulation of oligogalactolipids and triacylglycerols. | Awai et al. Proc. Natl. Acad. Sci. 103(28): 10817-22 (2006) |
| tgdl-1 | Compared to the wild type, mutant plants were consistently smaller and slightly pale. Mutant plants had aberrant accumulation of oligogalactolipids and triacylglycerols. Reduced growth, 50% of the seeds are aborted at the embryo heart stage, the seed chloroplasts have reduced galactolipids and leaves accumulated trigalactosyldiacylglycerol and triacylglycerol and phosphatidate | Awai et al. Proc. Natl. Acad. Sci. 103(28): 10817-22 (2006). Xu et al., Plant Cell 17: 3094-3110 (2005). |

Thus in one preferred embodiment, the inventors contemplate gene-silencing (knock down) methods for accumulating oil in vegetative tissues of the present inventions by reducing but not eliminating TGD protein production. However, one primary problem of several known problems encountered when engineering plants for gene silencing is target specificity. Full-length pieces of either a mutant cDNA or antisense cDNA sequence used in gene silencing constructs are more likely to bind to nontarget genes, which may or more typically may not be beneficial to desired plant oil production. Nontarget genes may have highly similar coding sequences when compared to the target gene or have high similarity in the uncoded region. Further, binding of mutant cDNA or antisense sequences expressed by silencing constructs to nontarget DNA may have adverse effects on agronomic traits necessary to commercial production. Thus in preferred embodiments, tgd sequences used in gene silencing constructs of the present inventions are fragments, i.e. partial DNA sequences for encoding mRNA of TGD proteins.

Additionally, the type of regulation by the target gene affects the success of gene silencing depending on whether the gene has effects which are dominant, co-dominate, recessive, dominant negative, pleiotropic effects, variable expressivity, complete or incomplete penetrance, etc. Thus, the inventors' encountered many problems with plant growth and reproduction when reducing tgd gene expression when producing plants mutant for tgd DNA sequences, such as stunted plant growth and embryonic lethality. For example, these problems were observed when a tgd mutant gene was used for silencing one homologous tgd gene, such as tgd2-1 silencing of tgd2. The inventors discovered through the use of these mutants that tgd genes were dominant negative, such that expressing a few mutant genes produced mutant protein that displaced wild-type functional TGD proteins within the lipid transporter molecule.

Thus, plants expressing mutant forms of tgd that interfered with wild-type tgd function showed a range of characteristics including a high rate of embryonic lethality, stunted growth, plants having yellow instead of green leaves and stems, and variability from plant to plant of amounts of oils stored in vegetative tissues. Therefore in preferred embodiments, the inventors contemplate the use of tgd RNAi silencing constructs for producing plants having similar levels, i.e. similar from plant to plant, of reduced TGD translation. Additionally, the use of a full-length tgd1 gene encoding the entire TGD1 protein for RNAi gene silencing in mutant tgd1-1 plants resulted in higher levels of sterile seeds or empty seed hulls and further diminished growth, Xu, et al., 2005, herein incorporated by reference in its entirety.

Thus in one example, the inventors made a RNAi construct using two copies of a full-length coding region of TGD1 as a cDNA in operable combination with a constitutive promoter, S35. In other words the construct consisted of a full-length sense tgd1 sequence, a glucuronidase intron in the spacer region, and a full-length tgd1 antisense sequence. However, as described, the expression of this construct in Arabidopsis plants resulted in variable reductions of TGD protein, reduced growth and sterility like those seen, for example, in Table 1 for the tgd mutants described in FIG. 1.

In order to overcome these limitations, the inventors contemplated the use of inducible constructs for turning on the RNAi constructs after a seed germinates and begins to grow in order to reduce effects on growth.

Further, the inventors contemplated overcoming the poor growth and reproductive characteristics of these tgd knock down plants by expressing additional or stacked heterologous genes, specifically, oil regulating transcription factors. Thus, the use of constructs for reducing TGD protein expression in combination with constructs overexpressing an oil regulating transcription factor can find use in the present inventions. Further, embodiments are contemplated for compositions and methods comprising RNAi constructs using fragments of tgd cDNA coding regions for use in plants expressing wild-type tgd genes for producing plants for use in establishing engineered plants having lowered TGD producing plant lines.

In one embodiment, engineered plants with lowered tgd translation from the use of a tgd RNAi gene silencing construct, would be used for breeding plant lines with genetically determined lowered amounts of tgd gene translation for increasing lipid expression in vegetative tissues. In further embodiments, expression of RNAi constructs using fragments of tgd cDNA coding regions are contemplated for use in plants for reducing targeted tgd gene translation at certain levels, i.e. reduced expression of TGD proteins between 0-25%, 25-50%, 50%-70%, up to 70%-90% of wild-type protein production. In a further embodiment, a reduction of TGD protein expression is combined with overexpression of a transcription factor. In preferred embodiments, plants expressing RNAi constructs for lowering TGD expression while overexpressing an oil regulating transcription factor, such as a WRI1 cDNA, for example, deposited at GenBank (AY254038), are contemplated.

In other embodiments contemplated for overcoming growth and reproductive defects observed in plants having decreased levels of either TGD proteins the inventors contemplate the use of plants having reduced expression of APS1, a gene encoding a major catalytic isoform of the small subunit of AGPase (ADP-glucose pyrophosphorylase). The inventors discovered that plants having reduced AGPase expression while concurrently ectopically expressing WRI1 increased the accumulation of TAG in Arabidopsis vegetative tissues. In fact, results showed that Arabidopsis ectopically expressing AGPRNAi-WRI1 accumulated less starch and 5.8-fold more TAG in the vegetative tissues. However the inventors contemplate that further increases in TAG content of vegetative tissues would be provided by plants having reduced APS1 along with reduced TGD expression while overexpressing WRI1.

Thus, in even further embodiments, plants expressing RNAi constructs for lowering TGD expression in combination with plants expressing RNAi constructs for lowering AGPase expression are contemplated. In additional embodiments, plants having lowered TGD expression and AGPase expression while overexpressing an oil regulating transcription factor are contemplated. Thus plants of the present inventions co-expressing RNAi constructs with vectors for overexpressing oil regulating transcription factors are contemplated to have increased oil in vegetative tissues while overcoming the greatly reduced growth and fertility observed in other plants having reduced TGD or AGPase.

A. Production of Seed Oil.

For producing edible oils, industrial oils, and oil biofuel uses, an increase in seed oil content is desirable and a major goal of oilseed engineering. There are at least three major biosynthetic events involved in the production of seed oils. The first involves the synthesis of fatty acids in plastids. The second involves a modification of these fatty acids by enzymes located primarily in the endoplasmic reticulum (ER) of plastid cells. The third involves packaging of nascent fatty acids into triacylglycerols (TAGs), which subsequently accumulate in oil bodies that bud off from the Endoplasmic Reticulum within cells. Research information is currently available regarding synthesis and modification of fatty acid-containing oil body structures in seeds. For example, see, Ohlrogge et al., Plant Cell 7:957-970. (1995); and Shanklin et al., Annu Rev. Plant Physiol. Plant Mol. Biol. 49:611-641 (1998), all of which are herein incorporated by reference in their entirety.

However, methods of increasing seed oil content by manipulation of oil regulating genes and transcription factors were not generally successful. One problem was that when seed oil was increased to high levels then fertility, i.e. viability, decreased. For example, several schemes were developed to modify the fatty acid composition of seed oils by genetic engineering resulting in increased nutritional and industrial value (Voelker et al., 1996, herein incorporated by reference in its entirety). However, strategies targeting single rate-limiting enzymes to increase seed oil content were moderately successful (Thelen and Ohlrogge, 2002, herein incorporated by reference in its entirety). Therefore, there remains a need for increasing oil produced on a per plant or population of plants basis with a minimum effect upon seeds whose viability and numbers are needed for agricultural and economical use.

However, little is known about the interactions of enzymes and cellular mechanisms required for the selection and transfer of fatty acids into storage TAGs in other plant tissues. Even less understood was the interaction of oil production in vegetative tissues such as leaves and stems in relation to oil production in seeds.

B. TGD Associated Production of Oil in Vegetative Tissues.

Plants with mutations in certain genes whose translated proteins result in the reduction in synthesis of a particular fatty acid were found and named after the altered fatty acid. Thus mutated genes affecting TAG expression were identified and labeled trigalactosyldiacyl-glycerol (tgd) proteins, 1 and 2 while tgd3 and tgd4 were originally discovered under a different name and renamed due to their relation to function. Genetic analysis indicated that TGD1-3 formed a lipid transporter as a triprotein complex located in the membrane of the ER (endoplasmic reticulum).

Thus, each one of the TGD1-3 proteins of *Arabidopsis* was required for the biosynthesis of endoplasmic reticulum derived thylakoid lipids. TGD2 was contemplated to be the substrate-binding protein of a contemplated lipid transporter combined with TGD1 (permease) and TGD3 (ATPase) proteins. The TGD1, -2, and -3 proteins were localized in the inner chloroplast envelope membrane. TGD2 appeared to be anchored with an N-terminal membrane-spanning domain into the inner envelope membrane, whereas the C-terminal domain faced the intermembrane space. Subsequent research found that one additional gene discovered under a different name, with no significant homology to TGD1-3 was also involved with TAG production. Because the encoded proteins were also involved with the same fatty acid pathway as TGD1-3 it was designated as tgd4. When plants with any one defective tgd were analyzed, the inventors discovered that TAG was increased in vegetative tissues of the plants along with other changes (alterations) to fatty acid compositions of vegetative tissues and seeds. Thus, the inventors isolated a series of *Arabidopsis* mutant plants for each of the genes encoding TGD 1, 2, 3, and 4 proteins whose leaves and other vegetative tissues had higher oil content, i.e. accumulated amounts of oil. These mutant genes were generally leaky with varying levels of expression from plant to plant. However when any one of the tgd genes was completely disrupted the result was detrimental to plant growth and/or plant development and fertility at levels generally associated with disruption of each one of the four genes, see mutant structures in FIG. 1 and Table 1 for a summary of characteristics.

As one example, the inventors created a dominant negative mutation for TGD2 and tested it in *Arabidopsis*, Awai et al. 2006, PNAS 103(28):10817-10822, herein incorporated by reference in its entirety, however in addition to the dominant negative leaky gene resulting in a range of phenotypes, those plants whose leaves accumulated oil lacked agronomic traits for commercial production, including having infertility, i.e. embryo-lethality, and stunted growth. The inventor's then attempted to completely shut off TGD1 by using an RNAi construct comprising the entire coding unit of TGD1 expressed as the sense and antisense directions separated by a spacer sequence of a glucuronidase intron, in operable combination with a constitutive promoter, Cauliflower Mosaic Virus (CaMV) 35S Promoter (i.e. S35), in plants co-expressing TGD1 mutations. The expression of this construct on the *Arabidopsis* background of TGD1-plants resulted in highly stunted plants with high level of embryo lethality, for example, large numbers of sterile seeds or empty seed hulls were observed (Xu, et al., Plant Cell. 2005 November; 17(11):3094-3110, herein incorporated by reference in its entirety). The ratio of aborted seeds approached 90% (409 out of 481 total for RNAi line-1 and 519 out of 583 total for RNAi line-) for the tgd1-1/TGD1-RNAi lines. Approximately 50% of the seeds of the tgd1-1 mutant were aborted. When embryos forming in siliques of the tgd1-1 mutant line were directly examined from 2 to 6 d after flowering, many were found arrested at the heart stage (see, description of heart stage, Mansfield and Briarty, Can. J. Bot. 69, 461-476 (1991), herein incorporated by reference in its entirety) just before the greening of the plastid was expected to begin.

The inventors discovered that accumulation of oil in the leaves and stems was achieved by altering the function of the trigalactosyldiacylglycerol (TGD) proteins when an RNAi silencing sequence, comprising the entire coding region of tgd1 under control of a S35 constitutive promoter, was induced to express in transgenic plants. Additionally, these plants showed a range of phenotypes. Thus similar to the mutant tgd expressing plants, these plants with a full-length gene silencing construct showed undesirable agronomic traits of wide variations in capability of growth, variability in accumulation of oil in plant cells, leaves, and stem, and high levels of embryo lethality.

C. Trigalactosyldiacylglycerol (tgd) Genes and TGD Proteins.

Plant oil normally accumulates in seeds, which have less storage capacity than combined amounts in plant cells and plant tissues leaves and stems. Thus wild type plants with normally functioning TGD proteins do not accumulate oils, including TAGs, in a manner as described herein. However, the inventors discovered that a loss of function of any one of the tgd1-tgd4 genes caused accumulation of TAG and other plant fatty acids in leaves and stems. Specifically, the inventors discovered through the use of mutant TGD proteins and by transgenic expression of constitutive-transiently expressed mutant tgd1, 2 or 3 genes that when TGD mutant proteins were present there was a dominant-negative effect on function. Therefore, despite the presence of functional wild type TGD proteins, mutant TGD proteins were incorporated into the TGD1-3 complex causing variable levels of accumulation of oils in plant cells, plant leaf and stem tissues. However, plants comprising constitutive-transiently expressed mutant tgd genes showed leaky expression with a wide range of plant growth, embryonic lethality, and variable levels of oils accumulated in plant cells and vegetative tissues. As one example, a TGD3 inactivation line (SALK_040335) carrying a T-DNA 5' of the presumed ATG start codon of *Arabidopsis* gene At1g65410 showed accumulation of the oligogalactolipid. However in tgd1-3 plants, the plant accumulates oil in its plant cells and plant tissues leaves and stems at the expense of reduced plant growth and fertility.

1. Reduced Tgd4 Expression Increased Lipid Content in Leaves.

Plants were also made which had insertion mutations that disrupted the normal function of TGD4 protein. The malfunctioning TGD4 protein also caused plant oil to accumulate in the leaf and stem with variable effects on plant growth and fertility, Xu, et al. 2008. The inventors further discovered that comparatively, plants with reduced TGD4 protein appeared to accumulate more oil in vegetative tissues than plants with reduced TGD1 or TGD2 protein.

Figure 2A:
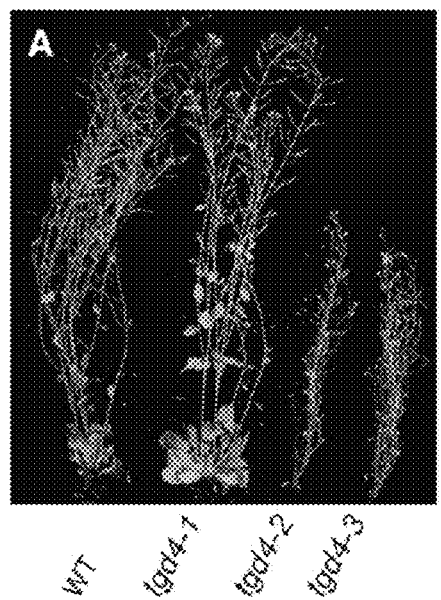
FIG. 2A-2B shows exemplary 7-week-old wild type and tgd4 mutant plants in FIG. 2A, and the lipid phenotype of isolated tgd4-1, tgd4-2, and tgd4-3 mutant plant oils compared to oil from wild type plants in FIG. 2B. A section of a thin layer chromatogram of lipid extracts stained for glycolipids is shown in FIG. 2B. The three galactoglycerolipids MGDG, DGDG, and TGDG are indicated.

Specifically, in a population of ethyl methane-sulfonate mutagenized population of *Arabidopsis* (ecotype Columbia [Col-2] that contained plants having T-DNA insertion, 3 plant lines were found with insertions in the tgd4 gene. Thus a tgd4-1 mutant was isolated during a screen for lines accumulating oligogalactolipids. The growth and lipid phenotypes of tgd4-1 are shown in FIG. 2. The tgd4-1 plant was slightly pale green but otherwise indistinguishable from the wild type in contrast to plants carrying the tgd4-2 and tgd4-3 T-DNA insertion alleles that were stunted, pale yellow in color, and infertile. A tgd4-1 phenotype included the presence of a lipid in leaf extracts that co-migrated during thin layer chromatography with trigalactosyl-diacylglycerol (TGDG) and stained positive for sugars. The total leaf fatty acid content of the severe tgd4-3 mutant was not reduced (wild type, 3.1 6 0.2, and tgd4-3, 3.1 6 0.1 mg/mg fresh weight; n=3, SD is given). A comparison of polar lipids in the wild type and the three mutant lines is shown in Table 2.

TABLE 2

Leaf Polar Lipid Composition of the Wild Type, tgd4-1, tgd4-2, and tgd4-3

| Lipids | Wild Type | tgd4-1 | tgd4-2 | tgd4-3 |
|---|---|---|---|---|
| MGDG | 37.4 ± 1.7 | 38.5 ± 7.5 | 34.4$^a$ ± 1.0 | 32.6$^a$ ± 1.1 |
| PtdGro | 8.9 ± 0.6 | 12.1$^a$ ± 1.2 | 12.3$^a$ ± 0.5 | 13.5$^a$ ± 0.2 |
| DGDG | 19.9 ± 0.5 | 15.2$^a$ ± 1.6 | 12.3$^a$ ± 0.9 | 12.6$^a$ ± 0.1 |
| SQDG | 3.1 ± 0.3 | 4.0 ± 0.6 | 3.5 ± 0.1 | 4.0$^a$ ± 0.2 |
| PtdIns | 1.1 ± 0.2 | 2.5$^a$ ± 0.9 | 1.2 ± 0.4 | 1.4 ± 0.2 |
| PtdEtn | 13.8 ± 0.1 | 10.0$^{a,b}$ ± 1.9 | 16.6$^{a,b}$ ± 0.3 | 16.8$^{a,b}$ ± 0.3 |
| PtdCho | 15.8 ± 0.3 | 15.8 ± 4.1 | 19.6$^a$ ± 0.7 | 19.1$^a$ ± 0.9 |

Values (mol %) of three independent samples were averaged and the SD is indicated. Plants were grown on soil for 4 weeks. PtdIns, phosphatidylinositol.
$^a$Values are significantly different from wild-type values based on Student's t test (95% confidence interval).
$^b$This lipid sample also contains TGDG at <1 mol %.

The mutants have slightly reduced amounts of galactoglycerolipids and slightly increased amounts of phosphatidylglycerol (PtdGro), phosphatidylethanolamine (PtdEtn), and phosphatidylcholine (PtdCho). The galactoglycerolipids are primarily found in plastids, while PtdGro and PtdCho are present in plastid and extraplastidic membranes, and PtdEtn is exclusively in extraplastidic membranes. Therefore, these lipid changes may reflect a decreased ratio of plastid-to-extraplastidic membranes in the mutants, which is consistent with the pale green color of the mutants indicative of reduced chlorophyll and photosynthetic membranes. The TGDG content of the mutants was <1 mol % of total fatty acids in leaves (e.g., 0.5 6 0.1 mol % for tgd4-3; n=3, SD is given). Viable seeds were obtained when wild-type pollen was transferred onto tgd4-2 or tgd4-3 pistils, but reciprocal transfer did not yield seeds, suggesting that the tgd4-2 and tgd4-3 mutations cause a pollen defect. Sequencing of cDNA for At3g06960 derived from tgd4-1 detected a mutation in nucleotide position 102 of the coding sequence (GenBank accession number NM_111576) in the first predicted exon of At3g06960. The mutation led to a Pro-to-Leu substitution in position 20 of the predicted protein). A wild-type cDNA derived from locus At3g06960 was fused to the open reading frame of green fluorescent protein (GFP) and when expressed in the tgd4-1 mutant under the control of the cauliflower mosaic virus (CaMV) 35S promoter and was able to restore the wild-type lipid phenotype. The point mutant allele and plants were designated tgd4-1, while two other plants having T-DNA insertion alleles affecting tgd4 expression corresponded to SAIL_760_F05, tgd4-2, and the T-DNA allele corresponding to SAIL_133_H06, tgd4-3. The use of these or other SALK lines with mutations for other tgd genes are contemplated to be problematic for use as founder plants for breeding plants expressing low tgd or for use as hosts for overexpressing other genes such as WRI1 or F-Box, as described herein. In part, due to the methods of making these lines, the plants are highly likely to have T-DNA insertions in other genes along with lacking desired agronomic traits. Further, these lines have variable "leaky" levels of gene expression increasing the variability of gene expression from plant to plant.

2. Reduced Expression from Certain Insertion Mutations in Each of Tgd1, Tgd2, Tgd3 and Tgd4 Genes Increased Lipid Accumulation in Plants.

Figure 2B:
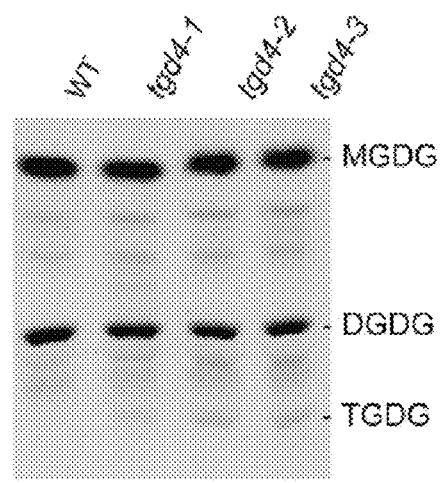
Figure 3A:
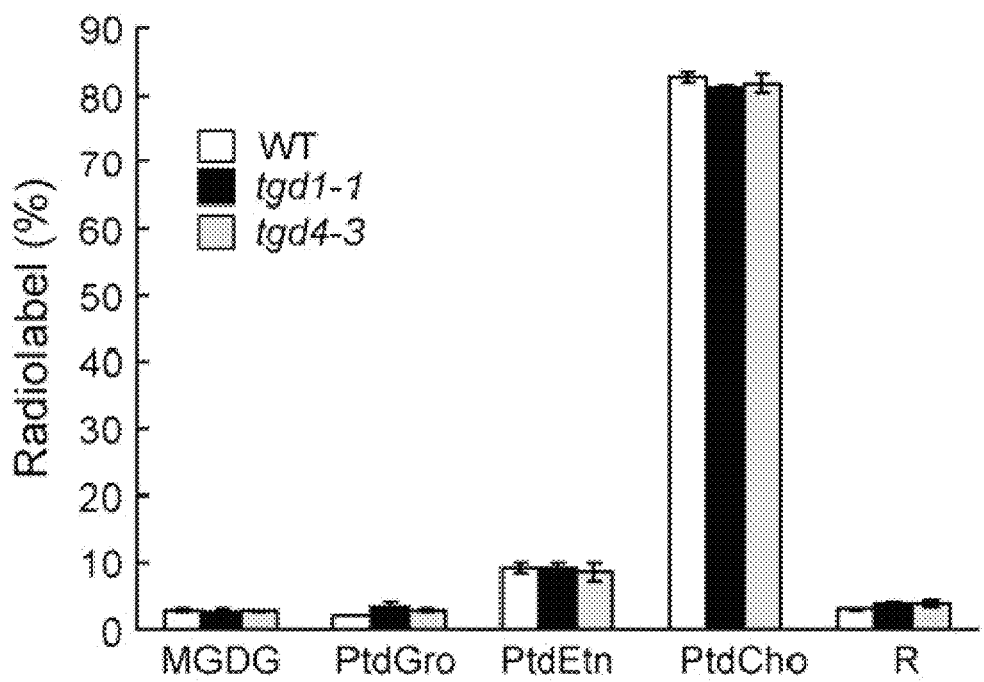
FIG. 3A-3C shows exemplary In Vivo Pulse-Chase Labeling of Polar Lipids with [1-$^{14}$C]-Oleate.
Figure 3B:
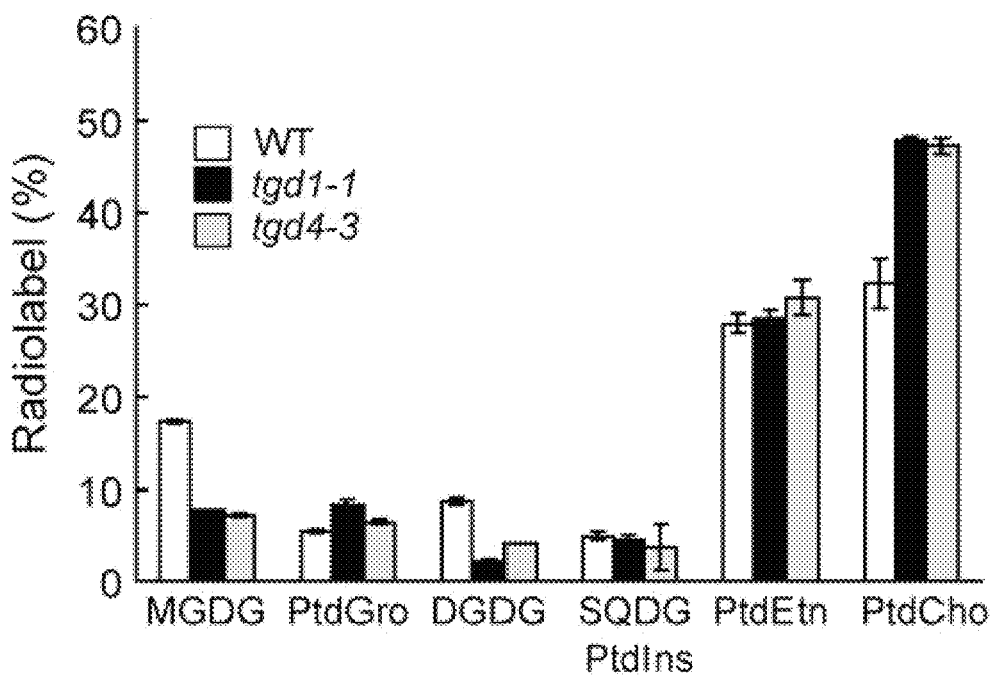
Figure 3C:
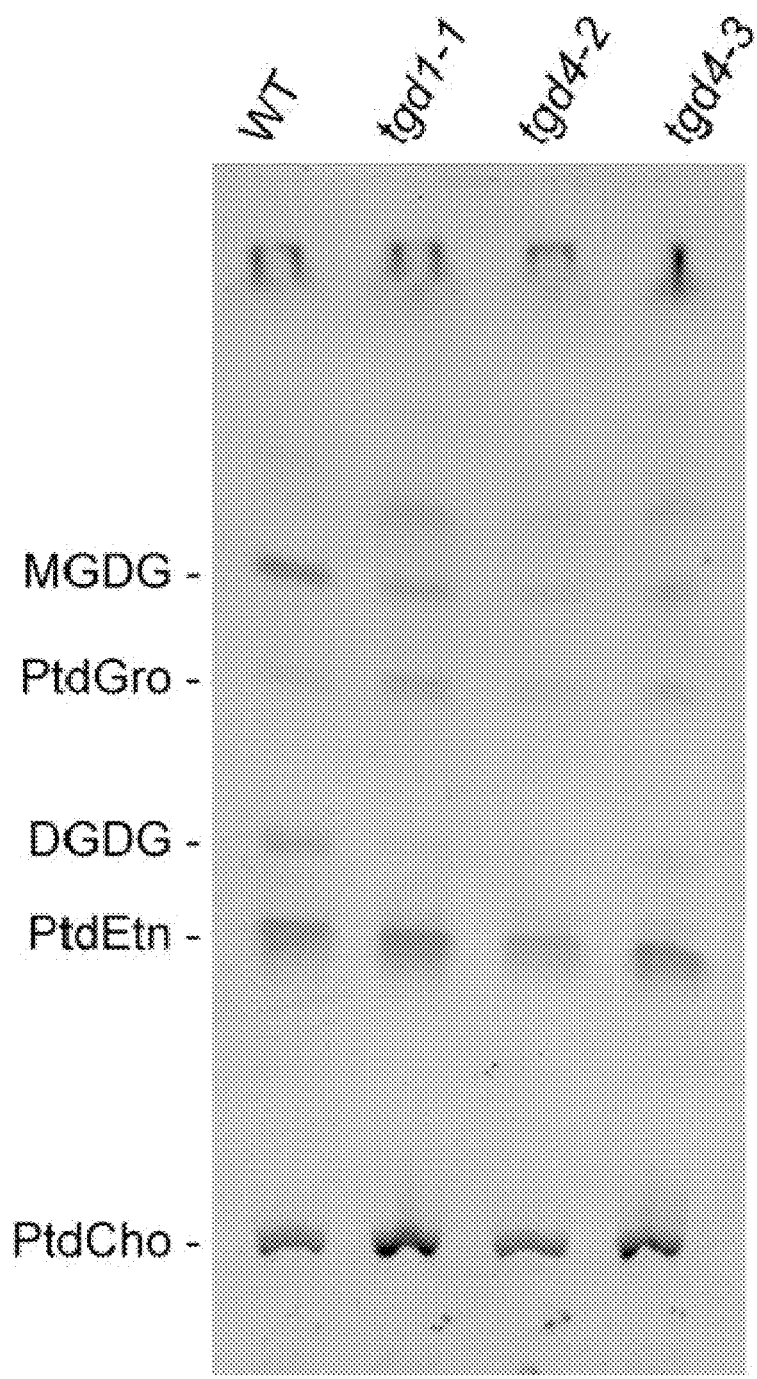
Figures 4A, 4B:
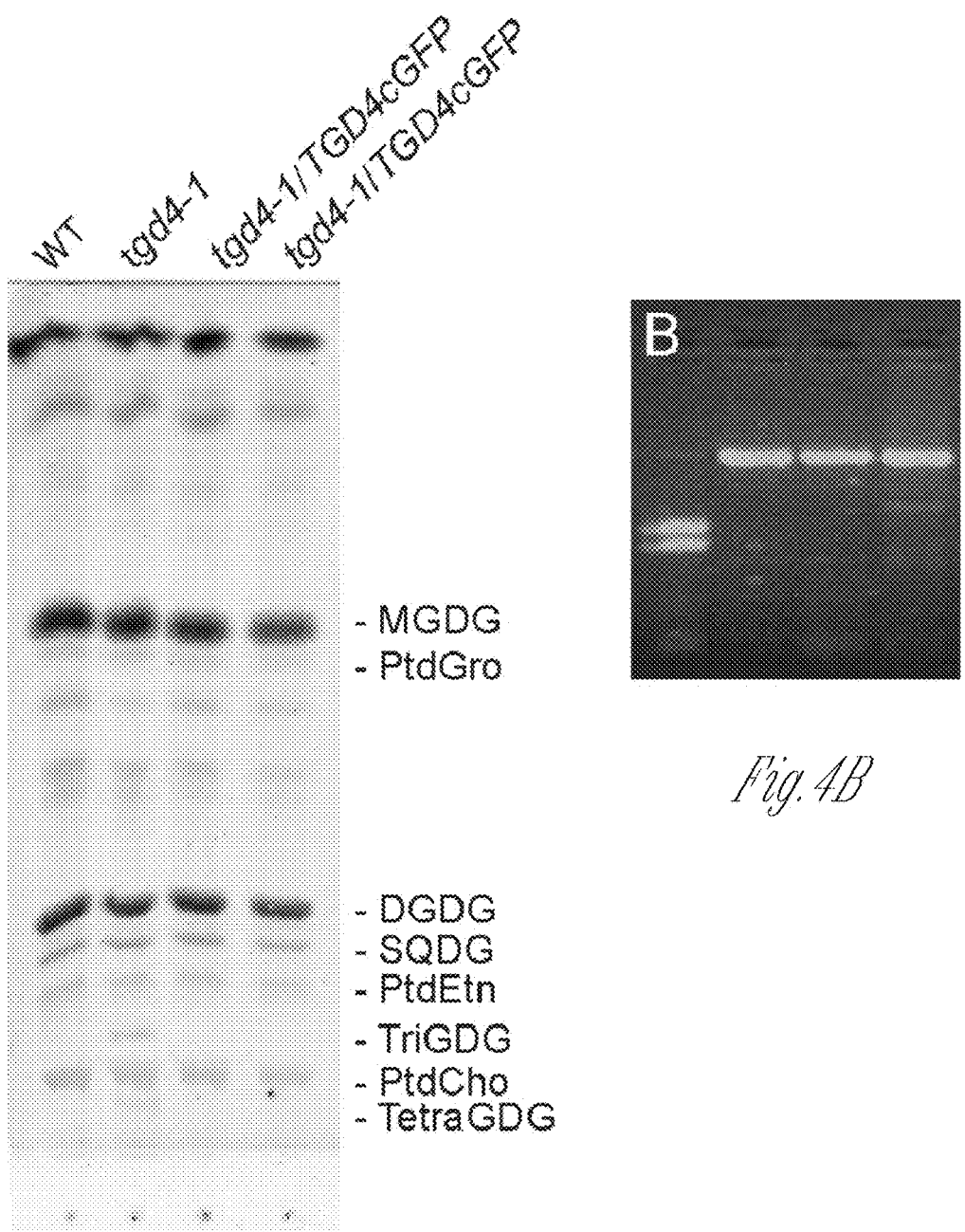
FIG. 4A-4B show exemplary reversal of increased lipid expression using a TGD4cGFP fusion construct.
Figure 5B:
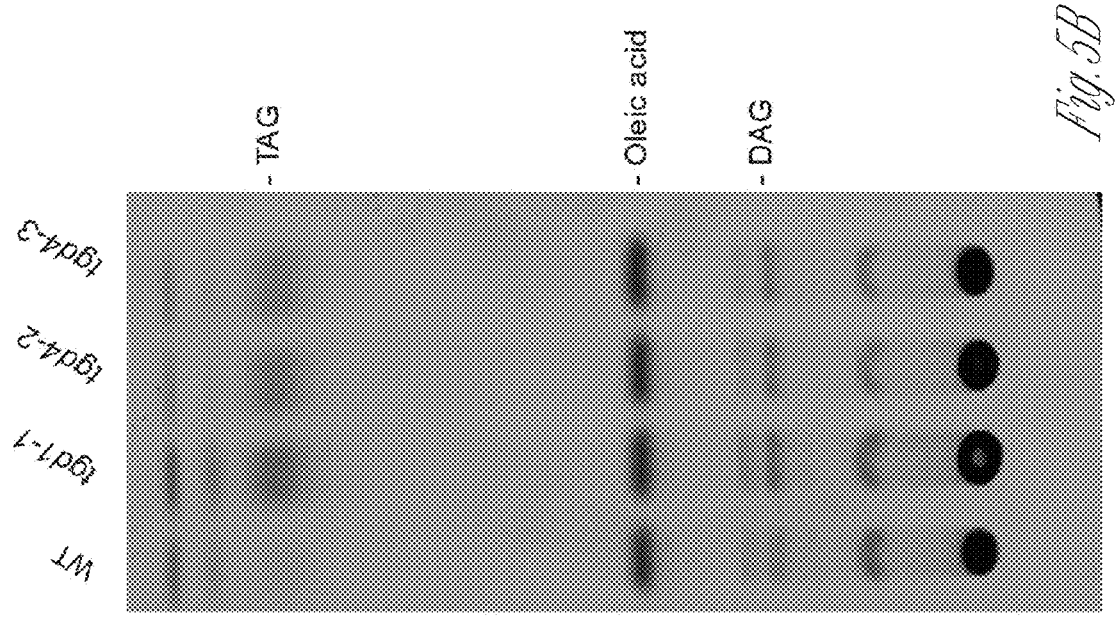
FIG. 5A-5B shows exemplary accumulation of triglycerides for tgd1-1 mutant plants and the tgd4-2 and tgd4-3 mutants.
Figure 5A:
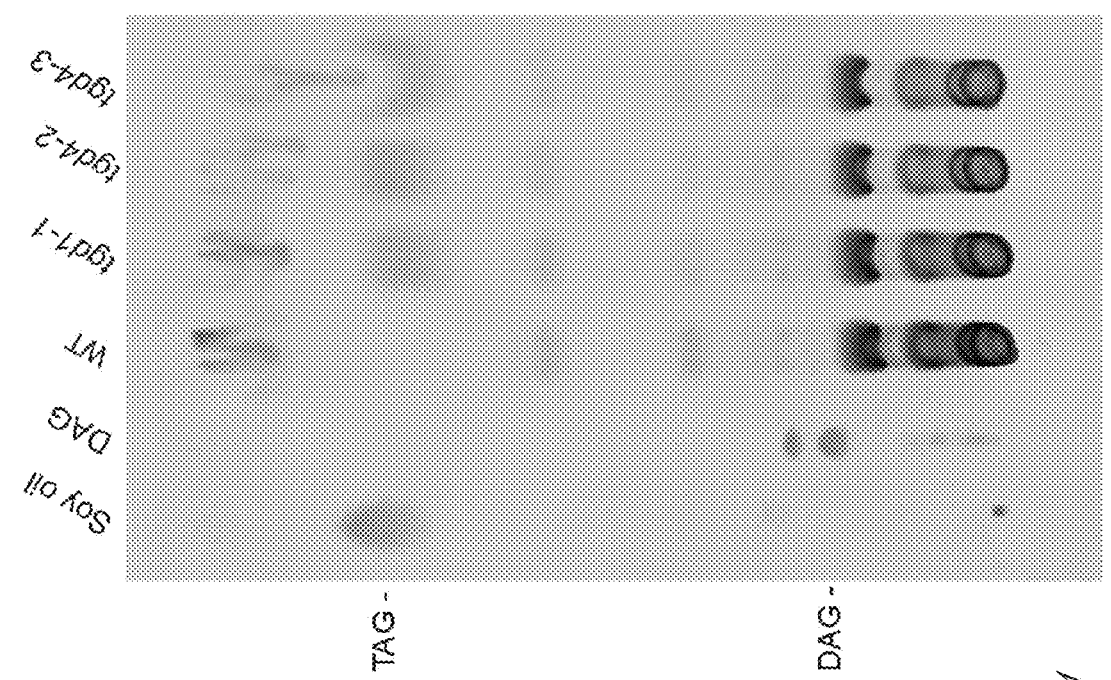

Analysis of neutral lipids in extracts of tgd4-1, tgd4-2 and tgd4-3 mutants revealed the accumulation of triacylglycerol (TGDG), see FIG. 2B. Comparative analysis of neutral lipids in extracts of lipids co-chromatographing with triacylglycerols in tgd4 mutants were shown in Table 2. Comparative analysis of neutral lipids in extracts of lipids co-chromatographing with triacylglycerols in tgd4 mutants were compared to a tgd1-1 mutant (FIG. 3). Triacylglycerol content of the mutant leaves was <1 mol % of total fatty acids (e.g., 0.5 6 0.2 mol % for tgd4-3; n=3, SD is given). Molecular species of galactoglycerolipids derived from the plastid pathway preferentially carry a 16-carbon fatty acyl group in the sn-2 position of the diacylglyceryl moiety, and ER-derived species preferentially carry an 18-carbon fatty acyl chain (Heinz and Roughan, 1983, herein incorporated by reference). Analysis of acyl chains following position specific lipase treatment of the two galactoglycerolipids from the wild type and different tgd4 mutants is shown in Table 3A.

TABLE 3A

Fatty Acid (FA) Composition at the sn-2 Position of the Two Major Galactoglycerolipids in the Wild Type, tgd4-1, tgd4-2, and tgd4-3

| | Fatty Acid Composition (Mol %)$^a$ | | | | | | | |
|---|---|---|---|---|---|---|---|---|
| FAs | 16:0 | 16:1 | 16:2 | 16:3 | 18:0 | 18:1 | 18:2 | 18:3 |
| | MGDG | | | | | | | |
| WT | 1.8 | 1.1 | ND$^b$ | 57.3 | 1.0 | ND | 2.7 | 35.9 |
| tgd4-1 | 5.3 | 2.8 | ND | 51.3 | 1.2 | ND | 5.8 | 33.4 |
| tgd4-2 | 18.3 | 7.3 | 1.5 | 59.7 | 2.4 | ND | 1.3 | 9.2 |
| tgd4-3 | 16.8 | 6.9 | 0.2 | 64.2 | 1.7 | ND | 1.1 | 8.8 |

TABLE 3A-continued

Fatty Acid (FA) Composition at the sn-2 Position of the Two Major Galactoglycerolipids in the Wild Type, tgd4-1, tgd4-2, and tgd4-3

| FAs | Fatty Acid Composition (Mol %)[a] | | | | | | | |
|---|---|---|---|---|---|---|---|---|
| | 16:0 | 16:1 | 16:2 | 16:3 | 18:0 | 18:1 | 18:2 | 18:3 |
| DGDG | | | | | | | | |
| WT | 19.0 | 1.2 | 0.4 | 3.8 | 4.2 | 2.0 | 3.0 | 64.4 |
| tgd4-1 | 29.2 | 1.8 | 0.4 | 1.2 | 7.4 | 4.5 | 5.4 | 49.3 |
| tgd4-2 | 65.4 | 1.7 | 0.5 | 0.6 | 8.6 | 4.4 | 2.9 | 14.7 |
| tgd4-3 | 74.0 | 1.1 | 0.6 | 3.6 | 3.7 | 2.7 | 1.9 | 11.9 |

[a]Three independent measurements were averaged for all samples, except for the tgd4-2 DGDG samples, for which only two samples were available. In all cases, the SD was <10%. Plants were 4 weeks old and grown on soil. Fatty acids (FAs) are designated with number of carbon atoms:number of double bonds.
[b]ND, not detected at a limit of 0.05 mol %.

Figures 6A, 6B:
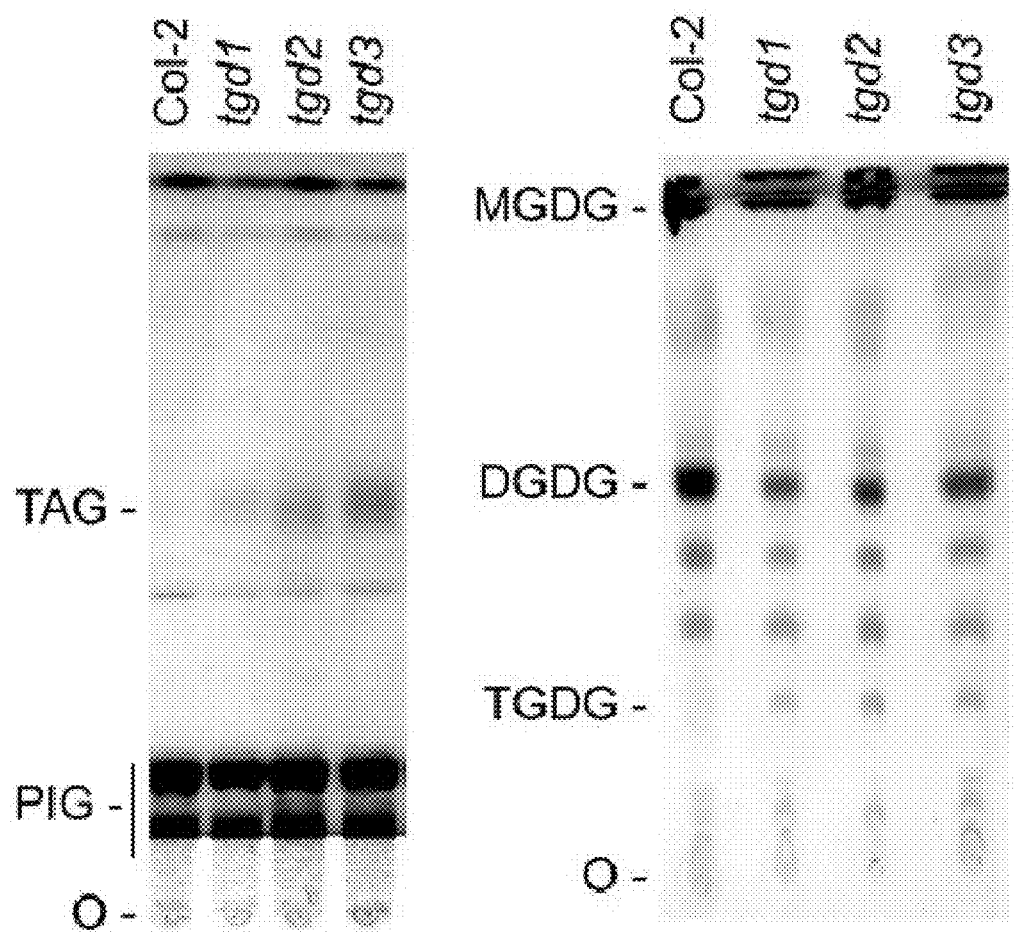
FIG. 6A-6B shows an exemplary lipid phenotype of the tgd3 mutant compared with the tgd1, tgd2 mutant and the Col-2 wild type. Total lipids were extracted from 4-week-old seedlings grown on MS agar plates containing 1% sucrose and separated by thin-layer chromatography.

Additional fatty acid analysis data for lipids in the wild type and the tgd4-2 and tgd4-3 mutants are provided in Table 3B, where the lipid abbreviations are: MGDG, monogalactosyldiacylglycerol; PtdGro, phosphatidylglycerol; DGDG, digalactosyldiacylglycerol; SQDG, sulfoquinovosyldiacylglycerol; PtdIns, phosphatidylinositol; PtdEtn, phosphatidylethanolamine; PtdCho, phosphatidylcholine. MGDG (sn-2) and DGDG (sn-2) refer to the fatty acids in the sn-2 position only of the respective lipid.

tgd4 genes, various amounts of oils accumulated in leaves and stems of these plants. Three tgd mutant alleles (tgd1-1, tgd2-1, tgd3-1) analyzed and discussed here were leaky, i.e. varying levels of expression in different plants, leading to attenuated phenotypes with up to 40% lethality, i.e. tgd1-1, tgd2-1. More severe impairment of the system as previously shown for TGD1 causes embryo-lethality making fully gene-disrupted mutants currently inaccessible to analysis. Therefore, leaf lipid extracts from the tgd1, tgd2 and the tgd3 lines were compared by thin-layer chromatography of neutral (FIG. 6A) and polar lipids (FIG. 6B). The tgd3 mutant extracts contained a lipid co-chromatographing with triacylglycerol (FIG. 6A), previously identified in the tgd1 mutant and shown also to accumulate in tgd2 mutant extracts. In addition, polar lipid extracts of the tgd3 mutant contained a new lipid staining with α-naphthol, which is diagnostic for the presence of hexoses (FIG. 6B). This lipid co-chromatographed with authentic trigalactosyldiacylglycerol accumulating in tgd1 and tgd2.

Figure 8A:
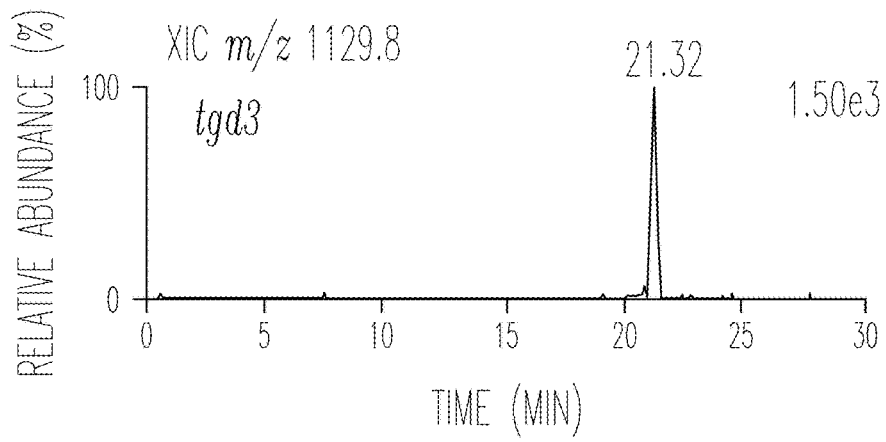
FIG. 8A-8F show exemplary LC/MS analyses of lipid extracts of tgd3 mutant and Col-2 wild type Arabidopsis leaves. Negative mode electrospray extracted ion chromatograms (XICs) for m/z 1129.6, the [M+acetate]-ion for TGDG 34:6, for extracts of tgd3 mutant leaves (FIG. 8A) and Col-2 wild type leaves (FIG. 8B).
Figure 8B:
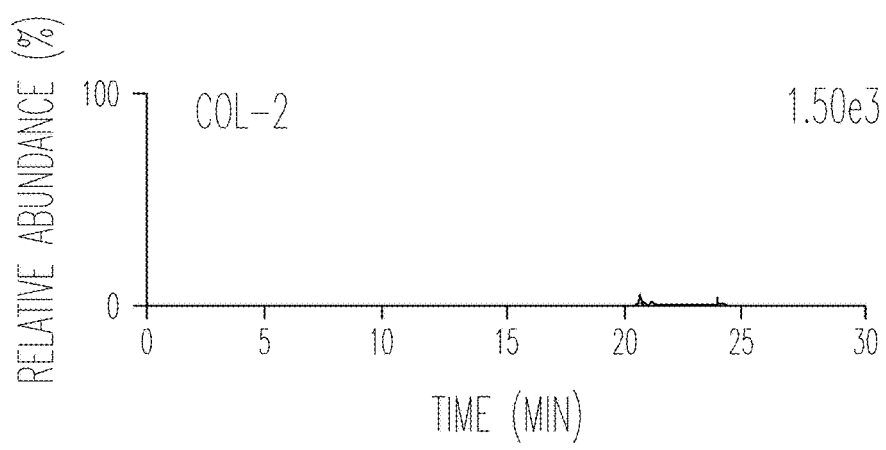
Figure 8C:
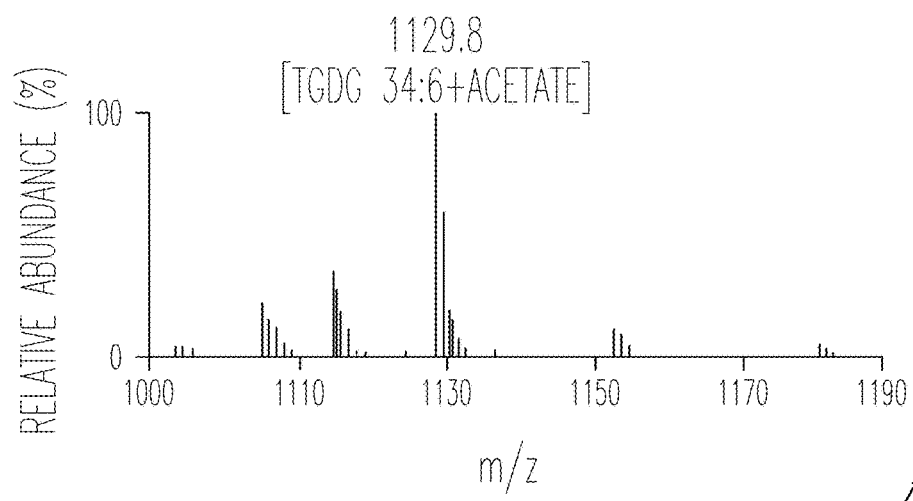

Further confirmation of the identities of TGDG and TAG lipids was provided by LC/MS analyses of leaf extracts of Col-2 wild type and tgd3 mutants (FIG. 8A-C). Extracted ion chromatograms (XICs) generated in negative ion mode yielded a strong peak at m/z 1129.6 for the tgd3 mutant corresponding to [M+acetate]—for TGDG 34:6 which was

TABLE 3B

Complete fatty acid composition data sets for wild type (WT), tgd4-2 and tgd4-3 mutants
Fatty Acid (mol %)

| | | 16:0 | 16:1 | 16:2 | 16:3 | 18:0 | 18:1 | 18:2 | 18:3 |
|---|---|---|---|---|---|---|---|---|---|
| WT | MGDG | 3.9 ± 1.4 | 0.4 ± 0.0 | 0.1 ± 0.1 | 23.8 ± 2.1 | 4.0 ± 4.2 | 0.0 ± 0.0 | 4.6 ± 1.0 | 63.3 ± 2.7 |
| | MGDG (sn-2) | 1.8 ± 0.1 | 1.1 ± 0.1 | 0.0 ± 0.0 | 57.3 ± 0.0 | 1.0 ± 0.2 | 0.0 ± 0.0 | 2.7 ± 0.3 | 35.9 ± 0.2 |
| | PtdGro | 25.1 ± 1.5 | 13.6 ± 2.3 | 0.4 ± 0.1 | 2.6 ± 0.1 | 9.4 ± 6.2 | 4.7 ± 0.8 | 9.5 ± 1.8 | 34.7 ± 0.1 |
| | DGDG | 12.6 ± 0.3 | 2.1 ± 0.3 | 0.1 ± 0.0 | 1.9 ± 0.0 | 2.3 ± 0.8 | 1.7 ± 0.0 | 4.6 ± 0.2 | 74.7 ± 1.1 |
| | DGDG (sn-2) | 19.0 ± 1.2 | 1.2 ± 0.0 | 0.3 ± 0.0 | 3.8 ± 3.0 | 4.2 ± 0.4 | 2.0 ± 0.0 | 3.0 ± 0.2 | 64.4 ± 3.6 |
| | SQDG | 31.0 ± 1.5 | 1.2 ± 0.2 | 0.3 ± 0.0 | 0.7 ± 1.0 | 13.0 ± 6.5 | 2.4 ± 0.1 | 4.8 ± 0.5 | 46.5 ± 3.1 |
| | PtdIns | 27.2 ± 0.2 | 1.5 ± 0.3 | 0.7 ± 0.6 | 0.0 ± 0.0 | 29.2 ± 4.9 | 2.3 ± 0.6 | 8.6 ± 1.2 | 30.4 ± 4.2 |
| | PtdEtn | 27.5 ± 0.3 | 0.4 ± 0.0 | 0.2 ± 0.0 | 0.0 ± 0.0 | 5.2 ± 1.1 | 3.6 ± 0.0 | 37.2 ± 0.9 | 25.8 ± 0.0 |
| | PtdCho | 18.5 ± 0.1 | 0.5 ± 0.0 | 0.2 ± 0.0 | 0.0 ± 0.0 | 4.3 ± 0.2 | 6.9 ± 0.0 | 36.1 ± 0.1 | 33.6 ± 0.1 |
| tgd4-2 | MGDG | 7.2 ± 0.1 | 2.6 ± 0.0 | 0.1 ± 0.0 | 24.6 ± 0.0 | 1.6 ± 0.1 | 9.0 ± 0.6 | 6.7 ± 0.4 | 48.2 ± 0.3 |
| | MGDG (sn-2) | 18.3 ± 1.2 | 7.3 ± 0.4 | 1.4 ± 0.1 | 59.7 ± 2.4 | 2.4 ± 0.2 | 0.0 ± 0.0 | 1.3 ± 0.1 | 9.2 ± 0.9 |
| | PtdGro | 23.7 ± 0.3 | 19.3 ± 0.1 | 0.0 ± 0.0 | 2.2 ± 0.3 | 4.3 ± 2.7 | 11.7 ± 0.1 | 9.2 ± 0.5 | 29.6 ± 0.6 |
| | DGDG | 37.2 ± 1.3 | 1.5 ± 0.5 | 0.3 ± 0.1 | 4.7 ± 0.1 | 4.7 ± 0.8 | 7.7 ± 0.1 | 10.8 ± 0.0 | 33.1 ± 0.2 |
| | DGDG (sn-2) | 65.4 ± 5.1 | 1.7 ± 0.1 | 0.5 ± 0.0 | 0.6 ± 0.1 | 8.6 ± 0.7 | 4.4 ± 0.4 | 2.9 ± 0.1 | 14.7 ± 1.3 |
| | SQDG | 50.4 ± 0.6 | 1.3 ± 0.0 | 0.2 ± 0.0 | 1.0 ± 1.4 | 10.3 ± 1.0 | 4.9 ± 0.3 | 4.2 ± 0.1 | 27.8 ± 1.1 |
| | PtdIns | 27.8 ± 2.1 | 1.0 ± 1.4 | 0.4 ± 0.4 | 0.0 ± 0.0 | 27.7 ± 0.2 | 6.8 ± 0.2 | 20.0 ± 3.3 | 16.5 ± 0.5 |
| | PtdEtn | 26.2 ± 0.4 | 0.7 ± 0.0 | 0.2 ± 0.0 | 2.3 ± 0.0 | 4.7 ± 0.2 | 14.1 ± 0.0 | 38.8 ± 0.5 | 13.1 ± 0.1 |
| | PtdCho | 14.1 ± 0.1 | 0.8 ± 0.1 | 0.1 ± 0.0 | 2.1 ± 0.0 | 4.2 ± 0.0 | 27.9 ± 0.3 | 32.6 ± 0.0 | 18.3 ± 0.2 |
| tgd4-3 | MGDG | 8.0 ± 0.3 | 3.4 ± 0.1 | 0.1 ± 0.0 | 22.6 ± 0.0 | 1.2 ± 0.0 | 11.6 ± 0.2 | 6.2 ± 0.1 | 46.9 ± 0.1 |
| | MGDG (sn-2) | 16.8 ± 0.2 | 6.9 ± 0.5 | 0.2 ± 0.0 | 64.2 ± 1.2 | 1.7 ± 0.1 | 0.0 ± 0.0 | 1.1 ± 0.1 | 8.8 ± 0.7 |
| | PtdGro | 23.9 ± 0.5 | 19.6 ± 0.6 | 0.0 ± 0.0 | 2.0 ± 0.4 | 3.4 ± 0.1 | 14.1 ± 0.4 | 8.9 ± 0.3 | 28.1 ± 0.8 |
| | DGDG | 37.7 ± 0.7 | 1.5 ± 0.2 | 0.2 ± 0.0 | 4.3 ± 0.0 | 3.2 ± 0.2 | 9.0 ± 0.0 | 9.9 ± 0.1 | 34.2 ± 1.0 |
| | DGDG (sn-2) | 74.0 ± 3.4 | 1.1 ± 0.0 | 0.6 ± 0.0 | 3.6 ± 0.3 | 3.7 ± 0.3 | 2.7 ± 0.2 | 1.9 ± 0.0 | 11.9 ± 0.0 |
| | SQDG | 50.6 ± 0.0 | 1.2 ± 0.0 | 0.3 ± 0.2 | 1.6 ± 0.2 | 5.3 ± 0.4 | 6.1 ± 0.4 | 5.3 ± 0.2 | 29.7 ± 0.3 |
| | PtdIns | 30.0 ± 0.4 | 2.1 ± 0.4 | 0.7 ± 0.0 | 0.0 ± 0.0 | 18.5 ± 0.2 | 10.9 ± 0.6 | 21.4 ± 3.1 | 16.3 ± 2.7 |
| | PtdEtn | 25.6 ± 0.0 | 0.9 ± 0.0 | 0.2 ± 0.0 | 2.3 ± 0.0 | 3.3 ± 0.1 | 19.4 ± 0.0 | 35.3 ± 0.2 | 13.1 ± 0.2 |
| | Ptdcho | 12.7 ± 0.2 | 1.0 ± 0.0 | 0.1 ± 0.0 | 1.9 ± 0.0 | 2.7 ± 0.0 | 36.2 ± 0.0 | 28.6 ± 0.1 | 16.9 ± 0.1 |
| | TGDG | 12.6 ± 1.2 | 5.7 ± 1.4 | 8.9 ± 3.7 | 28.2 ± 3.9 | 6.3 ± 1.4 | 7.6 ± 0.2 | 10.2 ± 0.3 | 20.5 ± 2.8 |
| | TAG | 41.7 ± 9.4 | 5.5 ± 4.0 | 11.7 ± 11.0 | 2.7 ± 1.9 | 17.9 ± 7.0 | 5.9 ± 1.3 | 10.3 ± 7.3 | 4.4 ± 5.5 |

It was apparent that 16-carbon fatty acids were highly enriched in the sn-2 position in the mutants consistent with an overabundance of molecular species derived from the plastid pathway. In other words, similar to the tgd1, tgd2, and tgd3 mutants, the ER pathway of galactoglycerolipid biosynthesis appeared to be disrupted in the tgd4 mutants.

Figure 7A:
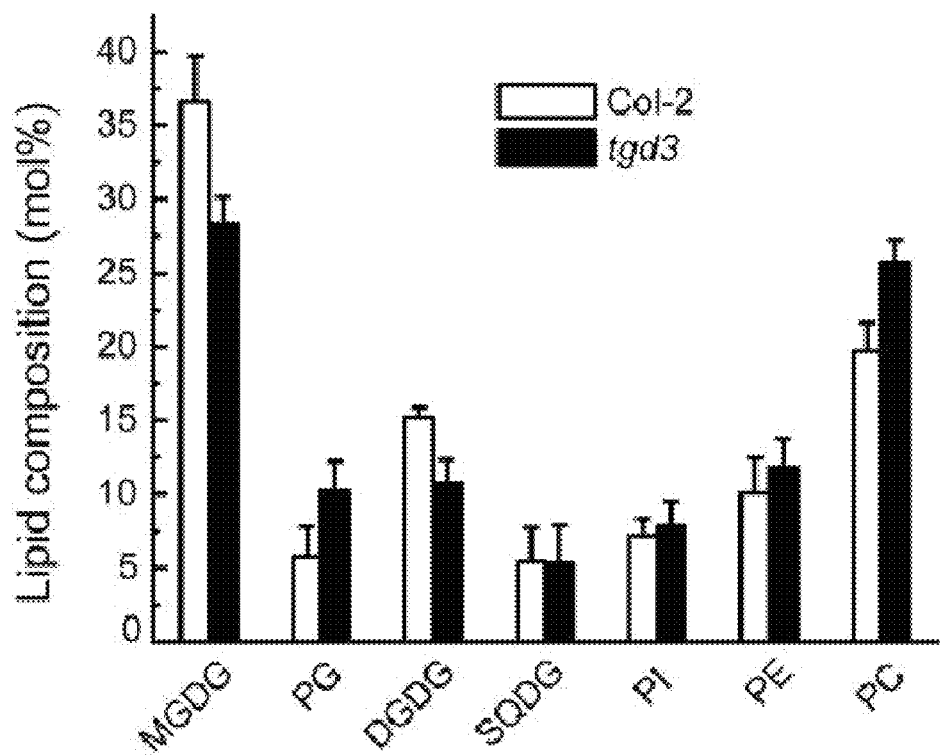
FIG. 7A-7C shows exemplary polar lipid composition and fatty acid content in the tgd3 mutant. Four-week-old Col-2 wild type and tgd3 mutant seedlings grown on the same MS agar plate were analyzed. Five replicates were averaged and the standard errors were shown.
Figure 8D:
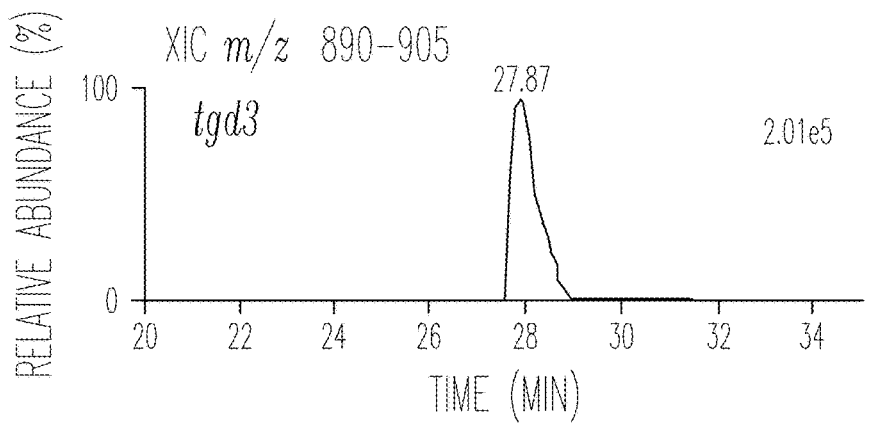
Figure 8E:
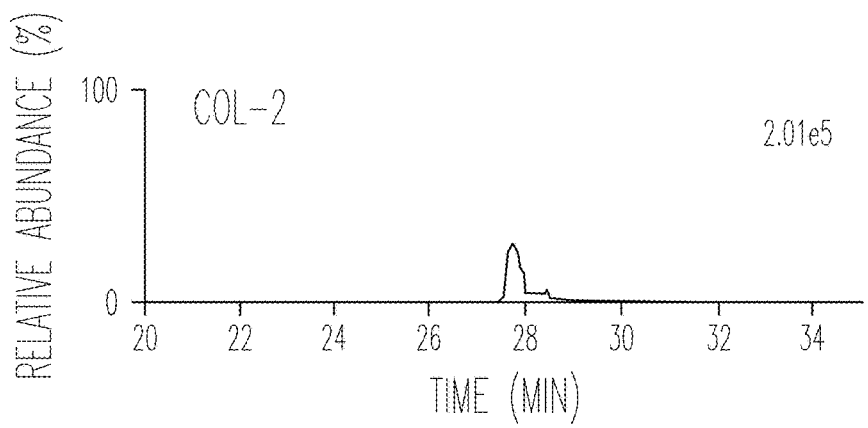
Figure 8F:
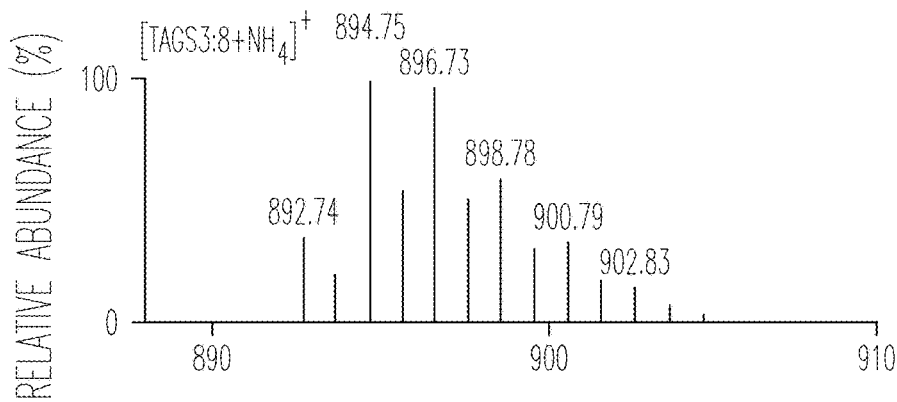

Thus, the inventors discovered that when the expression of one of these tgd genes was lowered through a mutation in one of tgd1-1 dgd1, or reduced tgd1, tgd2-1, and tgd3-1, and the dominant TGDG lipid detected, but minimal amounts in the wild-type extracts. The in-source CID spectra supported this assignment in the form of a fragment ion at m/z 277 corresponding to the C18:3 fatty acid anion. Triacylglycerols were characterized using positive ion electro spray ionization, displaying peaks at m/z 892.7 to 902.8 corresponding to [M+NH₄]+ of triacylglycerols with 54 carbons and a total number of double bonds ranging from 3 to 8 (FIG. 8F). Extracted ion chromatograms for signals in the range of m/z 890-905 showed about 5-fold greater signal in the tgd3 mutant than the wild type (FIG. 8D-8E). Ion abundances for both TGDG and TAG lipids peaks were consistent with quantitative analysis of fatty acid methylesters by gas chromatography coupled to flame ionization detection. The overall lipid composition of the tgd3 mutant differed from that of the wild type as shown in FIG. 7A. Most notably, the relative amounts of the major chloroplast lipids mono and digalactosyldiacylglycerol were decreased, while the presumed precursor of galactolipids derived from the endoplasmic reticulum (ER) pathway, phosphatidylcholine, was more abundant.

Figure 7B:
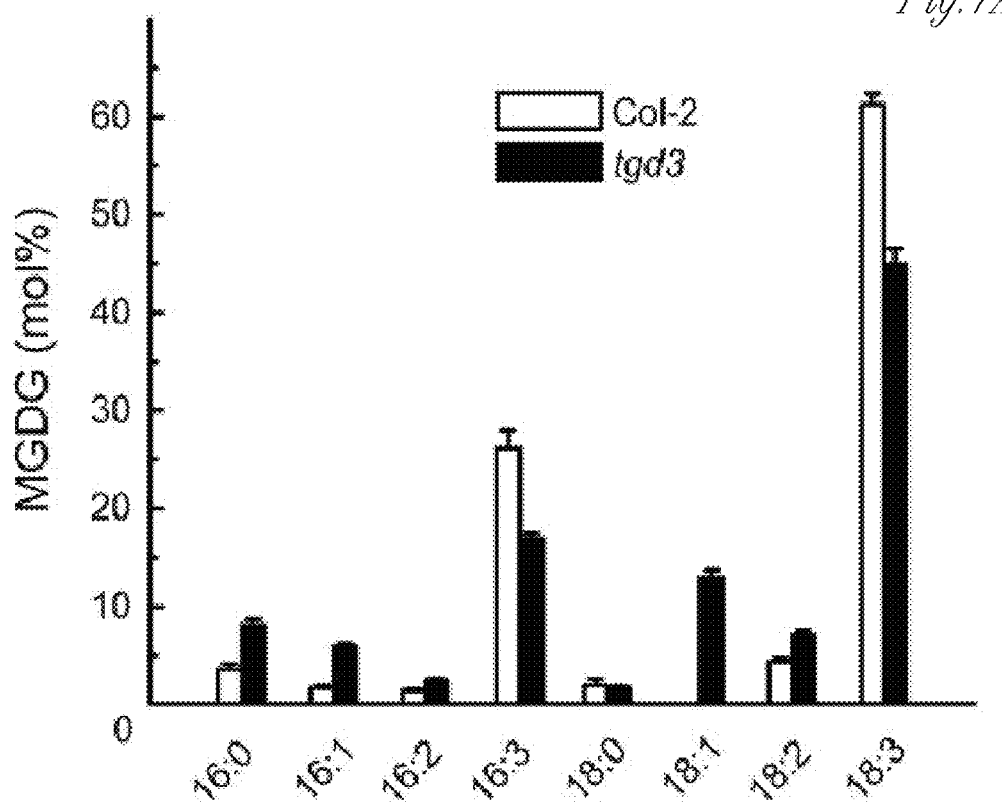

Analysis of the fatty acid composition of mono- and digalactosyldiacylglycerol revealed distinct changes in the fatty acid profiles in tgd3 as compared to the wild type (FIG. 7B, C). Most notably, fatty acids were generally more saturated and 18:3 fatty acid content was reduced. Moreover, the tgd3 fatty acid profile changes were very similar to those observed for the tgd1 and tgd2 mutants. In general, the tgd mutants impaired in the endoplasmic reticulum-pathway have an increased 16-carbon-to-18-carbon fatty acid ratio in their galactolipids. This is particularly visible for digalactosyldiacylglycerol, which is to a large extent derived from the endoplasmic reticulum-pathway.

Figure 7C:
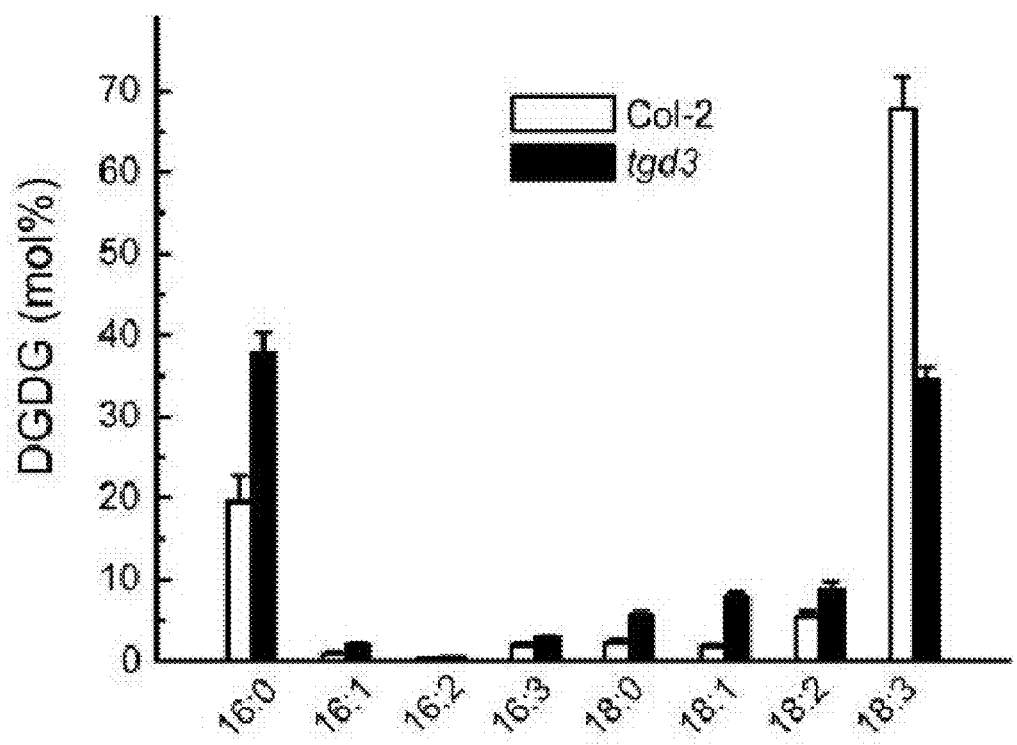
Figure 9A:
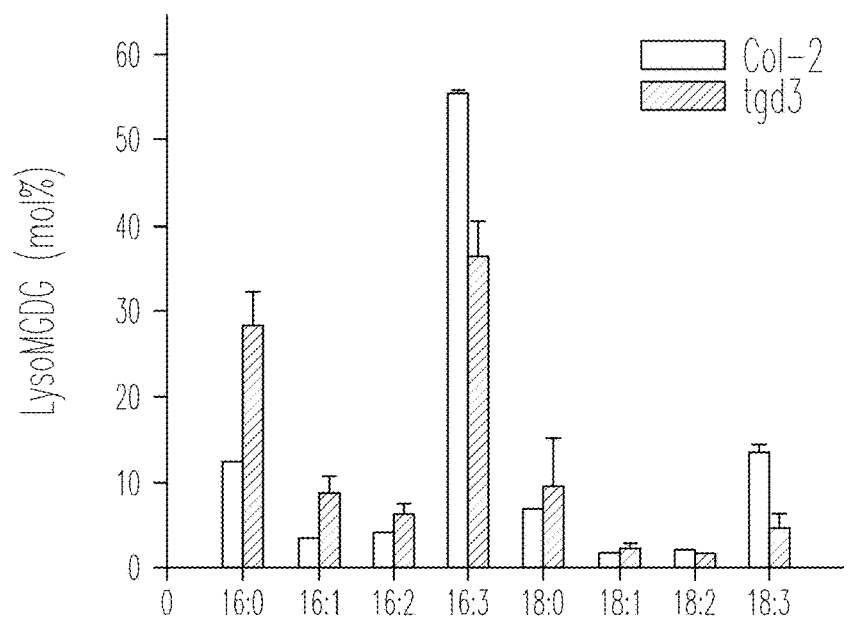
FIG. 9A-9B graphically illustrate the exemplary fatty acid composition of lyso-MGDG (FIG. 9A) and lyso-DGDG (FIG. 9B) in the tgd3 mutant and Col-2 wild type lines. Relative abundance (mol %) of 16 and 18-carbon fatty acids at the glycerol sn-2 position of MGDG and DGDG were determined from the lyso derivatives after digestion of the lipids with Rhizopus sp. lipase. Values represent the means of three measurements and the standard error is shown.
Figure 9B:
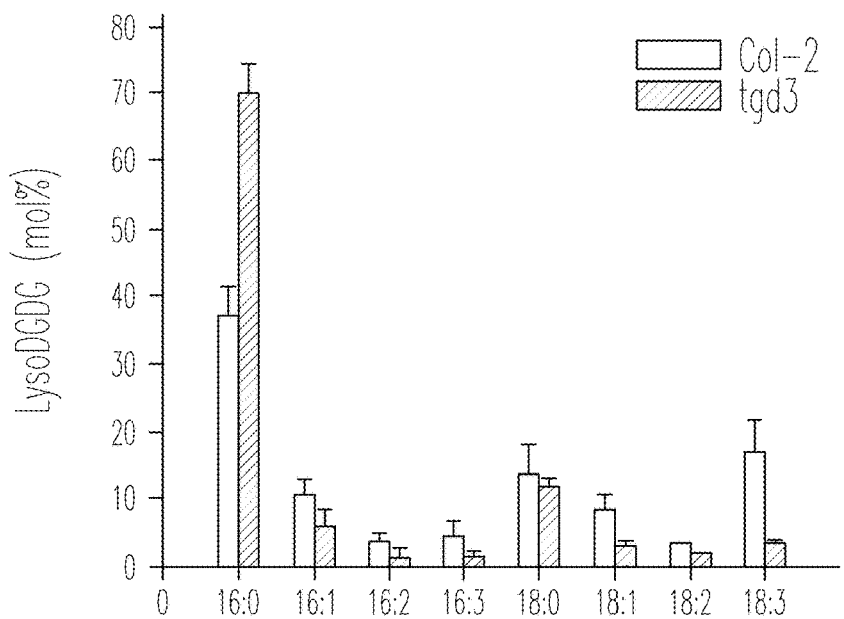

Accordingly, the 16-carbon-to-18-carbon ratio for the digalactolipid increased from 0.29 to 0.76 in the tgd3 mutant (FIG. 7C). This phenomenon was contemplated due to the substrate specificities of the different acyltransferases in the plastid and the ER leading to 18-carbon fatty acids at the sn-1 position and 16-carbon fatty acids at the sn-2 position of the diacylglycerol backbone for plastid derived lipids. Those lipids derived from the ER-pathway carry 18-carbon fatty acids in both positions. Positional analysis using *Rhizopus* lipase (FIG. 9) confirmed an increase in 16-carbon fatty acids in the sn-2 position of monogalactosyldiacylglycerol and digalactosyldiacylglycerol of the tgd3 mutant.

Overall, tgd3 has a complex lipid phenotype very similar to tgd1 and tgd2 that was consistent with an impairment of the endoplasmic reticulum-pathway of galactolipid biosynthesis. This similarity in phenotypes also indicated that the TGD1, TGD2, and TGD3 proteins are involved in the same biochemical process.

In summary, when expression of a trigalactosyldiacylglycerol (tgd) gene was disrupted by a T-DNA insertion or when a plant was induced to produce a malfunctioning protein that disrupted the TGD1-3 complex or TGD4 function, the presence of undesirable traits of the plants reduced the economic value of any plant lines developed from the mutant lines or use of mutant TGD genes.

Therefore, the inventors contemplated several methods as described herein in order to increase the value of plant lines having reduced TGD production with increased oil accumulation in nonseed parts. Thus in some embodiments, the inventors contemplated disruption of the expression of tgd gene translation after any one of the following developmental phases, i.e. after the plant germinated, early during seedling growth, later during seedling growth, after senescence, etc., by using an inducible RNAi construct or a construct whose expression was under control of a developmentally regulated promoter, such as a leaf promoter, a senescence promoter, i.e. a promoter turned on by the plant during or after seed formation, etc. In other embodiments, the inventors contemplated the use of a construct whose expression was limited to specific tissues, such as green tissues through the use of a ribusco promoter. In preferred embodiments, the technology described herein is contemplated for use by reduction (i.e. silencing) tgd gene translation for increasing the capacity of engineered plants to store oil while retaining desirable (or regaining by stacking heterologous gene expression) agronomic traits causing plant oils to accumulate in the leaf and stem structures of the plant.

D. *Brassica* Trigalactosyldiacylglycerol Genes and Encoded Proteins for Use in the Methods of the Present Inventions.

In one embodiment, the present invention contemplates making and using recombinant silencing constructs comprising gene fragments of Brassicaceae genes encoding trigalactosyldiacylglycerol (tgd) mRNA for translation into TGD proteins, i.e. TGD1, TGD2, TGD3, and TGD4. Brassicaceae genes from *Arabidopsis thaliana* plants are described herein. It is not meant to limit the inventions to the use of *Arabidopsis thaliana* tgd genes, such that tgd genes are contemplated for use from other Brassicaceae plants, such as rapeseed (canola). Even further, tgd gene sequences from other plants are contemplated for use, such as soybean, safflower, grape, rice, etc. Information on the biochemical characterization of mutant tgd genes and plants expressing these genes that can be used in the present inventions including information on tgd1-1 (including double tgd1-1 and dgd1) and tgd-2 (tgd2-1) mutant genes, and their role in oil biosynthesis, i.e. tgd1-1 dgd1 can be found in Xu et al., (2003) EMBO J. 22:2370-2379, Xu et al., The Plant Cell, Vol. 17, 3094-3110, (2005), tgd-2 Awai PNAS Jul. 11, 2006, 103(28):10817-10822, U.S. patent application Ser. No. 12/506,633, all of which are herein incorporated by reference in their entirety. Mutant genes for tgd3 (tgd3-1) and tgd4 (tgd4-1) and mutant plants were identified with their respective encoded proteins and plant phenotypes, Lu et al., 2007, The Journal of Biological Chemistry, 282:35945-35953, and Xu et al. The Plant Cell, 20:2190-2204, 2008, respectively, both of which are herein incorporated by reference in their entirety.

In one embodiment, expression of tgd silencing constructs in a plant cell, tissue or whole plant can be used for accumulation biosynthetic oil in plant cells, plant tissues, plant leaves, and plant stems. Thus in a preferred embodiment, the inventors contemplate accumulating consistently high levels of vegetative oils in plants of a plant line comprising a silenced tgd gene and agronomic traits for commercial production (e.g., SEQ ID NOs: 1, 3, 4, 6, 8, 9, 11) for reducing expression of their encoded proteins (e.g., SEQ ID NOs: 2, 5, 7, 10). In other preferred embodiments, tgd1 and tgd4 and their encoded proteins provide novel targets for engineering approaches with the goal of optimizing vegetative oil producing plant lines while reducing the loss of agronomic desirable traits. In one embodiment, the accumulated oil comprises triacylglycerols.

TABLE 5

Exemplary Trigalactosyldiacylglycerol sequences as RNAi targets for lowering amounts of translated protein in plant cells. Examples of gene polymorphism are provided as exemplary additional targets.

| Trigalactosyldiacylglycerol Genes; proteins in *Arabidopsis* plants | mRNA or cDNA | Protein SEQ ID NO: | Polymorphisms: Example of gene polymorphism |
|---|---|---|---|
| TGD4 PDE320 (PIGMENT DEFECTIVE 320) | Sequence: AT3G06960.1; TAIR Accession Locus: 20775621 | Protein: AT3G06960.1; TAIR Accession: AA Sequence: 10091186935 | 94% identity AT3G06960.2 (splice variant) 9 |
| TGD3 ATNAP11 (*ARABIDOPSIS THALIANA* NON-INTRINSIC ABC PROTEIN 11) | Sequence: AT1G65410.1; TAIR Accession Locus: 2206275 | Protein: AT1G65410.1; TAIR Accession AA Sequence: 10091049196 | NA |
| TGD2 | Sequence: AT3G20320.1; TAIR Accession Locus: 2092354 | Protein: AT3G20320.1; TAIR Accession: AA Sequence: 10091205107 | 83% identity overall; 88% to 3' area AT3G20320.2 (splice variant) |
| TGD1 | Sequence: AT1G19800.2; TAIR Accession Locus: 2013099 | Protein: AT1G19800.2; TAIR Accession: AA Sequence: 10091205108 | 99% identity AT1G19800.3 (splice variant) 98% identity AT1G19800.1 |

For example, an *Arabidopsis thaliana* pigment defective 320 Trigalactosyldiacylglycerol 4(tgd4) cDNA sequence is available with accession number AT3G06960.1 from the *Arabidopsis* information website at arabidopsis.org/servlets/TairObject?type=sequence&id=2002982503. This tgd4 cDNA has the following sequence (SEQ ID NO:1).

```
   1 AGCTGGGTGT AGAAATCGAG CGACGGCGGC GGAGACGACG
  41 GAGATGAACA GAATGAGATG GGTCGGAGAG GGAGACATCT
  81 GGGACCTCGA TATGTCAACT CCGGTGACGC TCGAGGGCAC
 121 CGCACGAGCT GTTCCTGACG ATCCTCTTCC TCTAGGTCTC
 161 TCTAGAGGCA CTCGTCTATC TCGCCCTAAG CAAGTTGAGT
 201 TCTTCCACCG CTTCATGGCC TCACCTCTCA TCCCTTCCTT
 241 CTCCCCTATC CGTCCCAACA CCGGAGATGG AGGCGGTGGT
 281 GGATTCTCTC TTCAAAGAGT CCTCACTCTT CCTTTCTCCA
 321 ACAACTGGCT TGTGTCTCTT CTGGGCCAAT TCGATGTTCA
 361 GAGATTCGTA ACGGAGATAG ATAAGACTAA AGCTTTTGGT
 401 CGAGGGTCTT CGTCTACAGT AGCTTCTCGT TTAAACACAA
 441 TTGGCAAGCA TTTGAAGGAT AAATCTTTGT ACGCATTGGG
 481 TTTTTGTTCT GAGTTTTTGT TATCACCAGA TGATACTTTG
 521 CTTCTTAGCT ATGATGCTTA CAAAGGTGAT CTCGATAAGA
 561 ATCCTAGAGC TAAGGCTATC TTCAATCACG AGTTTCCGCT
 601 TCACAATCTG ACAGCAGAAG CGGTTTGGCC TGGACTTTTT
 641 GTGGATAAAC ATGGTGAATA TTGGGATGTG CCACTCTCAA
 681 TGGCTATTGA TCTAGCATCT CTTCCTGCTG AATCTGGTCC
```

-continued

```
 721 AAGTTACCAT TTATGTTTAC ACCATAACAG CGGATCACCC
 761 AAGAAGTTAC ATTCTGATAC TATGGAAGTG CCTCCACCGT
 801 CACTGCTTCC TGGTTTGTCT CTGAAATCTG CAGTCTCTTA
 841 TAGGACAAAC ATGGATCTCT GGAGGGGTAC CACTCCAAAG
 881 CTCGAAACTT GCAAGCCCTA TGATGTCTTC CTCAGTAGTC
 921 CTCATGTCGC AGTATCTGGG ATTATCGGCT CTGTGATGAC
 961 CGCAGCATTT GGTGAAAATT CAATCAGATC AAAATTTGAA
1001 AATGATTCTG AGGGTGTTGG AGGGTTCTCT CTTCATTTTC
1041 CATCTGTAAA TTCCGGATTC ATGGCTGATG CCTTAGGGCG
1081 GGCATCACTC ACAGCTCAAT ATGGAAACTT CCAGAAATTC
1121 TTCTTTGATC TCACCCGTTT CCATGCTAGA TTAGACTTTC
1161 CGCATGGTTT GAGGTTTCTT ACCGGTGCCA CTAGCGTCGC
1201 ACAAGATCTT TTAAATTCTC GGCAGCCTAG TTTAGAAGCA
1241 TTTCAGAAAA TCTGCCCTGA AGTATTAGTT TCTCTACAGC
1281 AACAGATTGT TGGACCGTTT AGTTTCAAAG TGGAGTCTGG
1321 AATTGAGATC GATCTGAGGA ACGGAGCTAA CCCTGTGACT
1361 GTAGATAAGA CAGTATTTGC TATTGAATAT GCTCTTCAAG
1401 TGCTTCTTTC TGCCAAGGCT GTTGTTTCGT ACTCCCCAAA
1441 ACAGCAGAAG TTCATGGTTG AGCTTCGTTT CTTTGAGACA
1481 TAGTATCAGG ATTTTCCACT CAAAATGTCA AGCTTGATCC
1521 TGTGAAGATT GTAGTCTTGC AGAGAAGTAA ATACTAAATA
```

```
1561 GACAATGTTC TAATTGTTCA GTTTCTTATG TCAAACAGAA

1601 GAATGTTTCA ATAGAAGGGA AGTTTACATT TTGTTATAGT

1641 GTGATGTCTA CCAG
```

The TGD4 protein sequence encoded by the SEQ ID NO:1 cDNA has the following sequence (SEQ ID NO:2).

```
  1 MNRMRWVGEG DIWDLDMSTP VTLEGTARAV PDDPLPLGLS

41 RGTRLSRPKQ VEFFHRFMAS PLIPSFSPIR PNTGDGGGGG

81 FSLQRVLTLP FSNNWLVSLL GQFDVQRFVT EIDKTKAFGR

121 GSSSTVASRL NTIGKHLKDK SLYALGFCSE FLLSPDDTLL

161 LSYDAYKGDL DKNPRAKAIF NHEFPLHNLT AEAVWPGLFV

201 DKHGEYWDVP LSMAIDLASL PAESGPSYHL CLHHNSGSPK

241 KLHSDTMEVP PPSLLPGLSL KSAVSYRTNM DLWRGTTPKL

281 ETCKPYDVFL SSPHVAVSGI IGSVMTAAFG ENSIRSKFEN

321 DSEGVGGFSL HFPSVNSGFM ADALGRASLT AQYGNFQKFF

361 FDLTRFHARL DFPHGLRFLT GATSVAQDLL NSRQPSLEAF

401 QKICPEVLVS LQQQIVGPFS FKVESGIEID LRNGANPVTV

441 DKTVFAIEYA LQVLLSAKAV VSYSPKQNEF MVELRFFET
```

A variant of the *Arabidopsis thaliana* pigment defective 320 Trigalactosyldiacylglycerol 4(tgd4) cDNA sequence with 94% identity to the SEQ ID NO:1 sequence is available from the *Arabidopsis* database as accession number AT3G06960.2, which has the following sequence (SEQ ID NO:3).

```
  1 ATGAACAGAA TGAGATGGGT CGGAGAGGGA GACATCTGGG

41 ACCTCGATAT GTCAACTCCG GTGACGCTCG AGGGCACCGC

81 ACGAGCTGTT CCTGACGATC CTCTTCCTCT AGGTCTCTCT

121 AGAGGCACTC GTCTATCTCG CCCTAAGCAA GTTGAGTTCT

161 TCCACCGCTT CATGGCCTCA CCTCTCATCC CTTCCTTCTC

201 CCCTATCCGT CCCAACACCG GAGATGGAGG CGGAGAGGGA

241 TTCTCTCTTC AAAGAGTCCT CACTCTTCCT TTCTCCAACA

281 ACTGGCTTGT GTCTCTTCTG GGCCAATTCG ATGTTCAGAG

321 ATTCGTAACG GAGATAGATA AGACTAAAGC TTTTGGTCGA

361 GGGTCTTCGT CTACAGTAGC TTCTCGTTTA AACACAATTG

401 GCAAGCATTT GAAGGATAAA TCTTTGTACG CATTGGGTTT

441 TTGTTCTGAG TTTTTGTTAT CACCAGATGA TACTTTGCTT

481 CTTAGCTATG ATGCTTACAA AGGTGATCTC GATAAGAATC

521 CTAGAGCTAA GGCTATCTTC AATCACGAGT TTCCGCTTCA

561 CAATCTGACA GCAGAAGCGG TTTGGCCTGG ACTTTTTGTG

601 GATAAACATG GTGAATATTG GGATGTGCCA CTCTCAATGG

641 CTATTGATCT AGCATCTCTT CCTGCTGAAT CTGGTCCAAG

681 TTACCATTTA TGTTTACACC ATAACAGCGG ATCACCCAAG

721 AAGTTACATT CTGATACTAT GGAAGTGCCT CCACCGTCAC
```

```
761 TGCTTCCTGG TTTGTCTCTG AAATCTGCAG TCTCTTATAG

801 GACAAACATG GATCTCTGGA GGGGTACCAC TCCAAAGCTC

841 GAAACTTGCA AGCCCTATGA TGTCTTCCTC AGTAGTCCTC

881 ATGTCGCAGT ATCTGGGATT ATCGGTATGA TAAGTTTCTT

921 CAACTTATTT CAGAAGCATT TTATTGTCAA GACTGAAAGT

961 TTTGTGATTT CTCTAATAAG TTTTGTTCAA CTCTTATCAT

1001 TTGAGTTCTC CAATTCCAAT ATTTGA
```

An *Arabidopsis thaliana* Trigalactosyldiacylglycerol 3 (tgd3) cDNA sequence is available with accession number AT1G65410.1, and is shown below and identified herein as SEQ ID NO:4.

```
  1 CTTTGTTTCT GGGTTTCTCC TAAATCATCC AAATTGGTAT

41 CGAATTTGCC CTTCTCCGAT TCAATTTCTT CACGATCTCA

81 AAACCCAGAA GAAAGAATCA TGCTTTCGTT ATCATGCTCT

121 TCTTCTTCTT CTTCGTTGCT TCCTCCGAGT TTACACTACC

161 ACGGTTCTTC TTCTGTTCAG TCCATCGTTG TACCAAGAAG

201 GAGTCTTATC TCGTTTCGTC GGAAAGTCTC TTGCTGTTGC

241 ATAGCTCCAC CTCAGAACTT GGACAACGAT GCCACCAAAT

281 TCGATAGTCT TACCAAGTCT GGAGGAGGTA TGTTTAAAGA

321 GCGAGGGCTT AAGAATAATT CTGATGTTCT TATTGAATGT

361 AGAGATGTCT ATAAATCGTT TGGGGAGAAA CATATCTTGA

401 AAGGTGTTAG CTTTAAGATT AGACATGGTG AAGCTGTTGG

441 GGTGATTGGT CCTTCTGGAA CTGGAAAATC AACAATTTTA

481 AAGATTATGG CTGGTCTTCT TGCTCCAGAC AAGGGAGAAG

521 TTTATATACG AGGAAAAAAA CGAGCTGGTT TGATAAGTGA

561 TGAGGAAATA TCAGGACTTC GTATTGGCCT GGTATTTCAG

601 AGTGCAGCTC TCTTTGATTC ACTATCAGTT CGTGAAAATG

641 TTGGTTTTCT ACTTTATGAA AGGAAAAAAA TGTCCGAGAA

681 TCAAATATCT TAGCTTCTAA CACAAACCTT GGCAGCTGTT

721 GGTTTGAAGG GGGTTGAGAA TCGATTACCT TCTGAGCTAT

761 CTGGTGGAAT GAAGAAAAGG GTTGCTTTAG CTCGTTCACT

801 AATTTTTGAT ACAACAAAAG AGGTCATAGA GCCAGAGGTG

841 CTTTTGTACG ATGAGCCAAC TGCTGAACTT GATCCAATTG

881 CATCAACTGT AGTTGAAGAT CTTATACGGT CTGTTAACAT

921 AACAGACGAA GATGCAGTTG GAAAACCTGG AAAAATTGCG

961 TCTTATCTTG TTGTTACCCA TCAACATAGC ACCATTCAAA

1001 GAGCTGTAGA CAGGTTATTG TTTCTGTATG AAGGAAAGAT

1041 CGTTTGGCAA GGAATGATAC ATGTATTCAC AACCTCAACT

1081 AATCCAATAG TTCAACAGTT TGCTACAGGC AGCCTCGATG

1121 GACCAATCAG ATACTAGGGG AGGCAAACCG AGCCTAAAGA

1161 GGGACACTAA CCGATAATAG GGAACGCAAA CAAGTAATGG
```

```
1201 CTGACATACA CCACATGGCT GGATCAATTG GTTCAATACG

1241 ATGCTACTTG TAAACACTAT TTTTTCTTAG ATGCATAGAT

1281 CAGAAAAGCA TTGTCAGTTG
```

The TGD3 protein sequence encoded by the SEQ ID NO:4 cDNA has the following sequence (SEQ ID NO:5).

```
  1 MLSLSCSSSS SSLLPPSLHY HGSSSVQSIV VPRRSLISFR

41 RKVSCCCIAP PQNLDNDATK FDSLTKSGGG MCKERGLEND

81 SDVLIECRDV YKSFGEKHIL KGVSFKIRHG EAVGVIGPSG

121 TGKSTILKIM AGLLAPDKGE VYIRGKKRAG LISDEEISGL

161 RIGLVFQSAA LFDSLSVREN VGFLLYERSK MSENQISELV

201 TQTLAAVGLK GVENRLPSEL SGGMKKRVAL ARSLIFDTTK

241 EVIEPEVLLY DEPTAGLDPI ASTVVEDLIR SVHMTDEDAV

281 GKPGKIASYL VVTHQHSTIQ RAVDRLLFLY EGKIVWQGMT

321 HEFTTSTNPI VQQFATGSLD GPIRY
```

An *Arabidopsis thaliana* Trigalactosyldiacylglycerol 2 (tgd2) cDNA sequence is available with accession number AT3G20320.1, and is shown below and identified herein as SEQ ID NO:6.

```
  1 TATTCTCAGA TTCACGACAC CAGTTCGTCA CAAGCTTCGA

41 GCCCAGCTCG GAAAACAAAA TTGGAACTTG CTGCATAAAG

81 TTTAGTTTTT TTAATTGAAT TTGGAAGGAT GATTGGGAAT

121 CCAGTAATTC AAGTTCCATC ATCACTAATG CCATCATCCT

161 CCATGATTGC TTGTCCTCGA GTTTCACCCA ATGGGGTTCC

201 TTATCTTCCA CCAAAACCTA GAACTAGGCA TTTAGTGGTC

241 AGAGCTGCAT CCAATTCCGA TGCTGCTCAT GGTCAACCAT

281 CGTCTGATGG GGGGAAGAAT CCTCTCACCG TTGTTTTGGA

321 TGTGCCCAGG AATATATGGA GACAGACTTT AAAACCTTTG

361 AGTGATTTTG GGTTTGGTAA GAGAAGTATT TGGGAAGGTG

401 GTGTTGGTTT GTTTATTGTC TCTGGAGCTA CTCTTCTTGC

441 TCTTAGCTGG GCTTGGTTGC GAGGTTTTCA AATGCGGTCG

481 AAGTTTAGGA AATATCAGAC TGTGTTTGAG CTTAGTCATG

521 CTTCTGGTAT TTGCACGGGA ACACCGGTTA GGATCCGTGG

561 GGTTACTGTT GGTACGATTA TCCGTGTTAA TCCTTCCTTG

601 AAGAATATTG AAGCTGTTGC TGAGATAGAA GATGATAAGA

641 TTATTATCCC GAGGAATTCA TTGGTTGAGG TGAATCAGTC

681 TGGTCTTCTA ATGGAAACTA TGATCGACAT TATGCCTAGG

721 AATCCGATAC CAGAACCTTC AGTAGGACCT CTGCATCCTG

761 AATGTGGTAA GGAAGGTCTG ATCGTTTGTG ATAGGCAGAC

801 AATAAAAGGA GTGCAAGGAG TTAGTTTAGA TGAATTAGTT

841 GGAATTTTCA CTCGTATTGG ACGCGAAGTT GAGGCCATTG

881 GTGTTGCCAA TACGTATTCG CTTGCTGAGA GAGCTGCTTC

921 GGTTATTGAG GAAGCAAGGC CATTGCTCAA AAAGATTCAA

961 GCCATGGCTG AAGATGCTCA ACCTTTGCTC TCTGAGTTTC

1001 GTGATAGCGG CTTGCTCAAG GAAGTTGAGT GTCTTACTCG

1041 AAGCCTTACC CAAGCTTCTG ACGATTTGAG AAAGGTTAAT

1081 TCGTCAATTA TGACTCCTGA GAATACAGAA CTCATACAGA

1121 AGTCAATCTA CACTCTGGTT TATACTTTGA AGAACGTCGA

1161 GAGTATAAGC TCAGATATTC TGGGATTCAC AGGAGATGAA

1201 GCCACAAGAA AAAACCTTAA ACTACTCATC AAATCCCTAA

1241 GCAGGCTACT ATGATCAGCC TGTAGATTTT AGACTGGATA

1281 AATAAAATCC AGAATTTTTA TGGTAAGCAA GTTTTAAAAA

1321 TTCGAAAAAT GTGTTGTTTC TTCTTTAGAG TTATTTTTGT

1361 TTTCGTTTTG TGTTCTGAGA TTGGGGTTTA ATGGAGAGAC

1401 ATAATTCAGT TTTTATAAGA ACAAAAATGT TTGTTT
```

The TGD2 protein sequence encoded by the SEQ ID NO:6 cDNA has the following sequence (SEQ ID NO:7).

```
  1 MIGNPVIQVP SSLMPSSSMI ACPRVSPNGV PYLPPKPRTR

41 HLVVRAASNS DAAHGQPSSD GGKNPLTVVL DVPRNIWRQT

81 LKPLSDFGFG KRSIWEGGVG LFIVSGATLL ALSWAWLRGF

121 QMRSKFRKYQ TVFELSHASG ICTGTPVRIR GVTVGTIIRV

161 NPSLKNIEAV AEIEDDKIII PRNSLVEVNQ SGLLMETMID

201 IMPRNPIPEP SVGPLHPECG KEGLIVCDRQ TIKGVQGVSL

241 DELVGIFTRI GREVEAIGVA NTYSLAERAA SVIEEARPLL

281 KKIQAMAEDA QPLLSEFRDS GLLKEVECLT RSLTQASDDL

321 RKVNSSIMTP ENTELIQKSI YTLVYTLKNV ESISSDILGF

351 TGDEATRKNL KLLIKSLSRL L
```

A variant of the *Arabidopsis thaliana* tgd2 cDNA sequence with 83% identity to the SEQ ID NO:6 sequence is available from the *Arabidopsis* database as accession number AT3G20320.2, which has the following sequence (SEQ ID NO:8).

```
  1 CAGTTCGTCA CAAGCTTCGA GCCCAGGTAT TCTCTCTTTC

41 GCTCAAAAAC CCTAATCTCG ACTTATAATT CGATCGATAA

81 AGTAGAAGCT TCACGCAATT CACATGTTCT CTATCTTCTT

121 TCTAACTACA GCTCGGAAAA CAAAATTGGA ACTTGCTGCA

161 TAAAGTTTAG TTTTTTTATT GAATTTGGAA GGATGATTGG

201 GAATCCAGTA ATTCAAGTTC CATCATCACT AATGCCATCA

241 TCCTCCATGA TTGCTTGTCC TCGAGTTTCA CCCAATGGGG

281 TTCCTTATCT TCCACCAAAA CCTAGAACTA GGCATTTAGT

321 GGTCAGAGCT GCATCCAATT CCGATGCTGC TCATGGTCAA

361 CCATCGTCTG ATGGGGGGAA GAATCCTCTC ACCGTTGTTT
```

```
401 TGGATGTGCC CAGGAATATA TGGAGACAGA CTTTAAAACC
441 TTTGAGTGAT TTTGGGTTTG GTAAGAGAAG TATTTGGGAA
481 GGTGGTGTTG GTTTGTTTAT TGTCTCTGGA GCTACTCTTC
521 TTGCTCTTAG CTGGGCTTGG TTGCGAGGTT TTCAAATGCG
561 GTCGAAGTTT AGGAAATATC AGACTGTGTT TGAGCTTAGT
601 CATGCTTCTG GTATTTGCAC GGGAACACCG GTTAGGATCC
641 GTGGGGTTAC TGTTGGTACG ATTATCCGTG TTAATCCTTC
681 CTTGAAGAAT ATTGAAGCTG TTGCTGAGAT AGAAGATGAT
721 AAGATTATTA TCCCGAGGAA TTCATTGGTT GAGGTGAATC
761 AGTCTGGTCT TCTAATGGAA ACTATGATCG ACATTATGCC
801 TAGGAATCCG ATACCAGAAC CTTCAGTAGG ACCTCTGCAT
841 CCTGAATGTG GTAAGGAAGG TCTGATCGTT TGTGATAGGC
881 AGACAATAAA AGGAGTGCAA GGAGTTAGTT TAGATGAATT
921 AGTTGGAATT TTCACTCGTA TTGGACGCGA AGTTGAGGCC
961 ATTGGTGTTG CCAATACGTA TTCGCTTGCT GAGAGAGCTG
1001 CTTCGGTTAT TGAGGAAGCA AGGCCATTGC TCAAAAGTG
1041 ATGTCACAGA TTCAAGCCAT GGCTGAAGAT GCTCAACCTT
1081 TGCTCTCTGA GTTTCGTGAT AGCGGCTTGC TCAAGGAAGT
1121 TGAGTGTCTT ACTCGAAGCC TTACCCAAGC TTCTGACGAT
1161 TTGAGAAAGG TTAATTCGTC AATTATGACT CCTGAGAATA
1201 CAGAACTCAT ACAGAAGTCA ATCTACACTC TGGTTTATAC
1241 TTTGAAGAAC GTCGAGAGTA TAAGCTCAGA TATTCTGGGA
1281 TTCACAGGAG ATGAAGCCAC AAGAAAAAAC CTTAAACTAC
1321 TCATCAAATC CCTAAGCAGG CTACTATGAT CAGCCTGTAG
1361 ATTTTAGACT GGATAAATAA AATCCAGAAT TTTATGGTAA
1401 GCAAGTTTTA AAAATTCGAA AAATGTGTTG TTTCTTCTTT
1441 AGAGTTATTT TTGTTTTCGT TTTGTGTTCT GAGATTGGGG
1481 TTTAATGGAG AGACATAATT CAGTTTTTAT AAGAACAAAA
1521 ATGTTTGTTT CTC
```

An *Arabidopsis thaliana* Trigalactosyldiacylglycerol 1 (tgd1) cDNA sequence is available with accession number AT1G19800.2, and is shown below and identified herein as SEQ ID NO:9.

```
1 TGTGTGTTGT TGTTGTTGGC ACTGTGCCAC TTTCTCTCTC
41 GATGAACCCT CTCAAGCAAG CTTCTTCGAT CTTCCGAGCT
81 TAGTTTCGTT TCTAAATTAG AGATTTCACC TAGATTGGTC
121 CGTACATATC TTATACTGGG ATTCGAATTT GGCTGCCTCA
161 GAGTCAGAGA TTGATTAATT GATCAGATTC AGCTGTTGAA
201 ATCGTGCTTA TTGCTACAAA TTGAGAGGCA CTAAATCAGT
241 GAGGTCGTAA AGAAGAAGGC AACCACAATG ATGCAGACTT
281 GTTGTATCCA TCAATCGTTT TGTTTCCCTC ATAGAGTCTT
321 TCCACGGTTT GATGCTTCGA TTGGTATTAA GCCCCCAAAG
361 CTTTGTCAAG TTGGTTTCAT TGGAAAGACT CAATCTTATG
401 GGATTTCAAG TCCGATACGG CAAAGAAGAT TATATGTGAA
441 TTTGAATGCT AATGATGGTC ACCCATCCAT GTCTATGTTG
481 GAAGAAGAAA CCTCTACTGA AAACAACGCA CCCAGTCAAG
521 AAGCCGAGCT TCCGTTCAGC AAATGGTCAC CTTCTAAGTA
561 CATATGGAGA GGTTTATCAG TTCCTATTAT AGCAGGACAA
601 GTCGTTCTCC GGATTTTAAA GGGTAAGATT CACTGGAGAA
641 ACACTCTTCA ACAGCTGGAG AGAACCGGAC CGAAATCTCT
681 AGGAGTTTGT CTTCTGACTT CTACATTTGT TGGTATGGCT
721 TTCACAATCC AGTTCGTTAG AGAATTCACT AGACTAGGTC
761 TAAACAGATC CATTGGAGGT GTCTTGGCTT TAGCCTTCTC
801 TAGAGAGCTA AGTCCAGTCA TCACATCGAT TGTTGTTGCT
841 GGACGAATGG GAAGTGCATT TGCAGCTGAA CTAGGGACAA
881 TGCAAGTCTC AGAGCAAACT GATACACTCC GTGTTTTAGG
921 AGCTGACCCA ATTGATTATC TAATCACTCC AAGAGTCATC
961 GCCTCGTGTT TGGCTCTACC GTTTCTGACA CTCATGTGTT
1001 TCACTGTTGG TATGGCTTCA AGCGCTCTGC TCTCTGATGC
1041 AGTTTACGGG ATCAGCATTA ACATAATCAT GGACTCGGCT
1081 CACCGAGCAC TTAGACCATG GGACATTGTG AGTGCCATGA
1121 TTAAATCTCA AGTCTTTGGA GCTATAATAT CGGTAATTAG
1161 TTGTTCTTGG GGAGTAACCA CTACTGGAGG TGCTAAAGGT
1201 GTTGGAGAAT CTACAACTTC TGCTGTCGTC ATGTCTCTTG
1241 TCGGAATCTT CATCGCGGAC TTTGTGCTTT CTTCCTTCTT
1281 CTTTCAAGGT GCTGGAGATT CTTTGAAGAA CTGTGTTTGA
1321 CATATTATTT TCTGTCTTCT TTTGTTGTGG TTTAGATGGG
1361 TTTATGTAAA TCAGTTGTCT TAAATTGAGA AAGTAACATC
1401 ATTTTAGAAA GAACAGAAAG ATTGCTATAT TTCTATTCCA
1441 ATAATGATAC ACATTGAATA AT
```

The TGD1 protein sequence encoded by the SEQ ID NO:9 cDNA has the following sequence (SEQ ID NO:10).

```
1 MMQTCCIHQS FCFPHRVFPR FDASIGIKPP KLCQVGFIGK
41 TQSYGISSPI RQRRLYVNLN ANDGHPSMSM LEEETSTENN
81 APSQEAELPF SKWSPSKYIW RGLSVPIIAG QVVLRILKGK
121 IHWRNTLQQL ERTGPKSLGV CLLTSTFVGM AFTIQFVREF
161 TRLGLNRSIG GVLALAFSRE LSPVITSIVV AGRMGSAFAA
201 ELGTMQVSEQ TDTLRVLGAD PIDYLITPRV IASCLALPFL
241 TLMCFTVGMA SSALLSDAVY GISINIIMDS AHRALRPWDI
281 VSAMIKSQVF GAIISVISCS WGVTTTGGAK GVGESTTSAV
321 VMSLVGIFIA DFVLSSFFFQ GAGDSLKNCV
```

A variant of the *Arabidopsis thaliana* tgd1 cDNA sequence with 99% identity to the SEQ ID NO:9 sequence is available from the *Arabidopsis* database as accession number AT1G19800.3, which has the following sequence (SEQ ID NO:11).

```
   1 TGTGTGTGTT GTTGTTGTTG GCACTGTGCC ACTTTCTCTC
  41 TCGATGAACC CTCTCAAGCA AGCTTCTTCG ATCTTCCGAG
  81 CTTAGTTTCG TTTCTAAATA GATTTCACCT AGATTGGTCC
 121 GTACATATCT TATACTGGGA TTCGAATTTG GCTGCCTCAG
 161 AGTCAGAGAT TGATTAATTG ATCAGATTCA GCTGTTGAAA
 201 TCGTGCTTAT TGCTACAAAT TGAGAGGCAC TAAATCAGTG
 241 AGGTCGTAAA GAAGAAGGCA ACCACAATGA TGCAGACTTG
 281 TTTGTATCCAT CAATCGTTTT GTTTCCCTCA TAGAGTCTTT
 321 CCACGGTTTG ATGCTTCGAT TGGTATTAAG CCCCCAAAGC
 361 TTTGTCAAGT TGGTTTCATT GGAAAGACTC AATCTTATGG
 401 GATTTCAAGT CCGATACGGC AAAGAAGATT ATATGTGAAT
 441 TTGAATGCTA ATGATGGTCA CCCATCCATG TCTATGTTGG
 481 AAGAAGAAAC CTCTACTGAA AACAACGCAC CCAGTCAAGA
 521 AGCCGAGCTT CCGTTCAGCA AATGGTCACC TTCTAAGTAC
 561 ATATGGAGAG GTTTATCAGT TCCTATTATA GCAGGACAAG
 601 TCGTTCTCCG GATTTTAAAG GGTAAGATTC ACTGGAGAAA
 641 CACTCTTCAA CAGCTGGAGA GAACCGGACC GAAATCTCTA
 681 GGAGTTTGTC TTCTGACTTC TACATTTGTT GGTATGGCTT
 721 TCACAATCCA GTTCGTTAGA GAATTCACTA GACTAGGTCT
 761 AAACAGATCC ATTGGAGGTG TCTTGGCTTT AGCCTTCTCT
 801 AGAGAGCTAA GTCCAGTCAT CACATCGATT GTTGTTGCTG
 841 GACGAATGGG AAGTGCATTT GCAGCTGAAC TAGGGACAAT
 881 GCAAGTCTCA GAGCAAACTG ATACACTCCG TGTTTTAGGA
 921 GCTGACCCAA TTGATTATCT AATCACTCCA AGAGTCATCG
 961 CCTCGTGTTT GGCTCTACCG TTTCTGACAC TCATGTGTTT
1001 CACTGTTGGT ATGGCTTCAA GCGCTCTGCT CTCTGATGCA
1041 GTTTACGGGA TCAGCATTAA CATAATCATG GAACCGGACC
1081 ACCGAGCACT TAGACCATGG GACATTGTGA GTGCCATGAT
1121 TAAATCTCAA GTCTTTGGAG CTATAATATC GGTAATTAGT
1161 TGTTCTTGGG GAGTAACCAC TACTGGAGGT GCTAAAGGTG
1201 TTGGAGAATC TACAACTTCT GCTGTCGTCA TGTCTCTTGT
1241 CGGAATCTTC ATCGCGGACT TTGTGCTTTC TTCCTTCTTC
1281 TTTCAAGGTG CTGGAGATTC TTTGAAGAAC TGTGTTTGAC
1321 ATATTATTTT CTGTCTTCTT TTGTTGTGGT TTAGATGGGT
1361 TTATGTAAAT CAGTTGTCTT AAATTGAGAA AGTAACATCA
1401 TTTTAGAAAG AACAGAAAGA TTGCTATATT TCTATTCCAA
1441 TAATGATACA CATTGAATAA T
```

The methods of the present invention contemplate the use of at least one heterologous gene encoding a tgd RNAi of the present invention for use in a gene-silencing construct. Therefore, the inventors created exemplary gene constructs and methods comprising these gene constructs, as described herein, contemplated for increasing the amount of oils produced and stored in leaves and stems without stunting the growth of host plants. Even further the inventors contemplated that plants of the present inventions would have high fertility levels (at least greater than 60%) for increasing the amount of oil produced per plant in addition to having agronomical desirable traits.

Therefore, in one experiment designed to avoid stunted plant growth and embryo lethality while obtaining plants with a more consistent phenotype of accumulated, i.e. increased, oil in vegetative tissues, the inventors created an TGD3 RNAi construct using two copies of a fragment of the tgd3 gene, one in the sense direction and the other in an antisense direction, separated by a spacer sequence of a tgd3 intron, in operable combination with an inducible promoter.

Figure 10C:
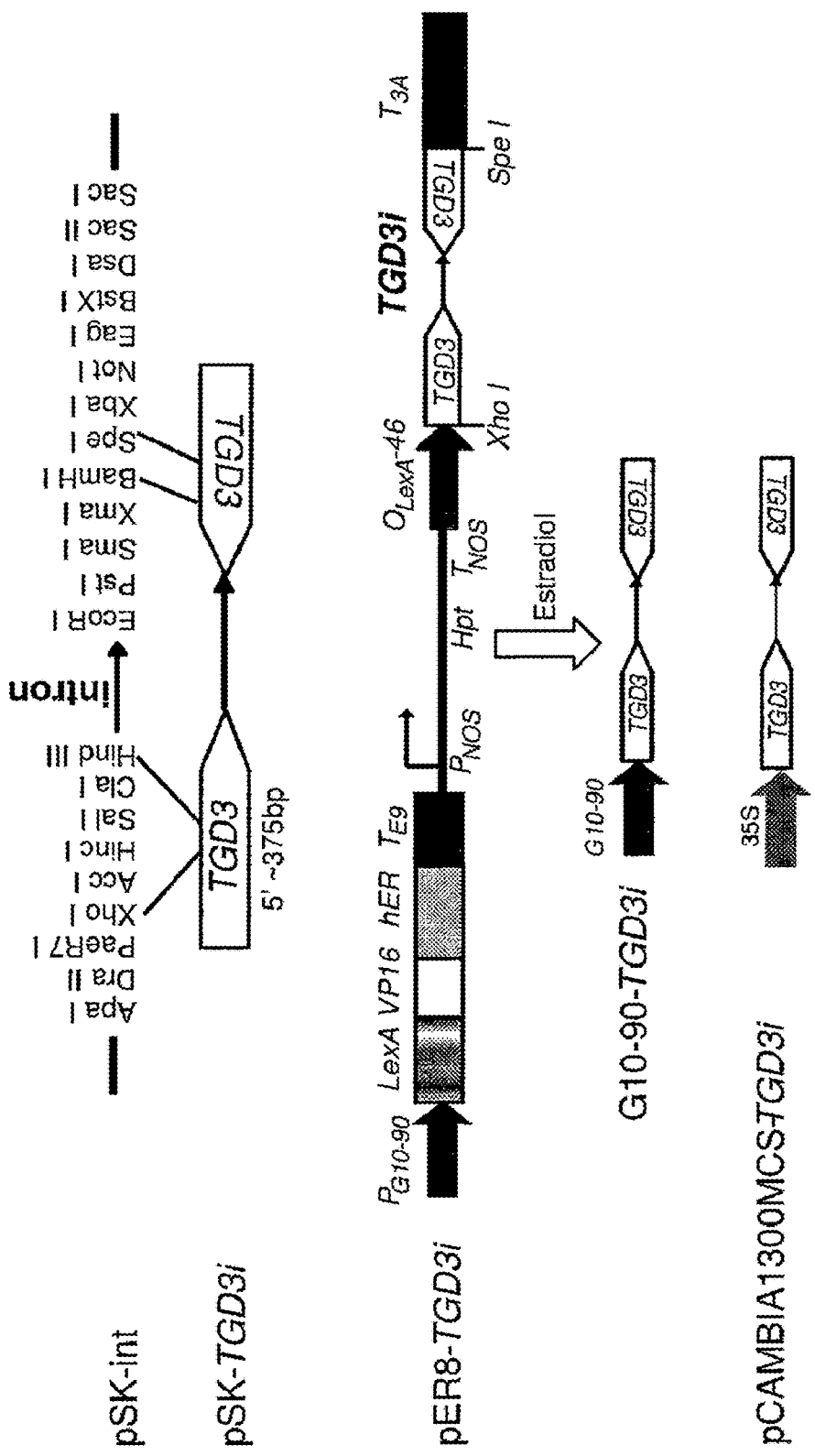

The tgd3 sense sequence of the RNAi construct containing 5' untranslated and 5' translated (underlined) regions of the cDNA is shown in FIG. 10 and below as SEQ ID NO:55.

```
   1 AAAAATGGCA ATGTGACTCA CTCAATCGGT GACTCGCTAT
  41 AGTCTGTGAA GAAAGGCCAA TTTCGCCATA AAGTTCACAC
  81 CTTTGATCTC CTTTGTTTCT GGGTTTCTCC TAAATCATCC
 121 AAATTGGTAT CGAATTTGCC CTTCTCCGAT TCAATTTCTT
 161 CACGATCTCA AAACCCAGAA GAAAGAATCA TGCTTTCGTT
 201 ATCATGCTCT TCTTCTTCTT CTTCGTTGCT TCCTCCGAGT
 241 TTACACTACC ACGGTTCTTC TTCTGTTCAG TCCATCGTTG
 281 TACCAAGAAG GAGTCTTATC TCGTTTCGTC GGAAAGTCTC
 321 TTGCTGTTGC ATAGCTCCAC CTCAGAACTT GGACAACGAT
 361 GCCACCAAAT TCGATT
```

This tgd3 RNAi construct was used to transform wildtype *Arabidopsis* plants (i.e. with functional TGD1, 2, 3 and 4). After germination, the roots of established control and RNAi construct-containing seedlings (around 3 weeks after sprouting) were soaked in the inducing chemical. Growing plant leaves of seedlings exposed to the inducing chemical began accumulating oil in their leaves. Thus, plants were able to grow normally before oil began accumulating in vegetative tissues. Exemplary analysis of these oils is shown in FIG. 11 and described herein in the Examples section.

Thus accumulation of the oil in the leaf and stem was achieved by altering the function of the trigalactosyldiacylglycerol (TGD) proteins after the plant is established (i.e. as a young seedling). The inventors were surprised that the resulting seedling plants accumulated substantial amounts of oils in leaves and stems with the use of either promoter. Also surprisingly, unlike plants engineered for a reduction in TGD1 and TGD2, separately, the use of a constitutive promoter for a construct reducing the production of TGD3 was not lethal in these TGD3 knock down plants.

Thus, in one embodiment, the inventors contemplate increasing the amount of oil produced and stored within a plant using either a constitutive promoter or an inducible promoter in operable combination with a gene silencing construct, i.e. a RNAi tgd gene fragment construct, comprising a fragment of a tgd gene as described herein.

Therefore, in some embodiments, tgd silencing constructs of under control of constitutive promoters. In other embodiments, tgd silencing constructs are under control of inducible promoters. In yet other embodiments, tgd silencing constructs are under control of developmental promoters. In yet further embodiments, tgd silencing constructs are under control of tissue specific promoters. The inventors additionally contemplate using other types of inducible RNAi tgd gene constructs for silencing tgd genes, such as an ethanol-inducible promoter, Peebles, et al., Biotechnology Progress, 23(5):1258-1260 (2007), herein incorporated by reference in its entirety, nonendogenous glucocorticoid promoter, and the like. In addition to using constructs with constitutive promoters for silencing tgd genes using RNAi constructs with DNA sequences, for examples, using tgd SEQ ID NOs:12-15.

E. Engineering Plants for Modifying Oil Content in Vegetative Tissues while Maintaining Plant Viability for Breeding Agronomically Desired Commercial Varieties Through the Use of Oil Regulating Transcription Factors.

Engineering the accumulation of triacylglycerols (TAGs) and other lipids in vegetative tissues is contemplated to support efforts for increasing yield of biofuels and/or edible lipids in relation to resources needed for crop growth. However as described, when oil production is manipulated in plants there is frequently a concurrent lowering of plant viability and seed fertility, such as shown when tgd expression is lowered. Thus, plants making larger amounts of oil having vigorous growth characteristics along with high fertility levels are needed. In one contemplated embodiment, the use of oil regulating transcription factors (TF) is contemplated to overcome these problems. As one example which succeeded in part, plants overexpressing WRINKLED1 having reduced amounts of AGPase proteins have increased amounts of TAGs in vegetative tissues. However, although the co-expression of WRINKLED1 increased oil levels in these plants also have not possessed reduced growth rates or fertility.

1. Use of Oil Regulating Transcription Factors for Increasing Oil Production in Vegetative Tissues of Plants.

Triacylglycerols (TAGs) derived from seed oils such as canola, soybean and palm are contemplated for use as a feedstock for biodiesel production (Durrett et al., 2008, herein incorporated by reference in its entirety) in addition to other types of uses. However, the current supply of these energy-rich compounds is limited because of low crop yield and arable land availability. For example, it has been estimated that 50%-75% increase in canola oil production will be required to meet the growing seed oil demand in Canada alone during the next 7-10 years (Weselake et al., 2009, herein incorporated by reference in its entirety). One contemplated approach to increase biodiesel feedstocks is to synthesize TAGs in vegetative tissues such as leaves, stems, roots and storage organs, using a metabolic engineering approach. For comparison, certain plants are naturally able to accumulate oils in nonseed tissues to various degrees, for instance, avocado mesocarp (Takenaga et al., 2008, herein incorporated by reference in its entirety), nut sedge roots (Stoller and Weber, 1975, herein incorporated by reference in its entirety) and stems of the 'oil firewood' Tetraena mongolica Maxim (Wang et al., 2007, herein incorporated by reference in its entirety). However these plants are not suitable for commercial agriculture nor do they produce the type of oils needed for commercial use.

The biochemistry of fatty acids (FA) and TAG synthesis in plants is complex, regulated by different factors in different cellular compartments, and each intermediate biochemical reaction was found to be catalyzed by specialized enzymes (Ohlrogge and Jaworski, 1997; Durrett et al., 2008, The Plant J, 54:593-607, all of which are herein incorporated by reference in their entirety). Photosynthate in the form of sugar from the source tissues of the parent plant was discovered as an import into developing seeds and converted via glycolysis into precursors of fatty acid biosynthesis (Durrett et al., 2008; Baud and Lepiniec, 2010, all of which are herein incorporated by reference in its entirety). Genetic studies in Arabidopsis revealed some of the factors that control the seed oil biosynthesis pathway. For example, a wri1-1 mutant, which was deficient in a transcription factor, had an 80% reduction in seed TAG content and required an external carbon source for germination (Focks and Benning, 1998, herein incorporated by reference in its entirety).

Similarly, several additional transcription factors such as LEAFY COTYLEDON1 (LEC1), LEAFY COTYLEDON2 (LEC2) and FUSCA3 (FUS3) were identified in Arabidopsis and discovered to play a role in seed maturation and oil biosynthesis (Baumlein et al., 1994; Meinke et al., 1994; Stone et al., 2001, all of which are herein incorporated by reference in their entirety). Thus earning the designation of oil regulating transcription factors. WRI1 in particular, a member of the APETALA2/ETHYLENE-RESPONSIVE ELEMENT BINDING (AP2/EREB) transcription factor family was discovered to have a role in oil regulation in both seeds and seedlings (Cernac and Benning, 2004; Cernac et al., 2006, all of which are herein incorporated by reference in their entirety). Analysis of gene expression in wri1-1 mutants and transgenic plants that expressed WRI1 cDNA or in a WRI1 enhancer-driven overexpression line showed targets of this transcription factor, including many genes encoding enzymes of the fatty acid biosynthesis pathway (Ruuska et al., 2002; Baud et al., 2007; Maeo et al., 2009, all of which are herein incorporated by reference in their entirety). A combination of molecular and biochemical approaches identified contemplated WRI1-binding motifs in some target genes (Baud et al., 2009; Maeo et al., 2009, all of which are herein incorporated by reference in their entirety). Overexpression of Brassica napus WRI1 in Arabidopsis and maize WRI1 in a low oil maize genetic (mutant) background enhanced oil accumulation in maize seeds (Liu et al., 2010; Shen et al., 2010, all of which are herein incorporated by reference in their entirety). However the mutant background was required. These results demonstrated that WRI1 regulated seed oil biosynthesis in both dicotyledonous and monocotyledonous plants. However, the numerous attempts to metabolically engineer TAG accumulation in seeds by targeting the expression of single genes or a combination of genes had moderate success (Thelen and Ohlrogge, 2002; Abbadi et al., 2004; Taylor et al., 2009, all of which are herein incorporated by reference in their entirety).

Another contemplated method for using an oil seed regulating transcription factor for overcoming the lack of success for increasing oil seed biosynthesis was the overexpression of LEC1 in Arabidopsis and LEC2 in the fatty acid break down mutant comatose (cts2), which led to the accumulation of oil in vegetative tissues (Mu et al., 2008; Slocombe et al., 2009, all of which are herein incorporated by reference in their entirety). In another test, transgenic tobacco engineered with DIACYLGLYCEROL ACYLTRANSFERASE 1 (DGAT1) and a transcription factor LEC2 showed accumulated oil surprisingly in the leaves of plants (Andrianov et al., 2010, herein incorporated by reference in its entirety).

In the case of developing seeds, carbon derived from photosynthesis was partitioned into different storage compounds. Therefore that carbon flux into oil was contemplated to be in competition with the use of carbon for other metabolic pathways (Vigeolas et al., 2004; Ekman et al., 2008, all of which are herein incorporated by reference in their entirety). One of these competing pathways is the biosynthesis of starch, which serves as a major carbon reserve in plants with up to 50% of photosynthate stored as starch. There are two types of starch, storage and transitory (Ballicora et al., 2004; Smith, 2008, all of which are herein incorporated by reference in their entirety). The synthesis and accumulation of starch in storage tissues is largely controlled by growth and development (Smith, 2008, herein incorporated by reference in its entirety). For example, seeds of Arabidopsis and B. napus accumulate starch early in development and later shift from synthesizing starch to oil (Focks and Benning, 1998; Vigeolas et al., 2004, all of which are herein incorporated by reference in their entirety).

Transitory starch is stored in the chloroplasts of leaves and is built up during the day. Its synthesis can consume up to half of the carbon fixed by photosynthesis. This starch is then broken down at night to provide a continuous source of carbon to the plant when $CO_2$ cannot be fixed by photosynthesis (Weise et al., 2004, herein incorporated by reference in its entirety). Adenosine Diphospho (ADP)-glucose pyrophosphorylase (AGPase) catalyzes the first committed step of starch biosynthesis and converts glucose-1-phosphate and ATP to ADP-glucose and inorganic pyrophosphate. ADP-glucose is subsequently turned into starch by multiple isoforms of starch synthase and branching enzyme (Ballicora et al., 2004; Smith, 2008, all of which are herein incorporated by reference in their entirety). Inactivation of AGPase in maize (Zea mays), rape seed (B. napus) and pea (Pisum sativum) led to considerable reduction in seed starch content (Vigeolas et al., 2004; Weigelt et al., 2009, all of which are herein incorporated by reference in their entirety). Therefore, several attempts were made to increase starch content through the genetic engineering of AGPase activity in crops (Stark et al., 1992; Smidansky et al., 2002; Ihemere et al., 2006, all of which are herein incorporated by reference in their entirety). However these plants had enhanced starch content not enhanced oil. This was due to the finding that starch and oil are competing pathways for use of carbon so when carbon is used for starch production it is less available for oil production.

Further, it was discovered that starch biosynthesis was partially blocked by suppression of the expression of APS1 while concurrently ectopically expressing WRI1 resulted in increased accumulation of TAG in Arabidopsis vegetative tissues. Arabidopsis plants that ectopically expressed AGPRNAi-WRI1 accumulated less starch and 5.8-fold more TAG in the vegetative tissues. Therefore it is contemplated that the amount of oil accumulated in plants would be improved further with the use of RNAi TGD (i.e. reduced translation of TGD) also having reduced APS1 while concurrently overexpressing WRI1. Hence a strategy was developed to divert carbon from starch to oil by silencing the expression of one of the AGPase gene. Thus resultant plants were contemplated to accumulate less starch and then have more available sugar for conversion into oil by concomitant expression of sugar sensitive WRI1 transcription factor.

In fact, in the AGPRNAi-WRI1 line 28, a 5.8-fold increased oil accumulation along with a 50% reduction in starch relative to wild type was observed in the vegetative tissues, compared to 2.6-2.8-fold oil accumulation in the transgenic lines expressing WRI1 cDNA alone. From data shown in FIGS. 21 and 22 for the wild type and the transgenic line 28, it was calculated that of the total carbon sequestered as TAG and starch, 20% was stored as TAG in transgenic line 28 compared to just 2% in wild-type plants. The amount of carbon accumulated as starch, sugars and TAG in the double transgenic line 28 was almost doubled. When these data were converted to energy density, the contribution of TAG compared to starch was 9.5-fold higher in line 28 compared to wild-type plants.

In most plants, TAGs are stored in oil droplets in the seeds, which support seedling growth after germination (Jolivet et al., distinct oil droplets in the leaf and root tissues as revealed by Nile red staining) These observations were consistent with increased oil accumulation in the AGPRNAi-WRI1 lines. Intriguingly, the presence of long-chain fatty acid containing TAG species typically found restricted to seeds in Arabidopsis were detected in the vegetative tissue of the AGPRNAi-WRI1 lines (FIG. 22C), suggesting that seed-like biosynthetic mechanisms was ectopically induced.

Figure 19A:
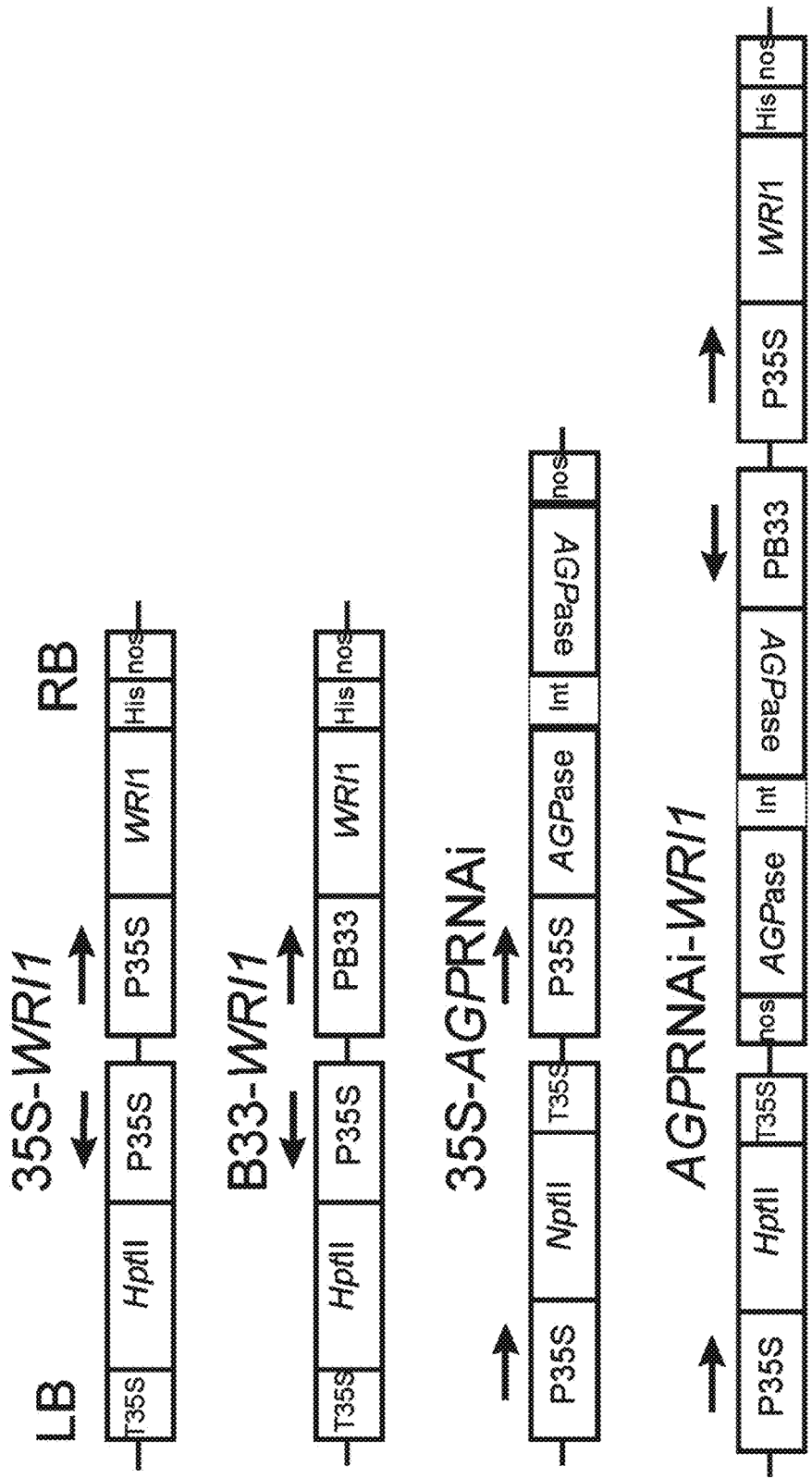
FIG. 19A-19D shows exemplary schematic diagrams of the T-DNA of the binary vectors and examples of the pale green phenotype of the WRINKLED1 (WRI1) over-expression and APS1 down-regulated AGPRNAi-WRI1 line.
Figure 19B:
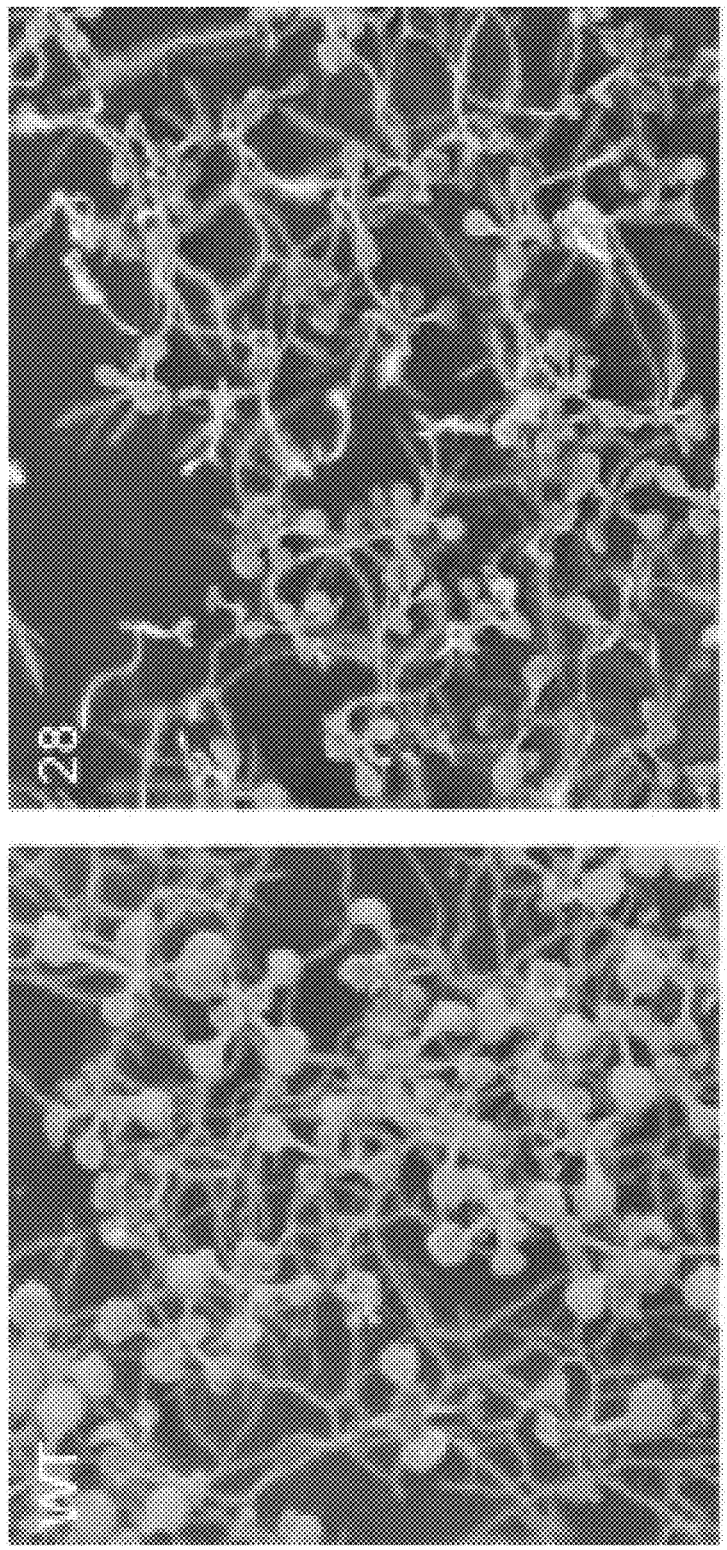
Figure 23:
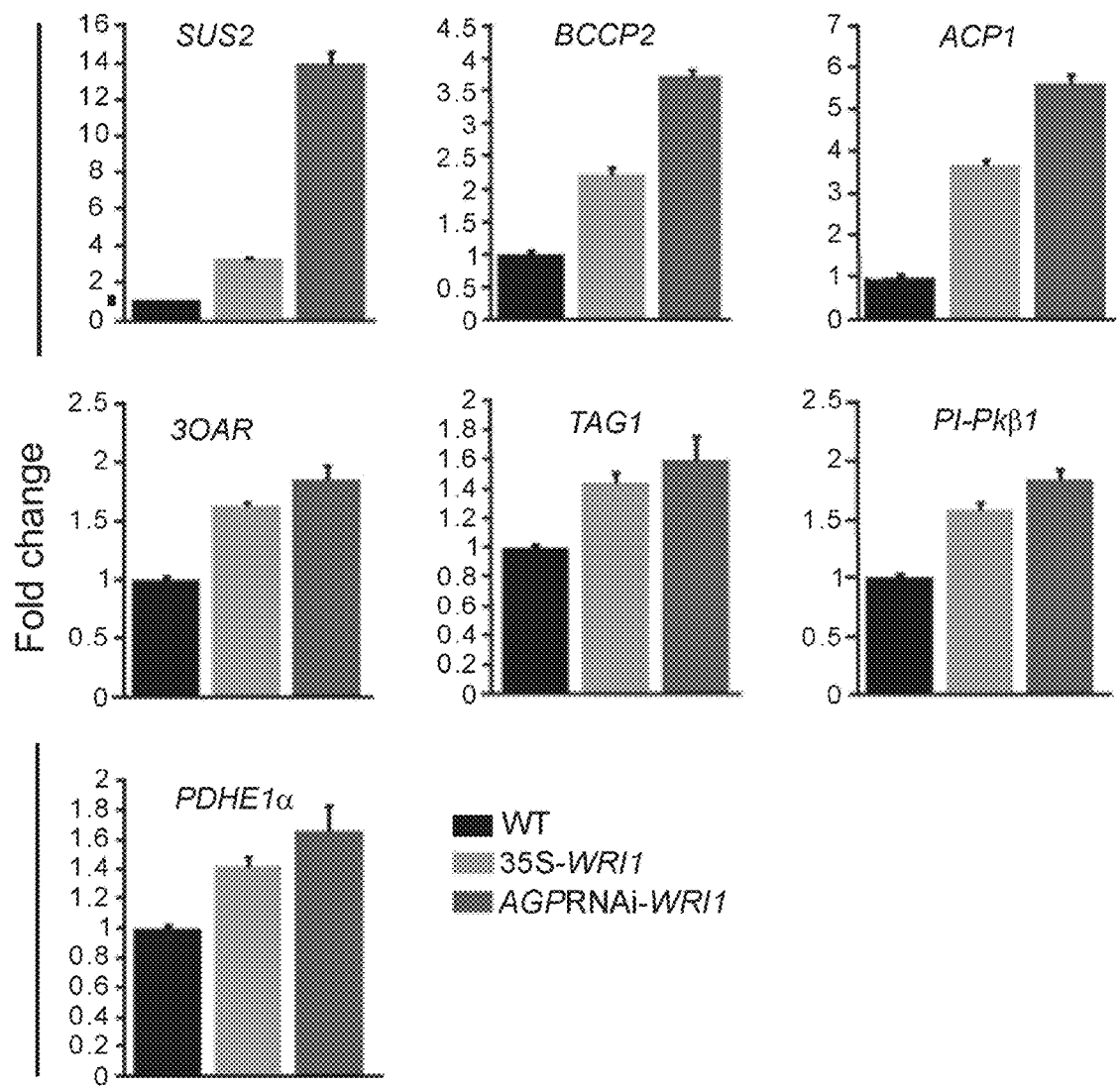
FIG. 23 graphically illustrates up-regulation of a series of WRINKLED1 (WRI1) target genes in 35S-WRI1 line 7 (light gray bars) and AGPRNAi-WRI1 line 28 (dark grey bars), compared to wild type (black bars). The error bars represent the standard deviation of the mean of three independent mRNA extractions.

The main cause for the reduction of starch levels in the 35S-AGPRNAi and AGPRNAi-WRI1 lines was the introduction of the RNAi cassette specifically targeting an AGPase small subunit that led to the down-regulation of APS1 expression (FIG. 19B). AGPase is a heterotetramer, composed of small and large subunits, and both subunits have regulatory roles required for the optimal activity of the enzyme. Thus, impairing one subunit effectively reduces AGPase activity and subsequently starch synthesis (Ballicora et al., 2004; Crevillen et al., 2005, all of which are herein incorporated by reference in their entirety). In support of these observations, previous studies in rape seeds showed that suppression of AGPase by sense or antisense orientation under the control of an embryo-specific promoter led to the reduction of starch in the developing seeds (Vigeolas et al., 2004, herein incorporated by reference in its entirety). In AGPRNAi-WRI1 lines inhibition of the starch biosynthesis pathway led to the accumulation of higher levels of sucrose, which in turn likely activated SUS2 to convert the available sugar pool into hexoses (FIG. 23). In addition to starch biosynthesis, these monosaccharides are also precursors for glycolysis, which in turn supplies substrates for oil biosynthesis. Previous studies showed that glucose/fructose in the agar medium led to the accumulation of long-chain fatty acids in transgenic Arabidopsis seedlings overexpressing WRI1 cDNA (Cernac and Benning, 2004, herein incorporated by reference in its entirety).

Figure 20A:
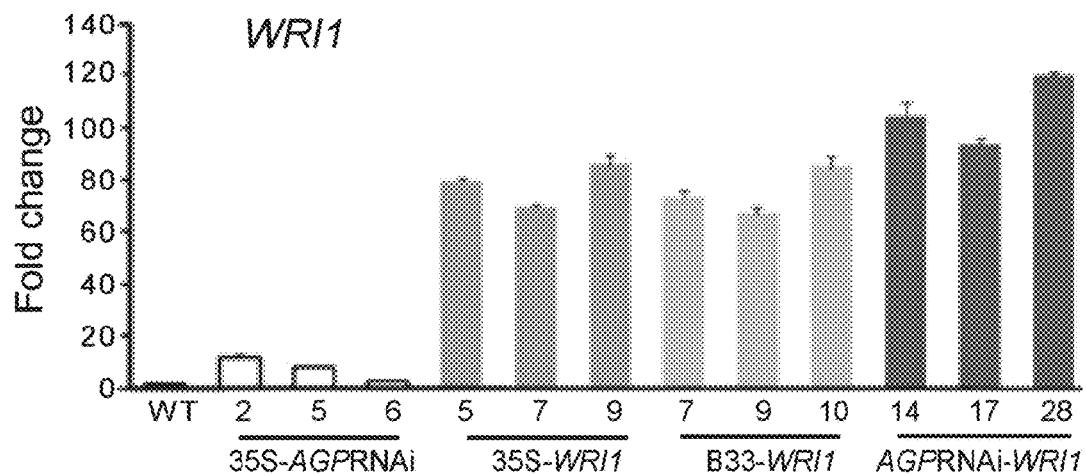
FIG. 20A-20B graphically illustrates the results of qRT-PCR analysis of WRINKLED1 (WRI1) and APS1 expression in different transgenic lines.

In addition to serving as an energy source, sugars play a role as signaling molecules in controlling gene expression in plants (Rolland et al., 2006, herein incorporated by reference in its entirety). In particular, the expression of WRI1 was regulated by various sugars. For example, glucose and fructose were necessary for seedlings ectopically overexpressing WRI1 to produce TAGs (Cernac and Benning, 2004, herein incorporated by reference in its entirety). It was demonstrated that WRI1 expression was enhanced by sucrose in Arabidopsis leaves (Masaki et al., 2005, herein incorporated by reference in its entirety). Consistent with these results, the expression of WRI1 in seedlings of 35S-AGPRNAi lines was increased 2.5-11-fold compared to wild-type plants (FIG. 20A). Thus, high sugar levels present in the AGPR-NAi-WRI1 lines also enhanced the expression of endogenous WRI1, leading to enhanced accumulation of WRI1 transcript in these plants relative to the 35S-WRI1 and B33-WRI1 overexpression lines.

However, the largest increase in WRI1 transcript levels in the AGPRNAi-WRI1 lines compared to wild-type lines was because of the expression of the 35S-WRI1 cassette (construct). Surprisingly, the relative expression level of SUS2 was considerably elevated in the AGPRNAi-WRI1 line (FIG. 23). SUS2 is an enzyme that reversibly cleaves sucrose into Uridine Diphosphate (UDP)-glucose and fructose in sink tissues (Angeles-Nunez and Tiessen, 2010, herein incorporated by reference in its entirety). In contrast expression of SUS2 was not elevated by overexpression of WRI1 in *Arabidopsis* seedlings (Baud et al., 2007; Maeo et al., 2009, herein incorporated by reference in their entirety). However, previous studies showed the presence of an AW-box in the promoter of SUS2, and co-expression of WRI1 in protoplasts transactivated a SUS2:LUC promoter:reporter (Maeo et al., 2009, herein incorporated by reference in its entirety). These observations combined with the results described herein show that although SUS2 is one of the WRI1 target genes, its expression may be directly controlled by sugars.

The relative expression of plastidic proteins involved in de novo fatty acid biosynthesis BCCP2 and ACP1 was enhanced in the AGPRNAi-WRI1 line. Previous studies showed that BCCP2 and ACP1 were WRI1 targets (Baud et al., 2007; Maeo et al., 2009, all of which are herein incorporated by reference in their entirety). Surprisingly, results described herein indicated moderate changes in the relative expression of some known WRI1 targets involved in the glycolysis and later stages of oil synthesis, for example PI-PKb1, 3OAR, PDHE1a and TAG1. It may be possible that in vegetative versus embryonic tissues, the expression of these genes or the activity of the encoded enzymes is differentially regulated based on the 'source/sink or sugar state' of the cells. For example, recent work has suggested that the activity of Nasturtium DGAT1 is regulated by its phosphorylation state (Xu et al., 2008, herein incorporated by reference in its entirety). Given the relatively high accumulation of TAG in these AGPRNAi-WRI1 lines, it is tempting to speculate that sugar signaling might be involved in such post-translational regulation of the activity of enzymes involved in TAG biosynthesis. Future detailed studies are needed to understand the effect of sugars on the WRI1 regulatory networks in vegetative tissues.

In conclusion, altering the carbon partitioning in the vegetative tissues in combination with up-regulation of TAG biosynthesis led to an enhanced accumulation of TAGs in transgenic seedlings, in principle enhancing the energy density of the biomass. Ultimately, TAGs need to be synthesized in the vegetative tissues of mature plants; these promising results are a first step towards that goal. However, further studies are necessary to understand possible factors which limit WRI1 expression, TAG synthesis and accumulation in the vegetative tissues to reach the amount needed to make an economically viable product. Following oil extraction, the remaining sugars and lignocellulose are still available for biofuel production. However, the greater energy density and compatibility with existing engine technology make TAG containing oils desirable such that the larger the TAG fraction in biomass, the higher is the crop value.

However, to be economically useful, changes in oil production must not come at the expense of overall seed yield, fertility, or at the loss of other high-value components, nor at a loss of agronomic traits desirable for commercial plant lines. For example, soybean is the largest source of vegetable oil, comprising 30% of the world market, and now constitutes over 80% of all dietary vegetable oils in the United States. Although termed an oilseed, soybean contains 18-22% oil on a seed dry-weight basis and is grown principally as a high-protein meal for animal feeds. Thus, increasing oil in soybean will in most cases not be useful if it comes at the expense of high-value soy protein that drives the crop's economics. By comparison, other oilseed crops (except cotton) are grown primarily for their oil and produce seeds with 40-60% oil. The wide range of seed oil percentage observed in nature suggests that this pathway might be amenable to metabolic engineering, particularly in "low-oil" oilseeds, provided mechanisms which control oil content are identified. Even further, the inventors contemplate that economically valuable increases in oil production in vegetative tissues combined with increases in seed oil content would provide plants and oil crops that would overcome current limitations.

2. WRINKLED1 Overexpression Increased Seed Oil Content.

A WRI1 gene encodes an APETALA2/ethylene-responsive element-binding protein transcription factor involved in the control of metabolism, particularly glycolysis, in the developing seeds. WRI1 encodes a putative transcription factor of the AP2/EREBP class (Jofuku et al., 1994; Riechmann et al., 2000; Weigel, 1995, all of which are herein incorporated by reference in its entirety). Examples of wild type *Arabidopsis* plants overexpressing a heterologous WRI1 gene showed lipid accumulation in seedlings, see, Cernac and Benning, The Plant Journal 40: 575-585 (2004), herein incorporated by reference in its entirety).

In the absence of sugar in the medium, seedlings of most of the transgenic plants lines were generally indistinguishable from wild type and developed into *Arabidopsis* plants which did not form ectopic embryos or show other obvious abnormalities. The requirement for sugar to bring about the aberrant phenotype may be simply explained by the fact that carbon skeletons and reducing power are needed to synthesize the large amounts of oil in these compromised seedlings. Plants grown from abnormal seedlings grown in the presence of sugar were often stunted in growth and yellowish suggesting reduced photosynthetic capability. They were often sterile as well. However, in the presence of sugar, oil-accumulated in seedlings in plant lines, which ectopically expressed WRI1. Essentially, the phenotype of these abnormal seedlings was consistent with an extension or reinitiation of the embryonic state of developing seeds during oil accumulation. However, ectopic expression of WRI1 did not lead to ectopic embryo formation as observed for LEC1 (Lotan et al., 1998, herein incorporated by reference in its entirety) in *Arabidopsis* or BABY BOOM in *Brassica* (Boutilier et al., 2002, herein incorporated by reference in its entirety).

Thus, ectopic expression of the WRI1 cDNA caused a sugar-inducible accumulation of seed-like oil in the transgenic seedlings. The general appearance of the transgenic seedlings suggested a resumption of embryonic development following germination. The overall conclusion was that the WRI1 gene product was involved in controlling seed development, in particular the phase of embryo maturation in which TAG accumulates, with sugar providing one part of the process (Cernac and Benning, 2004, herein incorporated by reference in its entirety). Moreover, the ectopic expression of WRI1 under the control of a CAMV 35S promoter led to an increase in WRI1 mRNA abundance in developing seedlings and concomitantly to an increase in the abundance of mRNA predicted to encode a plastidic isoform of the glycolytic enzyme pyruvate kinase. The expression of the WRI1 gene was observed in developing siliques and seeds isolated from the siliques in addition to roots and to a lower extent in young seedlings and flowers. Expression in strictly photosynthetic tissues was not detected by RNA/DNA hybridization. Specifically, a wild-type WRI1 cDNA (wri1)

under the control of the CAMV 35S promoter was introduced into *Arabidopsis* wild type plants and wri1-1 mutant plants. Thus, transgenic plants expressing the WRI1 cDNA under the control of the CAMV 35S promoter (wri1-cDNA, WT-cDNA) were made. In the case of the transgenic lines, 10 T2 seeds from 104 and 107 independently isolated lines were analyzed (mutant and wild-type background respectively). For wild type 10 seeds of 32 independent plants each and for the wri1 mutant 30 samples of 10 seeds each from a pooled seed batch were analyzed.

Figure 12A:
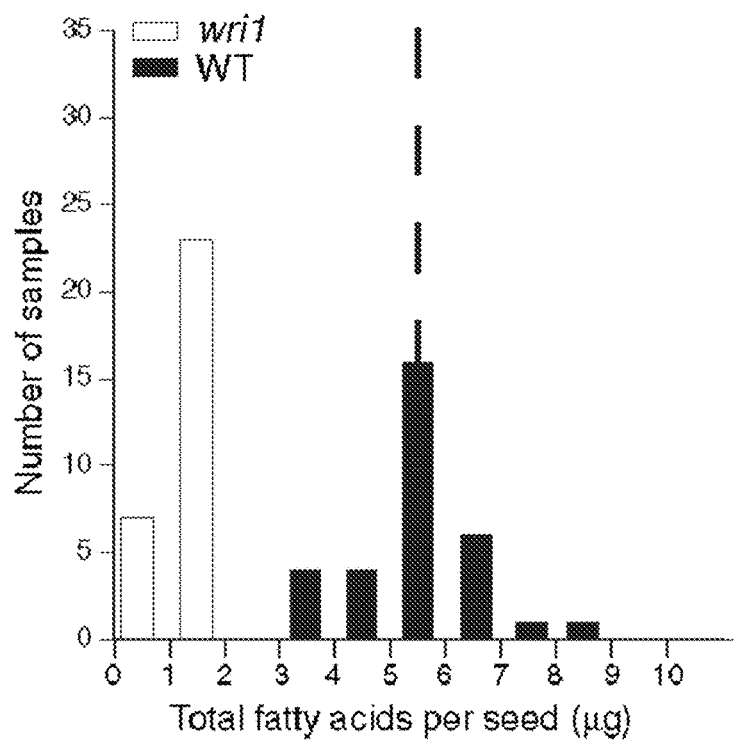
FIG. 12A-12C graphically illustrate the total fatty acids per seed for various WRINKLED plant types.
Figure 12B:
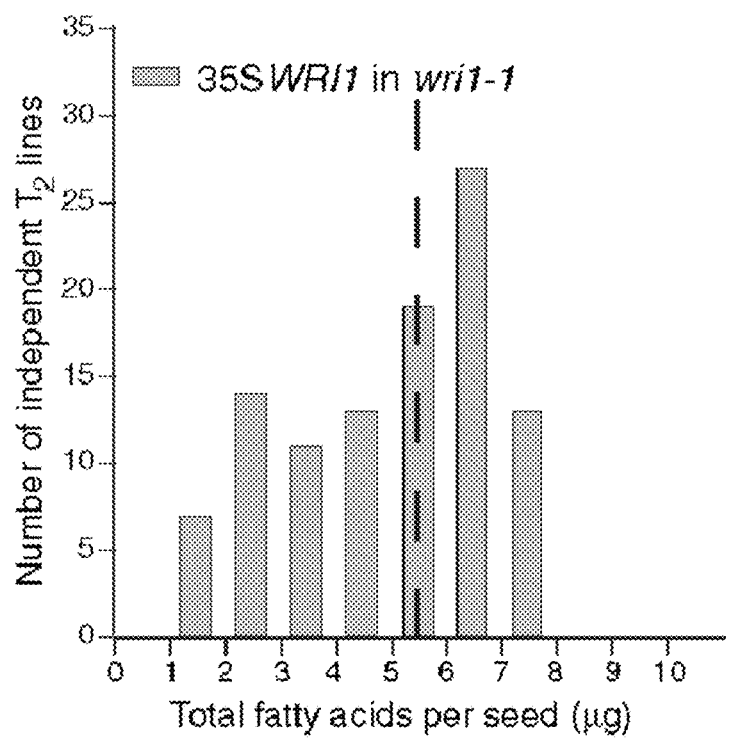
Figure 12C:
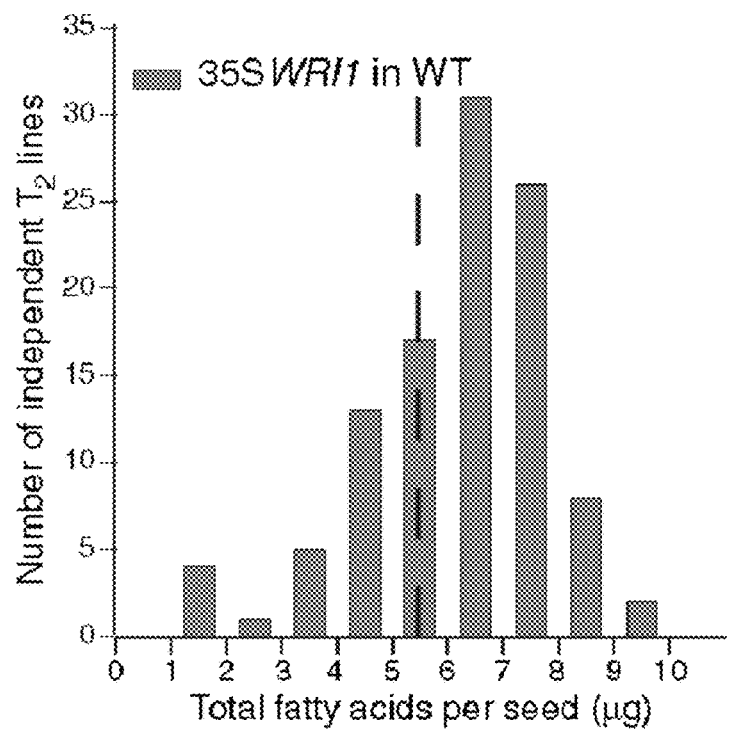

The transgenic lines were grown in parallel in 16 h light, 8 h dark, at 22° C. in the same chamber, while the untransformed lines were grown under identical conditions but in a different chamber to avoid cross-pollination between transgenic and untransformed lines. Individual plants were grouped in 1 µg intervals according to fatty acid content per seed. For better comparison, a broken line was centered through the peak of the wild type seed distribution, FIG. 12A-C. Total fatty acids were made as a measure of oil content, a distribution ranging from lines with very low to very high fatty acid content outside the range observed for wild-type plants was observed (FIG. 12A-C). Applying Student's t-test, the distributions for the wild type, transformed and untransformed, were statistically different (P<0.02). Although no WRI1 mRNA abundance data in the developing seeds for every line was available, independent transgenic lines were expected to have variable amounts of the WRI1 transcript due to positional or cosuppression effects accounting for the observed wide range of the distribution. To test the reproducibility of this effect through subsequent generations, T4 seeds of a number of lines distinguished by their high seed oil content in the T2 generation were analyzed. Several lines in the wild type and also one in the wri1-1 mutant background produced T4 seeds with 10-20% more oil per seed compared with the wild type grown in the same growth chamber. Total numbers of seeds per plant were not affected in the transgenic lines.

Figure 13A:
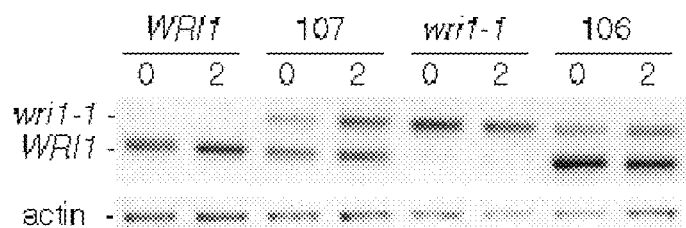
FIG. 13A-13B shows electrophoretically separated mRNAs illustrating the abundance of WRINKLED mRNAs in mutant, wild-type and transgenic lines.
Figure 13B:
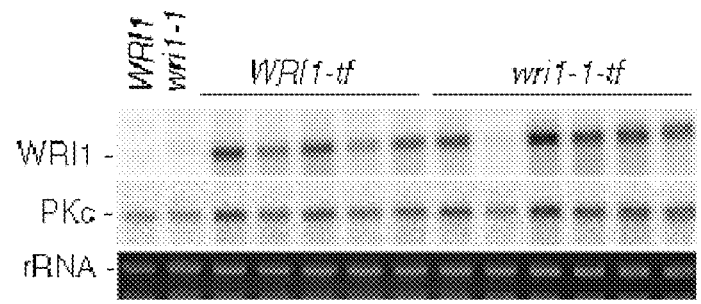

However, contrary to line 107 a small fraction of the plants of line 106 showed an abnormal morphological phenotype in the absence of sucrose. To be able to distinguish between the endogenous mutant wri1-1 RNA and the transgene-derived wild-type mRNA, semi-quantitative PCR was employed using diagnostic primers flanking the intron that was not removed in the mutant (FIG. 13A). The abundance of wild-type WRI1 mRNA derived from the transgene was clearly increased in 106 compared with the other lines. A clear-cut effect of sucrose on WRI1 RNA abundance was not visible in these experiments (FIG. 13A). Initially, this effect was not observed in the wild-type background. However, when the experiment was repeated by expressing the WRI1 cDNA under the control of the 35S promoter in a CAMBIA binary vector, transgenic lines in the wild-type and mutant backgrounds produced abnormal seedlings in the presence of sucrose. The abundance of WRI1 transcript was strongly increased in these transgenic lines compared with untransformed lines as shown in FIG. 13B. Moreover, the expression of one of the presumed target genes encoding a plastidic pyruvate kinase (PKc) was increased (FIG. 13B) in correlation with the appearance of abnormal seedlings in the presence of 2% sucrose in the medium.

3. Transgenic Seedlings Accumulated Triacylglycerols in the Presence of Sucrose.

Figure 14A:
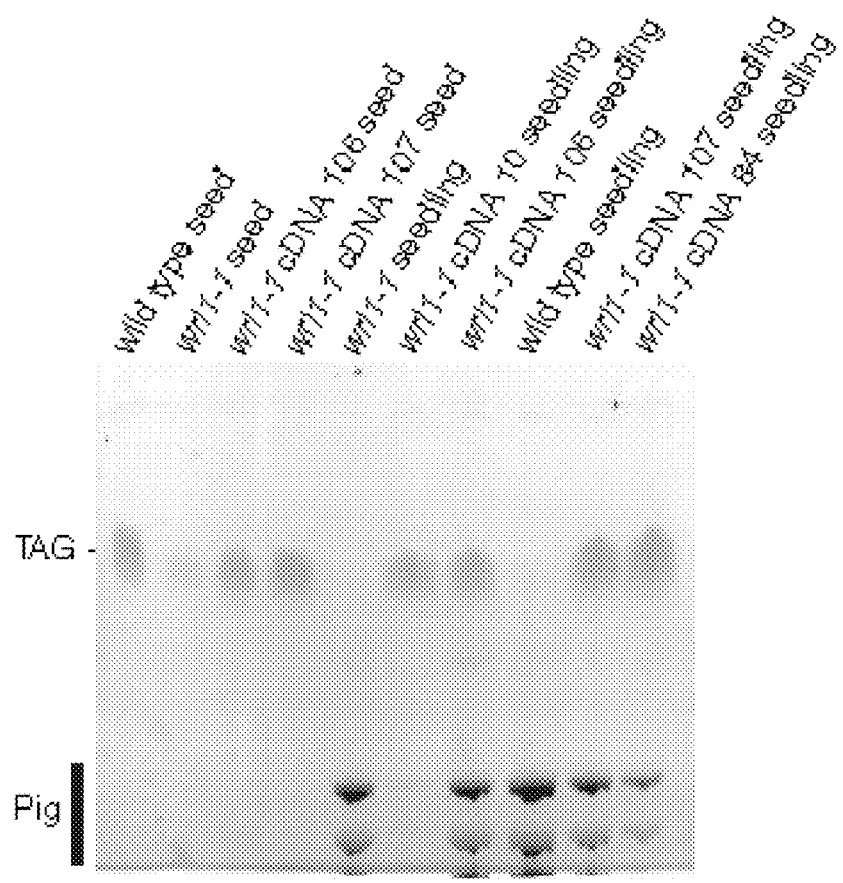
FIG. 14A-14D illustrates accumulation of triacylglycerols in transgenic seedlings.
Figure 14B:
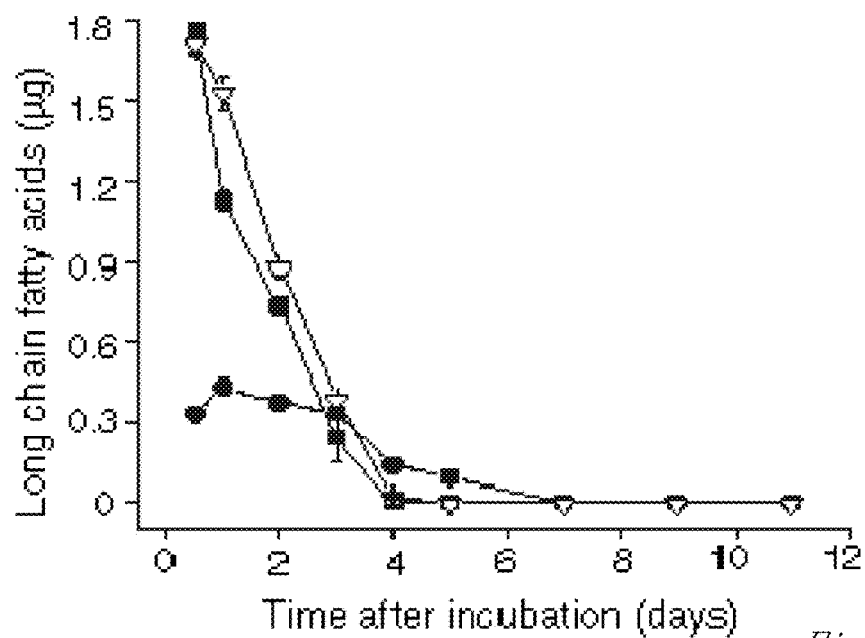
Figure 14C:
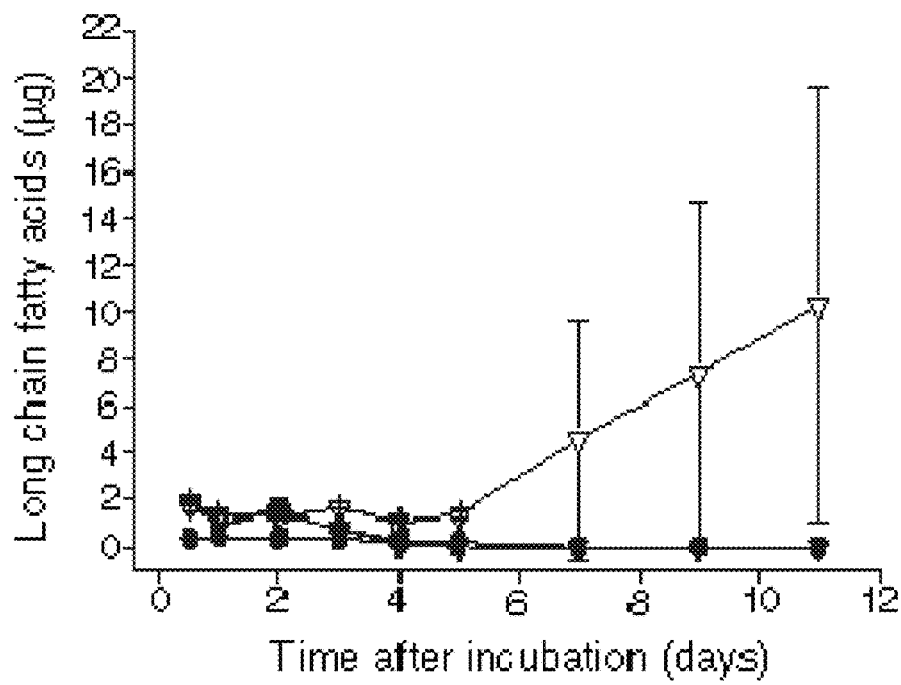
Figure 14D:
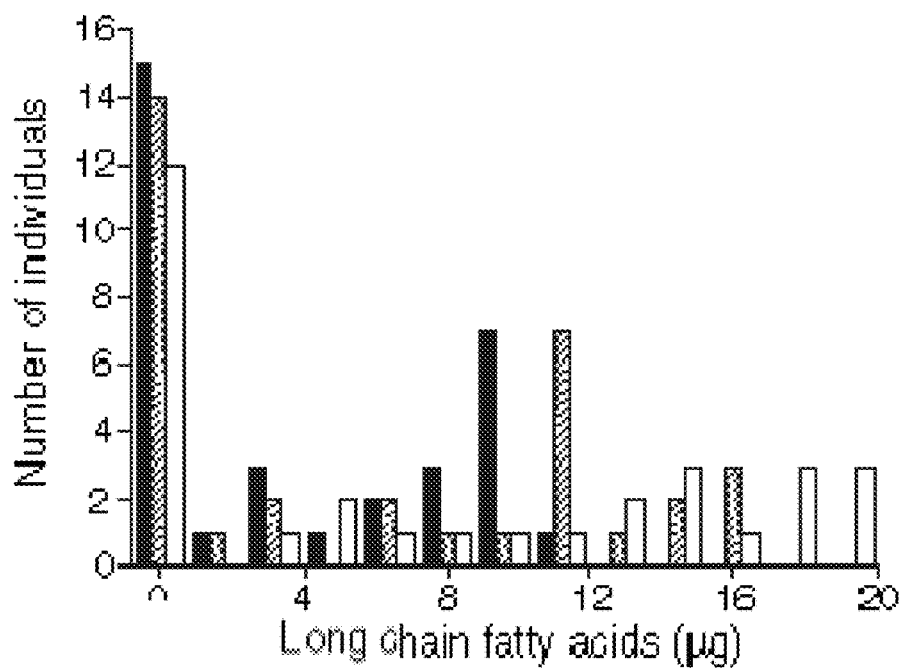

The abnormal seedlings of lines 106 and 107 and other transgenic lines were reminiscent of oil-accumulating embryos that had outgrown their seed coat. Indeed, seed oil was present in seedlings of these lines when grown on sucrose (FIG. 14A). Two additional independent transgenic lines, 10 and 84, both in the wri1-1 background were included to document that this phenomenon was not restricted to a few selected lines but generally occurs in lines which show abnormal seedling development on sucrose. To obtain more quantitative results, long-chain fatty acids (LFA) as markers for seed oil (Lu and Hills, 2002, herein incorporated by reference in its entirety) were compared for transgenic line 106, the wild type, and the wri1-1 mutant during a time course of 11 days following the incubation of stratified seeds on agar plates containing or lacking sucrose (FIG. 14B-D). In the absence of sucrose, line 106 and wild type were indistinguishable (FIG. 14B), while the wri1-1 mutant showed the characteristic low LFA content at these stages. After 3 days, LFAs were no longer detectable consistent with complete catabolism of seed oil. In the presence of sucrose (FIG. 14C), degradation of seed oil was delayed for the wild type and line 106 for approximately 1 day. Beginning with day 4, visibly aberrant seedlings were present for line 106 with yellow plants showing increasing amounts of LFAs. Following day 4, plants were no longer pooled but individually analyzed. The increasing standard deviation was due to the large variability among individual plants of line 106. Because line 106 is genetically stable showing no segregation of antibiotic-resistant and -sensitive plants, this variability reflected differences between seedlings in their ability to metabolize carbohydrates from the medium to triacylglycerols. To show this variability more explicitly, the class distribution for the amount of LFAs per individual plant of line 106 grown for 7, 9, and 11 days on sucrose-containing agar plates was determined (FIG. 14D). Remarkably, among the plants were individuals with amounts of LFAs in excess of 10-fold compared with the amount present in individual wild type seeds. Apparently, these seedlings actively synthesized triacylglycerols containing long chain fatty acids consistent with the TLC analysis (FIG. 14A). Similar, but less pronounced trends were observed for line 107). To explore whether the effect was specific for sucrose, LFAs in 11-day-old 35S-WRIT transgenic seedlings were analyzed, which were grown on different sugars as indicated in Table 4. Pools of 10 randomly picked seedlings included morphological normal and abnormal individuals of lines 106 and 107. Glucose or disaccharides giving rise to glucose seemed to be most effective (Table 4). Neither galactose, the epimer of glucose, nor the sugar alcohol sorbitol, had an effect.

TABLE 4

Sugar Specificity for Ectopic Oil Accumulation in 35S-WRI1 cDNA Transgenic Lines
Long Chain Fatty Acid Content (µg/seedling)

| Sugar type | Line 106 | Line 107 |
| --- | --- | --- |
| No sugar | 0.1 ± 0 | nd |
| Glucose | 5.1 ± 0.4 | 0.6 ± 0.2 |
| Fructose | 1.8 ± 0.4 | nd |
| Sucrose | 5.3 ± 0.3 | 0.9 ± 0.1 |
| Glucose/Fructose | 3.7 ± 0.3 | 0.9 ± 0.2 |
| Maltose | 2.9 ± 0.1 | nd |
| Sorbitol | 0.4 ± 0 | nd |
| Galactose | 0.5 ± 0.1 | nd |

In another embodiment, the engineered plants of the present inventions are contemplated for combining overexpression of WRINKLED1 with plants having reduced TGD proteins.

The inventors contemplated several methods for making inventive engineered plants with stacked genes for alterations in protein expression, i.e. one protein overexpressed while another protein has reduced expression. In one embodiment, plants engineered to overexpress a heterologous WRINKLED1 gene are used as breeding stock for introducing this heterologous gene into another transgenic engineered breeding stock having reduced TGD proteins. In a further embodiment, a heterologous WRINKLED1 gene is under control of a promoter, such as a constitutive promoter or an induced promoter or a tissue specific promoter, etc. As merely one example, the WRINKLED1 gene might be under the control of a constitutive promoter while as another example, the WRINKLED1 gene might be under the control of a ribusco promoter, etc. In a preferred embodiment, these overexpressing engineered plants are bred to engineered plants having reduced expression of a TGD protein resulting from the use of a TGD RNAi vector of the present inventions. The order of plant breeding strategy is not limited to one particular scheme. In other words the order of which plants are made and used is not important so long as the resulting engineered plant has increased expression of a WRINKLED1 gene along with reduced TGD protein for increasing lipid accumulation in vegetative tissues while retaining or regaining desirable agronomic traits. In an additional embodiment, aspects of the present inventions comprise overexpression of a heterologous WRINKLED1 gene in combination with reduced expression of a TGD protein for modifying and/or increasing lipid production in a plant or plant line. In one embodiment, TAG are increased in the vegetative tissues of engineered plants of the present inventions.

Accordingly, methods of making these engineered plants with increased TAG amounts in vegetative tissues comprises breeding WRINKLED1 overexpressing plants with engineered plants having reduced expression of a TGD gene as the result of transformation of the host plant with a TGD RNAi gene silencing vector of the present inventions. In a preferred embodiment, these methods of breeding further comprise using breeding stock with desired agronomic traits, such as large seed sizes, a particular oil composition, strong growth characteristics, growth characteristics for a particular hardiness zone, high levels of fertility, etc., and/or desirable economic traits, such as roundup ready varieties or other plant lines having glyphosate-resistance.

Thus methods of the present inventions further comprise transforming plants producing seed oil, in particular oil seed plants for expressing oil in vegetative tissues. Optimized agronomic traits of transgenic plants of the present inventions may be obtained by screening candidate plants for persistent expression of the transgene along with reduced TGD target proteins through multiple generations of breeding or rounds of vegetative propagation.

Therefore, with the discovery of the genes described herein and their effects upon oil production, described herein, the inventors' contemplated increasing the amount of oil per plant by increasing oil production in vegetative tissues. Further, the inventors contemplated that increasing the amount of oil per plant would be accomplished by increasing oil production in both vegetative tissues and seeds. Specifically, the inventors contemplated that by lowering tgd translation in plants through the use of tgd RNAi silencing constructs in specific amounts along with the overexpression of an oil regulating transcription factor, then a balance might be achieved between increased oil production and negative impacts on plant growth and fertility.

Additionally a AP2/EREB WRI1 protein described herein and in Cernac, 2004, herein incorporated by reference in its entirety, modified oil content in developing oil seeds and other tissues although it was discovered to control metabolic processes primarily for seed oil accumulation. The ectopic expression of WRI1 under the control of the CAMV 35S promoter was originally directed at the investigation of WRI1 function and not at engineering of oil content. However, even this crude expression system led to increases in seed oil content as well as the ectopic production of triacylglycerols in developing seedlings. Refined approaches toward the tissue-specific engineering of WRI1 RNA abundance as described herein, may well provide the means to control triacylglycerol biosynthesis in desirable tissues or at extended times of the life cycle of the plant.

F. F-Box Protein.

Further, an F-Box transcription protein was discovered whose overexpression in plants induced an increased production of plant oil. In fact, some of the inventors discovered that overexpression of F-box protein in transgenic *Arabidopsis* lines increased total oil content of plants by more than 10%. Therefore, the inventors contemplated that in some embodiments, by increasing the expression of the WRI1 gene and/or the F-Box gene in plants also having decreased production of TGD4, TGD3, TGD2 OR TGD1, then the resulting plants would have more desirable growth characteristics and fertility, i.e. in addition to other agronomic traits, than plants expressing normal amounts of any one of these genes or plants having lowered TGD production or overexpressing WRI1 or F-Box. In other words, engineered plants of the present inventions are contemplated to achieve a balance of highly increased lipid production in vegetative tissues and seeds balanced with desirable agronomic and commercial traits for use in producing commercially viable plant lines having significantly increased amounts of oil per plant. In one embodiment, TAG production is highly increased on a per plant and/or per acre basis.

Plants were engineered for lipid modification and/or increased lipid production in seeds using f-box genes. Indeed, this increase was confirmed over at least two generations of breeding engineered plants and the analysis was validated with two different approaches (i.e. total FAMEs and C:N ratio analysis). In particular, the overexpression of the *Arabidopsis thaliana* F-box protein gene (GenBank Accession Nos. NM_111499 (cDNA) and NP_566277 (protein) using the seed specific promoter phaseolin, produced seeds with a higher oil content phenotype (see FIGS. 15-18). Accordingly, in one aspect, the present invention provides genetic constructs for the overexpression of an F-box protein in plants. In general, such genetic constructs of the invention include embodiments described herein and in WO/2007/038345, herein incorporated by reference in its entirety. Thus, in one embodiment, plants engineered to overexpress an f-box protein gene are contemplated for use in the present inventions as original or source plants, in particular for use in breeding methods of the present inventions for introducing overexpression of F-Box into plants having lowered TGD protein. Alternatively, overexpression vectors for F-Box are used for transformation into plants having lowered TGD protein. Even further, plants overexpressing F-Box may be used as host plants where tgd RNAi is introduced into F-Box overexpressing plants. Specifically, aspects of the present inventions comprise engineering plants for overexpression of a heterologous F-box protein in plants in addition to reducing expression of a TGD protein, resulting in plants having a corresponding increase in TAG in vegetative tissues and seeds. Thus, in a preferred embodiment, plants are engineered for making increased amounts of oil in vegetative tissues while having vigorous growth rates and high levels of fertility.

In a further embodiment, the genetic constructs of the invention comprises a sequence that encodes the plant F-box protein has a polypeptide sequence that is at least 75% identical to the polypeptide sequence of an F-box/kelch-repeat protein from *Arabidopsis thaliana* (also disclosed as SEQ ID NO: 1 of WO 2007 038345, specifically incorporated by reference herein in its entirety), which is provided below as SEQ ID NO:56.

```
  1 MKAIQLLWEA IMEATKRERR REDDDGEKAS PESLVLPPEI
 41 ITEILLRLPA KSIGRFRCVS KLFCTLSSDP GFAKIHLDLI
 81 LRNESVRSLH RKLIVSSHNL YSLDFNSIGD GIRDLAAVEH
121 NYPLKDDPSI FSEMIRNYVG DHLYDDRRVM LKLNAKSYRR
161 NWVEIVGSSN GLVCISPGEG AVFLYNPTTG DSKRLPENFR
201 PKSVEYERDN FQTYGFGFDG LTDDYKLVKL VATSEDILDA
241 SVYSLKADSW RRICNLNYEH NDGSYTSGVH FNGAIHWVFT
281 ESRHNQRVVV AFDIQTEEFR EMPVPDEAED CSHRFSNFVV
321 GSLNGRLCVV NSCYDVHDDI WVMSEYGEAK SWSRIRINLL
361 YRSMKPLCST KNDEEVLLEL DGDLVLYNFE TNASSNLGIC
401 GVKLSDGFEA NTYVESLISP NSYGIES
```

In other embodiments, the plant F-box protein has a polypeptide sequence that is at least 90% identical to the polypeptide sequence of SEQ ID NO:56. In still further useful embodiments, the genetic constructs of the invention comprise a plant F-box protein having the polypeptide sequence of SEQ ID NO:56. In particular embodiments, the plant F-box protein is encoded by the nucleic acid sequence with NCBI accession number NM_111499, shown below and herein identified as SEQ ID NO:57

```
  1 TTTTTCAAAT CAAATCAGAA TACATTGATT CTGTATATCT
 41 TATTGAAAAA TCCATCAATT TACATCAACA ATTTTATATC
 81 TAATAATTAA TTTAAAGAGA AAATTTATAA AAGTTTATTA
121 GAGAGAAAGA CTCAAACTCG GATTTTATAG TCGTTATGAC
161 CCGGTTTGAC TATTGAACCG TTTAACCGAG AAATTGGGAC
201 TCAATTAAGA CAACCGAAAC TAGACCCGGA TCCAGTGTTA
241 GCGGGCTAGA TTAAGGTGTC GGGTCATAGC GGAGAAGCAA
281 CCAGACGCCA ACAATGAAAG CGATCCAGTT GCTGTGGGAA
321 GCGATAATGG AGGCGACGAA GAGAGAAAGA CGGAGAGAAG
361 ATGACGACGG CGAAAAAGCT TCACCGGAAT CACTCGTTCT
400 TCCACCAGAG ATCATTACAG AAATTCTTCT CCGATTACCA
441 GCCAAATCGA TCGGGCGATT CAGGTGCGTA TCAAAGCTCT
481 TTTGCACTTT ATCGTCAGAT CCAGGGTTCG CGAAGATTCA
521 CCTCGATCTG ATCCTTCGAA ACGAATCCGT AAGATCGCTC
561 CACCGTAAGC TCATTGTGTC TTCACATAAT CTGTACTCGT
601 TAGATTTCAA TTCGATCGGT GACGGAATTA GGGATTTAGC
641 GGCTGTGGAA CACAATTATC CTCTTAAAGA CGATCCAAGC
681 ATTTTCTCTG AGATGATTAG GAATTACGTG GGGGACCATC
721 TGTACGATGA TCGTCGCGTG ATGCTTAAGC TGAATGCGAA
761 ATCGTATCGA AGAAACTGGG TTGAGATCGT TGGATCTTCC
801 AATGGTTTAG TGTGTATCTC TCCTGGTGAA GGAGCTGTTT
841 TCTTGTATAA TCCAACTACC GGAGATTCCA AGAGATTACC
881 TGAAAATTTT CGTCCCAAAT CTGTAGAATA CGAAAGAGAT
921 AATTTCCAAA CTTATGGATT TGGTTTCGAT GGTCTCACTG
961 ATGATTACAA ATTGGTGAAG CTTGTTGCTA CCAGTGAAGA
1001 TATTCTCGAT GCTAGTGTCT ATTCCTTGAA GGCTGACTCA
1041 TGGAGACGGA TCTGCAATTT GAATTATGAG CACAACGATG
1081 GCTCCTACAC GTCCGGTGTG CATTTCAACG GTGCGATTCA
1121 CTGGGTGTTC ACAGAGAGTA GGCACAACCA AAGAGTGGTT
1161 GTAGCATTTG ATATTCAAAC CGAGGAGTTT CGAGAGATGC
1201 CAGTGCCTGA TGAAGCTGAA GATTGTTCCC ATAGGTTTAG
1241 CAACTTTGTG GTCGGAAGTC TCAATGGACG TCTCTGTGTG
1281 GTCAATAGTT GCTACGATGT GCATGATGAT ATATGGGTGA
1321 TGAGTGAGTA CGGTGAAGCT AAATCCTGGA GCAGAATTCG
1361 AATCAACTTG TTGTATAGGT CGATGAAACC GCTCTGTTCG
1401 ACTAAGAACG ATGAAGAGGT TCTTCTGGAG CTTGATGGAG
1441 ACCTGGTGTT GTACAACTTT GAAACCAATG CATCGAGTAA
1481 TCTAGGAATT TGTGGGGTTA AGCTCAGTGA CGGGTTCGAG
1521 GCAAATACAT ACGTAGAGAG CCTCATATCA CCCAACTCTT
1561 ATGGTATAGA GAGCTGAGGA AGTCTGCTTT TTGCTAAGAT
1601 ATAATAAACC AACATTCGGA TTAGAAATGT TTTAGAAACA
1641 TAATCATGTA ATATGTATCA TGTAATTAAC AACGAATGGT
1681 CAATGGGTAT TTTAAGTTTC TTTCTCCT
```

In further embodiments, the F-box protein is encoded by a nucleic acid that hybridizes to the nucleic acid sequence of SEQ ID NO: 57. In particularly useful embodiments, the F-box protein is encoded by a nucleic acid that hybridizes under stringent conditions to the nucleic acid sequence of SEQ ID NO:57.

In a further aspect, the invention provides a recombinant *Arabidopsis thaliana* plant cell having a heterologous genetic construct that includes a gene promoter sequence functionally linked to a plant F-box encoding sequence. In certain particularly useful embodiments, the F-box sequence encoded corresponds to the plant F-box polypeptide of SEQ ID NO: 56.

In yet another aspect, the invention provides a plant having a transgenic plant cell of the invention, as described above, or a part, propagule or progeny thereof comprising one of the genetic constructs of the invention.

Figure 15A:
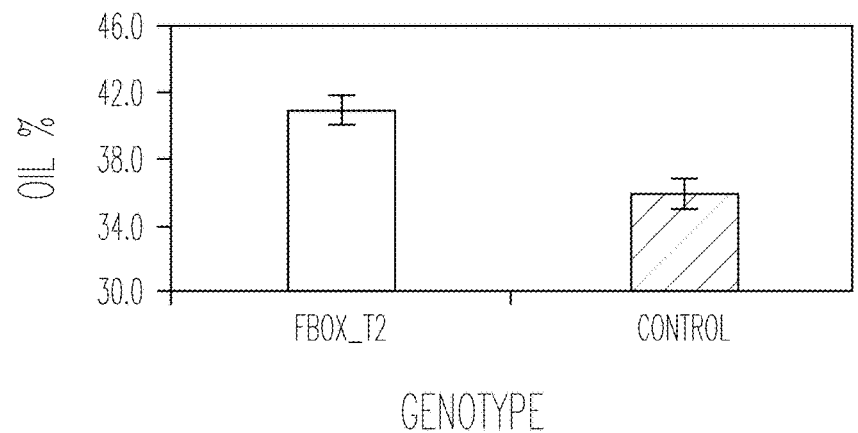
FIG. 15A-15B graphically illustrates the oil content of transgenic phaseolin-F-box lines compared with vector control lines.
Figure 15B:
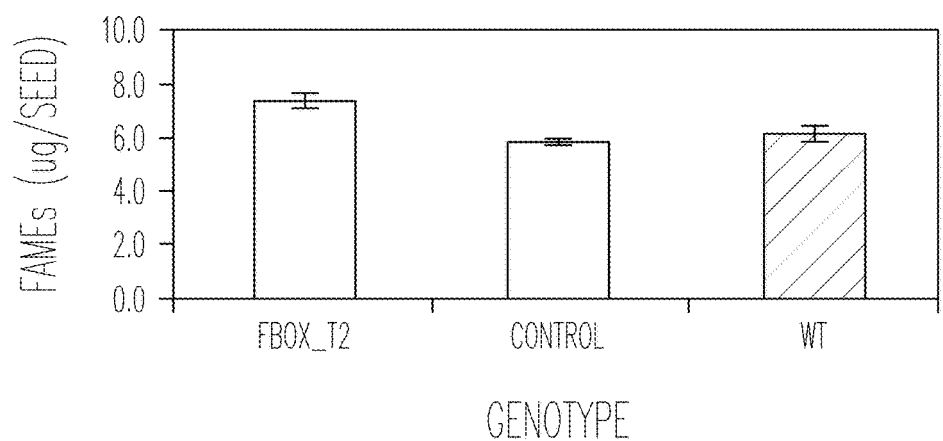
Figure 16A:
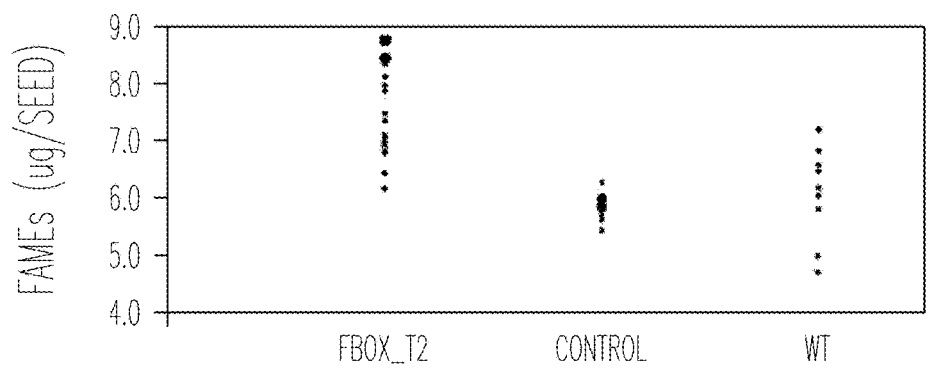
FIG. 16A-16B illustrate fatty acid methyl ester content and fatty acid types of wild type and transgenic lines.
Figure 16B:
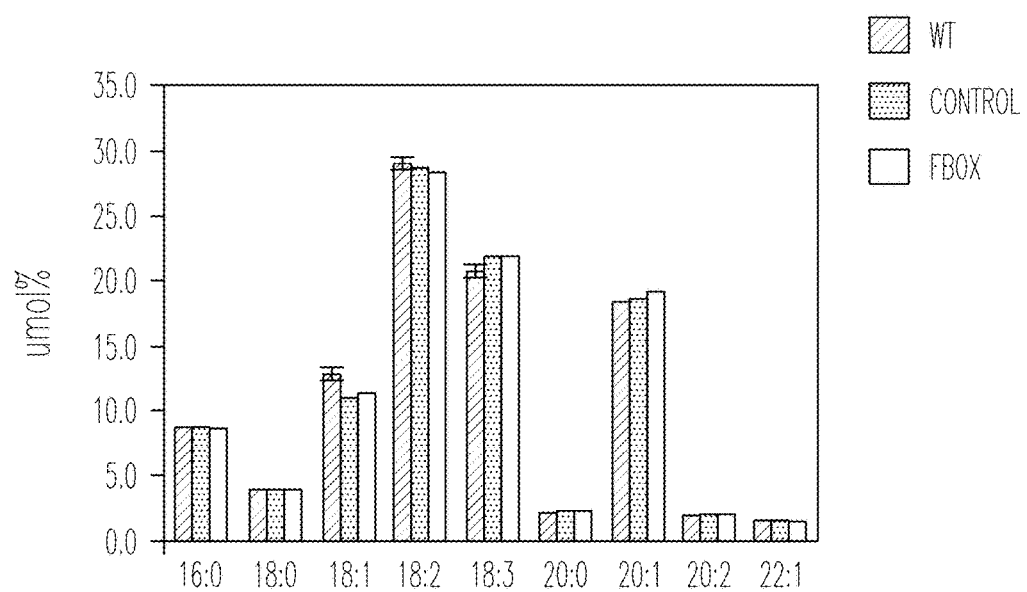

In still another aspect, the invention provides a method of modifying oil production in a plant by, first, stably incorporating into the genome of the plant a genetic construct of the invention, as described above, to provide a transformed plant, and, then, regenerating the transformed plant so that expression of the incorporated genetic construct modifies oil production in the plant. In particular embodiments, the plant modified is *Arabidopsis thaliana*. In other embodiments, the plant is an agricultural crop plant, such as corn or wheat. In further embodiments, the plant is an oil-producing agricultural crop such as soybean, palm, rapeseed or sunflower. In particular, FIG. 15A shows the oil content of transgenic phaseolin-F-box lines compared with vector control lines. Data shown are average of 18 lines (T2) and error bars are SE. FIG. 15B shows the total seed FAMEs of F-box transgenic lines compared to WT, and vector control lines (error bars are SE based on 18 lines: 3 duplicate for each line). FIG. 16A shows the total seed FAMEs of transgenic lines versus WT and vector control lines (large dots are the two lines with highest oil content and were named F-box2 and F-box3 later chosen for next generation analysis). FIG. 16B shows the fatty acid profile and fatty acid molar ratio composition of F-box transgenic lines versus control plants. Data in above section show that there is an >10% increase in oil content in F-box overexpressor lines comparing to wild type plants. This increase is confirmed both at a per mg basis and at a per seed basis. To further confirm this result, it is essential to determine changes in oil content for next generation. Furthermore, there is a small yet significant decrease in 18:1 and 18:2 in F-box overexpressors comparing to wild type, and there is a significant increase in 18:3 observed.

Figure 17A:
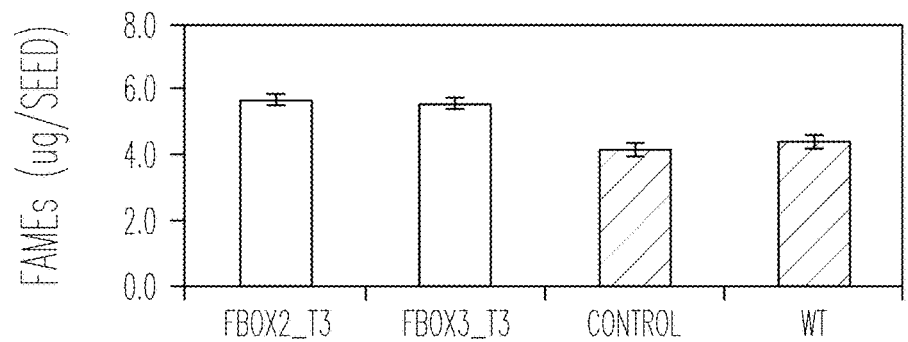
FIG. 17A-17B illustrate fatty acid methyl ester content and fatty acid types of wild type and transgenic lines.
Figure 17B:
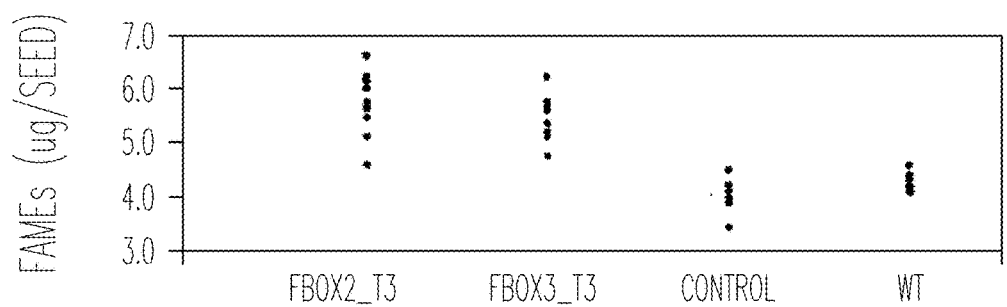
Figure 18A:
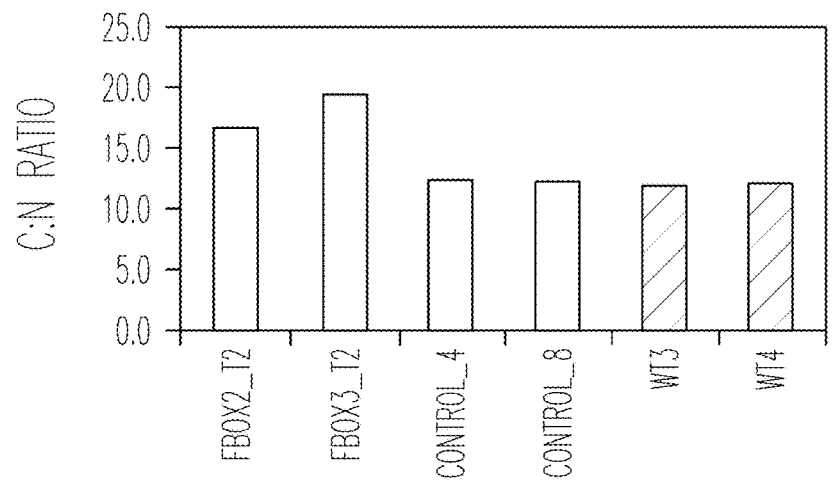
FIG. 18A-18B graphically illustrate the C:N ratios of F-box lines.
Figure 18B:
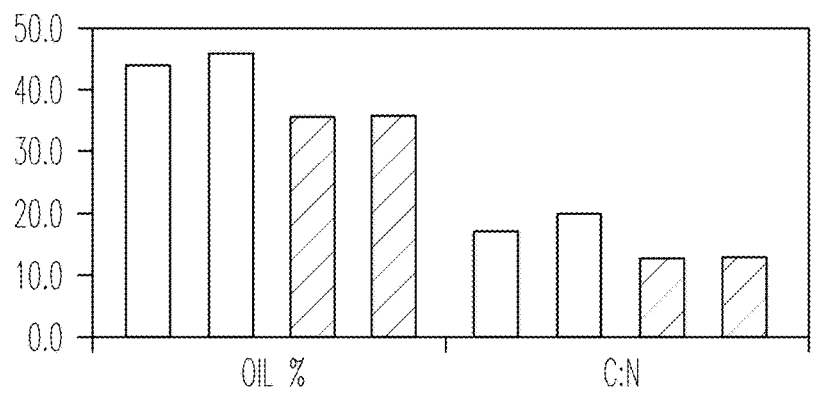

Evaluation of F-box gene at T3 generation: T2 plants from F-box2 and F-box3 lines (see FIG. 16A) were grown under standard conditions. To eliminate the potential effect of BASTA on seed metabolism, transformants were screened by PCR rather than by BASTA spray. F-box2 and F-box3 lines were grown together with WT and vector control lines. FAME analysis of T3 seeds was shown in FIG. 17A. FIG. 17A shows the total FAMEs per seed in F-box T3 seeds versus WT and vector control lines (the error bars are SE based on data obtained from 12 plants for F-box2 and F-box3 lines; 6 plants for WT and vector control lines; and the two lines here named F-box2 and F-box3 are the two data points indicated by big dots in FIG. 16A). FIG. 17B shows the total seed FAMEs of transgenic lines (F-box2 and F-box3) versus WT and vector control lines. C:N ratio analysis of T2 seeds: The two lines F-box2 and F-box3 were chosen for C:N ratio analysis. This analysis will confirm the changes the seed storage compounds (oil versus protein) (see FIG. 18). FIG. 18A shows the C:N ratio analysis for two independent lines F-box2 and F-box3. Error bars are SE based on six replicates. FIG. 18B shows the positive correlation between oil content and C:N ratio further that confirms the result (open columns are overexpressors F-box2 and F-box3; grey columns are Wild type *Arabidopsis* seeds). Thus, in some embodiments, the gene promoter sequence is a seed-specific promoter. In particularly useful embodiments, the gene promoter sequence is phaseolin. In certain particularly useful embodiments, the genetic construct comprises a pBB V-PHAS expression vector.

G. Plants Engineered for Lipid Modification and/or Increased Lipid Production in Vegetative Tissues Using at Least Two Oil Regulating Transcription Factors, for Example, a WRINKLED1 Gene and an f-Box Gene.

In another embodiment, the engineered plants of the present inventions are contemplated for combining overexpression of at least two heterologous transcriptional control genes, WRINKLED1 and f-box in combination with reduced TGD proteins. The inventors' contemplated several methods for making engineered plants of the present inventions. In one embodiment, plants engineered to overexpress an F-box protein gene are used as breeding stock for introducing this heterologous gene into another transgenic engineered breeding stock capable of overexpressing a heterologous WRINKLED1 gene such that the resulting plant overexpresses both the f-box gene and the WRINKLED1 gene. In a further embodiment, one or both heterologous genes are each under control of separate promoters, such as a constitutive promoter or an induced promoter or a tissue specific promoter, etc. As merely one example, the WRINKLED1 gene might be under the control of a constitutive promoter while the f-box gene might be under the control of a phaseolin promoter while as another example, the WRINKLED1 gene might be under the control of a ribusco promoter while the f-box gene might be under the control of a constitutive promoter, etc. In a further embodiment, these duel overexpressing engineered plants are bred to engineered plants having reduced expression of a TGD protein resulting from the use of a TGD RNAi vector of the present inventions. The order of plants used in a breeding strategy is not limited to one particular scheme. In other words the order of which plants are used in breeding is not important so long as the resulting engineered plant has increased expression of the f-box and WRINKLED1 genes along with reduced TGD protein. In an additional embodiment, aspects of the present inventions comprise overexpression of both a heterologous f-box protein gene and a WRINKLED1 gene in combination with reduced expression of a TGD protein for modifying and/or increasing lipid production in a plant or plant line. In one embodiment, TAG is increased in the vegetative tissues of engineered plants of the present inventions. In another embodiment, a vector construct is contemplated as comprising both a f-box gene and a WRINKLED1 gene for transformation and overexpression in a host plant. Further, each of these heterologous genes may be under the control of their own promoter, or both of these genes may be under control of a single promoter for making plants capable of overexpressing both of these heterologous genes. Regardless of how these new duel overexpressing engineered plants are made, the inventors' contemplated their use in making engineered plants having reduced expression of a TGD gene for substantially increasing TAG amounts in vegetative tissues with or without substantially increasing TAG amounts in seeds of these engineered plants.

Accordingly, methods of making these engineered plants with increased TAG amounts comprises breeding these f-box and WRINKLED1 overexpressing plants with engineered plants having reduced expression of a TGD gene as the result of transformation of the host plant with a TGD RNAi gene silencing vector of the present inventions. In a preferred embodiment, these methods of breeding further comprise using breeding stock with desired agronomic traits, such as large seed sizes, a particular oil composition, strong growth characteristics, growth characteristics for a particular hardiness zone, high levels of fertility, etc., and/or desirable economic traits, such as roundup ready varieties or other plant lines having glyphosate-resistance.

Thus, in one preferred embodiment, an overexpression construct of the present inventions is provided as a duel vector for overexpressing both an f-box protein gene and a WRINKLED1 gene in a host plant for increasing lipid production without significantly impacting host plant viability and fertility. Thus methods of the present inventions further comprise transforming plants, in particular oil seed plants, with a duel overexpression vector that when expressed increases oil production in the vegetative tissues of a plant. Such methods further include two primary means for making transgenic plants which further have reduced TGD expression, wherein a transgenic plant further comprises an RNAi vector of the present inventions for silencing a TGD gene. In another embodiment, a vector construct is contemplated as comprising both a f-box gene and a WRINKLED1 gene for transformation and overexpression in a host plant. Further, each of these heterologous genes may be under the control of their own promoter, or both of these genes may be under control of a single promoter for making plants capable of overexpressing both of these heterologous genes. Optimized transgenic plants of the invention may be obtained by screening candidate plants for persistent expression of the transgene through multiple generations of breeding or multiple rounds of vegetative propagation.

III. Use of Vectors and Plants Having Reduced APS1/AGPase while Overexpressing an Oil Regulating Transcription Factor, WRINKLED1 in Compositions and Methods of the Present Inventions.

*Arabidopsis thaliana* were engineered to ectopically overproduce the transcription factor WRINKLED1 (WRI1) involved in the regulation of seed oil biosynthesis. Furthermore, the misexpression (expression of a protein with reduced function compared to wild-type) and/or reduced expression of APS1 encoding a major catalytic isoform of the small subunit of ADP-glucose pyrophosphorylase involved in starch biosynthesis was reduced using an RNAi approach. The resulting AGPRNAi-WRI1 lines accumulated less starch and more hexoses. In addition, these lines produced 5.8-fold more oil in vegetative tissues than plants with WRI1 or AGPRNAi alone. Abundant oil droplets were visible in vegetative tissues. TAG molecular species contained long-chain fatty acids, similar to those found in seed oils. In AGPRNAi-WRI1 lines, the relative expression level of sucrose synthase 2 was considerably elevated and correlated with the level of sugars. The relative expression of the genes encoding plastidic proteins involved in de novo fatty acid synthesis, biotin carboxyl carrier protein isoform 2 and acyl carrier protein 1, was also elevated. The relative contribution of TAG compared to starch to the overall energy density increased 9.5-fold in one AGPRNAi-WRI1 transgenic line consistent with altered carbon partitioning from starch to oil.

IV. Gene Silencing for Knock Down of TGD Production.

Gene silencing (i.e. Gene knockdown) may or may not entirely eliminate the expression or translation of the target gene. Several methods can be used to silence a gene, in other words to reduce translations of a gene. In one method, antisense inhibition of protein production may be achieved by the use of an expression vector that overexpresses one copy of cDNA, orientated in the sense or antisense direction, which causes changes in encoded levels of proteins. However this process suffers from lack of specificity for the target sequence, incomplete efficacy, and inconsistent results. For example, expressing antisense sequences or sequences intended for co-suppression (examples of post-transcriptional gene silencing) was frequently observed in transgenic plants (Baulcombe, Plant Mol Biol 32:79-82 (1996); Jorgensen, Trends Genet. 1999; 15:11-2, all of which are herein incorporated by reference in their entirety). However, in some cases, partial functions were suppressed by antisense or co-suppression.

In contrast, methods of RNA silencing by RNAi inhibition may provide more consistent results and be amendable to controlling the amount of inhibition, such as desired in the present inventions where some translation of the targeted gene, i.e. tgd, is desired. Post-Transcriptional Gene Silencing (PTGS) is a RNA silencing pathway triggered by double stranded RNA (dsRNA). It includes antisense-mediated gene silencing, co-suppression, RNA interference (RNAi) and virus-induced gene silencing. Since RNAi may not totally abolish expression of the gene, this technique is sometimes referred as a 'knockdown,' to distinguish it from 'knockout' procedures in which expression of a gene is entirely eliminated. In preferred embodiments, tgd gene translation is "knock down" not "knock out." Post-transcriptional silencing may result in a strong reduction of mRNA accumulation in the cytoplasm without significant changes in the rate of transcriptional initiation in the nucleus. It can affect the expression of transgenes and homologous host genes, a phenomenon referred to as co-suppression (Chalcone synthase, van Blokland et al. 1994; glucanase, de Carvalho Niebel et al. 1995; chitinase, Kunz et al. 1996; nitrate reductase, Vaucheret et al. 1997). Thus, RNA molecules containing a nucleotide sequence identical to a portion of the target gene are preferred for inhibition. Although, RNA sequences with insertions, deletions, and single point mutations relative to the target sequence have also been found to be effective for inhibition. Therefore, sequence identity for use in RNAi constructs may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is also preferred.

Alternatively, the duplex region of the RNA may be defined functionally as a nucleotide sequence that is capable of hybridizing with a portion of the target gene transcript. The length of the identical nucleotide sequences may be at least 25, 50, 100, 200, 300 or 400 bases. There is no upper limit on the length of the dsRNA that can be used. For example, the dsRNA can range from about 21 base pairs (bp) of the gene to the full length of the gene or more. In one embodiment, the dsRNA used in the methods of the present invention is about 1000 bp in length. In another embodiment, the dsRNA is about 500 bp in length. In yet another embodiment, the dsRNA is about 22 bp in length. In some preferred embodiments, the sequences that mediate RNAi are from about 100 to about 200 nucleotides. The double stranded RNA of the present invention should be sufficiently similar to natural RNA that it has the ability to mediate RNAi for the target RNA.

Accordingly, in some embodiments, the present invention provides isolated RNA molecules (double-stranded or single-stranded) that are complementary to sequences required for oil biosynthesis. In some embodiments, the RNA molecules utilized mediate RNAi for one or more of the oil biosynthesis enzymes identified in FIG. 1. In some embodiments, the present invention provides transgenic plants that express dsRNA molecules that correspond to tgd RNA sequences, specifically, tgd genes. A heterologous gene encoding a tgd RNAi sequence of the present invention, which includes variants of the tgd RNAi, includes any suitable sequence that encodes a double stranded molecule specific for a target tgd RNA. Preferably, the heterologous gene is provided within an expression vector such that transformation with the vector results in expression of the double stranded RNA molecule; suitable vectors are described below. In a preferred embodiment, the tgd RNAi sequence comprises in operable combination two copies of a tgd gene or gene fragment, the 5' gene copy in the sense direction and downstream copy in the antisense direction separated by a spacer gene fragment. In another preferred embodiment, the first copy comprises a promoter DNA sequence in operable combination with the tgd sense gene (fragment). In another preferred embodiment, the first gene comprises a promoter DNA sequence in operable combination with the tgd gene as part of a RNAi expression vector construct. In another embodiment, each gene segment is ligated to each other and then ligated into an RNAi expression vector. In one embodiment the promoter is ligated to the first gene. In another embodiment the promoter is already part of the vector in which case the first gene is ligated into the RNAi vector in such a manner that the silencing sequence, i.e. sense, spacer and antisense sequence, is in operable combination with the promoter, i.e. when the promoter is active the entire tgd silencing construct is transcribed in the cell. In preferred embodiments, expression of the silencing gene construct reduces the amount of functional trigalactosyldiacylglycerol (tgd) proteins in a cell. In a preferred embodiment, the reduced amount of functional trigalactosyldiacylglycerol (tgd) proteins is in the range of 10-60%. RNAi constructs may be more effective that merely using antisense sequences, dominate negative sequences or knockout techniques that were often ineffective and required high levels of expression of the construct. In some embodiments, merely a few short double stranded RNA molecules per cell may be required for effective interference with translation of target tgd mRNA. In one preferred embodiment, an RNAi method is contemplated for use in silencing a tgd1, tgd2, tgd3 or tgd4 gene for increasing TAG and other plant oil production in vegetative tissues. Further, unlike methods comprising large copy numbers or entire cDNA sequences, RNAi molecules of the present inventions comprise 5' fragments of tgd genes in combination with constitutive promoters or regulatable, inducible promoters.

The use of inducible RNAi constructs and silencing gene constructs of the present inventions comprising inducible promoters is contemplated to avoid problems with abnormalities caused by a knocked down or knocked out gene in early developmental stages of plants. Thus in one embodiment, plants comprising silencing gene constructs of the present inventions having inducible promoters are exposed to the inducing compound after seed germination. In one embodiment, plants comprising silencing genes of the present inventions with inducible promoters are exposed to the inducing compound as seedling plants. In some embodiments, seedlings and immature plants are used to isolate oils from vegetative tissues instead of using mature plants.

There are several methods of using RNA sequences for controlling gene expression, especially for gene silencing, including RNA interference (RNAi), small interfering RNA (siRNA), small hairpin RNA (shRNA), small temporal RNAs (stRNA), microRNA (miRNA), and the like. In general, the term RNA interference (RNAi) describes the use of double-stranded RNA, comprising a sense and antisense nucleic acid for targeting specific endogenous mRNAs for degradation, thereby silencing their expression, in other words silencing translation. A dsRNA (RNAi, siRNA, shRNA, and the like) triggers destruction of a homologous mRNA that has the same sequence as one of the dsRNA strands.

V. Constructs.

The present invention relates to gene-specific silencing of genes involved in oil biosynthesis through RNA interference or other methods, and in particular, to vectors for expressing RNAi molecules that inhibit the expression of trigalactosyldiacylglycerol (tgd) protein genes in the oil biosynthesis pathway. In some embodiments, the present invention provides compositions and methods for inducible or constitutive expression of RNAi molecules, and/or for long-term expression of RNAi molecules. Hence the compositions and methods described herein are suitable for regulatable and/or sustained gene-specific silencing in cells, and further for silencing genes altering oil biosynthesis. In one embodiment, the lowering of tgd genes available for translation results in accumulation of a biosynthetic oil, in vegetative leaves and stems. In one embodiment, the biosynthetic oil comprises large amounts of triacylglycerol.

In some embodiments, the present invention provides methods and gene constructs for silencing otherwise known as down regulating one or more of the oil biosynthesis tgd enzymes. In preferred embodiments, corn-specific gene constructs encoding RNAi's specific for targeting one or more of the tgd enzymes are introduced into oil seed plants, including Brassica oil seed plants, preferably elite oil seed plants comprising agronomic traits. In some embodiments, oil content of plant parts, comprising leaves, stems, roots and seeds, of each plant are isolated and compared with control non-transgenic plants of the same age. In some preferred embodiments, oil content of plant parts, comprising leaves, stems, roots and seeds, of each plant are isolated and used for producing commercial oil products.

A. RNAi Constructs.

The present invention contemplates the use of RNA interference (RNAi) constructs to downregulate the translation of tgd genes. In some embodiments, the dsRNA used to initiate RNAi, may be isolated from native source or produced by known means, e.g., transcribed from DNA. The promoters and vectors described in more detail below are suitable for producing dsRNA. RNA is synthesized either in vivo or in vitro. In some embodiments, endogenous RNA polymerase of the cell may mediate transcription in vivo, or cloned RNA polymerase can be used for transcription in vivo or in vitro. In other embodiments, the RNA is provided transcription from a transgene in vivo or an expression construct. In some embodiments, the RNA strands are polyadenylated; in other embodiments, the RNA strands are capable of being translated into a polypeptide by a cell's translational apparatus. In still other embodiments, the RNA is chemically or enzymatically synthesized by manual or automated reactions. In further embodiments, the RNA is synthesized by a cellular RNA polymerase or a bacteriophage RNA polymerase (e.g., T3, T7, SP6). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with little or a minimum purification in order to avoid losses due to sample processing. In some embodiments, the RNA was dried for storage or dissolved in an aqueous solution. In other embodiments, the solution contains buffers or salts to promote annealing, and/or stabilization of the duplex strands. In some embodiments, the dsRNA is transcribed from the vector as two separate stands. When the dsRNA is thus-produced, the DNA sequence to be transcribed is flanked by two promoters, one controlling the transcription of one of the strands, and the other that of the complementary strand. These two promoters may be identical or different. In some embodiments, a DNA duplex provided at each end with a promoter sequence can directly generate RNAs of defined length, and which can join in pairs to form a dsRNA. See, e.g., U.S. Pat. No. 5,795,715, incorporated herein by reference. In some embodiments, the dsRNA is transcribed from the vector as one strand which forms a secondary structure which causes inhibition of translation. Inhibition is sequence-specific in that nucleotide sequences corresponding to the duplex region of the RNA are targeted for inhibition of translation of the target gene. RNA molecules containing a nucleotide sequence identical to or nearly identical to a portion of the target gene are preferred for inhibition.

Accordingly, in some embodiments, the present invention provides isolated RNA molecules (double-stranded or single-stranded) that are complementary to sequences required for oil biosynthesis. In some embodiments, the RNA molecules utilized mediate RNAi for one or more of the oil biosynthesis enzymes identified in FIG. 1. In some embodiments, probes that are specific for an oil biosynthesis pathway gene of interest are amplified from a DNA sample prepared from maize by using primers designed from maize genomic DNA or cDNA. Genes amplified from maize DNA are then used as probes for homologous genes from a genomic or cDNA libraries prepared from a maize line of interest. These genes are then inserted into an expression vector so that a nematode double stranded RNA corresponding to the gene of interest is produced when the vector is used to transfect a plant.

In some embodiments, the present invention provides transgenic plants that express dsRNA molecules that correspond to target tgd RNA. A heterologous gene encoding at least a portion of the RNAi of the present invention, which includes variants of the RNAi gene, includes any suitable sequence that encodes a double stranded molecule specific for a tgd target RNA. Preferably, the heterologous gene is provided within an expression vector such that transformation with the vector results in expression of the double stranded RNA molecule; suitable vectors are described below in the Examples.

B. Spacer Sequences for RNAi Constructs.

In preparing a construct comprising a nucleic acid sequence encoding a RNAi sequence of the present invention, various DNA fragments can be used to separate the 2 copies of the sequences for use in gene silencing. This sequence is known as a 'spacer' sequence. A spacer sequence can be manipulated, so as to provide for the DNA sequences in the desired orientation (e.g., sense or antisense) orientation. Hirai, et al. The effects of spacer sequences on silencing efficiency of plant RNAi vectors, Plant Cell Reports Volume 26, Number 5, 651-659, herein incorporated by reference in its entirety. The frequency of RNA silencing was more affected by spacer sequence than by spacer length, at least between 100 and 1800 bp. A broad range of the RNAi-induced silencing phenotypes can be generated by replacing the spacer sequence of RNAi construct tgd RNAi construct. In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Calais et al. (1987) Genes Develop. 1:1183; herein incorporated by reference in its entirety). Intron sequences have been routinely incorporated into plant transformation vectors, typically within the non-translated leader.

C. Constructs for Expression of Stacked Genes.

Heterologous genes, such as WRINKLED1 alone or in combination with AGPRNAi and F-Box, intended for expression in plants as stacked genes along with reduced TGD protein production, i.e. tgd RNAi constructs, are assembled in expression cassettes comprising a promoter. Methods which are well known to those skilled in the art may be used to construct expression vectors containing a heterologous gene and appropriate transcriptional and translational control elements. These methods include in vitro recombinant DNA techniques, synthetic techniques, and in vivo genetic recombination. Such techniques are widely described in the art (See e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y., all of which are herein incorporated by reference in their entirety). More specific examples of constructs for overexpressing heterologous genes, i.e. WRIL1 and F-box, and plants engineered for expressing these constructs are provided as described herein, and in Cernac and Benning, The Plant J, 40:575-585 (2004) and WO 2007 038345 respectively, herein incorporated by reference in their entirety.

In some embodiments, WRIL1 and/or F-box genes are expressed constitutively throughout the whole plant, for example, the CaMV 35S promoter is contemplated for use.

D. Promoters.

The methods of the present invention contemplate the use of at least one heterologous gene encoding a tgd gene silencing sequence of the present invention, or other heterologous sequence, operably linked to a promoter. Heterologous genes intended for expression in plant cells are operably connected to a promoter before or during ligation into expression constructs and cassettes. Many methods may be used to construct expression vectors containing a heterologous gene and appropriate transcriptional and translational control elements. These methods include, but are not limited to, in vitro recombinant DNA techniques, synthetic techniques, and in vivo genetic recombination. Such techniques are widely described in the art (See for example, Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.).

Promoters include but are not limited to constitutive promoters, tissue-, organ-, and developmentally specific promoters, and inducible promoters. Examples of promoters include but are not limited to: constitutive promoter 35S of cauliflower mosaic virus; a wound-inducible promoter from tomato, leucine amino peptidase ("LAP," Chao et al. (1999) Plant Physiol 120: 979-992; herein incorporated by reference); a chemically inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat. No. 5,187,267; herein incorporated by reference in its entirety); a tetracycline-inducible promoter (U.S. Pat. No. 5,057,422; herein incorporated by reference); and seed-specific promoters, such as those for seed storage proteins (e.g., phaseolin, napin, oleosin, and a promoter for soybean beta conglycin (Beachy et al. (1985) EMBO J. 4: 3047-3053; herein incorporated by reference in its entirety). In some preferred embodiments, the promoter is a phaseolin promoter.

In one embodiment, the promoter is a constitutive promoter such that the cell continuously expresses the genes in operable combination with the promoter. In another embodiment, the promoter is part of an inducible promoter system, for examples, see, Xu, et al. EMBO J., 2003, 22(10):2370-9; Lu et al., 2007, The Journal of Biological Chemistry, 282: 35945-35953; and Benning Progress in Lipid Research 47, Issue 5, 2008, 381-389, all of which are herein incorporated by reference in their entirety. In yet other embodiments of the present invention, a transgenic plant comprises a heterologous gene encoding a RNAi sequence of the present invention operably linked to an inducible promoter, and is grown either in the presence of the an inducing agent, or is grown and then exposed to an inducing agent. In still other embodiments of the present invention, a transgenic plant comprises a heterologous gene encoding a RNAi sequence of the present invention operably linked to a promoter which is either tissue specific or developmentally specific, and is grown to the point at which the tissue is developed or the developmental stage at which the developmentally-specific promoter is activated. Such promoters include seed and root specific promoters. In still other embodiments of the present invention, the transgenic plant comprises an RNAi sequence of the present invention operably linked to constitutive promoter. In further embodiments, the transgenic plants of the present invention express at least one double stranded RNA molecule at a level sufficient to reduce the proliferation of nematodes as compared to the proliferation of nematodes observed in a nontransgenic plant. Promoters. An estrogen receptor-based chemical-inducible system for use in transgenic plants. A chimeric transcription activator, XVE, was assembled by fusion of the DNA-binding domain of the bacterial repressor LexA (X), the acidic transactivating domain of VP16 (V) and the regulatory region of the human estrogen receptor (E; ER). The transactivating activity of the chimeric XVE factor, whose expression was controlled by the strong constitutive promoter G10-90, was strictly regulated by estrogens. In transgenic *Arabidopsis* and tobacco plants, stradiolactivated XVE can stimulate expression of a GFP reporter gene controlled by the target promoter, which consists of eight copies of the LexA operator fused upstream of the −46 35S minimal promoter. Upon induction by estradiol, GFP expression levels can be eightfold higher than that transcribed from a 35S promoter, whereas the uninduced controls have little detectable GFP transcripts, as monitored by Northern blot analysis. Neither toxic nor adverse physiological effects of the XVE system have been observed in transgenic *Arabidopsis* plants under the conditions tested. The XVE system thus appears to be a reliable and efficient chemical-inducible system for regulating trans gene expression in plants (Zuo, et al., Plant J. 2000 October; 24(2):265-73, herein incorporated by reference in its entirety).

E. Vectors.

In general, these vectors comprise a nucleic acid sequence encoding a RNAi silencing construct of the present invention (as described above) operably linked to a promoter and other regulatory sequences (e.g., enhancers, polyadenylation signals, etc.) required for expression in a plant. In one embodiment, the present invention contemplates a composition comprising a nucleic acid sequence encoding a tgd translation regulator of the present invention that is operatively linked to an appropriate promoter and inserted into a suitable vector for a particular transformation technique. Many methods may be used to construct expression vectors containing a heterologous gene and appropriate transcriptional and translational control elements. These methods include, but are not limited to, in vitro recombinant DNA techniques, synthetic techniques, and in vivo genetic recombination. Such techniques are widely described in the art (See for example, Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y., all of which are herein incorporated by reference in their entirety). Numerous transformation vectors are available for plant cell transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan et al. (1983) Nature 304:184, all of which are herein incorporated by reference in their entirety), the bar gene which confers resistance to the herbicide phosphinothricin (White et al. (1990) Nucl Acids Res. 18:1062; Spencer et al. (1990) Theor. Appl. Genet. 79:625, all of which are herein incorporated by reference in their entirety), the hph gene which confers resistance to the antibiotic hygromycin (Blochlinger and Diggelmann (1984) Mol. Cell. Biol. 4:2929, herein incorporated by reference in its entirety), and the dhfr gene, which confers resistance to methotrexate (Bourouis et al. (1983) EMBO J., 2:1099, herein incorporated by reference in its entirety).

In one embodiment, the present invention contemplates a composition comprising a nucleic acid sequence encoding a tgd RNAi construct of the present invention that is operatively linked to an appropriate promoter and inserted into a suitable vector for a particular transformation technique. Recombinant DNA, such as that described above, can be introduced into a plant cell in a number of ways. The choice of any specific method might depend on the type of plant targeted for transformation. In some embodiments, a vector is maintained episomally (i.e., for example, transient transformation). In other embodiments, a vector is integrated into the genome (i.e., for example, stable transformation). In one embodiment, any gene whose use in an RNAi expression vector results in the accumulation of oil in vegetative tissues such as leaf and stem is contemplated.

In yet other embodiments, the nucleic acids of the present invention are utilized to construct vectors derived from plant (+) RNA viruses (i.e., for example, brome mosaic virus, tobacco mosaic virus, alfalfa mosaic virus, cucumber mosaic virus, tomato mosaic virus, and combinations and hybrids thereof). Generally, the inserted polynucleotide of the present invention can be expressed from these vectors as a fusion protein (for example, coat protein fusion protein) or from its own subgenomic promoter or other promoter. Methods for the construction and use of such viruses are described. U.S. Pat. Nos. 5,846,795; 5,500,360; 5,173,410; 5,965,794; 5,977,438; and 5,866,785, all of which are incorporated herein by reference in their entirety.

In some embodiments of the present invention the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278, herein incorporated by reference in its entirety).

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan et al. (1983) Nature 304:184; all of which are herein incorporated by reference), the bar gene which confers resistance to the herbicide phosphinothricin (White et al. (1990) Nucl Acids Res. 18:1062; Spencer et al. (1990) Theor. Appl. Genet. 79:625; all of which are herein incorporated by reference), the hph gene which confers resistance to the antibiotic hygromycin (Blochlinger and Diggelmann (1984) Mol. Cell. Biol. 4:2929; herein incorporated by reference), and the dhfr gene, which confers resistance to methotrexate (Bourouis et al. (1983) EMBO J., 2:1099; herein incorporated by reference).

In some embodiments, the vector is adapted for use in an *Agrobacterium* mediated transfection process (See e.g., U.S. Pat. Nos. 5,981,839; 6,051,757; 5,981,840; 5,824,877; and 4,940,838; all of which are incorporated herein by reference). Construction of recombinant plasmids encoding a tgd RNAi construct in addition to recombinant Ti and Ri plasmids in general follows methods typically used with common bacterial vectors, such as pBR322. Additional use can be made of accessory genetic elements sometimes found with endogenous plasmids and sometimes constructed from foreign sequences. These may include but are not limited to structural genes for antibiotic resistance as selection genes.

Exemplary systems of using recombinant plasmid vectors that are compatible with the present invention include, but are not limited to the "cointegrate" and "binary" systems. In the "cointegrate" system, the shuttle vector containing the gene of interest is inserted by genetic recombination into a non-oncogenic plasmid that contains both the cis-acting and trans-acting elements required for plant cell transformation as, for example, in the pMLJ1 shuttle vector and the non-oncogenic plasmid pGV3850. The second system is called the "binary" system in which two plasmids are used; the gene of interest is inserted into a shuttle vector containing the cis-acting elements required for plant transformation. The other necessary functions are provided in trans by the non-oncogenic plasmid as exemplified by the pBIN19 shuttle vector and the non-oncogenic plasmid PAL4404. These and other vectors useful for these systems are commercially available.

In one embodiment, plant transformation was achieved by the floral dip method (Clough and Bent, 1998). Resistant seedlings were selected on MS medium containing 40 mg/mL of kanamycin.

Recombinant DNA, such as that described above, can be introduced into a plant cell in a number of ways. The choice of any specific method might depend on the type of plant targeted for transformation. In some embodiments, a vector is maintained episomally (i.e., for example, transient transformation). In preferred embodiments, a vector is integrated into the genome (i.e., for example, stable transformation).

F. Other Parts of Silencing Vector and Overexpression Vector Constructs.

The expression cassettes for both RNAi and overexpression vector constructs may further comprise any sequences required for expression of the silencing sequences and heterologous sequence constructs. Such additional sequences include, but are not limited to, transcription terminators, enhancers such as introns, viral sequences, and sequences intended for the targeting of the gene product to specific organelles, cell compartments, tissues, etc. A heterologous gene encoding a tgd silencing construct or overexpressed gene of the of the present invention, including variants or mutations of tgd RNAi constructs or overexpression vectors for WRI1 and F-Box, includes any suitable sequence of the inventions as described herein. Preferably, the tgd RNAi construct is provided within an expression vector such that transformation with the vector results in expression of the ds RNA for reducing translation of at least one type of TGD protein. In further embodiments, the heterologous gene is provided within an expression vector such that transformation with the vector results in expression of the heterologous protein, i.e. WRIK1 and/or F-Box polypeptide. Examples of suitable vectors are described herein.

For example, adapters or linkers can be used to join (ligate) the DNA sequence fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (See e.g., Odell et al. (1985) Nature 313:810; Rosenberg et al. (1987) Gene, 56:125; Guerineau et al. (1991) Mol. Gen. Genet., 262:141; Proudfoot (1991) Cell, 64:671; Sanfacon et al. Genes Dev., 5:141; Mogen et al. (1990) Plant Cell, 2:1261; Munroe et al. (1990) Gene, 91:151; Ballad et al. (1989) Nucleic Acids Res. 17:7891; Joshi et al. (1987) Nucleic Acid Res., 15:9627; all of which are herein incorporated by reference). Another form of gene regulation for altering oil content is using and expressing a dominant negative mutation in plants, for example, see, European Patent Application EP0945514. Oil production was also modified by the use of a silencing construct that instead of interfering with endogenous transcription or translation revealed a dominant negative form of regulation.

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Calais et al. (1987) Genes Develop. 1:1183; herein incorporated by reference). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Calderone et al. (1984) Cell 39:499; Lassoer et al. (1991) Plant Molecular Biology 17:229; all of which are herein incorporated by reference), a plant translational consensus sequence (Joshi (1987) Nucleic Acids Research 15:6643; herein incorporated by reference), an intron (Luehrsen and Walbot (1991) Mol. Gen. Genet. 225:81; herein incorporated by reference), and the like, operably linked to the nucleic acid sequence encoding a TGD.

G. Transformation Techniques.

In some embodiments of the present invention the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E.* *coli* GUS gene and the CaMV 35S transcriptional terminator (WO 93/07278; herein incorporated by reference).

Once a nucleic acid sequence encoding a tgd RNAi construct of the present invention is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, the vector is introduced through ballistic particle acceleration (i.e. gene gun) using devices (e.g., available from Agracetus, Inc., Madison, Wis. and Dupont, Inc., Wilmington, Del.). (See e.g., U.S. Pat. No. 4,945,050; and McCabe et al. (1988) Biotechnology 6:923). See also, Weissinger et al. (1988) Annual Rev. Genet. 22:421; Sanford et al. (1987) Particulate Science and Technology, 5:27 (onion); Svab et al. (1990) Proc. Natl. Acad. Sci. USA, 87:8526 (tobacco chloroplast); Christou et al. (1988) Plant Physiol., 87:671 (soybean); McCabe et al. (1988) Bio/Technology 6:923 (soybean); Klein et al. (1988) Proc. Natl. Acad. Sci. USA, 85:4305 (maize); Klein et al. (1988) Bio/Technology, 6:559 (maize); Klein et al. (1988) Plant Physiol., 91:4404 (maize); Fromm et al. (1990) Bio/Technology, 8:833; and Gordon-Kamm et al. (1990) Plant Cell, 2:603 (maize); Koziel et al. (1993) Biotechnology, 11:194 (maize); Hill et al. (1995) Euphytica, 85:119 and Koziel et al. (1996) Annals of the New York Academy of Sciences 792:164; Shimamoto et al. (1989) Nature 338: 274 (rice); Christou et al. (1991) Biotechnology, 9:957 (rice); Datta et al. (1990) Bio/Technology 8:736 (rice); European Patent Application EP 0 332 581 (orchardgrass and other Pooideae); Vasil et al. (1993) Biotechnology, 11: 1553 (wheat); Weeks et al. (1993) Plant Physiol., 102:1077 (wheat); Wan et al. (1994) Plant Physiol. 104: 37 (barley); Jahne et al. (1994) Theor. Appl. Genet. 89:525 (barley); Knudsen and Muller (1991) Planta, 185:330 (barley); Umbeck et al. (1987) Bio/Technology 5: 263 (cotton); Casas et al. (1993) Proc. Natl. Acad. Sci. USA 90:11212 (sorghum); Somers et al. (1992) Bio/Technology 10:1589 (oat); Torbert et al. (1995) Plant Cell Reports, 14:635 (oat); Weeks et al. (1993) Plant Physiol., 102:1077 (wheat); Chang et al., WO 94/13822 (wheat) and Nehra et al. (1994) The Plant Journal, 5:285 (wheat); all of which are herein incorporated by reference.

In other embodiments, direct transformation in the plastid genome is used to introduce the vector into the plant cell (See e.g., U.S. Pat. Nos. 5,451,513; 5,545,817; 5,545,818; PCT application WO 95/16783; all of which are herein incorporated by reference). The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al. (1990) PNAS, 87:8526; Staub and Maliga, (1992) Plant Cell, 4:39; all of which are herein incorporated by reference). The presence of cloning sites between these markers allowed creation of a plastid targeting vector introduction of foreign DNA molecules (Staub and Maliga (1993) EMBO J., 12:601; all of which are herein incorporated by reference). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga (1993) PNAS, 90:913; herein incorporated by reference). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway (1985) Mol. Gen. Genet, 202:179; herein incorporated by reference). In still other embodiments, the vector is transferred into the plant cell by using polyethylene glycol (Krens et al. (1982) Nature, 296:72; Crossway et al. (1986) BioTechniques, 4:320; all of which are herein incorporated by reference); fusion of protoplasts with other entities, either mini cells, cells, lysosomes or other fusible lipid-surfaced bodies (Fraley et al. (1982) Proc. Natl. Acad. Sci., USA, 79:1859; herein incorporated by reference); protoplast transformation (EP 0292435; herein incorporated by reference); direct gene transfer (Paszkowski et al. (1984) EMBO J., 3:2717; Hayashimoto et al. (1990) Plant Physiol. 93:857; all of which are herein incorporated by reference).

In still further embodiments, the vector may also be introduced into the plant cells by electroporation (Fromm, et al. (1985) Proc. Natl. Acad. Sci. USA 82:5824; Riggs et al. (1986) Proc. Natl. Acad. Sci. USA 83:5602; all of which are herein incorporated by reference). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus which are grown into whole plants.

H. Agrobacterium-Mediated Plant Transformation.

In some embodiments, the vectors comprising a nucleic acid sequence encoding a tgd RNAi construct or overexpression construct of the present invention are used in Agrobacterium-mediated transformation (Gelvin, Stanton B. and Schilperoort, Robert A, Plant Molecular Biology Manual, 2nd ed. Kluwer Academic Publ., Dordrecht 1995 in Sect., Ringbuc Zentrale Signatur: BT11-P; Glick, Bernard R. and Thompson, John E. Methods in Plant Molecular Biology and Biotechnology, S. 360, CRC Press, Boca Raton 1993; herein incorporated by reference). For example, Agrobacterium mediated transformation can be performed using the GV3 (pMP90) (Koncz and Schell 1986, Mol. Gen. Genet. 204:383-396) or LBA4404 (Clontech) Agrobacterium tumefaciens strain. Arabidopsis thaliana can be grown and transformed according to standard conditions (Bechtold 1993, Acad. Sci. Paris. 316:1194-1199; Bent et al. 1994, Science 265:1856-1860). Additionally, rapeseed can be transformed with the constructs of the present inventions via cotyledon or hypocotyl transformation (Moloney et al., 1989, Plant cell Report 8:238-242; De Block et al., 1989, Plant Physiol. 91:694-701). Use of antibiotic for Agrobacterium and plant selection depends on the binary vector and the Agrobacterium strain used for transformation. Rapeseed selection is normally performed using kanamycin as selectable plant marker. Additionally, Agrobacterium mediated gene transfer to flax can be performed using, for example, a technique described by Mlynarova et al. (1994, Plant Cell Report 13:282-285). Alternatively, plants may be transformed in vivo, such as by transformation of a whole plant by Agrobacteria infiltration of adult plants, as in a "floral dip" method (Bechtold N, Ellis J, Pelletier G (1993) Cr. Acad. Sci. III—Vie 316:1194-1199; herein incorporated by reference). Transformation of soybean can be performed using for example a technique described in EP 0424 047, U.S. Pat. No. 5,322,783 (Pioneer Hi-Bred International) or in EP 0397 687, U.S. Pat. No. 5,376,543 or U.S. Pat. No. 5,169,770 (University Toledo). Soybean seeds are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to moisture content less than 20% (fresh weight) in a sealed Petri dish until further use. The method of plant transformation is also applicable to Brassica and other crops. In particular, seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. The seed coats are removed and the seeds are air dried overnight in a half-open sterile Petri dish. During this period, the seeds lose approximately 85% of their water content. The seeds are then stored at room temperature in a sealed Petri dish until further use. Agrobacterium tumefactions culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and re-suspended in MS (Murashige and Skoog, 1962) medium supplemented with 100 µM acetosyringone. Bacteria cultures are incubated in this pre-induction medium for 2 hours at room temperature before use. The axis of soybean zygotic seed embryos at approximately 44% moisture content were imbibed for 2 hours at room temperature with the pre-induced Agrobacterium suspension culture. (The imbibition of dry embryos with a culture of Agrobacterium was also applicable to maize embryo axes). The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the Agrobacteria. The liquid medium is used to moisten the sterile filter paper. The embryos are incubated during 4 weeks at 25° C., under 440

μmol m⁻²sec⁻¹ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 440~mol m-2 sec-1 and 12 hours photoperiod for about 80 days. Samples of the primary transgenic plants (T0) are analyzed by PCR to confirm the presence of T-DNA. These results are confirmed by Southern hybridization wherein DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labeled probe by PCR, and used as recommended by the manufacturer.

I. Host Plants.

Host cells, tissues and plants that are transformed with a heterologous recombinant silencing gene encoding a tgd gene or tgd gene fragment of the present invention include, but are not limited to, those plant organisms that naturally express oils comprising triacylglycerols (TAGs) and those plant organisms in which it is commercially feasible to grow for harvesting large amounts of the TAG products. The methods of the present invention are not limited to any particular plant, including monocotyledons (monocots) and dicotyledons (dicots). Such plant organisms include but are not limited to, oleaginous plants. Examples of oleaginous plants include oil seed-producing plants, such as soybean, rutabaga, rapeseed (*Brassica napus* L. and *B. campestris* (canola)), sunflower, cotton, corn, cocoa, safflower, oil palm, coconut palm, flax, castor, peanut, rice, etc. Many commercial cultivars of these plants, i.e. elite cultivars, may be transformed with heterologous recombinant silencing genes of the present inventions. In a preferred embodiment, a host plant is a mustard family (Brassicaceae; Cruciferae) plant, such as *Arabidopsis thaliana, Brassica napus* L. and *B. campestris* plants, rutabaga plants, rape plants, field cabbage plants, for harvesting oils, such as rape oil, canola oil, mustard oil, oil of Colza, and the like. In a preferred embodiment, a host organism comprises a heritable heterologous recombinant silencing gene passed on to progeny plants. In another aspect, the invention provides transgenic plant cells comprising any of the genetic constructs described herein. In certain useful embodiments, the transgenic plant cell is *Arabidopsis thaliana*. In some embodiments, the plant cells is a cell from an oil-producing agricultural crop such as soybean, palm, rapeseed (canola), safflower, grape seed or sunflower. In other embodiments, the transgenic plant cell is an agricultural crop plant, such as corn or rice.

In one embodiment, the inventors contemplate inserting vectors comprising heterologous transgenic tgd RNAi silencing genes into a plant host cell and plant host tissue. A heterologous recombinant silencing gene comprising a tgd gene or tgd gene fragment of the present invention, including variants or mutations of a tgd gene or tgd gene fragment, includes any suitable tgd sequence that results in accumulation of oil in plant cells, plant leaf tissue and plant stem tissue in addition to the entire plant. Whole plants will be grown from transformed host cells or tissues, for example, from protoplast cells, such as hypocotyls protoplasts, cotyledons, shoots, embryo, plantlet meristem tissue, shoots, in vitro microspore culture, and the like. In one embodiment, the inventors contemplate inserting a silencing vector of the present invention comprising a heterologous transgenic tgd RNAi silencing gene into any plant cell or plant tissue capable of being grown into a first generation whole plant, for example, mesophyllprotoplasts, hypocotyl explants, cotyledon explants, an embryo, callus, embryogenic callus, a plantlet, and the like.

Preferably, the recombinant-silencing gene comprising a tgd gene is provided within an expression vector comprising a promoter in operable combination with the tgd silencing gene such that transformation with the vector results in expression of the silencing gene. In some embodiments, expression is contingent upon induction of the prompter. In preferred embodiments, the silencing gene constructs are integrated into the plant genome. Suitable vectors are described herein.

In yet other embodiments of the present invention, a transgenic organism (i.e., for example, a transgenic plant cell, plant seed, plant tissue or plant seedling) comprises a gene encoding a heterologous recombinant silencing gene of the present invention operably linked to an inducible promoter, is grown either in either the presence or absence of the inducing agent and/or inducing environmental condition (i.e., for example, where the inducing agent is a chemical), or is germinated or grown into a seedling or mature plant and then exposed to an inducing agent. In still other embodiments of the present invention, a transgenic organism comprises a gene encoding a heterologous recombinant silencing gene comprising a tgd gene of the present invention is operably linked to a promoter which is either species, cell, and/or tissue specific or developmentally specific, and is grown to the point at which the organism is developed or the developmental stage at which the developmentally-specific promoter is activated. Such promoters include, but are not limited to, tissue specific promoters.

In some embodiments, when gene expression is silenced, i.e. reduced, one result is increased oil content of a plant tissue. It is not intended to limit the type of plant tissue. Indeed, a variety of plant tissues are contemplated for use for producing oil of the present inventions including but not limited to ground tissue, parenchyma tissue, leaf tissue, petiole tissue, stem tissue, stalk tissue, shoot tissue, epidermal tissue, dermal tissue, phloem tissue, vascular tissue, pith tissue, photosynthetic tissue, lamina tissue, chlorenchyma tissue, mesophyll tissue, stoma tissue, etc. In some embodiments, the invention provides an RNAi expression vector for silencing a gene in a cell. In particular for silencing genes for altering oil biosynthesis. In some embodiments, the silenced gene increases oil content of a plant cell. It is not intended to limit the type of plant cell used for increasing oil content. Indeed, a variety of plant cells are contemplated for producing oil of the present inventions including but not limited to a meristem cell, a mesophyll cell, a spongy mesophyll cell, a protoplast cell, a dermal cell, an epidermal cell, a parenchyma cell, collenchyma, a sclerenchyma cell, a companion cell, a guard cell, a subsidiary cell, an epidermal hair cell (a trichome), etc. In one embodiment, a plant cell for use in the present inventions comprises a plastid. In one embodiment, a plant cell for use in the present inventions comprises a chromoplast. In one embodiment, a plant cell for use in the present inventions comprises a leucoplast, such as a leucoplast exposed to light. In a preferred embodiment, a plant cell for use in the present inventions comprises chlorophyll. In another preferred embodiment, a plant cell for use in the present inventions comprises a chloroplast. In a further embodiment, the silencing genes result in an increase of production of fatty acids. In a further embodiment, increase of production of fatty acids refers to an increase (accumulation) of a fatty acid including but not limited to a fatty acid for use in a biofuel. Indeed, a fatty acid accumulated by the compositions and methods of the present inventions include but are not limited to monogalactosyldiacylglycerol (MGDG), monogalactosyl-diacylglycerol (MGDG) (sn-2) trigalactosyldiacylglycerol (TGDG), triacylglycerol (TAG) and triacylglycerol (TAG) 18:0, diacylglycerol (DAG), alpha-naphthol straining fatty acid, trigalactosyldiacylglycerol (triGDG), digalactosyl diglycerides (DGDG), digalactosyl diglycerides (DGDG) (sn-2), SQDG tetragalactosyldiacylglycerol (TetraGDG), specifically 16:0, 16:1, 18:0 18:1. In one embodiment, a transgenic organism (i.e., for example, a transgenic Brassicaceae plant cell, plant seed, plant tissue or plant seedling) is grown under conditions sufficient to effect increased production of TAGs in vegetative tissues.

J. Growing and Breeding Plants of the Present Inventions.

The plant life cycle for oil production with this invention is 4 to 6 weeks in a laboratory environment. It takes 4 weeks for the plants to form canopies, at which time alteration of a TGD gene occurs. The promoter system controlling the TGD gene function is inducible by using estrogen. Disruption of the genes prior to plant growth and development is harmful to the health of the plant, and causes the plant to turn yellow. Hence, the plant must be harvested after the oil accumulates in the leaf and stem structures. Harvesting is contemplated 1 to 2 weeks after disruption of the TGD gene.

1. Growing Transformed Cells into Plants.

After selecting for transformed plant material that can express the heterologous gene encoding a tgd RNAi construct of the present invention, whole plants are regenerated. Plant regeneration from cultured protoplasts is described in Evans et al. (1983) Handbook of Plant Cell Cultures, Vol. 1: (MacMillan Publishing Co. New York); and Vasil I. R. (ed.), Cell Culture and Somatic Cell Genetics of Plants, Acad. Press, Orlando, Vol. I (1984), and Vol. III (1986); herein incorporated by reference. It is known that many plants can be regenerated from cultured cells or tissues, including but not limited to all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

Transgenic lines are established from transgenic plants by tissue culture propagation. The presence of nucleic acid sequences encoding a tgd RNAi construct of the present invention (including mutants or variants thereof) may be transferred to related varieties by traditional plant breeding techniques. In some embodiments of the present invention, a plant oil comprising TAG is produced in vivo, by providing an organism transformed with a heterologous gene encoding a tgd RNAi construct of the present invention and growing the transgenic organism under conditions sufficient to effect production of TAGs.

In other embodiments of the present invention, a plant oil comprising TAG is produced in vivo by transforming an organism with a heterologous gene encoding a tgd RNAi construct of the present invention and growing the transgenic organism under conditions sufficient to effect production of TAGs.

2. Breeding Transgenic Plants.

After each first generation transgenic plant is constructed, progeny from each of the first generation transgenic plants are bred, for example as in cross-breeding by sexual fertilization to produce second generation transgenic plants comprising various combinations of both a silencing construct, and in some embodiments an overexpression vector, and commercially desired traits. In a further embodiment, transgenic plants with one silencing gene are cross-bred to transgenic plants comprising other silencing genes. For example, various combinations of progeny from the first generation transgenic plants are crossbred to other corn plants in order to produce second generation transgenic showing a reduction in oil content. Progeny of the second generation ($F_2$) transgenic plants are cross-bred by man using sexual fertilization to other $F_2$ generation plants or with first generation transgenic plants to produce third generation transgenic plants that contain one or more silenced genes, or combinations thereof. For example, in one embodiment, cross-breeding a second generation transgenic plant with a reduction in tgd expression with another second generation transgenic plant with a reduction in tgd expression produces a third generation transgenic plant with reduced tgd expression that is economically desirable for (accumulating) oil in vegetative tissues. In other embodiments, transgenic plants with various combinations of reduced oil enzymes can be made by cross-breeding progeny from a particular transgenic plants. For example, Zhang et al, Theor. Appl. Genet. 92: 752-761, (1996), Zhong et al, Plant Physiol. 110:1097-1107, (1996), and Zhong et al, Planta, 187:483-489, (1992), herein incorporated by reference, provide methods for making transgenic plants by sexual fertilization.

Plants provided by the present inventions are contemplated for use in breeding to other plants, for producing commercial plant lines have increased oil in vegetative tissues along with other desired agronomic traits, such as insect resistance, pathogen resistance, drought resistance, cold resistance, fertility, etc.

Alternatively, plant material is transformed as above with a plasmid containing a heterologous RNAi expression cassette encoding a tgd-silencing construct. The transgenic plant is grown from the transformed plant material. Next, plant material from this transgenic plant is transformed with a second plasmid containing a heterologous expression cassette encoding a different tgd silencing construct and a second selectable marker for stacking tgd-silencing constructs. The double transgenic plant is then grown from the transformed plant material. Such that any desired combination of silenced genes in transgenic plants are contemplated. In a preferred embodiment, the above heterologous RNAi sequence expression cassettes further include therein nucleotide sequences that encode one or more selectable markers that enable selection and identification of transgenic plants that express the modified oil of the present invention. In some embodiments, the selectable markers confer additional benefits to the transgenic plant such as herbicide resistance, insect resistance, and/or resistance to environmental stress.

Alternatively, the above transformations are performed by co-transforming the plant material with a first plasmid containing a gene expression cassette encoding a selectable marker and a second plasmid containing a heterologous RNAi sequence expression cassette encoding a silencing construct. The advantage of using a separate plasmid is that after transformation, the selectable marker can be removed from the transgenic plant by segregation, which enables the selection method for recovering the transgenic plant to be used for recovering transgenic plants in subsequent transformations with the first transgenic plant. Examples of preferred markers that provide resistance to herbicides include, but are not limited to, the bar gene from *Streptomyces hygroscopicus* encoding phosphinothricin acetylase (PAT), which confers resistance to the herbicide glufonsinate; mutant genes which encode resistance to imidazalinone or sulfonylurea such as genes encoding mutant form of the ALS and AHAS enzyme as described by Lee at al. EMBO J. 7: 1241 (1988) and Miki et al., Theor. Appl. Genet. 80: 449 (1990), respectively, and in U.S. Pat. No. 5,773,702, all of which are herein incorporated by reference genes which confer resistance to glycophosphate such as mutant forms of EP SP synthase and aroA; resistance to L-phosphinothricin such as the glutamine synthetase genes; resistance to glufosinate such as the phosphinothricin acetyl transferase (PAT and bar) gene; and resistance to phenoxy propionic acids and cyclohexones such as the ACCAse inhibitor-encoding genes (Marshall, et al. Theor. Appl. Genet. 83: 435 (1992), herein incorporated by reference). The above list of genes which can import resistance to an herbicide is not inclusive and other genes not enumerated herein but which have the same effect as those above are within the scope of the present invention. Examples of preferred genes which confer resistance to pests or disease include, but are not limited to, genes encoding a *Bacillus thuringiensis* protein such as the delta-endotoxin, which is disclosed in U.S. Pat. No. 6,100,456, herein incorporated by reference; genes encoding lectins, (Van Damme et al., Plant Mol. Biol. 24: 825 (1994), herein incorporated by reference); genes encoding vitamin-binding proteins such as avidin and avidin homologs which can be used as larvicides against insect pests; genes encoding protease or amylase inhibitors, such as the rice cysteine proteinase inhibitor (Abe, et al., J. Biol. Chem. 262: 16793 (1987), herein incorporated by reference) and the tobacco proteinase inhibitor I (Hubb, et al., Plant Mol. Biol. 21:985 (1993)); genes encoding insect-specific hormones or pheromones such as ecdysteroid and juvenile hormone, and variants thereof, mimetics based thereon, or an antagonists or agonists thereof; genes encoding insect-specific peptides or neuropeptides which, upon expression, disrupts the physiology of the pest; genes encoding insect-specific venom such as that produced by a wasp, snake, etc.; genes encoding enzymes responsible for the accumulation of monoterpenes, sesquiterpenes, asteroid, hydroxamine acid, phenylpropanoid derivative or other non-protein molecule with insecticidal activity; genes encoding enzymes involved in the modification of a biologically active molecule (see U.S. Pat. No. 5,539,095 to Sticklen et al., which discloses a chitinase that functions as an anti-fungal); genes encoding peptides which stimulate signal transduction; genes encoding hydrophobic moment peptides such as derivatives of Tachyplesin which inhibit fungal pathogens; genes encoding a membrane permease, a channel former or channel blocker (for example, cecropin-beta lytic peptide analog renders transgenic tobacco resistant to *Pseudomonas solanacerum*) (Jaynes, et al. Plant Sci. 89:43 (1993), herein incorporated by reference); genes encoding a viral invasive protein or complex toxin derived therefrom (viral accumulation of viral coat proteins in transformed cells of some transgenic plants impart resistance to infection by the virus the coat protein was derived as shown by Beachy, et al. Ann. Rev. Phytopathol. 28:451 (1990); genes encoding an insect-specific antibody or antitoxin or a virus-specific antibody (Tavladoraki, et al. Nature 366: 469 (1993), herein incorporated by reference); and genes encoding a developmental-arrestive protein produced by a plant, pathogen or parasite which prevents disease. The above list of genes which can import resistance to disease or pests is not inclusive and other genes not enumerated herein but which have the same effect as those above are within the scope of the present invention. Examples of genes which confer resistance to environmental stress include, but are not limited to, mtld and HVA1, which are genes that confer resistance to environmental stress factors; rd29A and rd19B, which are genes of *Arabidopsis thaliana* that encode hydrophilic proteins which are induced in response to dehydration, low temperature, salt stress, or exposure to abscisic acid and enable the plant to tolerate the stress (Yamaguchi-Shinozaki, et al., Plant Cell 6: 251-264 (1994)).

3. Evaluation of Seed Viability/Fertility.

An exemplary method for determining viability, i.e. germination levels of seeds from plants of the present inventions is contemplated as a Warm Germination Test. Seeds may be placed in a row on a piece of wet filter paper, covered by another piece of wet filter paper, rolled up, then wrapped with a piece of waxed paper and placed in a large beaker with 1 inch of water at the bottom. The beaker is incubated in a growth chamber at 25° C. Seed germination is evaluated at day 5 of incubation.

4. Evaluation of Agronomic Traits by Field Trials.

In one embodiment, the transgenic plants are evaluated for agronomic performance associated with a silenced tgd gene. Agronomic field trials may be conducted as two row plots planted and thinned to a density of 30,000 plants per acre. Field trials are contemplated for being conducted as two-row plots seeded at nine seeds per foot in 12-foot rows with a 3-foot border on 30-inch-row spacing. Seed may be sampled from every plot and submitted for proximate analysis using near-infrared transmittance. Oil and protein data may be reported on a dry matter basis. Outlier analysis based on deleted studentized residuals using Statistical Analysis Software (SAS) may be performed on data prior to statistical analysis. Statistical analyses may be run using mixed model procedures in SAS. The analysis may be performed using a split-plot model to compare positive to negative isolines within the transgenic event. The analysis may be run across locations, with locations, replications within locations, and their interactions with the fixed effects considered random effects.

K. Harvesting/Isolating Oils from Plants of The Present Inventions.

In some embodiments of the present invention, the methods for accumulating oils in vegetative tissues, i.e. including TAGs, further comprise isolating the oils and TAGs produced. Several methods have been reported, and include harvesting the transgenic plants and extracting TAGs (see, for example, Christie, (1982) Lipid Analysis. 2nd Edition (Pergamon Press, Oxford); and Kates, (1986) Techniques of Lipidology (Elsevier, Amsterdam)). Extraction procedures preferably include solvent extraction, and typically include disrupting cells, as by chopping, mincing, grinding, and/or sonicating, prior to solvent extraction. In one embodiment, lipids are extracted from the tissue according to the method of Bligh and Dyer (1959) (Can J Biochem Physiol 37: 911-917). In yet other embodiments of the present invention, the TAGs are further purified, as for example by thin layer liquid chromatography (TLC), gas-liquid chromatography, counter current chromatography, high performance liquid chromatography, and the like.

In one exemplary embodiment, leaf lipid extracts of the wild type and the tgd1-1 and tgd2-1 mutants were compared by TLC. In the tgd2-1 sample a lipid staining positive for sugar and co-chromatographing with authentic trigalactolipid of tgd1-1 is present. See, FIG. 6A. A lipid co-chromatographing with authentic triacylglycerol accumulating in tgd1-1 leaves was present in the tgd2-1 sample as well. See, FIG. 6B. Quantitative analysis of the polar lipids indicated similar changes in the two mutants with relative amounts of the monogalactolipid and digalactolipid reduced and relative amounts of phosphatidylcholine increased. See, FIG. 6C. In addition, trigalactolipid was present to a similar extent in both mutants (tgd 1-1, 2.7±1.4 mol %; tgd 2-1, 1.6±0.4 mol %; n=4; data are ±SD) but was not detectable in the wild type. Analyzing the fatty acid composition of the two galactolipids indicated a reduction of 18-carbon fatty acids and an increase in 16-carbon fatty acids to the same extent in both mutants. See, FIG. 10D. These overall fatty acid compositions for the tgd 2-1 mutant imply a change in molecular species distribution in the two galactolipids consistent with a reduction of molecular species derived from the ER pathway. In addition, similar to the tgd 1-1 mutant carrying a weak chemically-induced mutant allele, the tgd 2-1 mutant produced a fraction 43%, 281 of 651 in a representative sample) of aborted seeds.

In summary, for exemplary plants such as *Arabidopsis thaliana* plants, tgd-1, 2, and 3 mutant genes were shown to contribute significantly to TAG accumulation in leaves of TAGs through ER mechanisms using a variety of mutant tgd gene genotypes with a range of phenotypes. In general, tgd mutants were impaired in the ER-pathway while showing an increased 16-carbon-to-18-carbon fatty acid ratio in their galactolipids. (Awai (2006) Proc. Natl. Acad. Sci. U.S.A. 103, 10817-10822). This was particularly visible for digalactosyldiacylglycerol, which is to a large extent derived from the ER-pathway (Heinz, (1983) Plant Physiol. 72:273-279). Accordingly, for example, the 16-carbon-to-18-carbon ratio for the digalactolipid increased from 0.29 to 0.76 in the tgd3 mutant (Table 3). This phenomenon was contemplated as due to the substrate specificities of the different acyltransferases in the plastid and the ER leading to 18-carbon fatty acids at the sn-1 position and 16-carbon fatty acids at the sn-2 position of the diacylglycerol backbone for plastid derived lipids. Those lipids derived from the ER-pathway carry 18-carbon fatty acids in both positions (Heinz, (1983) Plant Physiol. 72:273-279). Positional analysis using *Rhizopus* lipase confirmed an increase in 16-carbon fatty acids in the sn-2 position of monogalactosyldiacylglycerol and digalactosyldiacylglycerol of the tgd3 mutant.

Processes for extracting plant oils from seeds for biofuel feedstock are well known and practiced. The inventors contemplate using an oil extraction process for leaves and stems similar to the process used for extracting oil from peppermint leaves. In an exemplary embodiment, vegetative oils and seed oil may be isolated. Starting with 50 g of ground plant tissues or seeds suspended in buffer, centrifugation (20,000 g, 30 min) yielded a floating fat pad, liquid fraction containing soluble and membrane-associated proteins, and a pellet.

VI. Nucleic Acid and Protein Detection.

In some embodiments, the inventors contemplate monitoring the expression of a gene silencing construct of the present inventions in a plant cell, plant tissue or plant seed. In some embodiments, the expression of the gene-silencing construct is by integration of a marker gene in the construct. In some embodiments, the residual expression of the TGD protein in monitored.

Leaves of developing T1 (F1) plants may be analyzed in a PCR-based assay designed to quantitate the amount of a specific DNA target to determine if the plants were homozygous, heterozygous, or null for the trans gene. Events where the transgene and the selectable marker are linked (closely co-localized on the same chromosome) can be identified by Southern analysis.

A. Detection of DNA and RNA.

In some embodiments, the inventors contemplate monitoring the level of gene silencing by determining the amount of expressed TGD genes. DNA and mRNA expression may be measured by any suitable method, including but not limited to, those disclosed below. In some embodiments, RNA is detection by Northern blot analysis. Northern blot analysis involves the separation of RNA and hybridization of a complementary labeled probe.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized. Exemplary, semi-quantitative RT-PCR analysis of TGD3 mRNA levels in wild-type (Col-2) and tgd3 plants, FIG. 2, Lu et al., 2007; TGD2 FIG. 3, Awai, et al., 2006. In still further embodiments, RNA (or corresponding cDNA) is detected by hybridization to a oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

B. Detection of TGD Protein.

In some embodiments, the inventors contemplate monitoring the level of gene silencing by determining the amount of expressed TGD proteins. Thus, in some embodiments, gene expression may be detected by measuring the expression of a protein or polypeptide. Protein expression may be detected by any suitable method. In some embodiments, proteins are detected by immunohistochemistry. In other embodiments, proteins are detected by their binding to an antibody raised against the protein. The generation of antibodies is described below. In one example, a polyclonal antibody against TGD2 was made and used for detecting TGD2, Awai, et al., 2006. Similar methods are contemplated for making antibodies for detecting TGD1, TGD3, and TGD4.

Antibody binding may be detected by many different techniques including, but not limited to, (e.g., immunoelectron microscopy, radioimmunoassay, ELISA (enzyme-linked immunosorbent assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled.

VII. Summary.

While attempting to overcome limitations from using mutant tgd genes in plants for increasing accumulated oil in vegetative tissues, the inventors developed at least two types of RNAi tgd gene fragment constructs. One under control of a constitutive promoter and one under control of an inducible promoter along with methods comprising this RNAi construct for controlling the initiation of oil accumulation in leaves, stems and shoots. Thus in some embodiments, compositions and methods are used to produce whole plants, such as seedlings, immature, mature and senescing plants, whose vegetative tissues have accumulated oils, including accumulated TAGs. In some embodiments, plants having accumulated oils are plants having reduced TGD3 protein. In other embodiments, plants having accumulated oils in vegetative tissues are plants have reduced TGD4 protein. In yet other embodiments, plants having accumulated oils in vegetative tissues have reduced TGD2. In yet further embodiments, plants having accumulated oils in vegetative tissue are plants having reduced TGD1. In even further embodiments, having accumulated oils in vegetative tissues have more than one TGD protein that is reduced. The engineered plants of the present inventions are contemplated for use in a variety of ways, including but not limited to increasing the total amount of oil harvested from an individual plant since harvesting oil from vegetative tissues in addition to seeds. Additional advantages of making and using engineered plants would be the added flexibility of growing these plants for a shorter amount of time since oil produced in vegetative tissues were harvested before the plant matured and produced seeds. Thus growing and harvesting oil in young plants would reduce the overall cost of growing the plants. Further, the inventors contemplate growing several crops per growing season instead of one crop due to the early production of vegetative oils before seeds are ready for harvesting. Further, engineered plants having reduced production of TGDs would produce higher levels of TAGs in younger plants. The inventors further contemplate the following additional benefits of using the compositions and methods of the present inventions: enables more efficient feedstock crops per plant, increases the capacity of feedstock crops to store oil, hence, more oil can be produced, stored, and harvested per crop acreage, thus reducing the cost of biodiesel feedstock, while increasing efficiencies gained from higher oil yielding crops reduce oils costs and translate into lower biodiesel costs, technology is stackable and compatible with other transgenic crop technologies, and technology can be coupled with other transgenic crop technologies that aim to provide more advantageous feedstock. The oil obtained from vegetative tissues and seeds of engineered plants is contemplated for several uses including but not limited to biodiesel production, biofuels, and bioplastics production in manufacturing plants.

EXPERIMENTAL

The following examples serve to illustrate certain embodiments and aspects of the present invention and are not to be construed as liming the scope thereof. In the experimental disclosures which follow, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); pg (picograms); L and l (liters); ml (milliliters); µl (microliters); cm (centimeters); mm (millimeters); µm (micrometers); nm (nanometers); U (units); min (minute); s and sec (second); k (kilometer); deg (degree); ° C. (degrees Centigrade/Celsius), and polymerase chain reaction (PCR).

Example I

This example describes exemplary materials and methods used during the development of the present inventions.

Briefly, exemplary lipid assays were used for analyzing lipid content in lipids extracted from Col-2 wild type, seeds and plants of the present inventions. In some examples, tgd mutant seedlings were grown on Murashige and Skoog (MS) medium with 1% sucrose. In particular, fatty acid methylesters were prepared as described by Dörmann (Plant Cell 7:1801-1810 (1995), herein incorporated by reference in its entirety) and quantified by gas chromatography according to Rossak, et al. (Arch. Biochem. Biophys. 340:219-230 (1997), herein incorporated by reference in its entirety). Polar lipids were analyzed as described by Dörmann (Plant Cell 7:1801-1810 (1995), herein incorporated by reference in its entirety) on activated ammonium sulfate-impregnated silica gel TLC plates (Si250PA; Mallinckrodt, Baker, N.J.) developed with chloroform/methanol/acetic acid/water (85/25/10/4, v/v). Neutral lipids were separated on untreated TLC plates developed with petroleum ether/ether/acetic acid (80/20/1, v/v). Lipids were visualized by brief exposure to iodine vapor or staining with α-naphthol to detect glycolipids (Benning, et al., Arch. Biochem. Biophys. 317:103-111 (1995), herein incorporated by reference in its entirety). The fatty acid compositions at the sn-2 position of individual lipids were determined using *Rhizopus* lipase (Sigma, St. Louis, Mo.) digestion according to (Siebertz, et al., Naturforsch. 32:193-205 (1977), herein incorporated by reference in its entirety), with modifications as described in (Miguel, et al., Plant Physiol. 117, 923-930 (1998), herein incorporated by reference in its entirety). Fatty acid methyl esters were formed from lyso-lipids, and the fatty acid methylesters were quantified by gas chromatography.

Exemplary mass spectrometry methods were used to characterize lipid extracts using liquid chromatography/mass spectrometry (LC/MS) on a Waters LCT Premier time-of-flight mass spectrometer equipped with Shimadzu LC-20AD pumps and SIL-5000 autosampler. Extracts were analyzed using V-mode operation and electrospray ionization in both positive and negative ion modes similar to described protocols (Houjou, et al., Rapid Commun. Mass Spectrom. 19:654-666 (2005), herein incorporated by reference in its entirety) except that, in place of MS/MS spectra, mass spectra were acquired in alternating acquisition functions at low (15 V) and high (75 V) potentials on aperture one to generate spectra with, and without in-source collision-induced dissociation (CID). The latter conditions allow for production of characteristic fragment ions that support structure assignments. HPLC separations were performed using a Restek Allure C18 column (1×150 mm) using a ternary gradient based on: (a) 10 mM aqueous ammonium acetate, (b) methanol, and (c) 2-propanol.

Example II

This example describes exemplary compositions and methods for making RNAi constructs of the present inventions.

Various tgd RNAi silencing constructs were made using a 5' fragment of a cDNA coding region of TGD. Specifically, the inventors designed RNAi sequences for silencing a tgd gene, i.e. a sense tgd fragment (for examples, see, Table 6A) and antisense tgd fragment (for examples, see, Table 6B) attached with a spacer sequence, for example, a fragment of a tgd3 intron, see, Table 6C. Examples of TGD RNAi silencing constructs examples, see, Table 6C.

TABLE 6A

Exemplary tgd sense gene sequences for use in tgd gene silencing as part of RNAi construct sequences.

| Target gene for silencing: | Exemplary sequence for use in gene silencing vectors: Sense sequence, i.e. when promoter is located 5': 5'-3' | SEQ ID NO: |
|---|---|---|
| TGD4 AT3G06960 | ATGAACAGAATGAGATGGGTCGGAGAGGGAGACATCTGGG ACCTCGATATGTCAACTCCGGTGACGCTCGAGGGCACCGC ACGAGCTGTTCCTGACGATCCTCTTCCTCTAGGTCTCTCT AGAGGCACTCGTCTATCTCGCCCTAAGCAAGTTGAGTTCT TCCACCGCTTCATGGCCTCACCTCTCATCCCTTCCTTCTC CCCTATCCGTCCCAACACCGGAGATGGAGGCGGTGGTGGA TTCTCTCTTCAAAGAGTCCTCACTCTTCCTTTCTCCAACA ACTGGCTTGTGTCTCTTCTGGGCCAATTCGATGTTCAGAG ATTCGTAACGGAGATAGATAAGACTAAAGCTTTTGGTCGA GGGTCTTCGTCTACAGTAGCTTCTCGTTTAAACACAATTG GCAAGCATTTGAAGGATAAATCTTTGTACGCATTGGGTTT TTGTTCTGAGTTTTTGTTATCACCAGATGATACTTTGCTT CTTAGCTATGATGCTTACAA | 12 |
| TGD4 PDE320 (PIGMENT DEFECTIVE 320) | ATGAACAGAATGAGATGGGTCGGAGAGGGAGACATCTGGG ACCTCGATATGTCAACTCCGGTGACGCTCGAGGGCACCGC ACGAGCTGTTCCTGACGATCCTCTTCCTCTAGGTCTCTCT AGAGGCACTCGTCTATCTCGCCCTAAGCAAGTTGAGTTCT TCCACCGCTTCATGGCCTCACCTCTCATCCCTTCCTTCTC CCCTATCCGTCCCAACACCGGAGATGGAGGCGGTGGTGGA TTCTCTCTTCAAAGAGTCCTCACTCTTCCTTTCTCCAACA ACTGGCTTGTGTCTCTTCTGGGCCAATTCGATGTTCAGAG ATTCGTAACGGAGATAGATAAGACTAAAGC | 13 |
| TGD3 ATNAP11 ATNAP11 (Arabidopsis thaliana non-intrinsic abc protein 11) | AACGAAAAATGGCAATGTGACTCACTCAATCGGTGACTCG CTATAGTCTGTGAAGAAAGGCCAATTTCGCCATAAAGTTC ACACCTTTGATCTCCTTTGTTTCTGGGTTTCTCCTAAATC ATCCAAATTGGTATCGAATTTGCCCTTCTCCGATTCAATT TCTTCACGATCTCAA | 14 |
| TGD2 AT3G20320 | ATGATTGGGAATCCAGTAATTCAAGTTCCATCATCACTAA TGCCATCATCCTCCATGATTGCTTGTCCTCGAGTTTCACC CAATGGGGTTCCTTATCTTCCACCAAAACCTAGAACTAGG CATTTAGTGGTCAGAGCTGCATCCAATTCCGATGCTGCTC ATGGTCAACCATCGTCTGATGGGGGGAAGAATCCTCTCAC CGTTGTTTTGGATGTGCCCAGGAATATATGGAGACAGACT TTAAAACCTTTGAGTGATTTTGGGTTTGGTAAGAGAAGTA TTTGGGAAGGTGGTGTTGGTTTGTTTATTGTCTCTGGAGC TACTCTTCTTGCTCTTAGCTGGGCTTGGTTGCGAGGTTTT CAAATGCGGTCGAAGTTTAGGAAATATCAGACTGTGTTTG AGCTTAGTCATGCTTCTGGTATTTGCACGGGAACACCGGT TAGGATCCGTGGGGTTACTGTTGGTACGATTATCCGTGTT AATCCTTCCTTGAAGAATAT | 15 |
| TGD2 | CCTAGAACTAGGCATTTAGTGGTCAGAGCTGCATCCAATT CCGATGCTGCTCATGGTCAACCATCGTCTGATGGGGGGAA GAATCCTCTCACCGTTGTTTTGGATGTGCCCAGGAATATA TGGAGACAGACTTTAAAACCTTTGAGTGATTTTGGGTTTG GTAAGAGAAGTATTTGGGAAGGTGGTGTTGGTTTGTTTAT TGTCTCTGGAGCTACTCTTCTTGCTCTTAGCTGGGCTTGG TTGCGAGGTTTTCAAATGCGGTCGAAGTTTAGGAAATATC AGACTGTGTTTGAGCTTAGTCATGCTTCTGGTATTTGCAC | 16 |

TABLE 6A-continued

Exemplary tgd sense gene sequences for use
in tgd gene silencing as part of RNAi construct sequences.

| Target gene for silencing: | Exemplary sequence for use in gene silencing vectors: Sense sequence, i.e. when promoter is located 5': 5'-3' | SEQ ID NO: |
|---|---|---|
| | GGGAACACCGGTTAGGATCCGTGGGGTTACTGTTGGTACG<br>ATTATCCGTGTTAATCCTTCCTTGAAGAATATTGAAGCTG<br>TTGCTGAGATAGAAGATGA | |
| TGD1 | ATGATGCAGACTTGTTGTATCCATCAATCGTTTTGTTTCC<br>CTCATAGAGTCTTTCCACGGTTTGATGCTTCGATTGGTAT<br>TAAGCCCCCAAAGCTTTGTCAAGTTGGTTTCATTGGAAAG<br>ACTCAATCTTATGGGATTTCAAGTCCGATACGGCAAAGAA<br>GATTATATGTGAATTTGAATGCTAATGATGGTCACCCATC<br>CATGTCTATGTTGGAAGAAGAAACCTCTACTGAAAACAAC<br>GCACCCAGTCAAGAAGCCGAGCTTCCGTTCAGCAAATGGT<br>CACCTTCTAAGTACATATGGAGAGGTTTATCAGTTCCTAT<br>TATAGCAGGACAAGTCGTTCTCCGGATTTTAAAGGGTAAG<br>ATTCACTGGAGAAACACTCTTCAACAGCTGGAGAGAACCG<br>GACCGAAATCTCTAGGAGTTTGTCTTCTGACTTCTACATT<br>TGTTGGTATGGCTTTCACAATCCAGTTCGTTAGAGAATTC<br>ACTAGACTAGGTCTAAACAG | 17 |
| TGD1 | TGTGTGTTGTTGTTGTTGGCACTGTGCCACTTTCTCTCTC<br>GATGAACCCTCTCAAGCAAGCTTCTTCGATCTTCCGAGCT<br>TAGTTTCGTTTCTAAATTAGAGATTTCACCTAGATTGGTC<br>CGTACATATCTTATACTGGGATTCGAATTTGGCTGCCTCA<br>GAGTCAGAGATTGATTAATTGATCAGATTCAGCTGTTGAA<br>ATCGTGCTTATTGCTACAAATTGAGAGGCACTAAATCAGT<br>GAGGTCGTAAAGAAGAAGGCAACCACAATGATGCAGACTT<br>GTTGTATCCATCAATCGTTTTGTTTCCCTCATAGAGTCTT<br>TCCACGGTTTGATGCTTCGATTGGTATTAAGCCCCCAAAG<br>CTTTGTCAAGTTGGTTTCATTGGAAAGACTCAATCTTATG<br>GGATTTCAAGTCCGATACGGCAAAGAAGATTATATGTGAA<br>TTTGAATGCTAATGATGGTCACCCATCCATGTCTATGTTG<br>GAAGAAGAAACCTCTACTGAAAACAACGCACCCAGTCAAG<br>AAGCCGAGCTTCCGTTCAGCAAATGGTCACCTTCTAAGTA<br>CATATGGAGAGGTTTATCAGTTCCTATTATAGCAGGACAA<br>GTCGTTCTCCGGATTTTAAAGGGTAAGATTCACTGGAGAA<br>ACACTCTTCAACAGCTGGAGAGAACCGGACCGAAATCTCT<br>AGGAGTTTGTCTTCTGACTTCTACATTTGTTGGTATGGCT<br>TTCACAATCCAGTTCGTTAGAGAATTCACTAGACTAGGTC<br>TAAACAGATCCATTGGAGGTGTCTTGGCTTTAGCCTTCTC<br>TAGAGAGCTAAGTCCAGTCATCACATCGATTGTTGTTGCT<br>GGACGAATGGGAAGTGCATTTGCAGCTGAACTAGGGACAA<br>TGCAAGTCTCAGAGCAAACTGATACACTCCGTGTTTTAGG<br>AGCTGACCCAATTGATTATCTAATCACTCCAAGAGTCATC<br>GCCTCGTGTTTGGCTCTACCGTTTCTGACACTCATGTGTT<br>TCACTGTTGGTATGGCTTCAAGCGCTCTGCTCTCTGATGC<br>AGTTTACGGGATCAGCATTAACATAATCATGGACTCGGCT<br>CACCGAGCACTTAGACCATGGGACATTGTGAGTGCCATGA<br>TTAAATCTCAAGTCTTTGGAGCTATAATATCGGTAATTAG<br>TTGTTCTTGGGGAGTAACCACTACTGGAGGTGCTAAAGGT<br>GTTGGAGAATCTACAACTTCTGCTGTCGTCATGTCTCTTG<br>TCGGAATCTTCATCGCGGACTTTGTGCTTTCTTCCTTCTT<br>CTTTCAAGGTGCTGGAGATTCTTTGAAGAACTGTGTTTGA<br>CATATTATTTTCTGTCTTCTTTTGTTGTGGTTTAGATGGG<br>TTTATGTAAATCAGTTGTCTTAAATTGAGAAAGTAACATC<br>ATTTTAGAAAGAACAGAAAGATTGCTATATTTCTATTCCA<br>ATAATGATACACATTGAATAAT | 18 |

TABLE 6B

Exemplary tgd antisense gene sequences for use in tgd gene silencing
as part of RNAi construct sequences.

| Target gene for silencing: | Exemplary sequence for use in gene silencing vectors: antisense sequence, i.e. when promoter is located 5': 5'-3' | SEQ ID NO: |
|---|---|---|
| TGD4: | TTGTAAGCATCATAGCTAAGAAGCAAAGTATCATCTGGTGATAACAAAAACTCAGAACA<br>AAAACCCAATGCGTACAAAGATTTATCCTTCAAATGCTTGCCAATTGTGTTTAAACGAG<br>AAGCTACTGTAGACGAAGACCCTCGACCAAAAGCTTTAGTCTTATCTATCTCCGTTACG<br>AATCTCTGAACATCGAATTGGCCCAGAAGAGACACAAGCCAGTTGTTGGAGAAAGGAAG<br>AGTGAGGACTCTTTGAAGAGAGAATCCACCACCGCCTCCATCTCCGGTGTTGGGACGGA<br>TAGGGGAGAAGGAAGGGATGAGAGGTGAGGCCATGAAGCGGTGGAAGAACTCAACTTGC | 51 |

TABLE 6B-continued

Exemplary tgd antisense gene sequences for use in tgd gene silencing
as part of RNAi construct sequences.

| Target gene for silencing: | Exemplary sequence for use in gene silencing vectors: antisense sequence, i.e. when promoter is located 5': 5'-3' | SEQ ID NO: |
|---|---|---|
| | TTAGGGCGAGATAGACGAGTGCCTCTAGAGAGACCTAGAGGAAGAGGATCGTCAGGAAC AGCTCGTGCGGTGCCCTCGAGCGTCACCGGAGTTGACATATCGAGGTCCCAGATGTCTC CCTCTCCGACCCATCTCATTCTGTTCAT | |
| TGD3: | ATGCTTTCGTTATCATGCTCTTCTTCTTCTTCTTCGTTGCTTCCTCCGAGTTTACACTA CCACGGTTCTTCTTCTGTTCAGTCCATCGTTGTACCAAGAAGGAGTCTTATCTCGTTTC GTCGGAAAGTCTCTTGCTGTTGCATAGCTCCACCTCAGAACTTGGACAACGAT | 52 |
| TGD2: | ATATTCTTCAAGGAAGGATTAACACGGATAATCGTACCAACAGTAACCCCACGGATCCT AACCGGTGTTCCCGTGCAAATACCAGAAGCATGACTAAGCTCAAACACAGTCTGATATT TCCTAAACTTCGACCGCATTTGAAAACCTCGCAACCAAGCCCAGCTAAGAGCAAGAAGA GTAGCTCCAGAGACAATAAACAAACCAACACCACCTTCCCAAATACTTCTCTTACCAAA CCCAAAATCACTCAAAGGTTTTAAAGTCTGTCTCCATATATTCCTGGGCACATCCAAAA CAACGGTGAGAGGATTCTTCCCCCCATCAGACGATGGTTGACCATGAGCAGCATCGGAA TTGGATGCAGCTCTGACCACTAAATGCCTAGTTCTAGGTTTTGGTGGAAGATAAGGAAC CCCATTGGGTGAAACTCGAGGACAAGCAATCATGGAGGATGATGGCATTAGTGATGATG GAACTTGAATTACTGGATTCCCAATCAT | 53 |
| TGD1: | CTGTTTAGACCTAGTCTAGTGAATTCTCTAACGAACTGGATTGTGAAAGCCATACCAAC AAATGTAGAAGTCAGAAGACAAACTCCTAGAGATTTCGGTCCGGTTCTCTCCAGCTGTT GAAGAGTGTTTCTCCAGTGAATCTTACCCTTTAAAATCCGGAGAACGACTTGTCCTGCT ATAATAGGAACTGATAAACCTCTCCATATGTACTTAGAAGGTGACCATTTGCTGAACGG AAGCTCGGCTTCTTGACTGGGTGCGTTGTTTTCAGTAGAGGTTTCTTCTTCCAACATAG ACATGGATGGGTGACCATCATTAGCATTCAAATTCACATATAATCTTCTTTGCCGTATC GGACTTGAAATCCCATAAGATTGAGTCTTTCCAATGAAACCAACTTGACAAAGCTTTGG GGGCTTAATACCAATCGAAGCATCAAACCGTGGAAAGACTCTATGAGGGAAACAAAACG ATTGATGGATACAACAAGTCTGCATCAT | 54 |

TABLE 6C

Exemplary silencing sequences comprising in operable combination,
sense and antisense fragments, where a spacer element sequence is
located in between the sense and antisense sequences.

| Target gene for silencing: | Exemplary sequence for use in gene vectors: In operable combination: sense sequence-spacer-antisense, i.e. when promoter is located 5': 5'-3' (Sense underlined- spacer sequence in BOLD-antisense in lower case) | SEQ ID NO: |
|---|---|---|
| TGD4: AT3G06960 | <u>Atgaacagaatgagatgggtcggagagggagacatctgggacctcgatatgtcaac tccggtgacgctcgagggcaccgcacgagctgttcctgacgatcctcttcctctag gtctctctagaggcactcgtctatctcgccctaagcaagttgagttcttccaccgc ttcatggcctcacctctcatcccttccttctccctatccgtcccaacaccggaga tggaggcggtggtggattctctcttcaaagagtcctcactcttccttctccaaca actggcttgtgtctcttctgggccaattcgatgttcagagattcgtaacggagata gataagactaaagcttttggtcgagggtcttcgtctacagtagcttctcgtttaaa cacaattggcaagcatttgaaggataaatctttgtacgcattgggttttgttctg agttttgttatcaccagatgatactttgcttcttagctatgatgcttacaa</u>AACC CAGAAGAAAGAATCttgtaagcatcatagctaagaagcaaagtatcatctggtgat aacaaaaactcagaacaaaaacccaatgcgtacaaagatttatccttcaaatgctt gccaattgtgtttaaacgagaagctactgtagacgaagaccctcgaccaaaagctt tagtcttatctatctccgttacgaatctctgaacatcgaattggcccagaagagac acaagccagttgttggagaaaggaagagtgaggactctttgaagagagaatccacc accgcctccatctccggtgttgggacggatagggagaaggaagggatgagaggtg aggccatgaagcggtggaagaactcaacttgcttagggcgagatagacgagtgcct ctagagagacctagaggaagaggatcgtcaggaacagctcgtgcggtgccctcgag cgtcaccggagttgacatatcgaggtcccagatgtctccctctccgacccatctca ttctgttcat | 19 |
| TGD3 Underlined region is 5'-3' exon1 | <u>AACGAAAAATGGCAATGTGACTCACTCAATCGGTGACTCGCTATAGTCTGTGAAGA AAGGCCAATTTCGCCATAAAGTTCACACCTTTGATCTCCTTTGTTTCTGGGTTTCT CCTAAATCATCCAAATTGGTATTGCCCTTCTCCGATTCAATTTCTTCACG ATCTCAA</u>AACCCAGAAGAAAGAATatgctttcgttatcatgctcttcttcttctt cttcgttgcttcctccgagtttacactaccacggttcttcttctgttcagtccatc gttgtaccaagaaggagtcttatctcgtttcgtcggaaagtctcttgctgttgcat agctccacctcagaacttggacaacgat | 20 |

TABLE 6C-continued

Exemplary silencing sequences comprising in operable combination, sense and antisense fragments, where a spacer element sequence is located in between the sense and antisense sequences.

| Target gene for silencing: | Exemplary sequence for use in gene vectors: In operable combination: sense sequence-spacer-antisense, i.e. when promoter is located 5': 5'-3' (Sense underlined- spacer sequence in BOLD-antisense in lower case) | SEQ ID NO: |
|---|---|---|
| TGD2: AT3G20320 | atgattgggaatccagtaattcaagttccatcatcactaatgccatcatcctccat gattgcttgtcctcgagtttcacccaatggggttccttatcttccaccaaaaccta gaactaggcatttagtggtcagagctgcatccaattccgatgctgctcatggtcaa ccatcgtctgatgggggaagaatcctctcaccgttgttttggatgtgcccaggaa tatatggagacagactttaaaacctttgagtgattttgggttggtaagagaagta tttgggaaggtggtgttggtttgtttattgtctctggagctactcttcttgctctt agctgggcttggttgcgaggttttcaaatgcggtcgaagtttaggaaatatcagac tgtgtttgagcttagtcatgcttctggtatttgcacgggaacaccggttaggatcc gtgggggttactgttggtacgattatccgtgttaatccttccttgaagaatatAACC CAGAAGAAAGAATCatattcttcaaggaaggattaacacggataatcgtaccaaca gtaaccccacggatcctaaccggtgttcccgtgcaaataccagaagcatgactaag ctcaaacacagtctgatatttcctaaacttcgaccgcatttgaaaacctcgcaacc aagcccagctaagagcaagaagagtagctccagagacaataaacaaaccaacacca ccttcccaaatacttctcttaccaaacccaaaatcactcaaaggttttaaagtctg tctccatatattcctgggcacatccaaaacaacggtgagaggattcttcccccat cagacgatggttgaccatgagcagcatcggaattggatgcagctctgaccactaaa tgcctagttctaggttttggtggaagataaggaaccccattgggtgaaactcgagg acaagcaatcatggaggatgatggcattagtgatgatggaacttgaattactggat tcccaatcat | 21 |
| TGD1: AT1 G19800 | atgatgcagacttgttgtatccatcaatcgttttgtttccctcatagagtctttcc acggtttgatgcttcgattggtattaagcccccaaagctttgtcaagttggtttca ttggaaagactcaatctatgggatttcaagtccgatacggcaaagaagattatat gtgaatttgaatgctaatgatggtcacccatccatgtctatgttggagaagaaac ctctactgaaaacaacgcacccagtcaagaagccgagcttccgttcagcaaatggt caccttctaagtacatatggagaggtttatcagttcctattatagcaggacaagtc gttctccggattttaaagggtaagattcactggagaaacactcttcaacagctgga gagaaccggaccgaaatctctaggagtttgtcttctgacttctacatttgttggta tggctttcacaatccagttcgttagagaattcactagactaggtctaaacagAACC CAGAAGAAAGAATCctgtttagacctagtctagtgaattctctaacgaactggatt gtgaaagccataccaacaaatgtagaagtcagaagacaaactcctagagatttcgg tccggttctctccagctgttgaagagtgtttctccagtgaatcttaccctttaaaa tccggagaacgacttgtcctgctataataggaactgataaacctctccatatgtac ttagaaggtgaccatttgctgaacggaagctcggcttcttgactgggtgcgttgtt ttcagtagaggtttcttcttccaacatagacatggatgggtgaccatcattagcat tcaaattcacatataatcttctttgccgtatcggacttgaaatcccataagattga gtctttccaatgaaaccaacttgacaaagctttgggggcttaataccaatcgaagc atcaaaccgtggaaagactctatgagggaaacaaaacgattgatggatacaacaag tctgcatcat | 22 |

In one tgd RNAi construct for reducing TGD3, SEQ ID NO:20 was used to make two types of constructs. One construct had a constitutive promoter (S35) and the other construct had an inducible gene silencing promoter (for general examples of inducible gene silencing see, Guo et al. (The Plant J. 34(3): 383-92 (2003)), incorporated herein by reference in its entirety). In this example, the spacer region DNA was an intron of tgd3. FIG. 10 shows an exemplary tgd RNAi silencing construct of the present inventions having in operable combination with a promoter sequences, a sense fragment-spacer element-antisense fragment.

TABLE 7

Exemplary primers used for providing sequences for use in RNAi constructs.

| Gene | Forward Primer-sense | Reverse Primer-antisense |
|---|---|---|
| TGD4 | 5'-CATGGATCCATGAACAG AATGAGATGGGT-3' SEQ ID NO: 23 | 5'-ACAGTCGACCTAGTGCTCAAA GAAACGAAGC-3' (XU, 2008) SEQ ID NO: 24 |

TABLE 7-continued

Exemplary primers used for providing sequences for use in RNAi constructs.

| Gene | Forward Primer-sense | Reverse Primer-antisense |
|---|---|---|
| TGD3 | 5'-ACGGTACCATGCTTTCG TTATCATGCTC-3' SEQ ID NO: 25 | 5'-CTGGTACCCTAGTATCTGATT GGTCCAT-3' SEQ ID NO: 26 Binbin, et al. JBC, 2007 |
| TGD2 | 5'-GTCGACATGATTGGGAA TCCAGTAATTCAAG-3' SEQ ID NO: 27 | 5'-GTCGACTCATAGTAGCCTGCT TAGGG-3' SEQ ID NO: 28 Awai et al, Proc Natl Acad Sci USA. 2006 |
| TGD1 | 5'-AATACTAGTGGCGCGCC ATGATGCAGACTTGTT-3' SEQ ID NO: 29 | 5'-CCAGGATCCATTTAAATTCAA ACACAGTTCTT-3' SEQ ID NO: 30 |

TABLE 8

Exemplary promoters for use with RNAi constructs and vectors.

| Promoter Type: | Examples: | SEQ ID NO: | Exemplary use |
|---|---|---|---|
| Inducible | β-estradiol promoter i.e. regulatory region of the human estrogen receptor carboxy terminal region residues 282-295), as one example, NCBI: NM_000125 encoding, for one example, SEQ ID NO: 31: SAGDMRAANLWPSPLMIKRSKKNSLALSLTADQMVS ALLDAEPPILYSEYDPTRPFSEASMMGLLTNLADRE LVHMINWAKRVPGFVDLTLHDQVHLLECAWLEILMI GLVWRSMEHPGKLLFAPNLLLDRNQGKCVEGMVEIF DMLLATSSRFRMMNLQGEEFVCLKSIILLNSGVYTF LSSTLKSLEEKDHIHRVLDKITDTLIHLMAKAGLTL QQQHQRLAQLLLILSHIRHMSNKGMEHLYSMKCKNV VPLYDLLLEMLDAHRLHAPTSRGGASVEETDQSHLA TAGSTSSHSLQKYYITGEAEGFPATV | SEQ ID NO: 32 tctgctggagacatgagagctgc caacctttggccaagcccgctcat gatcaaacgctctaagaagaacag cctggccttgtccctgacggccga ccagatggtcagtgccttgttgga tgctgagcccccatactctattc cgagtatgatcctaccagaccctt cagtgaagcttcgatgatgggctt actgaccaacctggcagacaggga gctggttcacatgatcaactgggc gaagagggtgccaggctttgtgga tttgaccctccatgatcaggtcca ccttctagaatgtgcctggctaga gatcctgatgattggtctcgtctg gcgctccatggagcacccagggaa gctactgtttgctcctaacttgct cttggacaggaaccagggaaaatg tgtagagggcatggtggagatctt cgacatgctgctggctacatcatc tcggttccgcatgatgaatctgca gggagaggagtttgtgtgcctcaa atctattattttgcttaattctgg agtgtacacatttctgtccagcac cctgaagtctctggaagagaagga ccatatccaccgagtcctggacaa gatcacagacactttgatccacct gatggccaaggcaggcctgaccct gcagcagcagcaccagcggctggc ccagctcctcctcatcctctccca catcaggcacatgagtaacaaagg catggagcatctgtacagcatgaa gtgcaagaacgtggtgcccctcta tgacctgctgctggagatgctgga cgcccaccgcctacatgcgcccac tagccgtggaggggcatccgtgga ggagacggaccaaagccacttggc cactgcgggctctacttcatcgca ttccttgcaaaagtattacatcac gggggaggcagagggtttccctgc cacggtctga | In combination with exemplary RNAi sequences |
| Constitutive | CaMV 35S promoter | SEQ ID NO: 33 tgagacttttt caacaaaggg taatatccgg aaacctcctc ggattccatt gcccagctat ctgtcacttt attgtgaaga tagtggaaaa ggaaggtggc tcctacaaat gccatcattg cgataaagga aaggccatcg ttgaagatgc ctctgccgac agtggtccca aagatggacc cccaccccac gaggagcatc gtggaaaaag aagacgttcc aaccacgtct tcaaagcaag tggattgatg tgatatctcc actgacgtaa gggatgacgc acaatccac tatccttcgc aagaccttc ctctatataa ggaagttcat ttcatttgga gagga | In combination with exemplary gene silencing sequence for RNAi sequences |
| Constitutive | 35S minimal promoter | cccac tatccttcgc aagaccctc ctctatataa ggaagttcat ttcatttgga gagga | Operably combined with genes turned on by inducible promoter |

TABLE 9

Exemplary spacer sequences
for separating sense and antisense DNA in RNAi vectors.

| spacer sequences: | | Exemplary use: |
|---|---|---|
| glucuronidase intronSEQ ID NO: 35 | tatacgccatttgaagccgatgtcacgccgt<br>atgttattgccgggaaaagtgtacgtatcac<br>cgtttgtgtgaacaacgaactgaactggcag<br>actatcccgccgggaatggtgattaccgacg<br>aaaacggcaagaaaaagcagtcttacttcca<br>tgatttctttaactacgccgggatccatcgc<br>agcgtaatgctctacaccacgccgaacacct<br>gggtggacgatatcaccgtggtgacgcatgt<br>cgcgcaagactgtaaccacgcgtctgttgac<br>tggcaggtggtggccaatggtgatgtcagcg<br>ttgaactgcgtgatgcggatcaacaggtggt<br>tgcaactggacaaggcaccagcgggactttg<br>caagtggtgaatccgcacctctggcaaccgg<br>gtgaagg ttatctctat gaactgtgcgtc<br>acagccaaaagccagacagagtgtgatatct<br>acccgctgcgcgtcggcatccggtcagtggc<br>agtgaa gggcgaacag ttcctgatca<br>accac | RNAi vectors using full length TGD1 |
| TGD3 intron | AACCCAGAAGAAAGAATC<br>SEQ ID NO: 36 | in combination with exemplary gene silencing sequence for TGD3 |

TABLE 10

Exemplary vectors.

| inducible vector | pER8, Zuo, (2000) An estrogen receptor-based transactivator XVE mediates highly inducible gene expression in transgenic plants. *Plant J.* 24, 265-273. |
|---|---|
| silencing vector | pGSA1285 (ABRC, Ohio State University, Columbus, OH; CD3-454) |

1. Silencing Tgd3 Using a Constitutive Promoter.

The construct TGD3RNAi was introduced into *Arabidopsis* wild-type Col-2 background by *Agrobacterium*-mediated transformation (Xu et al. Plant Cell 17: 3094-3110 (2005), herein incorporated by reference in its entirety). T2 seeds from independent transformation lines were germinated on the regular MS medium containing Hygromycin B. After two weeks, resistant plants were transferred into a liquid MS solution. Oils (plant samples) were harvested from these plants after 6 days in liquid MS solution without an inducing compound. Harvested oils were analyzed by TLC. Constitutive overexpression of TGD3RNAi produced plants having increased levels of TGDG and TAG, see, lane labeled tgd-3, FIGS. 11A and 11B.

2. Silencing Tgd3 Using a Chemical Inducible TGD3RNAi System.

The construct TGD3RNAi-pER8, see, FIG. 10, was introduced into *Arabidopsis* wild-type Col-2 background by *Agrobacterium*-mediated transformation (for an example of transformation, see, Xu et al. 2005, herein incorporated by reference in its entirety). The inventors contemplated that by turning on the silencing construct at least several weeks after germination then these engineered plants would overcome limitations of silencing a tgd gene. T2 seeds from independent transformation lines were germinated on regular MS medium containing Hygromycin B. After two weeks, resistant plants were transferred into a liquid MS solution containing β-estradiol for turning on the promoter of the silencing construct. Oils (plant samples) were harvested from these plants after 6 days in solution after being exposed to the inducing compound. Harvested oils were analyzed by TLC.

Figure 11A:
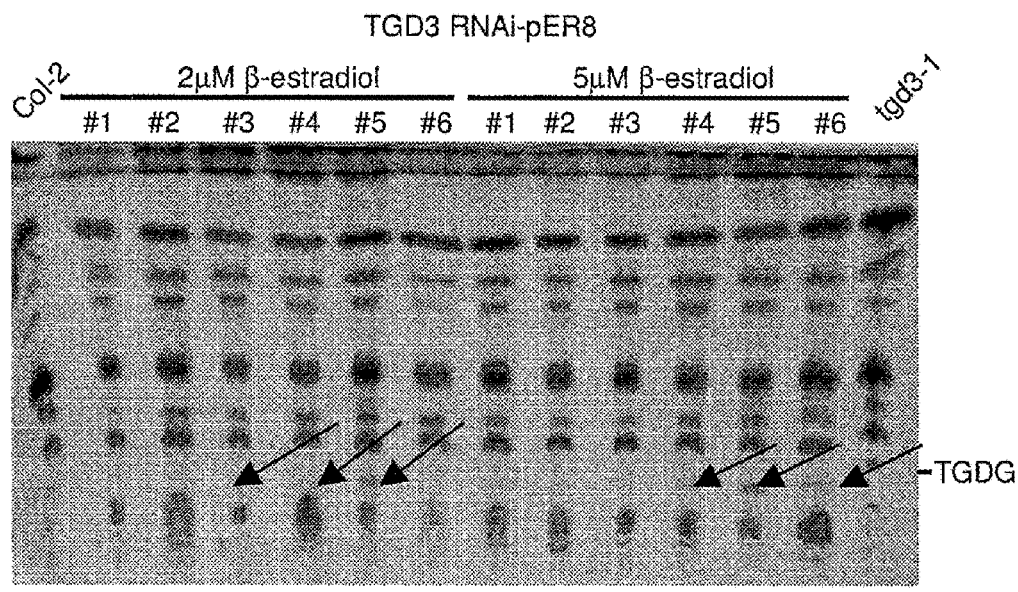
FIG. 11A-11B show exemplary results of TGDG3 silencing in plants.
Figure 11B:
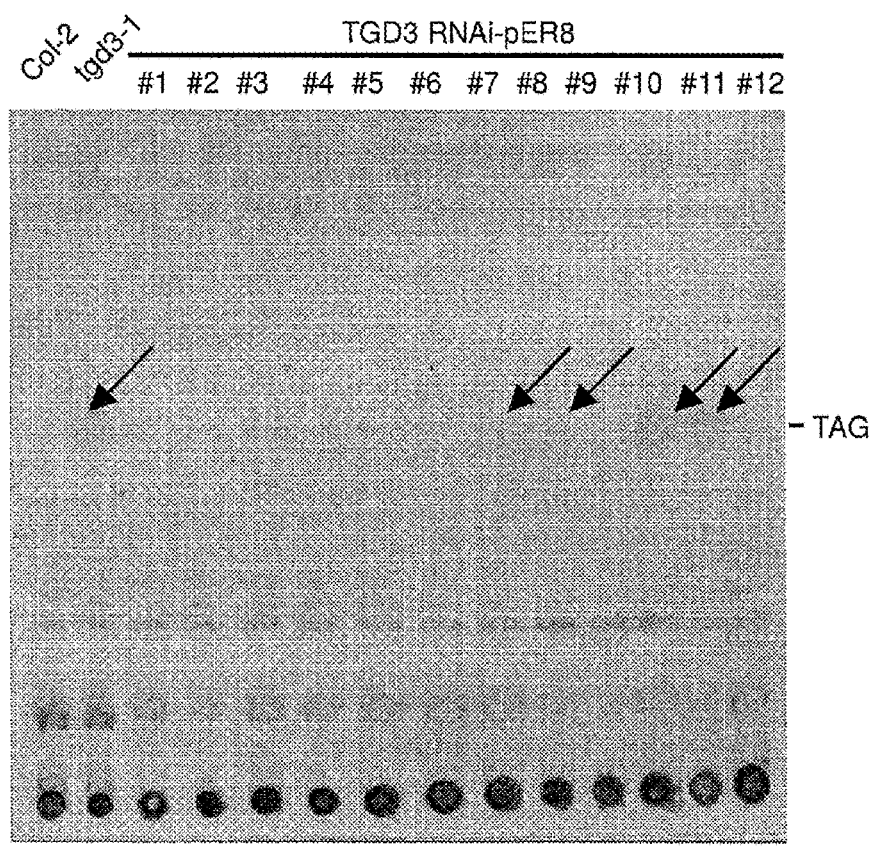

FIG. 11A shows an exemplary TGDG lipid phenotype of the seedlings after induction with 2 μM or 5 μM β-estradiol. Note the variability in TGDG production (i.e. band density) of different lines as shown at the arrows. FIG. 11B shows an exemplary TAG phenotype of the seedlings after induction with 2 μM β-estradiol. Note the variability in density of the TAG band at the arrows.

As shown in FIG. 11A, 3 out of the 6 lines tested have accumulated TGDG after β-estradiol induction for 6 days at a concentration as low as 2 μM. Similarly, 2 out of the 12 lines tested showed accumulation of triacylglycerols (TAG) (see FIG. 11B).

However, in the control wild type Col-2 plant treated the same way, a faint band migrated at the same position as TGDG was also observed, suggesting that the presence of extra oligogalactolipids in the controls might be due to a stress condition e.g. hypoxia (seedlings immersed under liquid solution for 6 days). Other ways of applying the β-estradiol inducer such as spraying the surface of leaves or direct germination of seeds on inducer-containing MS medium did not lead to these positive results.

Example III

This example describes a contemplated method for making and using plants having lowered tgd expression (i.e. expressing an RNAi construct of the present inventions) combined with overexpression of heterologous WRINKLED1 protein genes. RNAi vectors and methods of engineering plants comprising these gene silencing constructs for exemplary tgd 3 or tgd4 are described herein. Constructs for overexpressing heterologous genes, i.e. WRI1 and F-box, and plants engineered for expressing these constructs are provided as described herein, and in Cernac and Benning, The Plant J, 40:575-585 (2004) and WO 2007 038345 respectively, herein incorporated by reference in their entirety. In some embodiments, WRI1 and/or F-box genes are expressed constitutively within the whole plant, for example, the constitutive CaMV 35S promoter is contemplated for use.

A. Examples of Making Transgenic Plants Having Reduced TGD Protein.

Plants having reduced TGD protein are described herein, including in Example II. Such plants expressing tgd RNAi vector constructs are contemplated for use as host cells, tissues or plants for use in transfection with vectors as described herein for overexpressing WRI1 transcription factor proteins. In one embodiment, instead of using wild type seedlings, as described below, seedlings having reduced TGD proteins are used for transfection.

B. Examples of Making Transgenic Plants Overexpressing Heterologous WRINKLED1.

A complete cDNA for WRI1 DNA was obtained by RT-PCR employing a kit from Qiagen (Valencia, Calif., USA) using wild type (Col-2) silique RNA and the PCR primers 5'-GGTACCAAATCTAAACTTTCTCAGAG-3' (SEQ ID NO:60) and 5'-GGTACCGGCAAAGACATT-GATTATTC-3' (SEQ ID NO:61). The RT-PCR product was cloned using TA-overhangs into the pCR2.1TOPO vector from Invitrogen (Carlsbad, Calif., USA). Sequencing was performed at the MSU Genomics Technology Support Facility. The cDNA sequence for WRI1 was deposited at GenBank (AY254038). The cDNA was excised with KpnI and inserted into the binary vector pBinAR-Hyg (Dormann and Benning, 1998) or into a pCAMBIA1300 derivative (CAMBIA, Can berra, Australia), which contained the EcoRI/HindIII expression cassette from pBIN121 (Clontech, Palo Alto, Calif., USA).

One example of a WRI1 gene for use in a construct for overexpressing mRNA for WRI1 in a plant is an *Arabidopsis thaliana* WRINKLED1 (WRI1) with Accession number AY254038 (in FAST A format), provided below as SEQ ID NO:37.

```
   1 AAACCACTCT GCTTCCTCTT CCTCTGAGAA ATCAAATCAC

41 TCACACTCCA AAAAAAATC TAAACTTTCT CAGAGTTTAA

81 TGAAGAAGCG CTTAACCACT TCCACTTGTT CTTCTTCTCC

121 ATCTTCCTCT GTTTCTTCTT CTACTACTAC TTCCTCTCCT

161 ATTCAGTCGG AGGCTCCAAG GCCTAAACGA GCCAAAAGGG

201 CTAAGAAATC TTCTCCTTCT GGTGATAAAT CTCATAACCC

241 GACAAGCCCT GCTTCTACCC GACGCAGCTC TATCTACAGA

281 GGAGTCACTA GACATAGATG GACTGGGAGA TTCGAGGCTC

321 ATCTTTGGGA CAAAAGCTCT TGGAATTCGA TTCAGAACAA

361 GAAAGGCAAA CAAGTTTATC TGGGAGCATA TGACAGTGAA

401 GAAGCAGCAG CACATACGTA CGATCTGGCT GCTCTCAAGT

441 ACTGGGGACC CGACACCATC TTGAATTTTC CGGCAGAGAC

481 GTACACAAAG GAATTGGAAG AAATGCAGAG AGTGACAAAG

521 GAAGAATATT TGGCTTCTCT CCGCCGCCAG AGCAGTGGTT

561 TCTCCAGAGG CGTCTCTAAA TATCGCGGCG TCGCTAGGCA

601 TCACCACAAC GGAAGATGGG AGGCTCGGAT CGGAAGAGTG

641 TTTGGGAACA AGTACTTGTA CCTCGGCACC TATAATACGC

661 AGGAGGAAGC TGCTGCAGCA TATGACATGG CTGCGATTGA

721 GTATCGAGGC GCAAACGCGG TTACTAATTT CGACATTAGT

761 AATTACATTG ACCGGTTAAA GAAGAAAGGT GTTTTCCCGT

801 TCCCTGTGAA CCAAGCTAAC CATCAAGAGG GTATTCTTGT

841 TGAAGCCAAA CAAGAAGTTG AAACGAGAGA AGCGAAGGAA

881 GAGCCTAGAG AAGAAGTGAA ACAACAGTAC GTGGAAGAAC

921 CACCGCAAGA AGAAGAAGAG AAGGAAGAAG AGAAAGCAGA

961 GCAACAAGAA GCAGAGATTG TAGGATATTC AGAAGAAGCA

1001 GCAGTGGTCA ATTGCTGCAT AGACTCTTCA ACCATAATGG

1041 AAATGGATCG TTGTGGGGAC AACAATGAGC TGGCTTGGAA

1081 CTTCTGTATG ATGGATACAG GGTTTTCTCC GTTTTTGACT

1121 GATCAGAATC TCGCGAATGA GAATCCCATA GAGTATCCGG

1161 AGCTATTCAA TGAGTTAGCA TTTGAGGACA ACATCGACTT

1201 CATGTTCGAT GATGGGAAGC ACGAGTGCTT GAACTTGGAA

1241 AATCTGGATT GTTGCGTGGT GGGAAGAGAG AGCCCACCCT

1281 CTTCTTCTTC ACCATTGTCT TGCTTATCTA CTGACTCTGC

1321 TTCATCAACA ACAACAACAA CAACCTCGGT TTCTTGTAAC

1361 TATTTGGTCT GAGAGAGAGA GCTTTGCCTT CTAGTTTGAA

1401 TTTCTATTTC TTCCGCTTCT TCTTCTTTTT TTTCTTTTGT

1441 TGGGTTCTGC TTAGGGTTTG TATTTCAGTT TCAGGGCTTG

1481 TTCGTTGGTT CTGAATAATC AATGTCTTTG CCCCTTTTCT

1521 AATGGGTACC TGAAGGGCGA
```

Proper orientation and integrity were confirmed by restriction analysis and sequencing. For generation of transgenic plants, seedlings for wild type plants were grown and transferred to 3.5 inch pots that had been set up for dipping by mounding with potting soil and were covered with a plastic window screen with 20 evenly spaced holes of 0.5 cm diameter. Growth conditions were as described herein. When the primary inflorescence had bolted and the first three or four flowers had opened (approximately 4 weeks), the plants were transformed using the floral dip method (Clough and Bent, 1998, herein incorporated by reference in its entirety). Three to four pots were used per construct. The plants were dipped again in the same manner 2 or 3 weeks later. Competent cells of *Agrobacterium tumefaciens* strain GV3101, C58C1, pMP90 (Koncz and Schell, 1986, herein incorporated by reference in its entirety) were prepared and transformed according to Shen and Forde (1989). Transformation efficiencies ranged from 1 to 2% for pBinAR-Hyg or pCAMBIA constructs and 0.5-0.8% for pBIC20. Wild type plants transformed with the WRI1 cDNA were grown in separate flats in the same walk-in chamber and plants were individually tied to stakes. Leaf tissue taken for RNA analysis was harvested from 28-day-old rosettes. The stems used were taken from 35-day-old plants. Seedlings were 8 days old from the time the plates were placed into the incubator. Roots and shoots were excised from 10-day-old plantlets. Tissues were snap frozen in liquid nitrogen. Flowers consisted of the inflorescence meristem through the first three opened flowers. Whole silique tissue was harvested from approximately 40-day-old plants. Green siliques of each stage were taken. The age of the seed for the time course was determined by staging flowers as previously described (Focks and Benning, 1998, herein incorporated by reference in its entirety). Seeds were dissected out of the silique using fine tweezers. Seeds from 10 to 20 siliques were harvested onto a glass slide on ice and then gathered and placed into a 1.5 ml polypropylene tube in dry ice. This was repeated until the tagged siliques for each particular time point were harvested (10-14 h for one person). Tissue was stored at −80° C. until extraction. RNA extraction was performed according to the methods of Hosein (2001). Northern analysis (5 µg total RNA) was performed as previously described (Dörmann and Benning, 1998, herein incorporated by reference in its entirety).

The blots were analyzed using a phosphor imager (Molecular Dynamics, Amersham, Piscataway, N.J., USA). Background integrals of areas equal in size to those of the bands located between the wells and the bands on the blots were subtracted. Using the image quantification software provided by the manufacturer (image quant 5.2 and fragment analysis 1.1), the ratio of each background-corrected band intensity to the 16S rRNA band intensity for the respective time point was calculated and the lowest ratio was arbitrarily set to 1, to which other signals in each series were normalized. In experiments using RT-PCR, RNA was extracted from 11-day-old seedlings of each genotype using a Qiagen RN easy kit, as per the manufacturer's instructions. Reverse transcription was performed on 1 µg of total RNA using a Qiagen Omniscript kit. The primers used to distinguish WRI1 were designed to span the region of the first intron (5'-CCGACGCAGCTCTATCTACA-3' SEQ ID NO:38 and 5'-AGCCTCCCATCTTCCGTTGT-3' SEQ ID NO:39). Actin (At2g3762) was used for control purposes (5'-TGCGACAATGGAACTGGAATGG-3' SEQ ID NO:40 and 5'-AACAATCGATGGACCTGACTCG-3' SEQ ID NO:41). The cycle conditions were 3.5 min at 94° C., 0.5 min at 94° C., 0.75 min at 54° C., 1 min at 72° C., 30 cycles followed by 5 min at 72° C. In the wild type, the predicted PCR product is 358 bp, in the event of genomic DNA contamination; there is a product of 1080 bp. The same reaction conditions were used for the actin mRNA quantification, except that 25 cycles were used. For both, 1 unit of Invitrogen Taq polymerase was used with a final $MgCl_2$ concentration of 1.5 mM, dNTP concentration of 0.125 mM, and 10 pmol of each primer. Lipid extractions for the purpose of thin-layer chromatography were carried out as previously described (Focks and Benning, 1998) with the exception that the solvent system was 80:20:1, petroleum ether:ethyl ether:acetic acid. Seed oil quantitation by total fatty acid methylester analysis was carried out as previously described (Focks and Benning, 1998; Rossak et al., 1997). For time course experiments on seeds and seedlings, the sum of 20:0, 20:1, 22:0, and 22:1 LFA methylesters was reported.

Example IV

The following are examples of making transgenic plants overexpressing heterologous F-Box for lipid modification and/or increased lipid production in vegetative tissues using f-box genes.

This example describes a contemplated method for making and using plants having lowered tgd expression (i.e. expressing an RNAi construct of the present inventions) combined with overexpression of heterologous F-Box genes.

RNAi vectors and methods of engineering plants comprising these gene-silencing constructs for tgd 3 or tgd4 are described above. Constructs for overexpressing heterologous genes, i.e. F-box, and plants engineered for expressing these constructs are provided as described herein, and in WO 2007 038345, herein incorporated by reference in its entirety.

In some embodiments, plants of the present invention for increasing oil production in vegetative tissues were based, in part, upon incorporating the unexpected finding that overexpression of F-box genes in plants results in the increased production of plant oil. In particular, the overexpression of the *Arabidopsis thaliana* F-box protein gene (GenBank Accession Nos. NM_111499 (cDNA, SEQ ID NO:57) and NP 566277 (protein, SEQ ID NO:42) using the seed specific promoter phaseolin, produced seeds with a higher oil content phenotype (see, FIG. 17).

The sequence of the *Arabidopsis thaliana* F-box/Kelch-Repeat protein with GenBank Accession No. NP 566277 (protein, SEQ ID NO:42) is shown below.

```
  1 MKAIQLLWEA IMEATKRERR REDDDGEKAS PESLVLPPEI
 41 ITEILLRLPA KSIGRFRCVS KLFCTLSSDP GFAKIHLDLI
 81 LRNESVRSLH RKLIVSSHNL YSLDFNSIGD GIRDLAAVEH
121 NYPLKDDPSI FSEMIRNYVG DHLYDDRRVM LKLNAKSYRR
161 NWVEIVGSSN GLVCISPGEG AVFLYNPTTG DSKRLPENFR
201 PKSVEYERDN FQTYGFGFDG LTDDYKLVKL VATSEDILDA
241 SVYSLKADSW RRICNLNYEH NDGSYTSGVH FNGAIHWVFT
281 ESRHNQRVVV AFDIQTEEFR EMPVPDEAED CSHRFSNFVV
321 GSLNGRLCVV NSCYDVHDDI WVMSEYGEAK SWSRIRINLL
361 YRSMKPLCST KNDEEVLLEL DGDLVLYNFE TNASSNLGIC
401 GVKLSDGFEA NTYVESLISP NSYGIES
```

Accordingly, in one aspect, the present invention provides a genetic construct for the overexpression of an F-box protein in plants and plants overexpressing F-Box protein for use with tgd silencing constructs and plants expressing tgd silencing constructs of the present inventions. In general, such genetic constructs of the invention include embodiments described in WO/2007/038345, herein incorporated in its entirety in combination (i.e. stacked) with tgd RNAi of the present inventions. In particular, it is contemplated that aspects of the present inventions comprise overexpression of a heterologous F-box protein in plants in addition to reducing expression of a TGD gene resulting in lowered expressing of TGD proteins in the same plants resulting in a corresponding increase in TAG in vegetative tissues and seeds in plants having commercial value. In further embodiments, WRI1 and F-box genes are expressed within a plant having reduced TGD protein production.

Example V

This example describes exemplary generation of single transgenic lines for use in breeding double and multiple transgenic-engineered plants of the present inventions.

Double and multiple transgenic plant lines are contemplated to be established from individual transgenic plants. In one embodiment, transformed plants containing tgd RNAi constructs were grown to maturity and used in breeding methods of the present inventions. Thus, in one embodiment, a breeding method is contemplated comprising propagating transformed plants for use in developing plants and lines as source plants comprising RNAi constructs of the present inventions. In a further embodiment, these original or source plants are contemplated for breeding, such as in crossing, i.e. artificially or naturally, with other engineered plants in order to produce plants having additional modified gene expression of heterologous genes, i.e. stacked or pyramid genes. Thus, the presence of nucleic acid sequences encoding a heterologous wri1 gene and/or f-box gene of the present invention (including mutants or variants thereof) may be combined with traits of tgd RNAi transgenic plants by traditional plant breeding techniques. Such traditional techniques include but are not limited to artificial cross pollination, natural pollination, self-pollination, etc., and breeding methods including but not limited to back-crossing, in breeding, out crossing, hybridization, etc., wherein such crossing results in multiple generations for developing Accordingly, methods of making these engineered plants with increased TAG amounts comprises breeding these f-box or WRINKLED1 overexpressing plants with engineered plants having reduced expression of a TGD gene as the result of transformation of the host plant with a TGD RNAi gene silencing vector construct of the present interventions. In a preferred embodiment, these methods of breeding further comprise using breeding stock with desired agronomic traits, such as large amounts of TAG production, large seed sizes, a particular oil composition, strong growth characteristics, growth characteristics for a particular hardiness zone, high levels of fertility, etc., and/or desirable economic traits, such as roundup ready varieties or other plant lines having glyphosate-resistance.

Thus, in another embodiment, an overexpression construct of the present inventions is provided as a double gene vector for overexpressing both an AGPase RNAi silencing vector combined with an expression construct for an oil regulating transcript factor such as a WRINKLED1 gene in a host plant expressing a tgd RNAi construct having reduced TGD protein for increasing lipid production without significantly impacting host plant viability and fertility. Thus methods of the present inventions further comprise transforming plants, in particular oil seed plants, with a double gene overexpression vector that when expressed increases the amount of mRNA for encoding an oil transcription factor, such as encoding a WRI1 protein along with RNAi for reducing TGD proteins in a plant.

Example VI

This example describes material and methods comprising a double gene vector for overexpressing WRI1 in combination with reducing AGPRNAi.

Overexpression of WRI1 in combination with reduced AGPase (i.e. expressing a silencing construct AGPRNAi) caused a growth phenotype. Independent homozygous T3 transgenic *Arabidopsis* lines expressing a WRINKLED (WRI1) cDNA or suppressing the APS1 gene by RNAi under the control of the 35S cauliflower mosaic virus (CaMV) promoter or the Patatin B33 promoter in various combinations, summarized in FIG. 19A, were made.

The WRINKLED cDNA was obtained by PCR primers 5'CCAAggatcc-AAATCTAAACTTTCTCAGAGT3' (SEQ ID NO:58) and 5'CCTTacgcgtGGCAAA-GACATTGATT-ATT3' (SEQ ID NO:59). However, several WRINKLED cDNA sequences are available. For example, the WRINKLED cDNA can have the sequence provided with NCBI accession number NM_202701.2 (GI:145362489) and shown below as SEQ ID NO:44.

```
   1 CAGGGTTTAT TTAACTTGCC CTTTCTCGTT TCCTCCTTTT
  41 TTTCTTAAAC CACTCTGCTT CCTCTTCCTC TGAGAAATCA
  81 AATCACTCAC ACTCCAAAAA AAAATCTAAA CTTTCTCAGA
 121 GTTTAATGAA GAAGCGCTTA ACCACTTCCA CTTGTTCTTC
 161 TTCTCCATCT TCCTCTGTTT CTTCTTCTAC TACTACTTCC
 201 TCTCCTATTC AGTCGGAGGC TCCAAGGCCT AAACGAGCCA
 241 AAAGGGCTAA GAAATCTTCT CCTTCTGGTG ATAAATCTCA
 281 TAACCCGACA AGCCCTGCTT CTACCCGACG CAGCTCTATC
 321 TACAGAGGAG TCACTAGACA TAGATGGACT GGGAGATTCG
 361 AGGCTCATCT TTGGGACAAA AGCTCTTGGA ATTCGATTCA
 401 GAACAAGAAA GGCAAACAAG GTTTCGAGCA TATGACAGTG
 441 AAGAAGCAGC AGCACATACG TACGATCTGG CTGCTCTCAA
 481 GTACTGGGGA CCCGACACCA TCTTGAATTT TCCGGCAGAG
 521 ACGTACACAA AGGAATTGGA AGAAATGCAG AGAAGGAAGA
 561 AGGAAGAATA TTTGGCTTCT CTCCGCCGCC AGAGCAGTGG
 601 TTTCTCCAGA GGCGTCTCTA AATATCGCGG CGTCGCTAGG
 641 CATCACCACA ACGGAAGATG GGAGGCTCGG ATCGGAAGAG
 681 TGTTTGGGAA CAAGTACTTG TACCTCGGCA CCTATAATAC
 721 GCAGGAGGAA GCTGCTGCAG CATATGACAT GGCTGCGATT
 761 GAGTATCGAG GCGCAAACGC GGTTACTAAT TTCGACATTA
 801 GTAATTACAT TGACCGGTTA AAGAAGAAAG GTGTTTTCCC
 841 GTTCCCTGTG AACCAAGCTA ACCATCAAGA GGGTATTCTT
 881 GTTGAAGCCA AACAAGAAGT TGAAACGAGA GAAGCGAAGG
 921 AAGAGCCTAG AGAAGAAGTG AAACAACAGT AGAAGGAAGA
 961 ACCACCGCAA GAAGAAGAAG AGAAGGAAGA AGAGAAAGCA
1001 GAGCAACAAG AAGCAGAGAT TGTAGGATAT TCAGAAGAAG
1041 CAGCAGTGGT CAATTGCTGC ATAGACTCTT CAACCATAAT
1081 GGAAATGGAT CGTTGTGGGG ACAACAATGA GCTGGCTTGG
1121 AACTTCTGTA TGATGGATAC AGGGTTTTCT CCGTTTTTGA
1161 CTGATCAGAA TCTCGCGAAT GAGAATCCCA TAGAGTATCC
1201 GGAGCTATTC AATGAGTTAG CATTTGAGGA CAACAACAAC
1241 TTCATGTTCG ATGATGGGAA GCACGAGTGC TTGAACTTGG
1281 AAAATCTGGA TTGTTGCGTG GTGGGAAGAG AGAGCCCACC
1321 CTCTTCTTCT TCACCATTGT CTTGCTTATC TACTGACTCT
1361 GCTTCATCAA CAACAACAAC AACAACCTCG GTTTCTTGTA
1401 ACTATTTGGT CTGAGAGAGA GAGCTTTGCC TTCTAGTTTG
1441 AATTTCTATT TCTTCCGCTT CTTCTTCTTT TTTTTCTTTT
1481 GTTGGGTTCT GCTTAGGGTT TGTATTTCAG TTTCAGGGCT
1521 TGTTCGTTGG TTCTGAATAA TCAATGTCTT TGCCCCTTTT
1561 CTAATGCTCC AAGTTCAGAT
```

The AGPRNAi constructs were designed for this experiment and contemplated experiments with *B. napus* plants and therefore targeted a region of the sequence conserved across *Arabidopsis* and *Brassica*. A sequence from *B. napus* AGPase (accession AJ271162, SEQ ID NO:46) with 82% DNA sequence identity to the most similar *Arabidopsis* gene APS1 (At5g48300, SEQ ID NO:45) was used to design the RNAi construct. APS1 encodes one of the major catalytic isoforms of the small subunit of AGPase, which was found in the organs of the plant (Crevillen et al., 2005).

The following shows exemplary parts of an RNAi AGPase construct for use in operable combination with a promoter sequence. These parts are followed by an exemplary assembled construct for use in operable combination with a promoter.

The *Arabidopsis thaliana* ADPG pyrophosphorylase small subunit (APS1) with accession number At5g48300 is shown below and provided herein as SEQ ID NO:45.

```
   1 ATGGCGTCTG TATCTGCAAT TGGAGTTCTC AAGGTACCTC
  41 CTGCTTCGAC TTCCAATTCC ACCGGAAAAG CCACGGAGGC
  81 GGTTCCCACG AGGACTCTTT CTTTCTCCTC CTCTGTTACT
 121 TCATCCGACG ACAAGATTTC ACTCAAATCC ACCGTCTCCC
 161 GTCTTTGTAA ATCTGTTGTT CGCAGGAATC CGATCATCGT
 201 CTCTCCCAAA GCCGTCTCAG ATTCTCAAAA CTCTCAAACT
 241 TGTCTCGATC CTGATGCTAG CAGCAGTGTT TTGGGGATAA
 281 TCTTAGGAGG TGGAGCTGGA ACTCGTCTTT ATCCACTTAC
 321 GAAGAAGAGA GCGAAACCAG CTGTGCCTCT TGGTGCTAAC
 361 TATAGGCTTA TTGATATTCC TGTGAGCAAC TGTTTGAATA
 401 GCAACATATC CAAGATCTAT GTTCTTACTC AGTTCAATTC
 441 CGCGTCTTTG AATCGTCATC TTTCACGAGC TTATGCTAGT
 481 AACATGGGAG GTTATAAGAA TGAAGGATTC GTTGAAGTTC
 521 TCGCTGCTCA ACAGAGTCCT GAAAACCCCA ACTGGTTCCA
 561 GGGGACAGCT GATGCCGTCA GGCAATACTT GTGGTTGTTC
 601 GAGGAGCATA ATGTCTTGGA GTATCTCATT CTTGCTGGGG
 641 ATCATTTGTA TAGAATGGAC TATGAGAAGT TTATTCAAGC
 681 ACATAGGGAG ACTGATGCTG ATATCACAGT AGCTGCATTA
 721 CCAATGGACG AGCAACGAGC CACTGCTTTT GGGCTGATGA
 761 AGATTGATGA GGAAGGACGT ATTATTGAAT TTGCTGAAAA
 801 ACCAAAAGGG GAGCACCTAA AGGCCATGAA GGTTGACACA
 841 ACAATTCTAG GTCTTGATGA TCAGAGAGCC AAGGAGATGC
 881 CTTTCATTGC TAGTATGGGT ATTTATGTTG TAAGCAGAGA
 921 TGTAATGCTA GACTTACTAC GGAATCAGTT TCCTGGAGCT
 961 AATGACTTTG GAAGTGAAGT CATTCCCGGT GCCACTTCCC
1001 TTGGACTGAG GGTGCAAGCT TACCTATATG ATGGTTACTG
1041 GGAAGACATT GGTACTATAG AGGCATTTTA TAACGCTAAT
1081 CTTGGAATCA CCAAGAAACC AGTTCCTGAT TTTAGTTTCT
1121 ATGACCGTTC TGCTCCGATC TACACACAGC CGCGTTATTT
1161 ACCACCGTCT AAGATGCTTG ATGCTGATGT TACTGACAGT
1201 GTCATCGGAG AGGGCTGTGT TATCAAGAAC TGCAAAATTC
1241 ATCACTCTGT GGTTGGACTC CGTTCCTGCA TATCAGAAGG
1281 TGCTATTATT GAAGATTCGT TATTAATGGG AGCTGATTAT
1321 TACGAGACTG CTACGGAAAA GAGCCTCTTA AGCGCGAAAG
1361 GAAGTGTACC CATAGGTATT GGGAAAAACT CGCACATCAA
1401 AAGGGCCATC ATCGACAAAA ACGCACGTAT CGGTGACAAT
1441 GTCAAGATCA TAAACAGCGA CAACGTGCAA GAGGCAGCGA
1481 GAGAGACTGA TGGATATTTC ATAAAGAGCG GAATTGTAAC
1521 GGTTATCAAA GACGCCTTAA TCCCAACCGG CACTGTCATC
1561 TGAAGTACAC ATAATGCTCC TTTGTTTATT TCTT
```

Fragments can be used of a *Brassica napus* mRNA of cDNA encoding an ADP-glucose pyrophosphorylase small subunit (AGPase), for example, accession number AJ271162 (gi: 7688094), provided herein as SEQ ID NO:46.

```
   1 AAGAGTGAAG CTCCTCCTCT CGAACAACAA CAATGGCGAC
  41 AATGGCTGCA ATCGGATCCT TAAAAGTCCC TTCCTCTTCC
  81 TCGAACCACA CCCGTAGATT ATCATCTTCT TCTCAACGGA
 121 AGACTCTCTC GTTCTCGTCG TCTTCTCTTA CCGGAGAGAA
 161 ACTCAACCCG ACGCAGGAGA TCATCATCTC CAATCTCCCA
 201 CGTGGCAACG AGAGAAGAAC GCCATCGATC GTCTCTCCAA
 241 AAGCAGTTTC CGATTCGCAA AACTCGCAAA CTTGCCTTGA
 281 TCCTGACGCT AGCAGAAGTG TGTTGGGGAT AATTCTGGGA
 321 GGTGGTGCTG GAACGAGATT GTATCCGCTA ACGAAGAAGA
 361 GAGCGAAGCC AGCTGTTCCT CTCGGCGCTA ACTACCGTCT
 401 CATTGATATC CCAGTGAGCA ATTGCTTGAA CAGTAACATC
 441 TCCAAGATCT ATGTCCTTAC TCAGTTCAAC TCAGCTTCTC
 481 TCAACCGCCA TCTCTCCCGA GCTTACGCCA GCAACATGGG
 521 TGGTTACAAG AACGAAGGCT TCGTCGAGGT TCTTGCTGCT
 561 CAACAGAGTC CGAGAATCC CAATTGGTTT CAGGGGACTG
 601 CTGATGCAGT GAGGCAGTAC TTGTGGCTGT TGAAGAGCA
 641 CAATGTGTTG GAGTTTTTGG TTCTTGCAGG GGATCATTTG
 681 TACCGTATGG ACTACGAGAA GTTCATTCAA GCGCATCGTG
 721 AGACCGACGC TGATATCACT GTTGCTGCTC TTCCTATGGA
 761 TGAGAAACGT GCCACGGCTT TTGGACTTAT GAAGATTGAT
 801 GACGAAGGAA GGATCATTGA GTTTGCTGAG AAGCCTAAAG
 841 GAGAGCAGTT AAAGGCTATG AAGGTTGATA CAACAATCTT
 881 GGGACTTGAT GACGAAAGGG CCAAAGAGAT GCCCTTTATT
 921 GCTAGTATGG GGATATATGT TGTTAGCAAG AATGTGATGT
 961 TGGACTTGCT CCGAGACCAG TTCCCTGGAG CTAATGACTT
1001 CCGGAGAGAA GTTATCCCTG GTGCTACTGA TCTTGGACTC
1041 AGAGTGCAAG CTTATCTGTA TGATGGATAC TGGGAAGATA
```

```
1081 TTGGTACCAT TGAAGCCTTT TACAATGCTA ATCTTGGGAT

1121 CACCAAGAAA CCGAGACCAG ATTTCAGCTT CTATGACCGT

1161 TCAGCACCAA TCTACACACA GCCTCGGTAC TTACCTCCAT

1201 CCAAGATGCT TGATGCCGAT GTTACCGATA GTGTGATCGG

1241 TGAAGGTTGT GTCATCAAGA ATTGCAAAAT CCACCATTCC

1281 GTCATTGGTC TTCGGTCTTG CATATCGGAG GGTGCAATCA

1321 TAGAAGACAC CTTGTTGATG GGTGCTGACT ACTACGAGAC

1361 TGATGCGGAT AGGACACTCC TGGCTGCAAA AGGCAGCATC

1401 CCGATTGGCA TTGGCCGAGA CTCTCACATT AAAAGAGCTA

1441 TCATTGACAA GAATGCTCGT ATTGGTGACA ACGTCAAGAT

1481 CATCAACACG GACAATGTGC AAGAAGCTGC CAGAGAGACG

1521 GATGGATACT TCATCAAGAG CGGCATTGTT ACAGTGATCA

1561 AGGATGCTCT GATTCCTAGT GGAACTGTTA TCTAAGAGAC

1601 ACCACCACCC CGTTTGACAA TCTTCTTAAT ATCTCATGGT

1641 TTTGACCTCG AGTTAGCTTC CACTGATGCT ATCTCTAATG

1681 TTATCCGAGG TCAGGGCCTA TGCATCCTCC TGCCTTATCC

1721 CTAAATAATA TTCTCTACTT TGTATTCTAG TCTTTGGCGA

1761 T
```

For an RNAi construct (e.g., an RNAi cassette) one example of an AGPase sense sequence for RNAi is the following sequence identified herein as SEQ ID NO:47:

```
  1 5'-GGACTACGAG AAGTTCATTC AAGCGCATCG TGAGACCGAC

41 GCTGATATCA CTGTTGCTGC TCTTCCTATG GATGAGAAAC

81 GTGCCACGGC TTTTGGACTT ATGAAGATTG ATGACGAAGG

121 AAGGATCATT GAGTTTGCTG AGAAGCCTAA AGGAGAGCAG

161 TTAAAGGCTA TGAAGGTTGA TACAACAATC TTGGGACTTG

201 ATGACGAAAG GGCCAAAGAG ATGCCCTTTA TTGCTAGTAT

241 GGGGATATAT GTTGTTAGCA AGAATGTGAT GTTGGACTTG

281 CTCCGAGACC AGTTCCCTGG AGCTAATGAC TTCGGGAGTG

321 AAGTTATCCC TGGTGCTACT GATCTTGGAC TCAGAGTGCA

361 AGCTTATCTG TATGATGGAT ACTGGGAAGA TATTGGTACC

401 ATTGAAGCCT TTTACAATGC TAATCTTGGG ATCACCAAGA

441 AACCAGTACC AGATTTCAGC TTCTATGACC GTTCAGCACC

481 AATCTACACA CAGCCTCGGT-3'
```

A spacer DNA sequence with SEQ ID NO:48.

```
  1 5'-AGCTCCTGCT CTGTGAATTT CTCCGCTCAC
    GATAGATCTG

41 CTTATACTCC TTACATTCAA CCTTAGATCT GGTCTCGATT

81 TCTGTTTCTC TGTTTTTTTC TTTTGGTCGA GAATCTGATG

121 TTTGTTTATG TTCTGTCACC ATTAATAATA ATGAACTCTC
```

```
161 TCATTCATAC AATGATTAGT TTCTCTCGTC TACAAAACGA

201 TATGTTGCAT TTTCACTTTT CTTCTTTTTT TCTAAGATGA

241 TTTGCTTTGA CCAATTTGTT TAGATCTTTA TTTTATTTTA

281 TTTTCTGGTG GGTTGGTGGA AAGGAAAACA AAAAAAAAAC

321 AGCATAAATT GTTATTTGTT AATGTATTCA TTTTTTGGCT

361 ATTTGTTCTG GGTAAAAATC TGCTTCTACT ATTGAATCTT

401 TCCTGGATTT TTTACTCCTA TTGGGTTTTT AAGGAAAACA

441 TACATAATAA AAGGAAAACA AAGTTTTAT AGATTCTCTT

481 AAACCCCTTA CGATAAAGT TGGAATCAAA ATAATTCAGG

521 ATCAGATGCT CTTTGATTGA TTCAGATGCG ATTACAGTTG

561 CATGGCAAAT TTTCTAGATC CGTCGTCACA TTTTATTTTC

601 TGTTTAAATA TCTAAATCTG ATATATGATG TCGACAAATT

641 CTGGTGGCTT ATACATCACT TCAACTGTTT TCTTTTGGCT

681 TTGTTTGTCA ACTTGGTTTT CAATACGATT TGTGATTTCG

721 ATCGCTGAAT TTTTAATACA AGCAAACTGA TGTTAACCAC

761 AAGCAAGAGA TGTGACCTGC CTTATTAACA TCGTATTACT

801 TACTACTAGT CGTATTCTCA ACGCAATCGT TTTTGTATTT

841 CTCACATTAT GCCGCTTCTC TACTCTTTAT TCCTTTTGGT

881 CCACGCATTT TCTATTTGTG GCAATCCCTT TCACAACCTG

921 ATTTCCCACT TTGGATCATT TGTCTGAAGA CTCTCTTGAA

961 TCGTTACCAC TTGTTTCTTG TGCATGCTCT GTTTTTTAGA

1001 ATTAATGATA AAACTATTCC ATAGTCTTGA GTTTTCAGCT

1041 TGTTGATTCT TTTGCTTTTG GTTTTCTGCA GGTCAATTC-3'
```

The AGPase antisense sequence for the RNAi was as follows (with SEQ ID NO:49).

```
  1 5'-ACCGAGGCTG TGTGTAGATT GGTGCTGAAC GGTCATAGAA

41 GCTGAAATCT GGTACTGGTT TCTTGGTGAT CCCAAGATTA

81 GCATTGTAAA AGGCTTCAAT GGTACCAATA TCTTCCCAGT

121 ATCCATCATA CAGATAAGCT TGCACTCTGA GTCCAAGATC

161 AGTAGCACCA GGGATAACTT CACTCCCGAA GTCATTAGCT

201 CCAGGGAACT GGTCTCGGAG CAAGTCCAAC ATCACATTCT

241 TGCTAACAAC ATATATCCCC ATACTAGCAA TAAAGGGCAT

281 CTCTTTGGCC CTTTCGTCAT CAAGTCCCAA GATTGTTGTA

321 TCAACCTTCA TAGCCTTTAA CTGCTCTCCT TTAGGCTTCT

361 CAGCAAACTC AATGATCCTT CCTTCGTCAT CAATCTTCAT

401 AAGTCCAAAA GCCGTGGCAC GTTTCTCATC CATAGGAAGA

441 GCAGCAACAG TGATATCAGC GTCGGTCTCA CGATGCGCTT

481 GAATGAACTT CTCGTAGTCC-3'
```

One full sequence for an RNAi construct is as follows (SEQ ID NO:50).

```
    5'-GGACTACGAG AAGTTCATTC AAGCGCATCG
       TGAGACCGAC
  41 GCTGATATCA CTGTTGCTGC TCTTCCTATG GATGAGAAAC
  81 GTGCCACGGC TTTTGGACTT ATGAAGATTG ATGACGAAGG
 121 AAGGATCATT GAGTTTGCTG AGAAGCCTAA AGGAGAGCAG
 161 TTAAAGGCTA TGAAGGTTGA TACAACAATC TTGGGACTTG
 201 ATGACGAAAG GGCCAAAGAG ATGCCCTTTA TTGCTAGTAT
 241 GGGGATATAT GTTGTTAGCA AGAATGTGAT GTTGGACTTG
 281 CTCCGAGACC AGTTCCCTGG AGCTAATGAC TTCGGGAGTG
 321 AAGTTATCCC TGGTGCTACT GATCTTGGAC TCAGAGTGCA
 361 AGCTTATCTG TATGATGGAT ACTGGGAAGA TATTGGTACC
 401 ATTGAAGCCT TTTACAATGC TAATCTTGGG ATCACCAAGA
 441 AACCAGTACC AGATTTCAGC TTCTATGACC GTTCAGCACC
 481 AATCTACACA CAGCCTCGGT AGCTCCTGCT CTGTGAATTT
 521 CTCCGCTCAC GATAGATCTG CTTATACTCC TTACATTCAA
 561 CCTTAGATCT GGTCTCGATT TCTGTTTCTC TGTTTTTTC
 601 TTTTGGTCGA GAATCTGATG TTTGTTTATG TTCTGTCACC
 641 ATTAATAATA ATGAACTCTC TCATTCATAC AATGATTAGT
 681 TTCTCTCGTC TACAAAACGA TATGTTGCAT TTTCACTTTT
 721 CTTCTTTTTT TCTAAGATGA TTTGCTTTGA CCAATTTGTT
 761 TAGATCTTTA TTTTATTTTA TTTTCTGGTG GGTTGGTGGA
 801 AAGGAAAACA AAAAAAAAC AGCATAAATT GTTATTTGTT
 841 AATGTATTCA TTTTTTGGCT ATTTGTTCTG GGTAAAAATC
 881 TGCTTCTACT ATTGAATCTT TCCTGGATTT TTTACTCCTA
 921 TTGGGTTTTT AAGGAAAACA TACATAATAA AAGGAAAACA
 961 AAAGTTTTAT AGATTCTCTT AAACCCCTTA CGATAAAGT
1001 TGGAATCAAA ATAATTCAGG ATCAGATGCT CTTTGATTGA
1041 TTCAGATGCG ATTACAGTTG CATGGCAAAT TTTCTAGATC
1081 CGTCGTCACA TTTTATTTTC TGTTTAAATA TCTAAATCTG
1121 ATATATGATG TCGACAAATT CTGGTGGCTT ATACATCACT
1161 TCAACTGTTT TCTTTTGGCT TTGTTTGTCA ACTTGGTTTT
1201 CAATACGATT TGTGATTTCG ATCGCTGAAT TTTTAATACA
1241 AGCAAACTGA TGTTAACCAC AAGCAAGAGA TGTGACCTGC
1281 CTTATTAACA TCGTATTACT TACTACTAGT CGTATTCTCA
1321 ACGCAATCGT TTTTGTATTT CTCACATTAT GCCGCTTCTC
1361 TACTCTTTAT TCCTTTTGGT CCACGCATTT TCTATTTGTG
1401 GCAATCCCTT TCACAACCTG ATTTCCCACT TTGGATCATT
1441 TGTCTGAAGA CTCTCTTGAA TCGTTACCAC TTGTTTCTTG
1481 TGCATGCTCT GTTTTTTAGA ATTAATGATA AAACTATTCC
1521 ATAGTCTTGA GTTTTCAGCT TGTTGATTCT TTTGCTTTTG
1561 GTTTTCTGCA GGTCAATTCA CCGAGGCTGT GTGTAGATTG
1601 GTGCTGAACG GTCATAGAAG CTGAAATCTG GTACTGGTTT
1641 CTTGGTGATC CCAAGATTAG CATTGTAAAA GGCTTCAATG
1681 GTACCAATAT CTTCCCAGTA TCCATCATAC AGATAAGCTT
1721 GCACTCTGAG TCCAAGATCA GTAGCACCAG GGATAACTTC
1761 ACTCCCGAAG TCATTAGCTC CAGGGAACTG GTCTCGGAGC
1801 AAGTCCAACA TCACATTCTT GCTAACAACA TATATCCCCA
1841 TACTAGCAAT AAAGGGCATC TCTTTGGCCC TTTCGTCATC
1881 AAGTCCCAAG ATTGTTGTAT CAACCTTCAT AGCCTTTAAC
1721 TGCTCTCCTT TAGGCTTCTC AGCAAACTCA ATGATCCTTC
1761 CTTCGTCATC AATCTTCATA AGTCCAAAAG CCGTGGCACG
1801 TTTCTCATCC ATAGGAAGAG CAGCAACAGT GATATCAGCG
1841 TCGGTCTCAC GATGCGCTTG AATGAACTTC TCGTAGTCC-3'
```

Figure 19C:
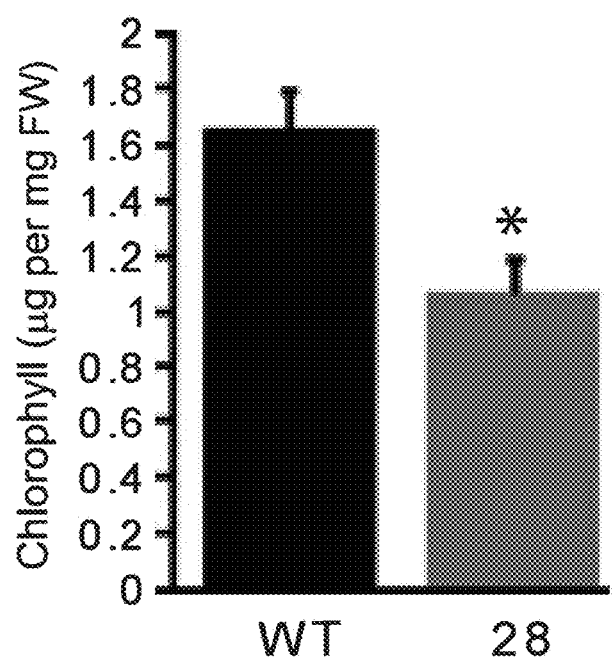

Three representative lines were selected from each group for further analysis. On ½ MS medium supplemented with 1% sucrose, the transgenic lines with single-gene constructs germinated and established into complete seedlings within 10-15 days. However, delayed development and expansion of cotyledons and leaves were observed in two of the AGPRNAi-WRI1 double gene transgenic lines 14 and 28, with these seedlings developing a glossy pale green appearance (FIG. 19B). Consistent with the pale green phenotype, the total chlorophyll content of AGPRNAi-WRI1 line 28 was almost 30% lower than that of wild-type plants (FIG. 19C).

Figure 19D:
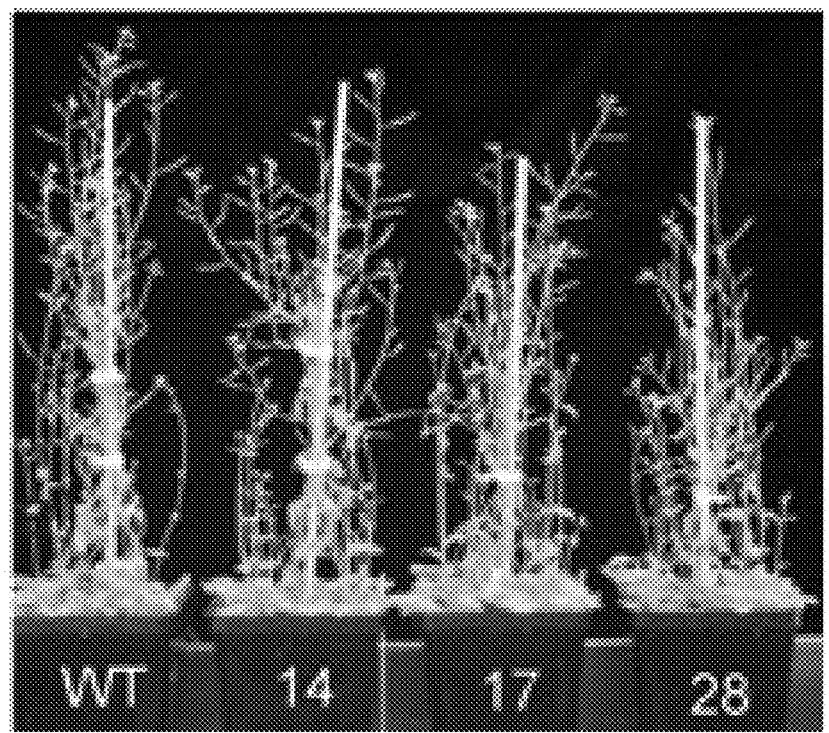

On soil, the AGPRNAi-WRI1 lines established well and underwent normal growth and development compared to wild-type plants (FIG. 19D). The distinct pale green appearance of the lines carrying the double-gene construct led us to further investigate the combinatorial role of WRI1 overexpression and AGPRNAi in these transgenic plants. The abundance of WRI1 and APS1 mRNA in the transgenic plants was determined with qRT-PCR. In the 35S-WRI1 and B33-WRI1 lines, levels of WRI1 mRNA in 15-day-old seedlings were between 67- and 85-fold higher compared to wild-type seedlings, with few notable differences depending on the type of promoter used (FIG. 20A). In 35S-AGPRNAi transgenic lines, the expression of WRI1 was increased between 2.5- and 11-fold compared to wild-type plants (FIG. 20A). Surprisingly, WRI1 transcript abundance was generally further enhanced in the AGPRNAi-WRI1 lines where WRI1 overexpression was combined with AGPRNAi, with WRI1 transcript levels between 93- and 120-fold that of wild type.

Figure 20B:
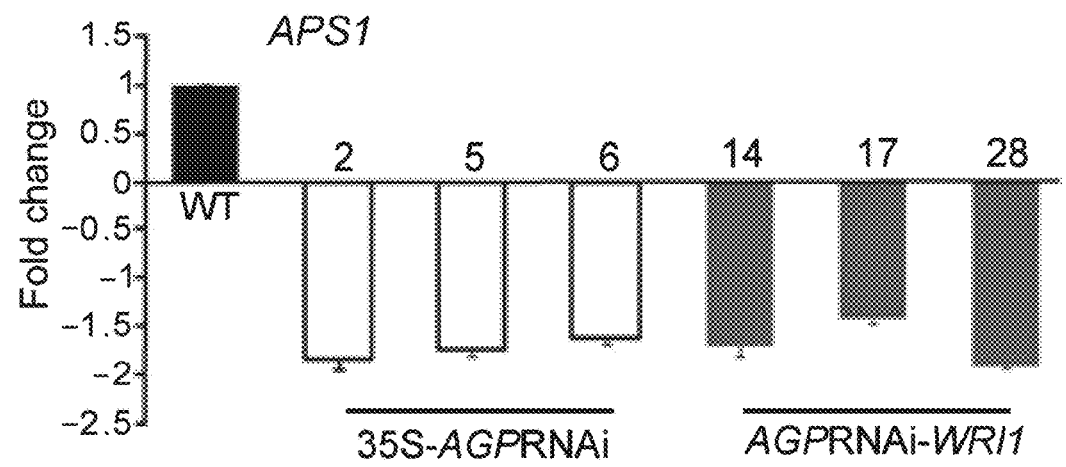

As APS1 (At5g48300) was the most similar *Arabidopsis* gene to the *B. napus* AGPase-encoding sequence chosen for the RNAi constructs, the relative expression of APS1 mRNA in the transgenic lines was analyzed. In 15-day-old seedlings of AGPRNAi-WRI1 lines, in which the AGPRNAi cassette was expressed under the control of the Patatin B33 promoter, the abundance of APS1 mRNA was decreased between −1.4-fold and −1.9-fold (FIG. 20B). In the 35S-AGPRNAi transgenic lines, in which the AGPRNAi construct was expressed under the control of the 35S CaMV promoter, the abundance of APS1 transcript was reduced between −1.6-fold and −1.8-fold, respectively. Thus, irrespective of the promoter used, reduction in APS1 mRNA was similar and had no deleterious effect on overall growth and development.

Figure 21A:
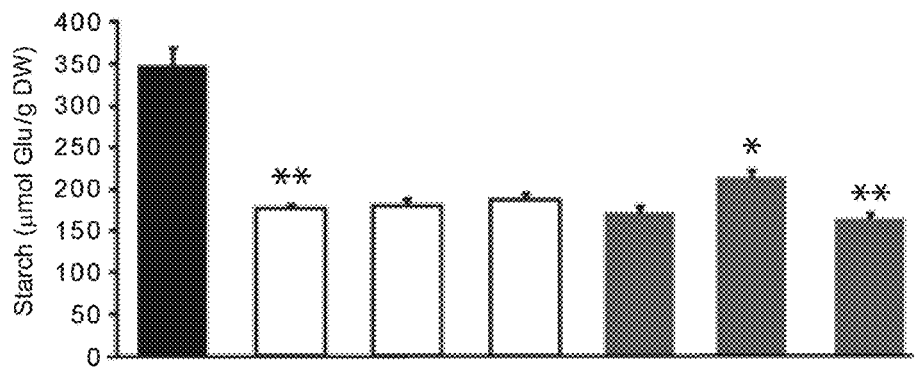
FIG. 21A-21D graphically illustrates starch and sugars level in T3 homozygous 35S-AGPRNAi lines (open bars), AGPRNAi-WRI1 lines (grey bars) compared to wild-type plants (dark bars).

Presence of AGPRNAi led to the inhibition of starch biosynthesis and accumulation of sugars. To determine the effects of the transgenes on carbohydrate metabolism, starch, sucrose, glucose and fructose levels of 15-day-old seedlings from the two types of AGPRNAi lines were analyzed. Compared to wild-type plants, the level of starch was reduced by about half in the 35S-AGPRNAi and AGPRNAi-WRI1 lines (FIG. 21A). The reduction of starch levels was almost the same in all the AGPRNAi lines irrespective of the type of promoter used to drive the AGPRNAi construct.

Figure 21B:
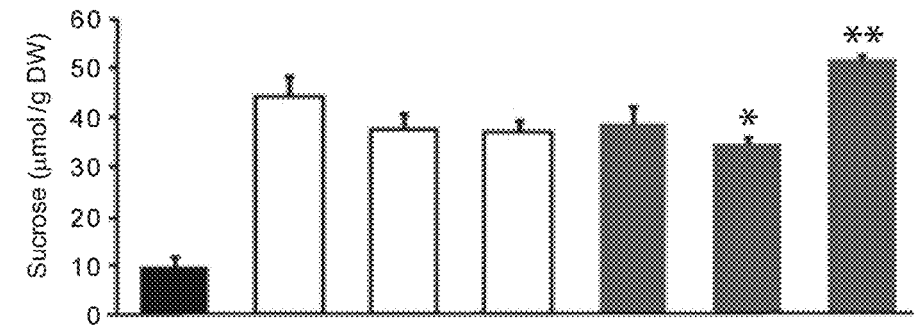
Figure 21C:
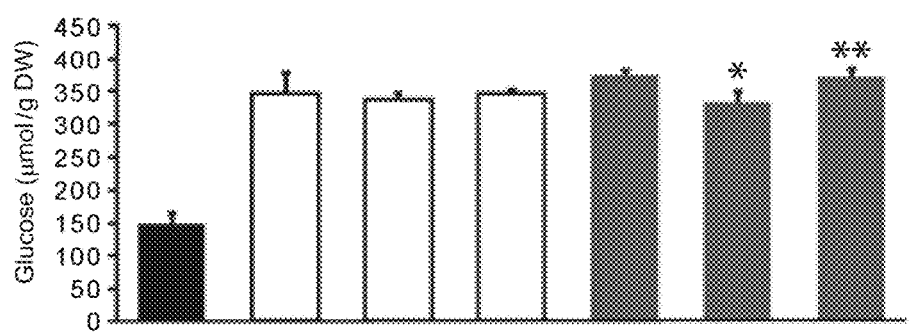
Figure 21D:
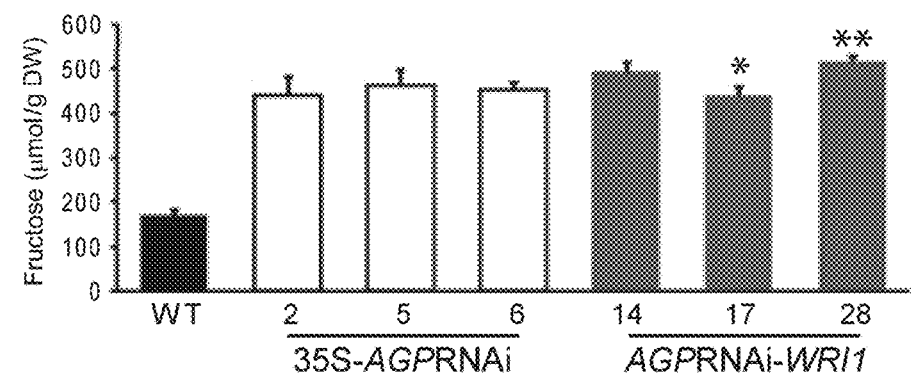

These results confirmed that the construct was effective in targeting starch biosynthesis and reducing carbon partitioning into starch. 35S-AGPRNAi and AGPRNAi-WRI1 lines accumulated considerably higher levels of sucrose, with a three to four-fold increase compared to wild-type plants (FIG. 21B). Similarly, the levels of glucose and fructose were higher (approximately 2-3-fold) in all these transgenic lines compared to wild type (FIG. 21C-D). AGPRNAi-WRI1 line 28 accumulated even higher levels of sucrose (5.3-fold), glucose (2.8-fold) and fructose (three-fold) than other lines (FIG. 21B-D). These results suggested that lower starch levels and higher levels of sugars are mainly because of the down-regulation of APS1. It is also apparent that the WRI1 mRNA production in AGPRNAi-WRI1 lines was elevated in the respective lines. For example, in AGPRNAi-WRI1 line 17, comparatively lower sucrose levels were observed compared to the other two AGPRNAi-WRI1 lines, 14 and 28 (FIG. 21B).

Correspondingly line 17 possessed comparatively lower WRI1 mRNA levels (90-fold) than the other two lines, in which the expression was almost 105-120-fold that of wild type (FIG. 20A). The vegetative tissues of AGPRNAi-WRI1 transgenic lines accumulate higher levels of TAGs. Electrospray ionization mass spectrometry (ESI-MS) was used to quantify the TAGs present in 15-day-old wild-type and transgenic seedlings grown on 1% sucrose. The AGPRNAi-WRI1 lines 14 and 28 showed considerably higher levels of oil, 3.7- and 5.8-fold higher (3 and 4.5 nmoles/mg DW), respectively, compared to wild type (FIG. 22A). The overall accumulation of TAG in the transgenic lines expressing WRI1 alone was between 2.6- and 2.8-fold higher than the wild type, irrespective of the promoter used. In 35S-AGPRNAi line 6, the TAG level in vegetative tissues was not different compared to wild type; lines 2 and 5 accumulated slightly more TAG (1.4- and 1.3-fold) than wild type. Taken together, these data provide evidence that the expression of the AGPRNAi alone was not sufficient to enhance the accumulation of oil in the seedlings. However, the combination of WRI1 overexpression along with AGPRNAi enhanced vegetative oil accumulation to levels higher than that with WRI1 ectopic expression alone. Analysis of the ESI-MS spectra of neutral lipid extracts from the AGPRNAi-WRI1 line 28 revealed the presence of TAG molecular species containing the longer fatty acids 20:1 and 22:1 typically found in seed oils (FIG. 22C). In contrast, their relative abundance was low in wild type (FIG. 22B). The presence of these seed-specific fatty acids was further confirmed by ESI-MS2, which produced the expected daughter fragments (FIG. 22D).

The first leaf pair and main root of the high oil accumulator line 28 and of a wild type was analyzed by confocal microscopy. As revealed by Nile red staining, the numbers and size of oil droplets were very distinct and high in line 28 leaf and root samples. The droplets were distributed close to the chloroplast in the leaf. In contrast, very few oil droplets were observed in the wild-type leaf and root samples.

Expression of WRI1 target genes in high-oil lines is increased. To probe the efficacy of the WRI1 expression construct was examined. The relative mRNA abundance of known WRI1 target genes involved in glycolysis or fatty acid biosynthesis in 35S-WRI1 line 7, AGPRNAi-WRI1 line 28 and wild-type seedlings grown for 15 days on 1% sucrose. When normalized to wild-type values, the transcript levels for sucrose synthase 2 (SUS2) At5g49190 (14-fold), biotin carboxyl carrier protein isoform 2 (BCCP2) At5g15530 (3.7-fold) and acyl carrier protein 1 (ACP1) At3g05020 (5.6-fold) were considerably higher in AGPRNAi-WRI1 line 28 compared to 35S-WRI1 line 7 (3.2-, 2.2- and 3.6-fold, respectively; FIG. 23). Slight increases in the expression of the genes encoding plastidic pyruvate kinase beta subunit 1 (Pl-PKb1) At5g52920, 3-oxoacyl (acyl-carrier protein) reductase (3OAR) At1g24360, pyruvate dehydrogenase E1 alpha (PDHE1a) At1g01090 and diacylglycerol acyltransferase 1 (TAG1) At2g19450 were observed in both groups of transgenic lines relative to wild-type plants (FIG. 23). These results confirmed that elevated WRI1 expression and increased sugars levels in AGPRNAi-WRI1 line 28 promoted the expression of WRI1 target genes as tested. Thus, conversion of available sugars into oil could be carried out by the concerted activity of the proteins encoded by these genes in the AGPRNAi-WRI1 line 28. This mechanism was not apparent in the transgenic lines expressing the WRI1 cDNA alone or in wild-type plants.

TABLE 11

Triacylglycerol (TAG) contribution to carbon and energy density of dry biomass compared to carbohydrates.

| Carbon | Carbohydrate* (μmolC/gDW) | TAG (μmolC/gDW) | Carbohydrate* % | TAG % | Starch % | TAG % |
|---|---|---|---|---|---|---|
| WT | 4446.32 | 42.73 | 99.04 | 0.96 | 97.99 | 2.01 |
| 28 | 8619.19 | 248.52 | 97.2 | 2.8 | 79.83 | 20.17 |

| Energy density | Carbohydrate*,† (kJ/gDW) | TAG (μmolC/gDW) | Carbohydrate* % | TAG % | Starch % | TAG % |
|---|---|---|---|---|---|---|
| WT | 2.07 | 0.03 | 98.7 | 1.3 | 97.4 | 2.6 |
| 28 | 4.02 | 0.15 | 96.3 | 3.8 | 75.0 | 25.0 |

*Includes starch, sucrose, glucose and fructose.
†Based on 2803 kJ/mol for glucose CRC Handbook of Chemistry and Physics (2008), herein incorporated by reference.
‡Based on 35 114 kJ/mol for triolein (Freedman and Bagby, 1989, herein incorporated by reference).
§Energy stored in TAG as percentage. WT, wild type; 28: AGPRNAi-WRINKLED1.

TABLE 12

Primers used in methods described herein.

| Gene | Accession | F/R | Sequence |
|---|---|---|---|
| Actin2 | At3g18780 | F<br>R | TGTGACAATGGTACCGGTATGG<br>GCCCTGGGAGCATCATCTC<br>(SEQ ID NO: 62) |
| ACP1 | At3g05020 | F<br>R | TGTCTGGCAACAACAAGGATTAGT<br>GCGGAGGTTGAAGGATAGATTAGTC<br>(SEQ ID NO: 63) |
| 3OAR | At1g24360 | F<br>R | AAAGCCGTCGCGAAGCTA<br>GGAGCCAATTGTCGGATTTG<br>(SEQ ID NO: 64) |
| APS1 | At5g48300 | F<br>R | ATGGCGTCTGTATCTGCAATTGGAG<br>GGATTTGAGTGAAATCTTGTCGTCG<br>(SEQ ID NO: 65) |
| BCCP2 | At5g15530 | F<br>R | AACAGGCGGGTCGGATCT<br>GCGGCTGCCATCTTTGAG<br>(SEQ ID NO: 66) |
| PDHE1a | At1g01090 | F<br>R | GAGGCCAAGGTGGATCCAT<br>CAAAGCCACCAAGCATGTTG<br>(SEQ ID NO: 67) |
| P1-PKb1 | At5g52920<br>R | F | CCAACGGTGGATCTGTGTCTAC<br>TCACTGCAAAACTCGCTGGTT<br>(SEQ ID NO: 68) |
| SUS2 | AT5G49190 | F<br>R | CAGTCTGCAGAGGAAGCCATAGT<br>AGGTCTGGGACGTATAGCCAAA<br>(SEQ ID NO: 69) |
| TAG1 | At2g19450 | F<br>R | TGGATTCTGCTGGCGTTACTAC<br>AGCCTATCAAGATCGACGAACTCT<br>(SEQ ID NO: 70) |
| WRI1 | At3g54320 | F<br>R | AAACGAGCCAAAAGGGCTAAG<br>GGGCTTGTCGGGTTATGAGA<br>(SEQ ID NO: 71) |

F- = Forward
R = Reverse

Exemplary Materials and Methods.

Plasmid construction. A double gene construct was made for duel function: an RNAi cassette (construct) for reducing AGPase translation (i.e. silencing AGPase) while overexpressing WRI1, see Cernac et al., 2004, herein incorporated by reference in its entirety. The WRI1 cDNA insert from Arabidopsis thaliana (Cernac and Benning, 2004) was obtained by PCR primers 5'CCAAggatcc-AAATCTAAACTTTCTCAGAGT3' (SEQ ID NO:58) and 5'CCTTacgcgtGGCAAA-GACATTGATTATT3' (SEQ ID NO:59). A fragment of 1463 bp containing the complete open reading frame was digested with BamHI and MluI. This fragment was then placed between a CaMV 35S (35S)/Patatin B33 (B33) promoter (Koster-Topfer et al., 1989, herein incorporated by reference), and a nos terminator to form an intermediate vector p35S-WRI1-nos and sequencing was performed. A C-terminal His-Tag was introduced by site-directed mutagenesis with two inverse primers WRI1HisR 5' gtgatgatgGACCAAATAGTTA-CAAGAAAC3' (SEQ ID NO:72) and WRI1HisF 5' catcac-catTGAGAGAGAGAGCTTT3' (SEQ ID NO:73). This vector was then digested with SfiI and inserted into a pLH6000 vector (DNA cloning service, Hamburg, Germany) to form 35S-WRI1 and B33-WRI1 (FIG. 19A-B). B. napus AGPase DNA sequence was used, which was already proven to inhibit AGPase activity in B. napus (Vigeolas et al., 2004) under the control of the 35S or B33 promoter. A B. napus AGPase (accession AJ271162) fragment from 565 to 1157 bp was synthesized; the 500-bp fragment was used for the construction of RNAi cassette in vector p35-iF2-1DCS (DNA Cloning Service). The 35S/B33 promoter was inserted (Koster-Topfer et al., 1989, herein incorporated by reference) to give rise to 35S/B331F2-AGPRNAi (35S-AGPRNAi) (FIG. 19). Fragment 35S-WRI1His-nos was inserted into the NotI and NheI restriction sites of vector B331F2-AGPR-NAi to form vector B331F2-AGPRNAi-WRI1His. This cassette was cut with SfiI and cloned into the SfiI restriction site of pLH6500 (DNA Cloning Service) to form the double-gene construct AGPRNAi-WRI1 (FIG. 19A).

Plant material and transformation. Arabidopsis wild-type (Col2) seeds or transgenic seeds were surface sterilized and grown on ½ Murashige and Skoog (MS) agar plates containing 1% sucrose in a growth chamber set to 16 h light/8 h dark (70-80 lm/m 2/s) at 22° C. after 2 days of stratification at 4° C. Fifteen-day-old wild-type and transgenic plants were transferred onto soil and grown in a growth chamber at 16 h light/8 h dark (70-80 lm/m 2/s) and 22° C. The binary vectors were introduced into Agrobacterium strain GV3101 by electroporation, and the T-DNAs were mobilized into Arabidopsis by flower-dip transformation (Clough and Bent, 1998). Transgenic plants (T1) were selected on ½ MS agar plates containing 1% sucrose and 20 mg/L hygromycin or 100 mg/L kanamycin. In general, wild-type and homozygous transgenic seedlings were grown on the same shelf of the growth chamber when used for metabolite analysis and other assays.

Quantitative real-time PCR (qRT-PCR). Total RNA was extracted from 15-day-old plants using an RNeasy Plant Mini Kit (Qiagen, Valencia, Calif.), and samples were stored at −80° C. Approximately 0.5 µg of total RNA was reverse transcribed by SuperScript III (Invitrogen, Carlsbad, Calif.), according to the manufacturers protocol. The cDNA (1.0 µL) was used as a template in a 23-µL PCR consisting of forward and reverse gene-specific primers (Table 12) and Fast SYBR Green master mix (Applied Biosystems, Forest City, Calif.) on an Applied Biosystems PRISM 7000 Sequence Detection System. The copy numbers of the cDNAs were quantified using a standard curve method, and the copy numbers of each sample was standardized to ACTIN2. The relative expression (as fold change) was scaled such that the expression level of the wild type was equal to one in the graphs.

Metabolite analysis. Fifteen-day-old wild-type and transgenic Arabidopsis whole seedlings were freeze-dried. Neutral lipids were extracted from dried samples using chloroform:methanol with 100 µM internal standard tri15:0 TAG and separated on silica plate using a mixture of solvents consisting of petroleum ether:ethyl ether:acetic acid (80:20:1, by volume). After thin-layer chromatography (TLC), TAG bands were visualized with iodine vapor. For quantitative analysis, TAG bands were isolated from the TLC plate, dissolved in toluene with 1 µM internal standard tri13:0 TAG and assayed using ESI-MS as described previously (Durrett et al., 2010, herein incorporated by reference in its entirety). Starch and sugars were analyzed by using an NAD(P)H-linked assay (Lowry & Passonneau, A flexible system of enzymatic analysis (Academic Press NY 1972), herein incorporated by reference in its entirety). About 5- to 10-mg dried whole seedling samples were ground into fine powder in a Retsch Mill at a frequency of 30 (maximum speed) for 30 s, soluble sugars were extracted by the addition of 1 mL 3.5% perchloric acid. Tubes were incubated on ice for 5 min before being centrifuged at 20,000 g for 10 min at 4° C. Approximately 750 µL of supernatant was recovered and processed as described below for glucose, fructose and sucrose assays. The pellet was washed twice with 70% alcohol, resuspended in 500 µL 0.2 M KOH and incubated at 95° C. for 30 min. Samples were allowed to cool for 2-5 min before adding 90 μL of 1 M acetic acid to bring the pH to approximately 5. Starch in the pellet was broken down to glucose by the addition of an enzyme cocktail (50 μL) consisting of 6.6 U amyloglucosidase (E-AMGDF; Megazyme, Wicklow, Ireland) and 50 U of alpha-amylase (E-ANAAM; Megazyme) and incubated for 2 days on a shaker at room temperature. Samples were then centrifuged for 30 min at 20,000 g, and the supernatant was transferred to fresh microfuge tubes. Five to ten microliters of the starch sample were assayed for glucose as described below. The 750-μL supernatant recovered as described above was neutralized to pH 7 by the addition of 150 μL of buffer consisting of 2 M KOH, 150 mM Hepes and 10 mM KCl. Samples were frozen in liquid nitrogen to help precipitate salts. Samples were then thawed and centrifuged at 20,000 g, and the supernatant was transferred to a fresh microfuge tube. Both starch and soluble sugars were assayed on a plate reader (Spectra Max M2, Molecular devices, Sunnyvale, Calif.) using an NADP(H)-linked assay at 340 nm. Samples were read in triplicate, using standard 96-well clear bottom plates. Each well that was used was 15 mM $MgCl_2$, 3 mM EDTA, 500 nmol NADP, 500 nmol ATP and 0.4 U glucose-6-phosphate dehydrogenase (G-8529; Sigma, St Louis, Mo.). Five microliters of sample was added to each well, and the reaction was started by adding 0.5 U of Hexokinase (H-4502; Sigma). Fructose and sucrose were determined by the sequential addition of 4 U Phosphoglucose isomerase (P-9544; Sigma) and 25 U Invertase (I-4504; Sigma). Change in optical density (Δ OD) were determined by taking endpoint assays before and after the addition of each enzyme. Because the Spectra Max M2 plate reader can also determine the path length of aqueous samples, absorbance units were normalized to a 1-cm path length and absolute glucose amounts were determined using an extinction coefficient of 6220 L/mol/cm for Nicotinamide 2-phosphoadenine dinucleotide (NADPH) at 340 nm (Lowry and Passonneau, 1972, herein incorporated by reference).

Microscopy. For oil droplet visualization, the first pair of leaves and main root samples from 15-day-old wild-type and transgenic seedlings were used. Freshly harvested leaf and root samples mounted in Nile red (2.5 μg/mL methanol) in 75% glycerol on a slide were examined using an Olympus FluoView 1000 Laser Scanning Confocal Microscope. Oil droplets were observed at 570-630 nm emission following 559-nm excitation by a solid-state laser. Chloroplasts were observed at 655-755-nm emission using the same laser excitation. Images were captured with the Olympus FluoView 1000 ASW software (Olympus, Center Valley, Pa.).

Example VII

This example illustrates that plants generated using the methods described herein accumulate higher levels of triacylglycerols (TAGs) in their vegetative tissue.

*Arabidopsis* lines overexpressing WRINKLED1 (WRI1) alone, plants overexpressing WRINKLED with down-regulation of AGPase, and plants that overexpress WRINKLED with down regulation of AGPase in tgd1-1 mutant background were generated as described herein.

After growth for fifteen days, vegetative tissues were collected from seedlings and dried. Triacylglycerol (TAG) levels in these vegetative tissues of the 15-day-old-seedling were measured by electrospray ionization mass spectrometry (ESI-MS) quantification.

Figure 24:
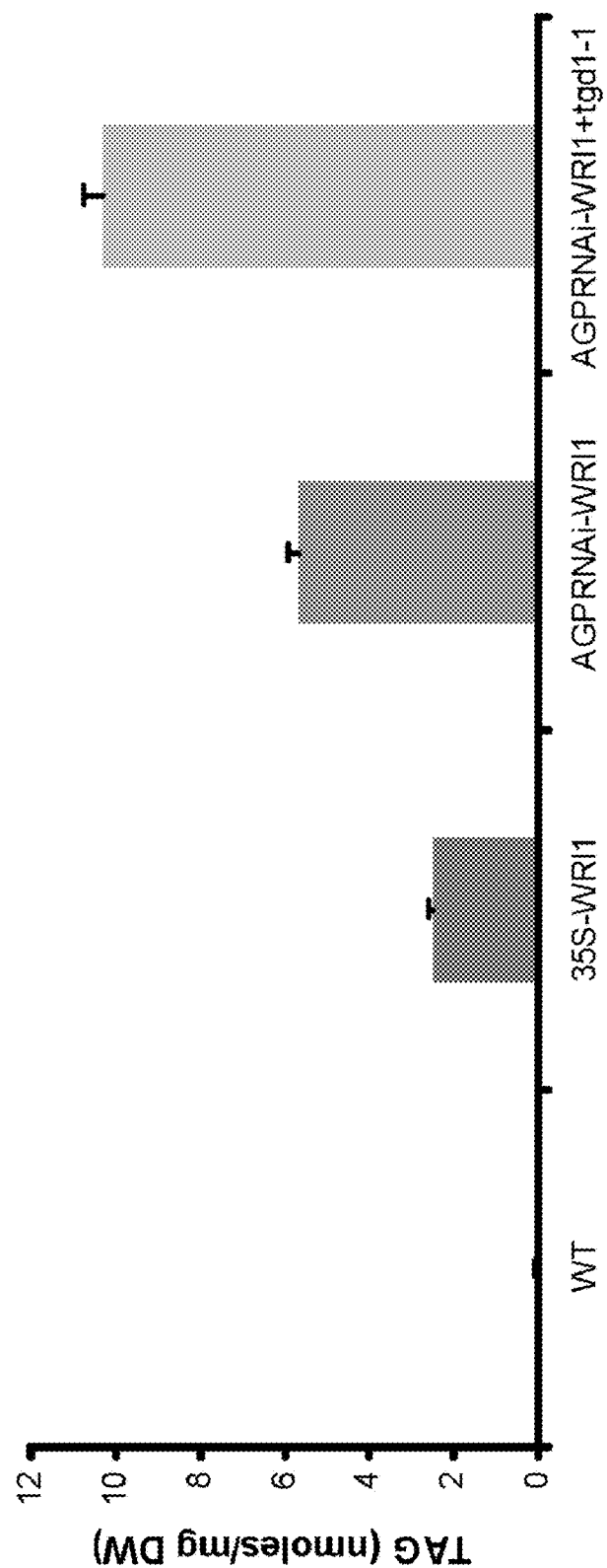
FIG. 24 graphically illustrates oil (triacylglycerol) content in *Arabidopsis* plants overexpressing WRINKLED1 (WRI1) alone, in plants overexpressing WRINKELD with down-regulation of APS1 (AGPRNAi), and in plants overexpressing WRINKLED, with down-regulation of APS1 in a tgd1-1 mutant background (plants having reduced TGD protein). As shown, plants having the combination of WRINKLED overexpression, down-regulation of APS1, and reduced TGD protein accumulate higher levels of triacylglycerols (TAGs) in their vegetative tissue of 15-day-old-seedling as measured by electrospray ionization mass spectrometry (ESI-MS) quantification. The error bars represent the standard deviation of the mean of three independent experiments (n=4).

FIG. 24 illustrates that while overexpression of WRINKLED and down regulation of AGPase can increase the level of triacylglycerols in the vegetative tissues of plants, the combination of WRINKLED overexpression, down regulation of AGPase, and reduced tgd function substantially increases the amount of triacylglycerols in plant vegetative tissues. For example, plants overexpression WRINKLED had about 2.2 nmoles triacylglycerols per mg dry weight (DW) of tissue, while plants overexpressing WRINKLED and down regulating AGPase had about 5.7 nmoles triacylglycerols per mg dry weight of tissue.

However, plants having combined WRINKLED overexpression, down regulation of AGPase, and reduced tgd function had about 10.3 nmoles triacylglycerols per mg dry weight of tissue. As illustrated wild type plants have substantially no detectable levels of triacylglycerols in their tissues.

These data show that the methods and genetic constructs described herein provide plants with significantly more oil content than is present in wild type plants, or even in plants with increased WRINKLED expression and reduced AGPase expression.

All publications and patents mentioned in the above specification are herein incorporated by reference in their entirety. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, plant biology, plant disease, agriculture, biofuels, biochemistry, chemistry, and plant pathogens or related fields are intended to be within the scope of the following claims. All references cited herein are incorporated in their entirety.

What is claimed:

1. A double gene vector construct, comprising two expression cassettes:
   a first gene RNAi silencing expression cassette comprising a first constitutive promoter in operable combination with a nucleic acid segment comprising:
   a first trigalactosyldiacylglycerol 3 (tgd3) fragment in its sense orientation with at least 95% sequence identity to a segment of SEQ ID NO: 14, 20 or 55, and
   a second tgd3 fragment in antisense orientation relative to the first tqd3 fragment; and
   a second gene expression cassette comprising a nucleic acid encoding a WRINKLED 1 transcription factor in operable combination with a second promoter.

2. The construct of claim 1, wherein said first trigalactosyldiacylglycerol 3 (tgd3) fragment in its sense orientation has SEQ ID NO: 14.

3. The construct of claim 1, wherein said second trigalactosyldiacylglycerol 3 (tgd3) fragment in its antisense orientation has SEQ ID NO: 52.

4. The construct of claim 1, further comprising a spacer nucleic acid sequence located in between said sense fragment and said antisense fragment.

5. The construct of claim 1, wherein said RNAi silencing expression cassette comprises SEQ ID NO: 20.

6. The construct of claim 1, wherein said WRINKLED1 nucleic acid has a sequence that comprises at least 95% sequence identity to SEQ ID NO: 37 or 44.

7. The construct of claim 1, wherein said second promoter is selected from the group consisting of a 35S cauliflower mosaic virus promoter and an Oleosin (OLE) promoter.

8. A reproductively competent plant comprising said construct of claim 1, wherein said plant has accumulated lipid in its vegetative tissues.

9. The construct of claim 1, wherein said WRINKLED1 nucleic acid encodes a WRINKLED1 protein encoded by a nucleic acid with at least 95% sequence identity to SEQ ID NO: 37 or 44.

10. The plant of claim 8, wherein said plant is an oleaginous plant.

11. The plant of claim 8, wherein said plant is selected from the group consisting of rice plants, beet plants, grape plants, *Arabidopsis* sp. plants, *Brassica* sp. plants, *Brassica napus* plants, grass plants and algae plants.

12. A plant seed comprising said construct of claim 1.

* * * * *

UNITED STATES PATENT AND TRADEMARK OFFICE
CERTIFICATE OF CORRECTION

PATENT NO. : 10,006,039 B2  
APPLICATION NO. : 14/046504  
DATED : June 26, 2018  
INVENTOR(S) : Benning et al.

Page 1 of 1

It is certified that error appears in the above-identified patent and that said Letters Patent is hereby corrected as shown below:

On the Title Page

In Column 2, item (56) under "Other Publications", Line 10, delete "ExtraplastidicTGD4" and insert --Extraplastidic TGD4-- therefor In Column 2, item (56) under "Other Publications", Line 32, delete "Establishmentl"," and insert --Establishment",-- therefor In the Specification In Column 1, Line 8-15, delete "This invention was made with government support under Grant No. MCB0453858 by The National Science Foundation (NSF), USDA-CSREES grant number 2005-35504-16195 from the United States Department of Agriculture, and Grant No. DE_FG02-07ER20356 from the Department of Energy (DOE) and Great Lakes Bioenergy Research Center Cooperative Agreement DE-FC02-07ER64494 by the DOE. The government has certain rights in the invention." and insert --This invention was made with government support under MCB0453858 awarded by the National Science Foundation, under DE-FG02-07er20356 and DE-FC02-07ER64494 awarded by the U.S. Department of Energy, and under 2005-35504-16195 awarded by the U.S. Department of Agriculture. The government has certain rights in the invention.-- therefor In the Claims In Column 179, Line 57, in Claim 1, delete "tqd3" and insert --tgd3-- therefor In Column 179, Line 59, in Claim 1, delete "WRINKLED 1" and insert --WRINKLED1-- therefor Signed and Sealed this  
Twenty-eighth Day of May, 2019

Andrei Iancu  
*Director of the United States Patent and Trademark Office*

SEQUENCE LISTING

<160> NUMBER OF SEQ ID NOS: 74

<210> SEQ ID NO 1
<211> LENGTH: 1654
<212> TYPE: DNA
<213> ORGANISM: Arabidopsis thaliana

<400> SEQUENCE: 1
agctgggtgt agaaatcgag cgacggcggc ggagacgacg gagatgaaca gaatgagatg      60
ggtcggagag ggagacatct gggacctcga tatgtcaact ccggtgacgc tcgagggcac     120

-continued

```
cgcacgagct gttcctgacg atcctcttcc tctaggtctc tctagaggca ctcgtctatc    180
tcgccctaag caagttgagt tcttccaccg cttcatggcc tcacctctca tcccttcctt    240
ctcccctatc cgtcccaaca ccggagatgg aggcggtggt ggattctctc ttcaaagagt    300
cctcactctt cctttctcca caactggctg tgtgtctctt ctgggccaat cgatgttca    360
gagattcgta acggagatag ataagactaa agcttttggt cgagggtctt cgtctacagt    420
agcttctcgt ttaaacacaa ttggcaagca tttgaaggat aaatctttgt acgcattggg    480
tttttgttct gagttttgt tatcaccaga tgatactttg cttcttagct atgatgctta    540
caaaggtgat ctcgataaga atcctagagc taaggctatc ttcaatcacg agtttccgct    600
tcacaatctg acagcagaag cggtttggcc tggactttt gtggataaac atggtgaata    660
ttgggatgtg ccactctcaa tggctattga tctagcatct cttcctgctg aatctggtcc    720
aagttaccat ttatgtttac accataacag cggatcaccc aagaagttac attctgatac    780
tatgaagtg cctccaccgt cactgcttcc tggtttgtct ctgaaatctg cagtctctta    840
taggacaaac atggatctct ggagggtac cactccaaag ctcgaaactt gcaagcccta    900
tgatgtcttc ctcagtagtc ctcatgtcgc agtatctggg attatcggct ctgtgatgac    960
cgcagcattt ggtgaaaatt caatcagatc aaatttgaa atgattctg agggtgttgg   1020
agggttctct cttcatttc catctgtaaa ttccggattc atggctgatg ccttagggcg   1080
ggcatcactc acagctcaat atggaaactt ccagaaatt ttctttgatc tcacccgttt   1140
ccatgctaga ttagactttc cgcatggttt gaggtttctt accggtgcca ctagcgtcgc   1200
acaagatctt ttaaattctc ggcagcctag tttagaagca tttcagaaaa tctgccctga   1260
agtattagtt tctctacagc aacagattgt tggaccgttt agtttcaaag tggagtctgg   1320
aattgagatc gatctgagga acggagctaa ccctgtgact gtagataaga cagtatttgc   1380
tattgaatat gctcttcaag tgcttctttc tgccaaggct gttgtttcgt actccccaaa   1440
acagaatgag ttcatggttg agcttcgttt ctttgagaca tagtatcagg attttccact   1500
caaaatgtca agcttgatcc tgtgaagatt gtagtcttgc agagaagtaa atactaaata   1560
gacaatgttc taattgttca gttcttatg tcaaacagaa gaatgtttca atagaaggga   1620
agtttacatt ttgttatagt gtgatgtcta ccag                               1654
```

<210> SEQ ID NO 2
<211> LENGTH: 479
<212> TYPE: PRT
<213> ORGANISM: Arabidopsis thaliana

<400> SEQUENCE: 2

```
Met Asn Arg Met Arg Trp Val Gly Glu Gly Asp Ile Trp Asp Leu Asp
  1               5                  10                  15

Met Ser Thr Pro Val Thr Leu Glu Gly Thr Ala Arg Ala Val Pro Asp
                 20                  25                  30

Asp Pro Leu Pro Leu Gly Leu Ser Arg Gly Thr Arg Leu Ser Arg Pro
             35                  40                  45

Lys Gln Val Glu Phe Phe His Arg Phe Met Ala Ser Pro Leu Ile Pro
         50                  55                  60

Ser Phe Ser Pro Ile Arg Pro Asn Thr Gly Asp Gly Gly Gly Gly
 65                  70                  75                  80

Phe Ser Leu Gln Arg Val Leu Thr Leu Pro Phe Ser Asn Asn Trp Leu
                 85                  90                  95

Val Ser Leu Leu Gly Gln Phe Asp Val Gln Arg Phe Val Thr Glu Ile
```

```
            100                 105                 110
Asp Lys Thr Lys Ala Phe Gly Arg Gly Ser Ser Thr Val Ala Ser
            115                 120                 125

Arg Leu Asn Thr Ile Gly Lys His Leu Lys Asp Lys Ser Leu Tyr Ala
            130                 135                 140

Leu Gly Phe Cys Ser Glu Phe Leu Leu Ser Pro Asp Asp Thr Leu Leu
145                 150                 155                 160

Leu Ser Tyr Asp Ala Tyr Lys Gly Asp Leu Asp Lys Asn Pro Arg Ala
                165                 170                 175

Lys Ala Ile Phe Asn His Glu Phe Pro Leu His Asn Leu Thr Ala Glu
                180                 185                 190

Ala Val Trp Pro Gly Leu Phe Val Asp Lys His Gly Glu Tyr Trp Asp
                195                 200                 205

Val Pro Leu Ser Met Ala Ile Asp Leu Ala Ser Leu Pro Ala Glu Ser
            210                 215                 220

Gly Pro Ser Tyr His Leu Cys Leu His His Asn Ser Gly Ser Pro Lys
225                 230                 235                 240

Lys Leu His Ser Asp Thr Met Glu Val Pro Pro Ser Leu Leu Pro
                245                 250                 255

Gly Leu Ser Leu Lys Ser Ala Val Ser Tyr Arg Thr Asn Met Asp Leu
                260                 265                 270

Trp Arg Gly Thr Thr Pro Lys Leu Glu Thr Cys Lys Pro Tyr Asp Val
                275                 280                 285

Phe Leu Ser Ser Pro His Val Ala Val Ser Gly Ile Ile Gly Ser Val
            290                 295                 300

Met Thr Ala Ala Phe Gly Glu Asn Ser Ile Arg Ser Lys Phe Glu Asn
305                 310                 315                 320

Asp Ser Glu Gly Val Gly Gly Phe Ser Leu His Phe Pro Ser Val Asn
                325                 330                 335

Ser Gly Phe Met Ala Asp Ala Leu Gly Arg Ala Ser Leu Thr Ala Gln
                340                 345                 350

Tyr Gly Asn Phe Gln Lys Phe Phe Asp Leu Thr Arg Phe His Ala
                355                 360                 365

Arg Leu Asp Phe Pro His Gly Leu Arg Phe Leu Thr Gly Ala Thr Ser
            370                 375                 380

Val Ala Gln Asp Leu Leu Asn Ser Arg Gln Pro Ser Leu Glu Ala Phe
385                 390                 395                 400

Gln Lys Ile Cys Pro Glu Val Leu Val Ser Leu Gln Gln Ile Val
                405                 410                 415

Gly Pro Phe Ser Phe Lys Val Glu Ser Gly Ile Glu Ile Asp Leu Arg
                420                 425                 430

Asn Gly Ala Asn Pro Val Thr Val Asp Lys Thr Val Phe Ala Ile Glu
                435                 440                 445

Tyr Ala Leu Gln Val Leu Leu Ser Ala Lys Ala Val Val Ser Tyr Ser
            450                 455                 460

Pro Lys Gln Asn Glu Phe Met Val Glu Leu Arg Phe Phe Glu Thr
465                 470                 475

<210> SEQ ID NO 3
<211> LENGTH: 1026
<212> TYPE: DNA
<213> ORGANISM: Arabidopsis thaliana

<400> SEQUENCE: 3
```

| | |
|---|---|
| atgaacagaa tgagatgggt cggagaggga gacatctggg acctcgatat gtcaactccg | 60 |
| gtgacgctcg agggcaccgc acgagctgtt cctgacgatc ctcttcctct aggtctctct | 120 |
| agaggcactc gtctatctcg ccctaagcaa gttgagttct tccaccgctt catggcctca | 180 |
| cctctcatcc cttccttctc ccctatccgt cccaacaccg gagatggagg cggtggtgga | 240 |
| ttctctcttc aaagagtcct cactcttcct ttctccaaca actggcttgt gtctcttctg | 300 |
| ggccaattcg atgttcagag attcgtaacg gagatagata agactaaagc ttttggtcga | 360 |
| gggtcttcgt ctacagtagc ttctcgttta aacacaattg gcaagcattt gaaggataaa | 420 |
| tctttgtacg cattgggttt ttgttctgag tttttgttat caccagatga tactttgctt | 480 |
| cttagctatg atgcttacaa aggtgatctc gataagaatc ctagagctaa ggctatcttc | 540 |
| aatcacgagt ttccgcttca caatctgaca gcagaagcgg tttggcctgg acttttgtg | 600 |
| gataaacatg gtgaatattg ggatgtgcca ctctcaatgg ctattgatct agcatctctt | 660 |
| cctgctgaat ctggtccaag ttaccattta tgtttacacc ataacagcgg atcacccaag | 720 |
| aagttacatt ctgatactat ggaagtgcct ccaccgtcac tgcttcctgg tttgtctctg | 780 |
| aaatctgcag tctcttatag gacaaacatg gatctctgga ggggtaccac tccaaagctc | 840 |
| gaaacttgca agcccatga tgtcttcctc agtagtcctc atgtcgcagt atctgggatt | 900 |
| atcggtatga taagtttctt caacttattt cagaagcatt ttattgtcaa gactgaaagt | 960 |
| tttgtgattt ctctaataag ttttgttcaa ctcttatcat tgagttctc caattccaat | 1020 |
| atttga | 1026 |

<210> SEQ ID NO 4
<211> LENGTH: 1300
<212> TYPE: DNA
<213> ORGANISM: Arabidopsis thaliana

<400> SEQUENCE: 4

| | |
|---|---|
| ctttgtttct gggtttctcc taaatcatcc aaattggtat cgaatttgcc cttctccgat | 60 |
| tcaatttctt cacgatctca aaacccagaa gaaagaatca tgctttcgtt atcatgctct | 120 |
| tcttcttctt cttcgttgct tcctccgagt ttacactacc acggttcttc ttctgttcag | 180 |
| tccatcgttg taccaagaag gagtcttatc tcgtttcgtc ggaaagtctc ttgctgttgc | 240 |
| atagctccac ctcagaactt ggacaacgat gccaccaaat tcgatagtct taccaagtct | 300 |
| ggaggaggta tgtttaaaga gcgagggctt aagaataatt ctgatgttct tattgaatgt | 360 |
| agagatgtct ataaatcgtt tggggagaaa catatcttga aggtgttag ctttaagatt | 420 |
| agacatggtg aagctgttgg ggtgattggt ccttctggaa ctggaaaatc aacaatttta | 480 |
| aagattatgg ctggtcttct tgctccagac aagggagaag tttatatacg aggaaaaaaa | 540 |
| cgagctggtt tgataagtga tgaggaaata tcaggacttc gtattggcct ggtatttcag | 600 |
| agtgcagctc tctttgattc actatcagtt cgtgaaaatg ttggttttct actttatgaa | 660 |
| agatcaaaaa tgtccgagaa tcaaatatct tagcttctaa cacaaacctt ggcagctgtt | 720 |
| ggtttgaagg gggttgagaa tcgattacct tctgagctat ctggtggaat gaagaaaagg | 780 |
| gttgctttag ctcgttcact aattttttgat acaacaaaag aggtcataga gccagaggtg | 840 |
| cttttgtacg atgagccaac tgctgaactt gatccaattg catcaactgt agttgaagat | 900 |
| cttatacggt ctgttaacat aacagacgaa gatgcagttg gaaaacctgg aaaaattgcg | 960 |
| tcttatcttt tgttacccca tcaacatagc accattcaaa gagctgtaga caggttattg | 1020 |
| tttctgtatg aaggaaagat cgtttggcaa ggaatgatac atgtattcac aacctcaact | 1080 |

```
aatccaatag ttcaacagtt tgctacaggc agcctcgatg gaccaatcag atactagggg    1140
aggcaaaccg agcctaaaga gggacactaa ccgataatag ggaacgcaaa caagtaatgg    1200
ctgacataca ccacatggct ggatcaattg gttcaatacg atgctacttg taaacactat    1260
tttttcttag atgcatagat cagaaaagca ttgtcagttg                          1300
```

<210> SEQ ID NO 5
<211> LENGTH: 345
<212> TYPE: PRT
<213> ORGANISM: Arabidopsis thaliana

<400> SEQUENCE: 5

```
Met Leu Ser Leu Ser Cys Ser Ser Ser Ser Ser Leu Leu Pro Pro
 1               5                  10                  15

Ser Leu His Tyr His Gly Ser Ser Val Gln Ser Ile Val Val Pro
                20                  25                  30

Arg Arg Ser Leu Ile Ser Phe Arg Arg Lys Val Ser Cys Cys Ile
                35                  40                  45

Ala Pro Pro Gln Asn Leu Asp Asn Asp Ala Thr Lys Phe Asp Ser Leu
 50                  55                  60

Thr Lys Ser Gly Gly Gly Met Cys Lys Glu Arg Gly Leu Glu Asn Asp
 65                  70                  75                  80

Ser Asp Val Leu Ile Glu Cys Arg Asp Val Tyr Lys Ser Phe Gly Glu
                85                  90                  95

Lys His Ile Leu Lys Gly Val Ser Phe Lys Ile Arg His Gly Glu Ala
                100                 105                 110

Val Gly Val Ile Gly Pro Ser Gly Thr Gly Lys Ser Thr Ile Leu Lys
                115                 120                 125

Ile Met Ala Gly Leu Leu Ala Pro Asp Lys Gly Glu Val Tyr Ile Arg
 130                 135                 140

Gly Lys Lys Arg Ala Gly Leu Ile Ser Asp Glu Glu Ile Ser Gly Leu
 145                 150                 155                 160

Arg Ile Gly Leu Val Phe Gln Ser Ala Ala Leu Phe Asp Ser Leu Ser
                165                 170                 175

Val Arg Glu Asn Val Gly Phe Leu Leu Tyr Glu Arg Ser Lys Met Ser
                180                 185                 190

Glu Asn Gln Ile Ser Glu Leu Val Thr Gln Thr Leu Ala Ala Val Gly
                195                 200                 205

Leu Lys Gly Val Glu Asn Arg Leu Pro Ser Glu Leu Ser Gly Gly Met
 210                 215                 220

Lys Lys Arg Val Ala Leu Ala Arg Ser Leu Ile Phe Asp Thr Thr Lys
 225                 230                 235                 240

Glu Val Ile Glu Pro Glu Val Leu Leu Tyr Asp Glu Pro Thr Ala Gly
                245                 250                 255

Leu Asp Pro Ile Ala Ser Thr Val Val Glu Asp Leu Ile Arg Ser Val
                260                 265                 270

His Met Thr Asp Glu Asp Ala Val Gly Lys Pro Gly Lys Ile Ala Ser
                275                 280                 285

Tyr Leu Val Val Thr His Gln His Ser Thr Ile Gln Arg Ala Val Asp
                290                 295                 300

Arg Leu Leu Phe Leu Tyr Glu Gly Lys Ile Val Trp Gln Gly Met Thr
 305                 310                 315                 320

His Glu Phe Thr Thr Ser Thr Asn Pro Ile Val Gln Gln Phe Ala Thr
                325                 330                 335
```

Gly Ser Leu Asp Gly Pro Ile Arg Tyr
                340                 345

<210> SEQ ID NO 6
<211> LENGTH: 1436
<212> TYPE: DNA
<213> ORGANISM: Arabidopsis thaliana

<400> SEQUENCE: 6

```
tattctcaga ttcacgacac cagttcgtca caagcttcga gcccagctcg gaaaacaaaa      60
ttggaacttg ctgcataaag tttagttttt taattgaat ttggaaggat gattgggaat     120
ccagtaattc aagttccatc atcactaatg ccatcatcct ccatgattgc ttgtcctcga    180
gtttcaccca atgggggttcc ttatcttcca ccaaaaccta gaactaggca tttagtggtc    240
agagctgcat ccaattccga tgctgctcat ggtcaaccat cgtctgatgg ggggaagaat    300
cctctcaccg ttgttttgga tgtgcccagg aatatatgga gacagacttt aaaacctttg    360
agtgattttg ggtttggtaa gagaagtatt tgggaaggtg tgttggttt gtttattgtc     420
tctggagcta ctcttcttgc tcttagctgg gcttggttgc gaggttttca aatgcggtcg    480
aagtttagga aatatcagac tgtgtttgag cttagtcatg cttctggtat ttgcacggga    540
acaccggtta ggatccgtgg ggttactgtt ggtacgatta ccgtgttaa tccttccttg     600
aagaatattg aagctgttgc tgagatagaa atgataaga ttattatccc gaggaattca     660
ttggttgagg tgaatcagtc tggtcttcta atggaaacta tgatcgacat tatgcctagg    720
aatccgatac cagaaccttc agtaggacct ctgcatcctg aatgtggtaa ggaaggtctg    780
atcgtttgtg ataggcagac aataaaagga gtgcaaggag ttagtttaga tgaattagtt    840
ggaattttca ctcgtattgg acgcgaagtt gaggccattg tgttgccaa tacgtattcg     900
cttgctgaga gagctgcttc ggttattgag gaagcaaggc cattgctcaa aaagattcaa    960
gccatggctg aagatgctca accttttgctc tctgagtttc gtgatagcgg cttgctcaag   1020
gaagttgagt gtcttactcg aagccttacc caagcttctg acgatttgag aaaggttaat   1080
tcgtcaatta tgactcctga gaatacagaa ctcatacaga agtcaatcta cactctggtt   1140
tatactttga agaacgtcga gagtataagc tcagatattc tgggattcac aggagatgaa   1200
gccacaagaa aaaaccttaa actactcatc aaatccctaa gcaggctact atgatcagcc   1260
tgtagatttt agactggata aataaaatcc agaatttta tggtaagcaa gttttaaaaa    1320
ttcgaaaaat gtgttgttc ttcttttagag ttatttttgt tttcgttttg tgttctgaga    1380
ttggggttta atggagagac ataattcagt ttttataaga acaaaaatgt ttgttt       1436
```

<210> SEQ ID NO 7
<211> LENGTH: 381
<212> TYPE: PRT
<213> ORGANISM: Arabidopsis thaliana

<400> SEQUENCE: 7

Met Ile Gly Asn Pro Val Ile Gln Val Pro Ser Ser Leu Met Pro Ser
 1               5                   10                  15

Ser Ser Met Ile Ala Cys Pro Arg Val Ser Pro Asn Gly Val Pro Tyr
                20                  25                  30

Leu Pro Pro Lys Pro Arg Thr Arg His Leu Val Val Arg Ala Ala Ser
            35                  40                  45

Asn Ser Asp Ala Ala His Gly Gln Pro Ser Ser Asp Gly Gly Lys Asn
        50                  55                  60

```
Pro Leu Thr Val Val Leu Asp Val Pro Arg Asn Ile Trp Arg Gln Thr
 65                  70                  75                  80

Leu Lys Pro Leu Ser Asp Phe Gly Phe Gly Lys Arg Ser Ile Trp Glu
                 85                  90                  95

Gly Gly Val Gly Leu Phe Ile Val Ser Gly Ala Thr Leu Leu Ala Leu
            100                 105                 110

Ser Trp Ala Trp Leu Arg Gly Phe Gln Met Arg Ser Lys Phe Arg Lys
            115                 120                 125

Tyr Gln Thr Val Phe Glu Leu Ser His Ala Ser Gly Ile Cys Thr Gly
130                 135                 140

Thr Pro Val Arg Ile Arg Gly Val Thr Val Gly Thr Ile Ile Arg Val
145                 150                 155                 160

Asn Pro Ser Leu Lys Asn Ile Glu Ala Val Ala Glu Ile Glu Asp Asp
                165                 170                 175

Lys Ile Ile Ile Pro Arg Asn Ser Leu Val Glu Val Asn Gln Ser Gly
            180                 185                 190

Leu Leu Met Glu Thr Met Ile Asp Ile Met Pro Arg Asn Pro Ile Pro
            195                 200                 205

Glu Pro Ser Val Gly Pro Leu His Pro Glu Cys Gly Lys Glu Gly Leu
210                 215                 220

Ile Val Cys Asp Arg Gln Thr Ile Lys Gly Val Gln Gly Val Ser Leu
225                 230                 235                 240

Asp Glu Leu Val Gly Ile Phe Thr Arg Ile Gly Arg Glu Val Glu Ala
                245                 250                 255

Ile Gly Val Ala Asn Thr Tyr Ser Leu Ala Glu Arg Ala Ala Ser Val
            260                 265                 270

Ile Glu Glu Ala Arg Pro Leu Leu Lys Lys Ile Gln Ala Met Ala Glu
            275                 280                 285

Asp Ala Gln Pro Leu Leu Ser Glu Phe Arg Asp Ser Gly Leu Leu Lys
290                 295                 300

Glu Val Glu Cys Leu Thr Arg Ser Leu Thr Gln Ala Ser Asp Asp Leu
305                 310                 315                 320

Arg Lys Val Asn Ser Ser Ile Met Thr Pro Glu Asn Thr Glu Leu Ile
                325                 330                 335

Gln Lys Ser Ile Tyr Thr Leu Val Tyr Thr Leu Lys Asn Val Glu Ser
            340                 345                 350

Ile Ser Ser Asp Ile Leu Gly Phe Thr Gly Asp Glu Ala Thr Arg Lys
            355                 360                 365

Asn Leu Lys Leu Leu Ile Lys Ser Leu Ser Arg Leu Leu
370                 375                 380

<210> SEQ ID NO 8
<211> LENGTH: 1533
<212> TYPE: DNA
<213> ORGANISM: Arabidopsis thaliana

<400> SEQUENCE: 8
cagttcgtca caagcttcga gcccaggtat tctctctttc gctcaaaaac cctaatctcg     60
acttataatt cgatcgataa agtagaagct tcacgcaatt cacatgttct ctatcttctt    120
tctaactaca gctcggaaaa caaaattgga acttgctgca taagtttag tttttttatt    180 gaatttggaa ggatgattgg gaatccagta attcaagttc catcatcact aatgccatca    240
tcctccatga ttgcttgtcc tcgagtttca cccaatgggg ttccttatct tccaccaaaa    300
```

```
cctagaacta ggcatttagt ggtcagagct gcatccaatt ccgatgctgc tcatggtcaa      360
ccatcgtctg atgggggaa  gaatcctctc accgttgttt tggatgtgcc caggaatata      420
tggagacaga ctttaaaacc tttgagtgat tttgggtttg gtaagagaag tatttgggaa      480
ggtggtgttg gtttgtttat tgtctctgga gctactcttc ttgctcttag ctgggcttgg      540
ttgcgaggtt ttcaaatgcg gtcgaagttt aggaaatatc agactgtgtt tgagcttagt      600
catgcttctg gtatttgcac gggaacaccg gttaggatcc gtggggttac tgttggtacg      660
attatccgtg ttaatccttc cttgaagaat attgaagctg ttgctgagat agaagatgat      720
aagattatta tcccgaggaa ttcattggtt gaggtgaatc agtctggtct tctaatggaa      780
actatgatcg acattatgcc taggaatccg ataccagaac cttcagtagg acctctgcat      840
cctgaatgtg gtaaggaagg tctgatcgtt tgtgataggc agacaataaa aggagtgcaa      900
ggagttagtt tagatgaatt agttggaatt ttcactcgta ttggacgcga agttgaggcc      960
attggtgttg ccaatacgta ttcgcttgct gagagagctg cttcggttat tgaggaagca     1020
aggccattgc tcaaaaagtg atgtcacaga ttcaagccat ggctgaagat gctcaacctt     1080
tgctctctga gtttcgtgat agcggcttgc tcaaggaagt tgagtgtctt actcgaagcc     1140
ttacccaagc ttctgacgat ttgagaaagg ttaattcgtc aattatgact cctgagaata     1200
cagaactcat acagaagtca atctacactc tggtttatac tttgaagaac gtcgagagta     1260
taagctcaga tattctggga ttcacaggag atgaagccac aagaaaaaac cttaaactac     1320
tcatcaaatc cctaagcagg ctactatgat cagcctgtag attttagact ggataaataa     1380
aatccagaat tttatggtaa gcaagtttta aaaattcgaa aaatgtgttg tttcttcttt     1440
agagttattt ttgttttcgt tttgtgttct gagattgggg tttaatggag agcataatt      1500 cagtttttat aagaacaaaa atgtttgttt ctc                                   1533

<210> SEQ ID NO 9
<211> LENGTH: 1462
<212> TYPE: DNA
<213> ORGANISM: Arabidopsis thaliana

<400> SEQUENCE: 9
tgtgtgttgt tgttgttggc actgtgccac tttctctctc gatgaaccct ctcaagcaag       60
cttcttcgat cttccgagct tagtttcgtt tctaaattag agatttcacc tagattggtc      120
cgtacatatc ttatactggg attcgaattt ggctgcctca gagtcagaga ttgattaatt      180
gatcagattc agctgttgaa atcgtgctta ttgctacaaa ttgagaggca ctaaatcagt      240
gaggtcgtaa agaagaaggc aaccacaatg atgcagactt gttgtatcca tcaatcgttt      300
tgtttccctc atagagtctt tccacggttt gatgcttcga ttggtattaa gcccccaaag      360
ctttgtcaag ttggtttcat tggaaagact caatcttatg ggatttcaag tccgatacgg      420
caaagaagat tatatgtgaa tttgaatgct aatgatggtc acccatccat gtctatgttg      480
gaagaagaaa cctctactga aaacaacgca cccagtcaag aagccgagct tccgttcagc      540
aaatggtcac cttctaagta catatggaga ggtttatcag ttcctattat agcaggacaa      600
gtcgttctcc ggatttaaaa gggtaagatt cactggagaa acactcttca acagctggag      660
agaaccggac cgaaatctct aggagtttgt cttctgactt ctacatttgt tggtatggct      720
ttcacaatcc agttcgttag agaattcact agactaggtc taaacagatc cattggaggt      780
gtcttggctt tagcccttctc tagagagcta agtccagtca tcacatcgat tgttgttgct      840
ggacgaatgg gaagtgcatt tgcagctgaa ctagggacaa tgcaagtctc agagcaaact      900
```

```
gatacactcc gtgttttagg agctgaccca attgattatc taatcactcc aagagtcatc    960
gcctcgtgtt tggctctacc gtttctgaca ctcatgtgtt tcactgttgg tatggcttca   1020
agcgctctgc tctctgatgc agtttacggg atcagcatta acataatcat ggactcggct   1080
caccgagcac ttagaccatg ggacattgtg agtgccatga ttaaatctca agtctttgga   1140
gctataatat cggtaattag ttgttcttgg ggagtaacca ctactggagg tgctaaaggt   1200
gttggagaat ctacaacttc tgctgtcgtc atgtctcttg tcggaatctt catcgcggac   1260
tttgtgcttt cttccttctt ctttcaaggt gctggagatt ctttgaagaa ctgtgtttga   1320
catattattt tctgtcttct tttgttgtgg tttagatggg tttatgtaaa tcagttgtct   1380
taaattgaga agtaacatc attttagaaa gaacagaaag attgctatat ttctattcca   1440
ataatgatac acattgaata at                                            1462
```

<210> SEQ ID NO 10
<211> LENGTH: 350
<212> TYPE: PRT
<213> ORGANISM: Arabidopsis thaliana

<400> SEQUENCE: 10

```
Met Met Gln Thr Cys Cys Ile His Gln Ser Phe Cys Phe Pro His Arg
 1               5                  10                  15

Val Phe Pro Arg Phe Asp Ala Ser Ile Gly Ile Lys Pro Pro Lys Leu
            20                  25                  30

Cys Gln Val Gly Phe Ile Gly Lys Thr Gln Ser Tyr Gly Ile Ser Ser
        35                  40                  45

Pro Ile Arg Gln Arg Arg Leu Tyr Val Asn Leu Asn Ala Asn Asp Gly
    50                  55                  60

His Pro Ser Met Ser Met Leu Glu Glu Thr Ser Thr Glu Asn Asn
65                  70                  75                  80

Ala Pro Ser Gln Glu Ala Glu Leu Pro Phe Ser Lys Trp Ser Pro Ser
                85                  90                  95

Lys Tyr Ile Trp Arg Gly Leu Ser Val Pro Ile Ala Gly Gln Val
            100                 105                 110

Val Leu Arg Ile Leu Lys Gly Lys Ile His Trp Arg Asn Thr Leu Gln
        115                 120                 125

Gln Leu Glu Arg Thr Gly Pro Lys Ser Leu Gly Val Cys Leu Leu Thr
    130                 135                 140

Ser Thr Phe Val Gly Met Ala Phe Thr Ile Gln Phe Val Arg Glu Phe
145                 150                 155                 160

Thr Arg Leu Gly Leu Asn Arg Ser Ile Gly Gly Val Leu Ala Leu Ala
                165                 170                 175

Phe Ser Arg Glu Leu Ser Pro Val Ile Thr Ser Ile Val Val Ala Gly
            180                 185                 190

Arg Met Gly Ser Ala Phe Ala Ala Glu Leu Gly Thr Met Gln Val Ser
        195                 200                 205

Glu Gln Thr Asp Thr Leu Arg Val Leu Gly Ala Asp Pro Ile Asp Tyr
    210                 215                 220

Leu Ile Thr Pro Arg Val Ile Ala Ser Cys Leu Ala Leu Pro Phe Leu
225                 230                 235                 240

Thr Leu Met Cys Phe Thr Val Gly Met Ala Ser Ser Ala Leu Leu Ser
                245                 250                 255

Asp Ala Val Tyr Gly Ile Ser Ile Asn Ile Ile Met Asp Ser Ala His
            260                 265                 270
```

Arg Ala Leu Arg Pro Trp Asp Ile Val Ser Ala Met Ile Lys Ser Gln
            275                 280                 285

Val Phe Gly Ala Ile Ile Ser Val Ile Ser Cys Ser Trp Gly Val Thr
        290                 295                 300

Thr Thr Gly Gly Ala Lys Gly Val Gly Glu Ser Thr Thr Ser Ala Val
305                 310                 315                 320

Val Met Ser Leu Val Gly Ile Phe Ile Ala Asp Phe Val Leu Ser Ser
                325                 330                 335

Phe Phe Phe Gln Gly Ala Gly Asp Ser Leu Lys Asn Cys Val
                340                 345                 350

<210> SEQ ID NO 11
<211> LENGTH: 1461
<212> TYPE: DNA
<213> ORGANISM: Arabidopsis thaliana

<400> SEQUENCE: 11

| | |
|---|---|
| tgtgtgtgtt gttgttgttg gcactgtgcc actttctctc tcgatgaacc ctctcaagca | 60 |
| agcttcttcg atcttccgag cttagtttcg tttctaaata gatttcacct agattggtcc | 120 |
| gtacatatct tatactggga ttcgaatttg gctgcctcag agtcagagat tgattaattg | 180 |
| atcagattca gctgttgaaa tcgtgcttat tgctacaaat tgagaggcac taaatcagtg | 240 |
| aggtcgtaaa gaagaaggca accacaatga tgcagacttg ttgtatccat caatcgtttt | 300 |
| gtttccctca tagagtcttt ccacggtttg atgcttcgat tggtattaag cccccaaagc | 360 |
| tttgtcaagt tggtttcatt ggaaagactc aatcttatgg gatttcaagt ccgatacggc | 420 |
| aaagaagatt atatgtgaat ttgaatgcta atgatggtca cccatccatg tctatgttgg | 480 |
| aagaagaaac ctctactgaa acaacgcac ccagtcaaga agccgagctt ccgttcagca | 540 |
| aatggtcacc ttctaagtac atatggagag gtttatcagt tcctattata gcaggacaag | 600 |
| tcgttctccg gattttaaag ggtaagattc actggagaaa cactcttcaa cagctggaga | 660 |
| gaaccggacc gaaatctcta ggagtttgtc ttctgacttc tacatttgtt ggtatggctt | 720 |
| tcacaatcca gttcgttaga gaattcacta gactaggtct aaacagatcc attggaggtg | 780 |
| tcttggcttt agccttctct agagagctaa gtccagtcat cacatcgatt gttgttgctg | 840 |
| gacgaatggg aagtgcattt gcagctgaac tagggacaat gcaagtctca gagcaaactg | 900 |
| atacactccg tgttttagga gctgacccaa ttgattatct aatcactcca agagtcatcg | 960 |
| cctcgtgttt ggctctaccg tttctgacac tcatgtgttt cactgttggt atggcttcaa | 1020 |
| gcgctctgct ctctgatgca gtttacggga tcagcattaa cataatcatg gactcggctc | 1080 |
| accgagcact tagaccatgg gacattgtga gtgccatgat taaatctcaa gtctttggag | 1140 |
| ctataatatc ggtaattagt tgttcttggg gagtaaccac tactggaggt gctaaaggtg | 1200 |
| ttggagaatc tacaacttct gctgtcgtca tgtctcttgt cggaatcttc atcgcggact | 1260 |
| ttgtgctttc ttccttcttc tttcaaggtg ctggagattc tttgaagaac tgtgtttgac | 1320 |
| atattatttt ctgtcttctt ttgttgtggt ttagatgggt ttatgtaaat cagttgtctt | 1380 |
| aaattgagaa agtaacatca ttttagaaag aacagaaaga ttgctatatt tctattccaa | 1440 |
| taatgataca cattgaataa t | 1461 |

<210> SEQ ID NO 12
<211> LENGTH: 500
<212> TYPE: DNA
<213> ORGANISM: Artificial Sequence

```
<220> FEATURE:
<223> OTHER INFORMATION: A synthetic RNAi sequence

<400> SEQUENCE: 12
atgaacagaa tgagatgggt cggagaggga gacatctggg acctcgatat gtcaactccg      60
gtgacgctcg agggcaccgc acgagctgtt cctgacgatc ctcttcctct aggtctctct     120
agaggcactc gtctatctcg ccctaagcaa gttgagttct tccaccgctt catggcctca     180
cctctcatcc cttccttctc ccctatccgt cccaacaccg agatggagg cggtggtgga      240 ttctctcttc aaagagtcct cactcttcct ttctccaaca actggcttgt gtctcttctg     300
ggccaattcg atgttcagag attcgtaacg gagatagata agactaaagc ttttggtcga     360
gggtcttcgt ctacagtagc ttctcgttta aacacaattg gcaagcattt gaaggataaa     420
tctttgtacg cattgggttt tgttctgag tttttgttat caccagatga tactttgctt      480
cttagctatg atgcttacaa                                                 500

<210> SEQ ID NO 13
<211> LENGTH: 350
<212> TYPE: DNA
<213> ORGANISM: Artificial Sequence
<220> FEATURE:
<223> OTHER INFORMATION: A synthetic RNAi sequence

<400> SEQUENCE: 13
atgaacagaa tgagatgggt cggagaggga gacatctggg acctcgatat gtcaactccg      60
gtgacgctcg agggcaccgc acgagctgtt cctgacgatc ctcttcctct aggtctctct     120
agaggcactc gtctatctcg ccctaagcaa gttgagttct tccaccgctt catggcctca     180
cctctcatcc cttccttctc ccctatccgt cccaacaccg agatggagg cggtggtgga      240 ttctctcttc aaagagtcct cactcttcct ttctccaaca actggcttgt gtctcttctg     300
ggccaattcg atgttcagag attcgtaacg gagatagata agactaaagc                350

<210> SEQ ID NO 14
<211> LENGTH: 175
<212> TYPE: DNA
<213> ORGANISM: Artificial Sequence
<220> FEATURE:
<223> OTHER INFORMATION: A synthetic RNAi sequence

<400> SEQUENCE: 14
aacgaaaaat ggcaatgtga ctcactcaat cggtgactcg ctatagtctg tgaagaaagg      60
ccaatttcgc cataaagttc acacctttga tctcctttgt ttctgggttt ctcctaaatc     120
atccaaattg gtatcgaatt tgcccttctc cgattcaatt tcttcacgat ctcaa          175

<210> SEQ ID NO 15
<211> LENGTH: 500
<212> TYPE: DNA
<213> ORGANISM: Artificial Sequence
<220> FEATURE:
<223> OTHER INFORMATION: A synthetic RNAi sequence

<400> SEQUENCE: 15
atgattggga atccagtaat tcaagttcca tcatcactaa tgccatcatc ctccatgatt      60
gcttgtcctc gagtttcacc caatgggggtt ccttatcttc caccaaaacc tagaactagg    120
catttagtgg tcagagctgc atccaattcc gatgctgctc atggtcaacc atcgtctgat    180 gggggggaaga atcctctcac cgttgttttg gatgtgccca ggaatatatg gagacagact    240
```

```
ttaaaaccctt tgagtgattt tgggtttggt aagagaagta tttgggaagg tggtgttggt      300
ttgtttattg tctctggagc tactcttctt gctcttagct gggcttggtt gcgaggtttt      360
caaatgcggt cgaagtttag gaaatatcag actgtgtttg agcttagtca tgcttctggt      420
atttgcacgg gaacaccggt taggatccgt ggggttactg ttggtacgat tatccgtgtt      480
aatccttcct tgaagaatat                                                  500

<210> SEQ ID NO 16
<211> LENGTH: 419
<212> TYPE: DNA
<213> ORGANISM: Artificial Sequence
<220> FEATURE:
<223> OTHER INFORMATION: A synthetic RNAi sequence

<400> SEQUENCE: 16
cctagaacta ggcatttagt ggtcagagct gcatccaatt ccgatgctgc tcatggtcaa       60
ccatcgtctg atgggggaa gaatcctctc accgttgttt tggatgtgcc caggaatata      120
tggagacaga ctttaaaacc tttgagtgat tttgggtttg gtaagagaag tatttgggaa      180
ggtggtgttg gtttgtttat tgtctctgga gctactcttc ttgctcttag ctgggcttgg      240
ttgcgaggtt ttcaaatgcg gtcgaagttt aggaaatatc agactgtgtt tgagcttagt      300
catgcttctg gtatttgcac gggaacaccg gttaggatcc gtggggttac tgttggtacg      360
attatccgtg ttaatccttc cttgaagaat attgaagctg ttgctgagat agaagatga      419

<210> SEQ ID NO 17
<211> LENGTH: 500
<212> TYPE: DNA
<213> ORGANISM: Artificial Sequence
<220> FEATURE:
<223> OTHER INFORMATION: A synthetic RNAi sequence

<400> SEQUENCE: 17
atgatgcaga cttgttgtat ccatcaatcg ttttgtttcc ctcatagagt ctttccacgg       60
tttgatgctt cgattggtat taagcccccca agctttgtc aagttggttt cattggaaag     120
actcaatctt atgggatttc aagtccgata cggcaaagaa gattatatgt gaatttgaat      180
gctaatgatg gtcacccatc catgtctatg ttggaagaag aaacctctac tgaaaacaac      240
gcacccagtc aagaagccga gcttccgttc agcaaatggt caccttctaa gtacatatgg      300
agaggtttat cagttcctat tatagcagga caagtcgttc tccggatttt aaagggtaag      360
attcactgga gaaacactct tcaacagctg gagagaaccg gaccgaaatc tctaggagtt      420
tgtcttctga cttctacatt tgttggtatg gctttcacaa tccagttcgt tagagaattc      480
actagactag gtctaaacag                                                  500

<210> SEQ ID NO 18
<211> LENGTH: 1462
<212> TYPE: DNA
<213> ORGANISM: Artificial Sequence
<220> FEATURE:
<223> OTHER INFORMATION: A synthetic RNAi sequence

<400> SEQUENCE: 18
tgtgtgttgt tgttgttggc actgtgccac tttctctctc gatgaaccct ctcaagcaag       60
cttcttcgat cttccgagct tagtttcgtt tctaaattag agatttcacc tagattggtc      120
cgtacatatc ttatactggg attcgaattt ggctgcctca gagtcagaga ttgattaatt      180
gatcagattc agctgttgaa atcgtgctta ttgctacaaa ttgagaggca ctaaatcagt      240
```

| | |
|---|---|
| gaggtcgtaa agaagaaggc aaccacaatg atgcagactt gttgtatcca tcaatcgttt | 300 |
| tgtttccctc atagagtctt tccacggttt gatgcttcga ttggtattaa gcccccaaag | 360 |
| ctttgtcaag ttggtttcat tggaaagact caatcttatg ggatttcaag tccgatacgg | 420 |
| caaagaagat tatatgtgaa tttgaatgct aatgatggtc acccatccat gtctatgttg | 480 |
| gaagaagaaa cctctactga aaacaacgca cccagtcaag aagccgagct tccgttcagc | 540 |
| aaatggtcac cttctaagta catatggaga ggtttatcag ttcctattat agcaggacaa | 600 |
| gtcgttctcc ggattttaaa gggtaagatt cactggagaa acactcttca acagctggag | 660 |
| agaaccggac cgaaatctct aggagtttgt cttctgactt ctacatttgt tggtatggct | 720 |
| ttcacaatcc agttcgttag agaattcact agactaggtc taaacagatc cattggaggt | 780 |
| gtcttggctt tagccttctc tagagagcta agtccagtca tcatcgat tgttgttgct | 840 |
| ggacgaatgg gaagtgcatt tgcagctgaa ctagggacaa tgcaagtctc agagcaaact | 900 |
| gatacactcc gtgttttagg agctgaccca attgattatc taatcactcc aagagtcatc | 960 |
| gcctcgtgtt tggctctacc gtttctgaca ctcatgtgtt tcactgttgg tatggcttca | 1020 |
| agcgctctgc tctctgatgc agtttacggg atcagcatta acataatcat ggactcggct | 1080 |
| caccgagcac ttagaccatg ggacattgtg agtgccatga ttaaatctca agtctttgga | 1140 |
| gctataatat cggtaattag ttgttcttgg ggagtaacca ctactggagg tgctaaaggt | 1200 |
| gttggagaat ctacaacttc tgctgtcgtc atgtctcttg tcggaatctt catcgcggac | 1260 |
| tttgtgcttt cttccttctt cttcaaggt gctggagatt cttgaagaa ctgtgtttga | 1320 |
| catattattt tctgtcttct tttgttgtgg tttagatggg tttatgtaaa tcagttgtct | 1380 |
| taaattgaga agtaacatc atttagaaa gaacagaaag attgctatat ttctattcca | 1440 |
| ataatgatac acattgaata at | 1462 |

<210> SEQ ID NO 19
<211> LENGTH: 1018
<212> TYPE: DNA
<213> ORGANISM: Artificial Sequence
<220> FEATURE:
<223> OTHER INFORMATION: A synthetic RNAi sequence

<400> SEQUENCE: 19

| | |
|---|---|
| atgaacagaa tgagatgggt cggagaggga gacatctggg acctcgatat gtcaactccg | 60 |
| gtgacgctcg agggcaccgc acgagctgtt cctgacgatc ctcttcctct aggtctctct | 120 |
| agaggcactc gtctatctcg ccctaagcaa gttgagttct tccaccgctt catggcctca | 180 |
| cctctcatcc cttccttctc ccctatccgt cccaacaccg gagatggagg cggtggtgga | 240 |
| ttctctcttc aaagagtcct cactcttcct ttctccaaca actggcttgt gtctcttctg | 300 |
| ggccaattcg atgttcagag attcgtaacg gagatagata agactaaagc ttttggtcga | 360 |
| gggtcttcgt ctacagtagc ttctcgttta aacacaattg gcaagcattt gaaggataaa | 420 |
| tctttgtacg cattgggttt tgttctgag tttttgttat caccagatga tactttgctt | 480 |
| cttagctatg atgcttacaa acccagaag aaagaatctt gtaagcatca tagctaagaa | 540 |
| gcaaagtatc atctggtgat aacaaaaact cagaacaaaa acccaatgcg tacaaagatt | 600 |
| tatccttcaa atgcttgcca attgtgttta acgagaagc tactgtagac gaagaccctc | 660 |
| gaccaaaagc tttagtctta tctatctccg ttacgaatct ctgaacatcg aattggccca | 720 |
| gaagagacac aagccagttg ttggagaaag gaagagtgag gactctttga agagagaatc | 780 |

```
caccaccgcc tccatctccg gtgttgggac ggataggga  gaaggaaggg atgagaggtg    840
aggccatgaa gcggtggaag aactcaactt gcttagggcg agatagacga gtgcctctag    900
agagacctag aggaagagga tcgtcaggaa cagctcgtgc ggtgccctcg agcgtcaccg    960
gagttgacat atcgaggtcc cagatgtctc cctctccgac ccatctcatt ctgttcat    1018

<210> SEQ ID NO 20
<211> LENGTH: 364
<212> TYPE: DNA
<213> ORGANISM: Artificial Sequence
<220> FEATURE:
<223> OTHER INFORMATION: A synthetic RNAi sequence

<400> SEQUENCE: 20
aacgaaaaat ggcaatgtga ctcactcaat cggtgactcg ctatagtctg tgaagaaagg     60
ccaatttcgc cataaagttc acacctttga tctcctttgt ttctgggttt ctcctaaatc    120
atccaaattg gtatcgaatt tgcccttctc cgattcaatt tcttcacgat ctcaaaaccc    180
agaagaaaga atcatgcttt cgttatcatg ctcttcttct tcttcttcgt tgcttcctcc    240
gagtttacac taccacggtt cttcttctgt tcagtccatc gttgtaccaa gaaggagtct    300
tatctcgttt cgtcggaaag tctcttgctg ttgcatagct ccacctcaga acttggacaa    360
cgat                                                                 364

<210> SEQ ID NO 21
<211> LENGTH: 1018
<212> TYPE: DNA
<213> ORGANISM: Artificial Sequence
<220> FEATURE:
<223> OTHER INFORMATION: A synthetic RNAi sequence

<400> SEQUENCE: 21
atgattggga atccagtaat tcaagttcca tcatcactaa tgccatcatc ctccatgatt     60
gcttgtcctc gagtttcacc caatgggggtt ccttatcttc caccaaaaacc tagaactagg    120 catttagtgg tcagagctgc atccaattcc gatgctgctc atggtcaacc atcgtctgat    180 gggggaaga atcctctcac cgttgttttg gatgtgccca ggaatatatg gagacagact    240
ttaaaacctt tgagtgattt tggggtttggt aagagaagta tttgggaagg tggtgttggt    300
ttgtttattg tctctggagc tactcttctt gctcttagct gggcttggtt gcgaggtttt    360
caaatgcggt cgaagtttag gaaatatcag actgtgtttg agcttagtca tgcttctggt    420
atttgcacgg gaacaccggt taggatccgt ggggttactg ttggtacgat atccgtgtt    480 aatccttcct tgaagaatat aacccagaag aaagaatcat attcttcaag gaaggattaa    540
cacggataat cgtaccaaca gtaaccccac ggatcctaac cggtgttccc gtgcaaatac    600
cagaagcatg actaagctca aacacagtct gatatttcct aaacttcgac cgcatttgaa    660
aacctcgcaa ccaagcccag ctaagagcaa gaagagtagc tccagagaca ataaacaaac    720
caacaccacc ttcccaaata cttctcttac caaacccaaa atcactcaaa ggttttaaag    780
tctgtctcca tatattcctg ggcacatcca aaacaacggt gagaggattc ttccccccat    840
cagacgatgg ttgaccatga gcagcatcgg aattggatgc agctctgacc actaaatgcc    900
tagttctagg ttttggtgga agataaggaa ccccattggg tgaaactcga ggacaagcaa    960
tcatggagga tgatggcatt agtgatgatg gaacttgaat tactggattc ccaatcat    1018

<210> SEQ ID NO 22
<211> LENGTH: 1018
```

<212> TYPE: DNA
<213> ORGANISM: Artificial Sequence
<220> FEATURE:
<223> OTHER INFORMATION: A synthetic RNAi sequence

<400> SEQUENCE: 22

```
atgatgcaga cttgttgtat ccatcaatcg ttttgtttcc ctcatagagt ctttccacgg        60
tttgatgctt cgattggtat taagccccca aagctttgtc aagttggttt cattggaaag       120
actcaatctt atgggatttc aagtccgata cggcaaagaa gattatatgt gaatttgaat       180
gctaatgatg gtcacccatc catgtctatg ttggaagaag aaacctctac tgaaaacaac       240
gcacccagtc aagaagccga gcttccgttc agcaaatggt caccttctaa gtacatatgg       300
agaggtttat cagttcctat tatagcagga caagtcgttc tccggatttt aaagggtaag       360
attcactgga gaaacactct tcaacagctg gagagaaccg gaccgaaatc tctaggagtt       420
tgtcttctga cttctacatt tgttggtatg gctttcacaa tccagttcgt tagagaattc       480
actagactag gtctaaacag aacccagaag aaagaatcct gtttagacct agtctagtga       540
attctctaac gaactggatt gtgaaagcca taccaacaaa tgtagaagtc agaagacaaa       600
ctcctagaga tttcggtccg gttctctcca gctgttgaag agtgtttctc cagtgaatct       660
tacccttttaa aatccggaga acgacttgtc ctgctataat aggaactgat aaacctctcc       720
atatgtactt agaaggtgac catttgctga acggaagctc ggcttcttga ctgggtgcgt       780
tgttttcagt agaggtttct tcttccaaca tagacatgga tgggtgacca tcattagcat       840
tcaaattcac atataatctt ctttgccgta tcggacttga aatcccataa gattgagtct       900
ttccaatgaa accaacttga caaagctttg ggggcttaat accaatcgaa gcatcaaacc       960
gtggaaagac tctatgaggg aaacaaaacg attgatggat acaacaagtc tgcatcat      1018
```

<210> SEQ ID NO 23
<211> LENGTH: 29
<212> TYPE: DNA
<213> ORGANISM: Artificial Sequence
<220> FEATURE:
<223> OTHER INFORMATION: A synthetic primer sequence

<400> SEQUENCE: 23

```
catggatcca tgaacagaat gagatgggt                                           29
```

<210> SEQ ID NO 24
<211> LENGTH: 31
<212> TYPE: DNA
<213> ORGANISM: Artificial Sequence
<220> FEATURE:
<223> OTHER INFORMATION: A synthetic primer sequence

<400> SEQUENCE: 24

```
acagtcgacc tagtgctcaa agaaacgaag c                                        31
```

<210> SEQ ID NO 25
<211> LENGTH: 28
<212> TYPE: DNA
<213> ORGANISM: Artificial Sequence
<220> FEATURE:
<223> OTHER INFORMATION: A synthetic primer sequence

<400> SEQUENCE: 25

```
acggtaccat gctttcgtta tcatgctc                                            28
```

<210> SEQ ID NO 26

-continued

<210> SEQ ID NO 26
<211> LENGTH: 28
<212> TYPE: DNA
<213> ORGANISM: Artificial Sequence
<220> FEATURE:
<223> OTHER INFORMATION: A synthetic primer sequence

<400> SEQUENCE: 26
ctggtaccct agtatctgat tggtccat                                      28

<210> SEQ ID NO 27
<211> LENGTH: 31
<212> TYPE: DNA
<213> ORGANISM: Artificial Sequence
<220> FEATURE:
<223> OTHER INFORMATION: A synthetic primer sequence

<400> SEQUENCE: 27
gtcgacatga ttgggaatcc agtaattcaa g                                  31

<210> SEQ ID NO 28
<211> LENGTH: 26
<212> TYPE: DNA
<213> ORGANISM: Artificial Sequence
<220> FEATURE:
<223> OTHER INFORMATION: A synthetic primer sequence

<400> SEQUENCE: 28
gtcgactcat agtagcctgc ttaggg                                        26

<210> SEQ ID NO 29
<211> LENGTH: 33
<212> TYPE: DNA
<213> ORGANISM: Artificial Sequence
<220> FEATURE:
<223> OTHER INFORMATION: A synthetic primer sequence

<400> SEQUENCE: 29
aatactagtg gcgcgccatg atgcagactt gtt                                33

<210> SEQ ID NO 30
<211> LENGTH: 32
<212> TYPE: DNA
<213> ORGANISM: Artificial Sequence
<220> FEATURE:
<223> OTHER INFORMATION: A synthetic primer sequence

<400> SEQUENCE: 30
ccaggatcca tttaaattca aacacagttc tt                                 32

<210> SEQ ID NO 31
<211> LENGTH: 314
<212> TYPE: PRT
<213> ORGANISM: Homo sapiens

<400> SEQUENCE: 31

Ser Ala Gly Asp Met Arg Ala Ala Asn Leu Trp Pro Ser Pro Leu Met
  1               5                  10                  15

Ile Lys Arg Ser Lys Lys Asn Ser Leu Ala Leu Ser Leu Thr Ala Asp
                 20                  25                  30

Gln Met Val Ser Ala Leu Leu Asp Ala Glu Pro Pro Ile Leu Tyr Ser
             35                  40                  45

Glu Tyr Asp Pro Thr Arg Pro Phe Ser Glu Ala Ser Met Met Gly Leu
         50                  55                  60

Leu Thr Asn Leu Ala Asp Arg Glu Leu Val His Met Ile Asn Trp Ala 65                  70                  75                  80
Lys Arg Val Pro Gly Phe Val Asp Leu Thr Leu His Asp Gln Val His
                    85                  90                  95

Leu Leu Glu Cys Ala Trp Leu Glu Ile Leu Met Ile Gly Leu Val Trp
                100                 105                 110

Arg Ser Met Glu His Pro Gly Lys Leu Leu Phe Ala Pro Asn Leu Leu
                115                 120                 125

Leu Asp Arg Asn Gln Gly Lys Cys Val Glu Gly Met Val Glu Ile Phe
130                 135                 140

Asp Met Leu Leu Ala Thr Ser Ser Arg Phe Arg Met Met Asn Leu Gln
145                 150                 155                 160

Gly Glu Glu Phe Val Cys Leu Lys Ser Ile Ile Leu Leu Asn Ser Gly
                165                 170                 175

Val Tyr Thr Phe Leu Ser Ser Thr Leu Lys Ser Leu Glu Glu Lys Asp
                180                 185                 190

His Ile His Arg Val Leu Asp Lys Ile Thr Asp Thr Leu Ile His Leu
                195                 200                 205

Met Ala Lys Ala Gly Leu Thr Leu Gln Gln Gln His Gln Arg Leu Ala
                210                 215                 220

Gln Leu Leu Leu Ile Leu Ser His Ile Arg His Met Ser Asn Lys Gly
225                 230                 235                 240

Met Glu His Leu Tyr Ser Met Lys Cys Lys Asn Val Val Pro Leu Tyr
                245                 250                 255

Asp Leu Leu Leu Glu Met Leu Asp Ala His Arg Leu His Ala Pro Thr
                260                 265                 270

Ser Arg Gly Gly Ala Ser Val Glu Glu Thr Asp Gln Ser His Leu Ala
                275                 280                 285

Thr Ala Gly Ser Thr Ser Ser His Ser Leu Gln Lys Tyr Tyr Ile Thr
                290                 295                 300

Gly Glu Ala Glu Gly Phe Pro Ala Thr Val
305                 310

<210> SEQ ID NO 32
<211> LENGTH: 945
<212> TYPE: DNA
<213> ORGANISM: Homo sapiens

<400> SEQUENCE: 32
tctgctggag acatgagagc tgccaacctt tggccaagcc cgctcatgat caaacgctct      60
aagaagaaca gcctggcctt gtccctgacg gccgaccaga tggtcagtgc cttgttggat     120
gctgagcccc ccatactcta ttccgagtat gatcctacca gacccttcag tgaagcttcg     180
atgatgggct tactgaccaa cctggcagac agggagctgg ttcacatgat caactgggcg     240
aagagggtgc caggctttgt ggatttgacc ctccatgatc aggtccacct tctagaatgt     300
gcctggctag agatcctgat gattggtctc gtctggcgct ccatgagcca cccagggaag     360
ctactgtttg ctcctaactt gctcttggac aggaaccagg gaaaatgtgt agagggcatg     420
gtggagatct tcgacatgct gctggctaca tcatctcggt tccgcatgat gaatctgcag     480
ggagaggagt ttgtgtgcct caaatctatt attttgctta attctggagt gtacacattt     540
ctgtccagca ccctgaagtc tctggaagag aaggaccata tccaccgagt cctggacaag     600
atcacagaca ctttgatcca cctgatggcc aaggcaggcc tgaccctgca gcagcagcac     660
cagcggctgg cccagctcct cctcatcctc tcccacatca ggcacatgag taacaaaggc     720

```
atggagcatc tgtacagcat gaagtgcaag aacgtggtgc ccctctatga cctgctgctg      780
gagatgctgg acgcccaccg cctacatgcg cccactagcc gtggaggggc atccgtggag      840
gagacggacc aaagccactt ggccactgcg ggctctactt catcgcattc cttgcaaaag      900
tattacatca cgggggaggc agagggtttc cctgccacgg tctga                     945

<210> SEQ ID NO 33
<211> LENGTH: 345
<212> TYPE: DNA
<213> ORGANISM: Artificial Sequence
<220> FEATURE:
<223> OTHER INFORMATION: A synthetic promoter sequence

<400> SEQUENCE: 33
tgagactttt caacaaaggg taatatccgg aaacctcctc ggattccatt gcccagctat       60
ctgtcacttt attgtgaaga tagtggaaaa ggaaggtggc tcctacaaat gccatcattg      120
cgataaagga aaggccatcg ttgaagatgc ctctgccgac agtggtccca aagatggacc      180
cccaccccac gaggagcatc gtggaaaaag aagacgttcc aaccacgtct tcaaagcaag      240
tggattgatg tgatatctcc actgacgtaa gggatgacgc acaatcccac tatccttcgc      300
aagacccttc ctctatataa ggaagttcat tcatttgga gagga                       345

<210> SEQ ID NO 34
<211> LENGTH: 60
<212> TYPE: DNA
<213> ORGANISM: Artificial Sequence
<220> FEATURE:
<223> OTHER INFORMATION: A synthetic promoter sequence

<400> SEQUENCE: 34
cccactatcc ttcgcaagac ccttcctcta tataaggaag ttcatttcat ttggagagga       60

<210> SEQ ID NO 35
<211> LENGTH: 525
<212> TYPE: DNA
<213> ORGANISM: Artificial Sequence
<220> FEATURE:
<223> OTHER INFORMATION: A synthetic spacer sequence

<400> SEQUENCE: 35
tatacgccat ttgaagccga tgtcacgccg tatgttattg ccgggaaaag tgtacgtatc       60
accgtttgtg tgaacaacga actgaactgg cagactatcc cgccgggaat ggtgattacc      120
gacgaaaacg gcaagaaaaa gcagtcttac ttccatgatt tctttaacta cgccgggatc      180
catcgcagcg taatgctcta caccacgccg aacacctggg tggacgatat caccgtggtg      240
acgcatgtcg cgcaagactg taaccacgcg tctgttgact ggcaggtggt ggccaatggt      300
gatgtcagcg ttgaactgcg tgatgcggat caacaggtgg ttgcaactgg acaaggcacc      360
agcgggactt tgcaagtggt gaatccgcac ctctggcaac cgggtgaagg ttatctctat      420
gaactgtgcg tcacagccaa aagccagaca gagtgtgata tctacccgct gcgcgtcggc      480
atccggtcag tggcagtgaa gggcgaacag ttcctgatca accac                      525

<210> SEQ ID NO 36
<211> LENGTH: 18
<212> TYPE: DNA
<213> ORGANISM: Artificial Sequence
<220> FEATURE:
<223> OTHER INFORMATION: A synthetic spacer sequence

<400> SEQUENCE: 36
```

```
aacccagaag aaagaatc                                                   18

<210> SEQ ID NO 37
<211> LENGTH: 1540
<212> TYPE: DNA
<213> ORGANISM: Arabidopsis thaliana

<400> SEQUENCE: 37
aaaccactct gcttcctctt cctctgagaa atcaaatcac tcacactcca aaaaaaaatc     60
taaactttct cagagtttaa tgaagaagcg cttaaccact tccacttgtt cttcttctcc    120
atcttcctct gtttcttctt ctactactac ttcctctcct attcagtcgg aggctccaag    180
gcctaaacga gccaaaaggg ctaagaaatc ttctccttct ggtgataaat ctcataaccc    240
gacaagccct gcttctaccc gacgcagctc tatctacaga ggagtcacta gacatagatg    300
gactgggaga ttcgaggctc atctttggga caaaagctct tggaattcga ttcagaacaa    360
gaaaggcaaa caagtttatc tgggagcata tgacagtgaa gaagcagcag cacatacgta    420
cgatctggct gctctcaagt actggggacc cgacaccatc ttgaattttc cggcagagac    480
gtacacaaag gaattggaag aaatgcagag agtgacaaag gaagaatatt tggcttctct    540
ccgccgccag agcagtggtt tctccagagg cgtctctaaa tatcgcggcg tcgctaggca    600
tcaccacaac ggaagatggg aggctcggat cggaagagtg tttgggaaca agtacttgta    660
cctcggcacc tataatacgc aggaggaagc tgctgcagca tatgacatgg ctgcgattga    720
gtatcgaggc gcaaacgcgg ttactaattt cgacattagt aattacattg accggttaaa    780
gaagaaaggt gttttcccgt tccctgtgaa ccaagctaac catcaagagg gtattcttgt    840
tgaagccaaa caagaagttg aaacgagaga agcgaaggaa gagcctagag aagaagtgaa    900
acaacagtac gtggaagaac caccgcaaga agaagaagag aaggaagaag agaaagcaga    960
gcaacaagaa gcagagattg taggatattc agaagaagca gcagtggtca attgctgcat   1020
agactcttca accataatgg aaatggatcg ttgtggggac aacaatgagc tggcttggaa   1080
cttctgtatg atggatacag ggttttctcc gttttttgact gatcagaaatc tcgcgaatga   1140 gaatcccata gagtatccgg agctattcaa tgagttagca tttgaggaca acatcgactt   1200
catgttcgat gatgggaagc acgagtgctt gaacttggaa atctggattt gttgcgtggt   1260
gggaagagag agcccaccct cttcttcttc accattgtct tgcttatcta ctgactctgc   1320
ttcatcaaca acaacaacaa caacctcggt ttcttgtaac tatttggtct gagagagaga   1380
gctttgcctt ctagtttgaa tttctatttc ttccgcttct tcttcttttt tttcttttgt   1440
tgggttctgc ttagggtttg tatttcagtt tcagggcttg ttcgttggtt ctgaataatc   1500
aatgtctttg cccctttcct aatgggtacc tgaagggcga                         1540

<210> SEQ ID NO 38
<211> LENGTH: 20
<212> TYPE: DNA
<213> ORGANISM: Artificial Sequence
<220> FEATURE:
<223> OTHER INFORMATION: A synthetic primer

<400> SEQUENCE: 38
ccgacgcagc tctatctaca                                                 20

<210> SEQ ID NO 39
<211> LENGTH: 20
<212> TYPE: DNA
```

```
<213> ORGANISM: Artificial Sequence
<220> FEATURE:
<223> OTHER INFORMATION: A synthetic primer

<400> SEQUENCE: 39
agcctcccat cttccgttgt                                        20

<210> SEQ ID NO 40
<211> LENGTH: 22
<212> TYPE: DNA
<213> ORGANISM: Artificial Sequence
<220> FEATURE:
<223> OTHER INFORMATION: A synthetic primer

<400> SEQUENCE: 40
tgcgacaatg gaactggaat gg                                     22

<210> SEQ ID NO 41
<211> LENGTH: 22
<212> TYPE: DNA
<213> ORGANISM: Artificial Sequence
<220> FEATURE:
<223> OTHER INFORMATION: A synthetic primer

<400> SEQUENCE: 41
aacaatcgat ggacctgact cg                                     22

<210> SEQ ID NO 42
<211> LENGTH: 427
<212> TYPE: PRT
<213> ORGANISM: Arabidopsis thaliana

<400> SEQUENCE: 42
```

Met Lys Ala Ile Gln Leu Leu Trp Glu Ala Ile Met Glu Ala Thr Lys
 1               5                  10                  15

Arg Glu Arg Arg Arg Glu Asp Asp Gly Glu Lys Ala Ser Pro Glu
            20                  25                  30

Ser Leu Val Leu Pro Pro Glu Ile Ile Thr Glu Ile Leu Leu Arg Leu
        35                  40                  45

Pro Ala Lys Ser Ile Gly Arg Phe Arg Cys Val Ser Lys Leu Phe Cys
    50                  55                  60

Thr Leu Ser Ser Asp Pro Gly Phe Ala Lys Ile His Leu Asp Leu Ile
65                  70                  75                  80

Leu Arg Asn Glu Ser Val Arg Ser Leu His Arg Lys Leu Ile Val Ser
                85                  90                  95

Ser His Asn Leu Tyr Ser Leu Asp Phe Asn Ser Ile Gly Asp Gly Ile
            100                 105                 110

Arg Asp Leu Ala Ala Val Glu His Asn Tyr Pro Leu Lys Asp Pro
        115                 120                 125

Ser Ile Phe Ser Glu Met Ile Arg Asn Tyr Val Gly Asp His Leu Tyr
    130                 135                 140

Asp Asp Arg Arg Val Met Leu Lys Leu Asn Ala Lys Ser Tyr Arg Arg
145                 150                 155                 160

Asn Trp Val Glu Ile Val Gly Ser Ser Asn Gly Leu Val Cys Ile Ser
                165                 170                 175

Pro Gly Glu Gly Ala Val Phe Leu Tyr Asn Pro Thr Thr Gly Asp Ser
            180                 185                 190

Lys Arg Leu Pro Glu Asn Phe Arg Pro Lys Ser Val Gly Tyr Glu Arg
        195                 200                 205

Asp Asn Phe Gln Thr Tyr Gly Phe Gly Phe Asp Gly Leu Thr Asp Asp
210                 215                 220

Tyr Lys Leu Val Lys Leu Val Ala Thr Ser Glu Asp Ile Leu Asp Ala
225                 230                 235                 240

Ser Val Tyr Ser Leu Lys Ala Asp Ser Trp Arg Arg Ile Cys Asn Leu
                245                 250                 255

Asn Tyr Glu His Asn Asp Gly Ser Tyr Thr Ser Gly Val His Phe Asn
            260                 265                 270

Gly Ala Ile His Trp Val Phe Thr Glu Ser Arg His Asn Gln Arg Val
        275                 280                 285

Val Val Ala Phe Asp Ile Gln Thr Glu Phe Arg Glu Met Pro Val
290                 295                 300

Pro Asp Glu Ala Glu Asp Cys Ser His Arg Phe Ser Asn Phe Val Val
305                 310                 315                 320

Gly Ser Leu Asn Gly Arg Leu Cys Val Val Asn Ser Cys Tyr Asp Val
                325                 330                 335

His Asp Asp Ile Trp Val Met Ser Glu Tyr Gly Glu Ala Lys Ser Trp
            340                 345                 350

Ser Arg Ile Arg Ile Asn Leu Leu Tyr Arg Ser Met Lys Pro Leu Cys
        355                 360                 365

Ser Thr Lys Asn Asp Glu Glu Val Leu Leu Glu Leu Asp Gly Asp Leu
370                 375                 380

Val Leu Tyr Asn Phe Glu Thr Asn Ala Ser Ser Asn Leu Gly Ile Cys
385                 390                 395                 400

Gly Val Lys Leu Ser Asp Gly Phe Glu Ala Asn Thr Tyr Val Glu Ser
                405                 410                 415

Leu Ile Ser Pro Asn Ser Tyr Gly Ile Glu Ser
            420                 425

<210> SEQ ID NO 43

<400> SEQUENCE: 43

000

<210> SEQ ID NO 44
<211> LENGTH: 1580
<212> TYPE: DNA
<213> ORGANISM: Artificial Sequence
<220> FEATURE:
<223> OTHER INFORMATION: A synthetic cDNA

<400> SEQUENCE: 44
cagggtttat taacttgcc ctttctcgtt tcctcctttt tttcttaaac cactctgctt      60
cctcttcctc tgagaaatca atcactcac actccaaaaa aaaatctaaa ctttctcaga    120
gtttaatgaa gaagcgctta accacttcca cttgttcttc ttctccatct tcctctgttt    180
cttcttctac tactacttcc tctcctattc agtcggaggc tccaaggcct aaacgagcca    240
aaagggctaa gaaatcttct ccttctggtg ataaatctca taccccgaca gccctgctt    300 ctacccgacg cagctctatc tacagaggag tcactagaca tagatggact gggagattcg    360
aggctcatct ttgggacaaa agctcttgga attcgattca gaacaagaaa ggcaaacaag    420
gtttcgagca tatgacagtg aagaagcagc agcacatacg tacgatctgg ctgctctcaa    480
gtactgggga cccgacacca tcttgaattt tccggcagag acgtacacaa aggaattgga    540
agaaatgcag agagtgacaa aggaagaata tttggcttct ctccgccgcc agagcagtgg    600

-continued

```
tttctccaga ggcgtctcta aatatcgcgg cgtcgctagg catcaccaca acggaagatg    660
ggaggctcgg atcggaagag tgtttgggaa caagtacttg tacctcggca cctataatac    720
gcaggaggaa gctgctgcag catatgacat ggctgcgatt gagtatcgag gcgcaaacgc    780
ggttactaat ttcgacatta gtaattcat tgaccggtta aagaagaaag gtgttttccc      840
gttccctgtg aaccaagcta accatcaaga gggtattctt gttgaagcca acaagaagt      900
tgaaacgaga gaagcgaagg aagagcctag agaagaagtg aaacaacagt acgtggaaga    960
accaccgcaa gaagaagaag agaaggaaga agagaaagca gagcaacaag aagcagagat   1020
tgtaggatat tcagaagaag cagcagtggt caattgctgc atagactctt caaccataat   1080
ggaaatggat cgttgtgggg acaacaatga gctggcttgg aacttctgta tgatggatac   1140
agggttttct ccgttttga ctgatcagaa tctcgcgaat gagaatccca tagagtatcc    1200
ggagctattc aatgagttag catttgagga caacatcgac ttcatgttcg atgatgggaa   1260
gcacgagtgc ttgaacttgg aaaatctgga ttgttgcgtg gtgggaagag agagcccacc   1320
ctcttcttct tcaccattgt cttgcttatc tactgactct gcttcatcaa caacaacaac   1380
aacaacctcg gtttcttgta actatttggt ctgagagaga gagctttgcc ttctagtttg   1440
aatttctatt tcttccgctt cttcttcttt tttttctttt gttgggttct gcttagggtt   1500
tgtatttcag tttcagggct tgttcgttgg ttctgaataa tcaatgtctt tgccccttt    1560
ctaatgctcc aagttcagat                                                1580
```

<210> SEQ ID NO 45
<211> LENGTH: 1594
<212> TYPE: DNA
<213> ORGANISM: Arabidopsis thaliana

<400> SEQUENCE: 45

```
atggcgtctg tatctgcaat tggagttctc aaggtacctc ctgcttcgac ttccaattcc     60
accggaaaag ccacggaggc ggttcccacg aggactcttt cttttctcctc ctctgttact   120
tcatccgacg acaagatttc actcaaatcc accgtctccc gtctttgtaa atctgttgtt    180
cgcaggaatc cgatcatcgt ctctcccaaa gccgtctcag attctcaaaa ctctcaaact   240
tgtctcgatc ctgatgctag cagcagtgtt ttggggataa tcttaggagg tggagctgga   300
actcgtcttt atccacttac gaagaagaga gcgaaaccag ctgtgcctct tggtgctaac   360
tataggctta ttgatattcc tgtgagcaac tgtttgaata gcaacatatc caagatctat   420
gttcttactc agttcaattc cgcgtctttg aatcgtcatc tttcacgagc ttatgctagt   480
aacatgggag gttataagaa tgaaggattc gttgaagttc tcgctgctca acagagtcct   540
gaaaacccca actggttcca ggggacagct gatgccgtca gcaatacttt gtggttgttc   600
gaggagcata atgtcttgga gtatctcatt cttgctgggg atcatttgta tagaatggac   660
tatgagaagt ttattcaagc acatagggag actgatgctg atatcacagt agctgcatta   720
ccaatggacg agcaacgagc cactgctttt gggctgatga agattgatga ggaaggacgt   780
attattgaat ttgctgaaaa accaaaaggg gagcacctaa aggccatgaa ggttgacaca   840
acaattctag gtcttgatga tcagagagcc aaggagatgc ctttcattgc tagtatgggt   900
atttatgttg taagcagaga tgtaatgcta gacttactac ggaatcagtt tcctggagct   960
aatgactttg gaagtgaagt cattcccggt gccacttccc ttggactgag ggtgcaagct  1020
tacctatatg atggttactg gaagacatt ggtactatag aggcatttta taacgctaat   1080
cttggaatca ccaagaaacc agttcctgat tttagtttct atgaccgttc tgctccgatc  1140
```

```
tacacacagc cgcgttattt accaccgtct aagatgcttg atgctgatgt tactgacagt   1200
gtcatcggag agggctgtgt tatcaagaac tgcaaaattc atcactctgt ggttggactc   1260
cgttcctgca tatcagaagg tgctattatt gaagattcgt tattaatggg agctgattat   1320
tacgagactg ctacgaaaaa gagcctctta agcgcgaaag gaagtgtacc cataggtatt   1380
gggaaaaact cgcacatcaa aagggccatc atcgacaaaa acgcacgtat cggtgacaat   1440
gtcaagatca taaacagcga caacgtgcaa gaggcagcga gagagactga tggatatttc   1500
ataaagagcg gaattgtaac ggttatcaaa gacgccttaa tcccaaccgg cactgtcatc   1560
tgaagtacac ataatgctcc tttgtttatt tctt                               1594

<210> SEQ ID NO 46
<211> LENGTH: 1761
<212> TYPE: DNA
<213> ORGANISM: Brassica napus

<400> SEQUENCE: 46
aagagtgaag ctcctcctct cgaacaacaa caatggcgac aatggctgca atcggatcct    60
taaaagtccc ttcctcttcc tcgaaccaca cccgtagatt atcatcttct tctcaacgga   120
agactctctc gttctcgtcg tcttctctta ccggagagaa actcaacccg acgcaggaga   180
tcatcatctc caatctccca cgtggcaacg agagaagaac gccatcgatc gtctctccaa   240
aagcagtttc cgattcgcaa aactcgcaaa cttgccttga tcctgacgct agcagaagtg   300
tgttggggat aattctggga ggtggtgctg gaacgagatt gtatccgcta acgaagaaga   360
gagcgaagcc agctgttcct ctcggcgcta actaccgtct cattgatatc ccagtgagca   420
attgcttgaa cagtaacatc tccaagatct atgtccttac tcagttcaac tcagcttctc   480
tcaaccgcca tctctcccga gcttacgcca gcaacatggg tggttacaag aacgaaggct   540
tcgtcgaggt tcttgctgct caacagagtc ccgagaatcc caattggttt caggggactg   600
ctgatgcagt gaggcagtac ttgtggctgt ttgaagagca caatgtgttg gagttttttgg   660 ttcttgcagg ggatcatttg taccgtatgg actacgagaa gttcattcaa gcgcatcgtg   720
agaccgacgc tgatatcact gttgctgctc ttcctatgga tgagaaacgt gccacggctt   780
ttggacttat gaagattgat gacgaaggaa ggatcattga gtttgctgag aagcctaaag   840
gagagcagtt aaaggctatg aaggttgata caacaatctt gggacttgat gacgaagggg   900
ccaaagagat gccctttatt gctagtatgg ggatatatgt tgttagcaag aatgtgatgt   960
tggacttgct ccgagaccag ttccctggag ctaatgactt cggagtgaa gttatccctg   1020 gtgctactga tcttggactc agagtgcaag cttatctgta tgatggatac tgggaagata  1080
ttggtaccat tgaagccttt tacaatgcta atcttgggat caccaagaaa ccagtaccag  1140
atttcagctt ctatgaccgt tcagcaccaa tctacacaca gcctcggtac ttacctccat  1200
ccaagatgct tgatgccgat gttaccgata gtgtgatcgg tgaaggttgt gtcatcaaga  1260
attgcaaaat ccaccattcc gtcattggtc ttcggtcttg catatcggag ggtgcaatca  1320
tagaagacac cttgttgatg ggtgctgact actacgagac tgatgcggat aggacactcc  1380
tggctgcaaa aggcagcatc ccgattggca ttggccgaga ctctcacatt aaaagagcta  1440
tcattgacaa gaatgctcgt attggtgaca acgtcaagat catcaacacg gacaatgtgc  1500
aagaagctgc cagagagacg gatggatact tcatcaagag cggcattgtt acagtgatca  1560
aggatgctct gattcctagt ggaactgtta tctaagagac accaccaccc cgtttgacaa  1620
```

```
tcttcttaat atctcatggt tttgacctcg agttagcttc cactgatgct atctctaatg    1680
ttatccgagg tcagggccta tgcatcctcc tgccttatcc ctaaataata ttctctactt    1740
tgtattctag tctttggcga t                                              1761

<210> SEQ ID NO 47
<211> LENGTH: 500
<212> TYPE: DNA
<213> ORGANISM: Artificial Sequence
<220> FEATURE:
<223> OTHER INFORMATION: A synthetic RNAi

<400> SEQUENCE: 47
ggactacgag aagttcattc aagcgcatcg tgagaccgac gctgatatca ctgttgctgc      60
tcttcctatg gatgagaaac gtgccacggc ttttggactt atgaagattg atgacgaagg     120
aaggatcatt gagtttgctg agaagcctaa aggagagcag ttaaaggcta tgaaggttga     180
tacaacaatc ttgggacttg atgacgaaag ggccaaagag atgcccttta ttgctagtat     240
ggggatatat gttgttagca agaatgtgat gttggacttg ctccgagacc agttccctgg     300
agctaatgac ttcgggagtg aagttatccc tggtgctact gatcttggac tcagagtgca     360
agcttatctg tatgatggat actgggaaga tattggtacc attgaagcct tttacaatgc     420
taatcttggg atcaccaaga aaccagtacc agatttcagc ttctatgacc gttcagcacc     480
aatctacaca cagcctcggt                                                500

<210> SEQ ID NO 48
<211> LENGTH: 1079
<212> TYPE: DNA
<213> ORGANISM: Artificial Sequence
<220> FEATURE:
<223> OTHER INFORMATION: A synthetic spacer

<400> SEQUENCE: 48
agctcctgct ctgtgaattt ctccgctcac gatagatctg cttatactcc ttacattcaa      60
ccttagatct ggtctcgatt tctgtttctc tgttttttc ttttggtcga aatctgatg      120 tttgtttatg ttctgtcacc attaataata atgaactctc tcattcatac aatgattagt     180
ttctctcgtc tacaaaacga tatgttgcat tttcacttt cttctttttt tctaagatga     240
tttgctttga ccaatttgtt tagatcttta ttttatttta ttttctggtg ggttggtgga     300
aattgaaaaa aaaaaaaac agcataaatt gttatttgtt aatgtattca tttttggct     360 atttgttctg ggtaaaaatc tgcttctact attgaatctt tcctggattt tttactccta     420 tttgggttttt atagtaaaaa tacataataa aaggaaaaca aaagttttat agattctctt     480
aaacccctta cgataaaagt tggaatcaaa ataattcagg atcagatgct ctttgattga     540
ttcagatgcg attacagttg catggcaaat tttctagatc cgtcgtcaca ttttattttc     600
tgtttaaata tctaaatctg atatatgatg tcgacaaatt ctggtggctt atacatcact     660
tcaactgttt tcttttggct tgttgtgtca acttggtttt caatacgatt tgtgatttcg     720
atcgctgaat ttttaataca agcaaactga tgttaaccac aagcaagaga tgtgacctgc     780
cttattaaca tcgtattact tactactagt cgtattctca acgcaatcgt ttttgtattt     840
ctcacattat gccgcttctc tactctttat tccttttggt ccacgcattt tctatttgtg     900
gcaatccctt tcacaacctg atttcccact ttggatcatt tgtctgaaga ctctcttgaa     960
tcgttaccac ttgtttcttg tgcatgctct gtttttaga attaatgata aaactattcc    1020
atagtcttga gttttcagct tgttgattct tttgcttttg gttttctgca ggtcaattc     1079
```

<210> SEQ ID NO 49
<211> LENGTH: 500
<212> TYPE: DNA
<213> ORGANISM: Artificial Sequence
<220> FEATURE:
<223> OTHER INFORMATION: A synthetic antisense sequence

<400> SEQUENCE: 49

```
accgaggctg tgtgtagatt ggtgctgaac ggtcatagaa gctgaaatct ggtactggtt      60
tcttggtgat cccaagatta gcattgtaaa aggcttcaat ggtaccaata tcttcccagt     120
atccatcata cagataagct tgcactctga gtccaagatc agtagcacca gggataactt     180
cactcccgaa gtcattagct ccagggaact ggtctcggag caagtccaac atcacattct     240
tgctaacaac atatatcccc atactagcaa taaagggcat ctctttggcc ctttcgtcat     300
caagtcccaa gattgttgta tcaaccttca tagcctttaa ctgctctcct ttaggcttct     360
cagcaaactc aatgatcctt ccttcgtcat caatcttcat aagtccaaaa gccgtggcac     420
gtttctcatc cataggaaga gcagcaacag tgatatcagc gtcggtctca cgatgcgctt     480
gaatgaactt ctcgtagtcc                                                 500
```

<210> SEQ ID NO 50
<211> LENGTH: 2079
<212> TYPE: DNA
<213> ORGANISM: Artificial Sequence
<220> FEATURE:
<223> OTHER INFORMATION: A synthetic RNAi

<400> SEQUENCE: 50

```
ggactacgag aagttcattc aagcgcatcg tgagaccgac gctgatatca ctgttgctgc      60
tcttcctatg gatgagaaac gtgccacggc ttttggactt atgaagattg atgacgaagg     120
aaggatcatt gagtttgctg agaagccaa aggagagcag ttaaaggcta tgaaggttga     180
tacaacaatc ttgggacttg atgacgaaag ggccaaagag atgccctta ttgctagtat     240
ggggatatat gttgttagca agaatgtgat gttggacttg ctccgagacc agttccctgg     300
agctaatgac ttcgggagtg aagttatccc tggtgctact gatcttggac tcagagtgca     360
agcttatctg tatgatggat actgggaaga tattggtacc attgaagcct tttacaatgc     420
taatcttggg atcaccaaga aaccagtacc agatttcagc ttctatgacc gttcagcacc     480
aatctacaca cagcctcggt agctcctgct ctgtgaattt ctccgctcac gatagatctg     540
cttatactcc ttacattcaa ccttagatct ggtctcgatt tctgtttctc tgtttttttc     600
ttttggtcga gaatctgatg tttgtttatg ttctgtcacc attaataata atgaactctc     660
tcattcatac aatgattagt ttctctcgtc tacaaaacga tatgttgcat ttcactttt      720
cttcttttt tctaagatga tttgctttga ccaatttgtt tagatcttta ttttatttta     780
ttttctggtg ggttggtgga aattgaaaaa aaaaaaaaac agcataaatt gttatttgtt     840
aatgtattca ttttttggct atttgttctg ggtaaaaatc tgcttctact attgaatctt     900
tcctggattt tttactccta ttgggttttt atagtaaaaa tacataataa aaggaaaaca     960
aaagttttat agattctctt aaacccctta cgataaaagt tggaatcaaa ataattcagg    1020
atcagatgct ctttgattga ttcagatgcg attacagttg catggcaaat tttctagatc    1080
cgtcgtcaca tttatttttc tgtttaaata tctaaatctg atatatgatg tcgacaaatt    1140
ctggtggctt atacatcact tcaactgttt tcttttggct ttgtttgtca acttggtttt    1200
```

```
caatacgatt tgtgatttcg atcgctgaat ttttaataca agcaaactga tgttaaccac      1260
aagcaagaga tgtgacctgc cttattaaca tcgtattact tactactagt cgtattctca      1320
acgcaatcgt ttttgtattt ctcacattat gccgcttctc tactctttat tccttttggt      1380
ccacgcattt tctatttgtg gcaatcccct tcacaacctg atttcccact ttggatcatt      1440
tgtctgaaga ctctcttgaa tcgttaccac ttgtttcttg tgcatgctct gttttttaga      1500
attaatgata aaactattcc atagtcttga gttttcagct tgttgattct tttgcttttg      1560
gttttctgca ggtcaattca ccgaggctgt gtgtagattg gtgctgaacg gtcatagaag      1620
ctgaaatctg gtactggttt cttggtgatc ccaagattag cattgtaaaa ggcttcaatg      1680
gtaccaatat cttcccagta tccatcatac agataagctt gcactctgag tccaagatca      1740
gtagcaccag ggataacttc actcccgaag tcattagctc cagggaactg gtctcggagc      1800
aagtccaaca tcacattctt gctaacaaca tatatcccca tactagcaat aaagggcatc      1860
tctttggccc tttcgtcatc aagtcccaag attgttgtat caaccttcat agcctttaac      1920
tgctctcctt taggcttctc agcaaactca atgatccttc cttcgtcatc aatcttcata      1980
agtccaaaag ccgtggcacg tttctcatcc ataggaagag cagcaacagt gatatcagcg      2040
tcggtctcac gatgcgcttg aatgaacttc tcgtagtcc                             2079

<210> SEQ ID NO 51
<211> LENGTH: 500
<212> TYPE: DNA
<213> ORGANISM: Artificial Sequence
<220> FEATURE:
<223> OTHER INFORMATION: A synthetic RNAi sequence

<400> SEQUENCE: 51
ttgtaagcat catagctaag aagcaaagta tcatctggtg ataacaaaaa ctcagaacaa        60
aaacccaatg cgtacaaaga tttatccttc aaatgcttgc caattgtgtt taaacgagaa      120
gctactgtag acgaagaccc tcgaccaaaa gctttagtct tatctatctc cgttacgaat      180
ctctgaacat cgaattggcc cagaagagac acaagccagt tgttggagaa aggaagagtg      240
aggactcttt gaagagagaa tccaccaccg cctccatctc cggtgttggg acggataggg      300
gagaaggaag ggatgagagg tgaggccatg aagcggtgga agaactcaac ttgcttaggg      360
cgagatagac gagtgcctct agagagacct agaggaagag gatcgtcagg aacagctcgt      420
gcggtgccct cgagcgtcac cggagttgac atatcgaggt cccagatgtc tccctctccg      480
acccatctca ttctgttcat                                                  500

<210> SEQ ID NO 52
<211> LENGTH: 171
<212> TYPE: DNA
<213> ORGANISM: Artificial Sequence
<220> FEATURE:
<223> OTHER INFORMATION: A synthetic RNAi sequence

<400> SEQUENCE: 52
atgctttcgt tatcatgctc ttcttcttct tcttcgttgc ttcctccgag tttacactac        60
cacggttctt cttctgttca gtccatcgtt gtaccaagaa ggagtcttat ctcgtttcgt      120
cggaaagtct cttgctgttg catagctcca cctcagaact tggacaacga t              171

<210> SEQ ID NO 53
<211> LENGTH: 500
<212> TYPE: DNA
<213> ORGANISM: Artificial Sequence
```

<220> FEATURE:
<223> OTHER INFORMATION: A synthetic RNAi sequence

<400> SEQUENCE: 53

| | | | | | |
|---|---|---|---|---|---|
| atattcttca | aggaaggatt | aacacggata | atcgtaccaa | cagtaacccc | acggatccta | 60 |
| accggtgttc | ccgtgcaaat | accagaagca | tgactaagct | caaacacagt | ctgatatttc | 120 |
| ctaaacttcg | accgcatttg | aaaacctcgc | aaccaagccc | agctaagagc | aagaagagta | 180 |
| gctccagaga | caataaacaa | accaacacca | ccttcccaaa | tacttctctt | accaaaccca | 240 |
| aaatcactca | aaggttttaa | agtctgtctc | catatattcc | tgggcacatc | caaaacaacg | 300 |
| gtgagaggat | tcttcccccc | atcagacgat | ggttgaccat | gagcagcatc | ggaattggat | 360 |
| gcagctctga | ccactaaatg | cctagttcta | ggttttggtg | aagataagg | aaccccattg | 420 |
| ggtgaaactc | gaggacaagc | aatcatggag | gatgatggca | ttagtgatga | tggaacttga | 480 |
| attactggat | tcccaatcat | | | | | 500 |

<210> SEQ ID NO 54
<211> LENGTH: 500
<212> TYPE: DNA
<213> ORGANISM: Artificial Sequence
<220> FEATURE:
<223> OTHER INFORMATION: A synthetic RNAi sequence

<400> SEQUENCE: 54

| | | | | | |
|---|---|---|---|---|---|
| ctgtttagac | ctagtctagt | gaattctcta | acgaactgga | ttgtgaaagc | cataccaaca | 60 |
| aatgtagaag | tcagaagaca | aactcctaga | gatttcggtc | cggttctctc | cagctgttga | 120 |
| agagtgtttc | tccagtgaat | cttacccttt | aaaatccgga | gaacgacttg | tcctgctata | 180 |
| ataggaactg | ataaacctct | ccatatgtac | ttagaaggtg | accatttgct | gaacggaagc | 240 |
| tcggcttctt | gactgggtgc | gttgtttca | gtagaggttt | cttcttccaa | catagacatg | 300 |
| gatgggtgac | catcattagc | attcaaattc | acatataatc | ttctttgccg | tatcggactt | 360 |
| gaaatcccat | aagattgagt | cttttccaatg | aaaccaactt | gacaaagctt | tggggggctta | 420 |
| ataccaatcg | aagcatcaaa | ccgtggaaag | actctatgag | ggaaacaaaa | cgattgatgg | 480 |
| atacaacaag | tctgcatcat | | | | | 500 |

<210> SEQ ID NO 55
<211> LENGTH: 376
<212> TYPE: DNA
<213> ORGANISM: Artificial Sequence
<220> FEATURE:
<223> OTHER INFORMATION: A synthetic RNAi sequence

<400> SEQUENCE: 55

| | | | | | |
|---|---|---|---|---|---|
| aaaaatggca | atgtgactca | ctcaatcggt | gactcgctat | agtctgtgaa | gaaaggccaa | 60 |
| tttcgccata | aagttcacac | ctttgatctc | ctttgtttct | gggtttctcc | taaatcatcc | 120 |
| aaattggtat | cgaatttgcc | cttctccgat | tcaatttctt | cacgatctca | aaacccagaa | 180 |
| gaaagaatca | tgctttcgtt | atcatgctct | tcttcttctt | cttcgttgct | tcctccgagt | 240 |
| ttacactacc | acggttcttc | ttctgttcag | tccatcgttg | taccaagaag | gagtcttatc | 300 |
| tcgtttcgtc | ggaaagtctc | ttgctgttgc | atagctccac | ctcagaactt | ggacaacgat | 360 |
| gccaccaaat | tcgatt | | | | | 376 |

<210> SEQ ID NO 56
<211> LENGTH: 427
<212> TYPE: PRT

<213> ORGANISM: Arabidopsis thaliana

<400> SEQUENCE: 56

```
Met Lys Ala Ile Gln Leu Leu Trp Glu Ala Ile Met Glu Ala Thr Lys
 1               5                  10                  15
Arg Glu Arg Arg Glu Asp Asp Gly Glu Lys Ala Ser Pro Glu
             20                  25                  30
Ser Leu Val Leu Pro Pro Glu Ile Ile Thr Glu Ile Leu Leu Arg Leu
                 35                  40                  45
Pro Ala Lys Ser Ile Gly Arg Phe Arg Cys Val Ser Lys Leu Phe Cys
 50                  55                  60
Thr Leu Ser Ser Asp Pro Gly Phe Ala Lys Ile His Leu Asp Leu Ile
 65                  70                  75                  80
Leu Arg Asn Glu Ser Val Arg Ser Leu His Arg Lys Leu Ile Val Ser
                 85                  90                  95
Ser His Asn Leu Tyr Ser Leu Asp Phe Asn Ser Ile Gly Asp Gly Ile
                100                 105                 110
Arg Asp Leu Ala Ala Val Glu His Asn Tyr Pro Leu Lys Asp Asp Pro
                115                 120                 125
Ser Ile Phe Ser Glu Met Ile Arg Asn Tyr Val Gly Asp His Leu Tyr
                130                 135                 140
Asp Asp Arg Arg Val Met Leu Lys Leu Asn Ala Lys Ser Tyr Arg Arg
145                 150                 155                 160
Asn Trp Val Glu Ile Val Gly Ser Ser Asn Gly Leu Val Cys Ile Ser
                165                 170                 175
Pro Gly Glu Gly Ala Val Phe Leu Tyr Asn Pro Thr Thr Gly Asp Ser
                180                 185                 190
Lys Arg Leu Pro Glu Asn Phe Arg Pro Lys Ser Val Glu Tyr Glu Arg
                195                 200                 205
Asp Asn Phe Gln Thr Tyr Gly Phe Gly Phe Asp Gly Leu Thr Asp Asp
                210                 215                 220
Tyr Lys Leu Val Lys Leu Val Ala Thr Ser Glu Asp Ile Leu Asp Ala
225                 230                 235                 240
Ser Val Tyr Ser Leu Lys Ala Asp Ser Trp Arg Arg Ile Cys Asn Leu
                245                 250                 255
Asn Tyr Glu His Asn Asp Gly Ser Tyr Thr Ser Gly Val His Phe Asn
                260                 265                 270
Gly Ala Ile His Trp Val Phe Thr Glu Ser Arg His Asn Gln Arg Val
                275                 280                 285
Val Val Ala Phe Asp Ile Gln Thr Glu Glu Phe Arg Glu Met Pro Val
                290                 295                 300
Pro Asp Glu Ala Glu Asp Cys Ser His Arg Phe Ser Asn Phe Val Val
305                 310                 315                 320
Gly Ser Leu Asn Gly Arg Leu Cys Val Val Asn Ser Cys Tyr Asp Val
                325                 330                 335
His Asp Asp Ile Trp Val Met Ser Glu Tyr Gly Glu Ala Lys Ser Trp
                340                 345                 350
Ser Arg Ile Arg Ile Asn Leu Leu Tyr Arg Ser Met Lys Pro Leu Cys
                355                 360                 365
Ser Thr Lys Asn Asp Glu Glu Val Leu Leu Glu Leu Asp Gly Asp Leu
                370                 375                 380
Val Leu Tyr Asn Phe Glu Thr Asn Ala Ser Ser Asn Leu Gly Ile Cys
385                 390                 395                 400
```

Gly Val Lys Leu Ser Asp Gly Phe Glu Ala Asn Thr Tyr Val Glu Ser
                405                 410                 415

Leu Ile Ser Pro Asn Ser Tyr Gly Ile Glu Ser
            420                 425

<210> SEQ ID NO 57
<211> LENGTH: 1708
<212> TYPE: DNA
<213> ORGANISM: Arabidopsis thaliana

<400> SEQUENCE: 57 ttttcaaat caaatcagaa tacattgatt ctgtatatct tattgaaaaa tccatcaatt      60
tacatcaaca attttatatc taataattaa tttaaagaga aaatttataa aagtttatta   120
gagcaaataa ctcaaactcg gattttatag tcgttatgac ccggtttgac tattgaaccg   180
tttaaccgag aaattgggac tcaattaaga caaccgaaac tagacccgga tccagtgtta   240
gcgggctaga ttaaggtgtc gggtcatagc ggagaagcaa ccagacgcca acaatgaaag   300
cgatccagtt gctgtgggaa gcgataatgg aggcgacgaa gagagaaaga cggagagaag   360
atgacgacgg cgaaaaagct tcaccggaat cactcgttct tccaccagag atcattacag   420
aaattcttct ccgattacca gccaaatcga tcgggcgatt caggtgcgta tcaaagctct   480
tttgcacttt atcgtcagat ccagggttcg cgaagattca cctcgatctg atccttcgaa   540
acgaatccgt aagatcgctc caccgtaagc tcattgtgtc ttcacataat ctgtactcgt   600
tagatttcaa ttcgatcggt gacggaatta gggatttagc ggctgtggaa cacaattatc   660
ctcttaaaga cgatccaagc atttctctg agatgattag gaattacgtg ggggaccatc   720
tgtacgatga tcgtcgcgtg atgcttaagc tgaatgcgaa atcgtatcga agaaactggg   780
ttgagatcgt tggatcttcc aatggtttag tgtgtatctc tcctggtgaa ggagctgttt   840
tcttgtataa tccaactacc ggagattcca agagattacc tgaaaatttt cgtcccaaat   900
ctgtagaata cgaaagagat aatttccaaa cttatggatt tggtttcgat ggtctcactg   960
atgattacaa attggtgaag cttgttgcta ccagtgaaga tattctcgat gctagtgtct  1020
attccttgaa ggctgactca tggagacgga tctgcaattt gaattatgag cacaacgatg  1080
gctcctacac gtccggtgtg catttcaacg gtgcgattca ctgggtgttc acagagagta  1140
ggcacaacca aagagtggtt gtagcatttg atattcaaac cgaggagttt cgagagatgc  1200
cagtgcctga tgaagctgaa gattgttccc ataggtttag caactttgtg gtcggaagtc  1260
tcaatggacg tctctgtgtg gtcaatagtt gctacgatgt gcatgatgat atatgggtga  1320
tgagtgagta cggtgaagct aaatcctgga gcagaattcg aatcaacttg ttgtataggt  1380
cgatgaaacc gctctgttcg actaagaacg atgaagaggt tcttctggag cttgatggag  1440
acctggtgtt gtacaacttt gaaaccaatg catcgagtaa tctaggaatt tgtggggtta  1500
agctcagtga cgggttcgag gcaaatacat acgtagagag cctcatatca cccaactctt  1560
atggtataga gagctgagga agtctgcttt ttgctaagat ataataaacc aacattcgga  1620
ttagaaatgt tttagaaaca taatcatgta atatgtatca tgtaattaac aacgaatggt  1680
caatgggtat tttaagtttc tttctcct                                     1708

<210> SEQ ID NO 58
<211> LENGTH: 21
<212> TYPE: DNA
<213> ORGANISM: Artificial Sequence
<220> FEATURE:
<223> OTHER INFORMATION: A synthetic primer

<400> SEQUENCE: 58
aaatctaaac tttctcagag t                                             21

<210> SEQ ID NO 59
<211> LENGTH: 29
<212> TYPE: DNA
<213> ORGANISM: Artificial Sequence
<220> FEATURE:
<223> OTHER INFORMATION: A synthetic primer

<400> SEQUENCE: 59
ccttacgcgt ggcaaagaca ttgattatt                                     29

<210> SEQ ID NO 60
<211> LENGTH: 26
<212> TYPE: DNA
<213> ORGANISM: Artificial Sequence
<220> FEATURE:
<223> OTHER INFORMATION: A synthetic primer

<400> SEQUENCE: 60
ggtaccaaat ctaaactttc tcagag                                        26

<210> SEQ ID NO 61
<211> LENGTH: 26
<212> TYPE: DNA
<213> ORGANISM: Artificial Sequence
<220> FEATURE:
<223> OTHER INFORMATION: A synthetic primer

<400> SEQUENCE: 61
ggtaccggca aagacattga ttattc                                        26

<210> SEQ ID NO 62
<211> LENGTH: 42
<212> TYPE: DNA
<213> ORGANISM: Artificial Sequence
<220> FEATURE:
<223> OTHER INFORMATION: A synthetic primer

<400> SEQUENCE: 62
tgtgacaatg gtaccggtat ggrgccctgg gagcatcatc tc                      42

<210> SEQ ID NO 63
<211> LENGTH: 50
<212> TYPE: DNA
<213> ORGANISM: Artificial Sequence
<220> FEATURE:
<223> OTHER INFORMATION: A synthetic primer

<400> SEQUENCE: 63
tgtctggcaa caacaaggat tagtrgcgga ggttgaagga tagattagtc              50

<210> SEQ ID NO 64
<211> LENGTH: 39
<212> TYPE: DNA
<213> ORGANISM: Artificial Sequence
<220> FEATURE:
<223> OTHER INFORMATION: A synthetic primer

<400> SEQUENCE: 64
aaagccgtcg cgaagctarg gagccaattg tcggatttg                          39

<210> SEQ ID NO 65

```
<211> LENGTH: 51
<212> TYPE: DNA
<213> ORGANISM: Artificial Sequence
<220> FEATURE:
<223> OTHER INFORMATION: A synthetic primer

<400> SEQUENCE: 65
atggcgtctg tatctgcaat tggagrggat ttgagtgaaa tcttgtcgtc g        51

<210> SEQ ID NO 66
<211> LENGTH: 37
<212> TYPE: DNA
<213> ORGANISM: Artificial Sequence
<220> FEATURE:
<223> OTHER INFORMATION: A synthetic primer

<400> SEQUENCE: 66
aacaggcggg tcggatctrg cggctgccat ctttgag                         37

<210> SEQ ID NO 67
<211> LENGTH: 40
<212> TYPE: DNA
<213> ORGANISM: Artificial Sequence
<220> FEATURE:
<223> OTHER INFORMATION: A synthetic primer

<400> SEQUENCE: 67
gaggccaagg tggatccatr caaagccacc aagcatgttg                      40

<210> SEQ ID NO 68
<211> LENGTH: 44
<212> TYPE: DNA
<213> ORGANISM: Artificial Sequence
<220> FEATURE:
<223> OTHER INFORMATION: A synthetic primer

<400> SEQUENCE: 68
ccaacggtgg atctgtgtct acrtcactgc aaaactcgct ggtt                 44

<210> SEQ ID NO 69
<211> LENGTH: 46
<212> TYPE: DNA
<213> ORGANISM: Artificial Sequence
<220> FEATURE:
<223> OTHER INFORMATION: A synthetic primer

<400> SEQUENCE: 69
cagtctgcag aggaagccat agtraggtct gggacgtata gccaaa               46

<210> SEQ ID NO 70
<211> LENGTH: 47
<212> TYPE: DNA
<213> ORGANISM: Artificial Sequence
<220> FEATURE:
<223> OTHER INFORMATION: A synthetic primer

<400> SEQUENCE: 70
tggattctgc tggcgttact acragcctat caagatcgac gaactct              47

<210> SEQ ID NO 71
<211> LENGTH: 42
<212> TYPE: DNA
<213> ORGANISM: Artificial Sequence
<220> FEATURE:
<223> OTHER INFORMATION: A synthetic primer

<400> SEQUENCE: 71
```

```
aaacgagcca aaagggctaa grgggcttgt cgggttatga ga                            42

<210> SEQ ID NO 72
<211> LENGTH: 30
<212> TYPE: DNA
<213> ORGANISM: Artificial Sequence
<220> FEATURE:
<223> OTHER INFORMATION: A synthetic primer

<400> SEQUENCE: 72
gtgatgatgg accaaatagt tacaagaaac                                          30

<210> SEQ ID NO 73
<211> LENGTH: 25
<212> TYPE: DNA
<213> ORGANISM: Artificial Sequence
<220> FEATURE:
<223> OTHER INFORMATION: A synthetic primer

<400> SEQUENCE: 73
catcaccatt gagagagaga gcttt                                               25

<210> SEQ ID NO 74
<211> LENGTH: 375
<212> TYPE: DNA
<213> ORGANISM: Artificial Sequence
<220> FEATURE:
<223> OTHER INFORMATION: A synthetic RNAi sequence

<400> SEQUENCE: 74
aaaaatggca atgtgactca ctcaatcggt gactcgctat agtctgtgaa gaaaggccaa         60
tttcgccata aagttcacac ctttgatctc ctttgtttct gggtttctcc taaatcatcc        120
aaattggtat cgaatttgcc cttctccgat tcaatttctt cacgatctca aaacccagaa        180
gaaagaatca tgctttcgtt atcatgctct tcttcttctt cttcgttgct tcctccgagt        240
ttacactacc acggttcttc ttctgttcag tccatcgttg taccaagaag gagtcttatc        300
tcgtttcgtc ggaaagtctc ttgctgttgc atagctccac ctcagaactt ggacaacgat        360
gccaccaaat tcgat                                                         375
```